United States Patent
Bryja et al.

(10) Patent No.: US 11,498,920 B2
(45) Date of Patent: Nov. 15, 2022

(54) 4-(1H-IMIDAZOL-5-YL)-1H-PYRROLO[2, 3-B] PYRIDINES FOR USE IN THE TREATMENT OF LEUKAEMIAS, LYMPHOMAS AND SOLID TUMORS

(71) Applicant: MASARYKOVA UNIVERZITA, Brno (CZ)

(72) Inventors: Vitezslav Bryja, Brno (CZ); Pavlina Janovska, Brno (CZ); Michaela Gregorova, Hradec Kralove (CZ); Vaclav Nemec, Brno—Bohunice (CZ); Prashant Khirsariya, Brno (CZ); Kamil Paruch, Tisnov (CZ)

(73) Assignee: MASARYKOVA UNIVERZITA, Brno (CZ)

( * ) Notice: Subject to any disclaimer, the term of this patent is extended or adjusted under 35 U.S.C. 154(b) by 316 days.

(21) Appl. No.: 16/963,766

(22) PCT Filed: Mar. 26, 2019

(86) PCT No.: PCT/EP2019/057595
§ 371 (c)(1),
(2) Date: Jul. 21, 2020

(87) PCT Pub. No.: WO2019/185631
PCT Pub. Date: Oct. 3, 2019

(65) Prior Publication Data
US 2021/0040086 A1    Feb. 11, 2021

(30) Foreign Application Priority Data

Mar. 29, 2018  (EP) .................................... 18164938

(51) Int. Cl.
*C07D 471/04*    (2006.01)
*C07D 519/00*    (2006.01)
*A61P 35/02*    (2006.01)

(52) U.S. Cl.
CPC ............ *C07D 471/04* (2013.01); *A61P 35/02* (2018.01); *C07D 519/00* (2013.01)

(58) Field of Classification Search
CPC ...... C07D 471/04; C07D 519/00; A61P 35/02
USPC ...................................................... 514/210.21
See application file for complete search history.

(56) References Cited

FOREIGN PATENT DOCUMENTS

| WO | 2011085269 A1 | 7/2011 |
| WO | 2014023271 A1 | 2/2014 |
| WO | 2014100533 A1 | 6/2014 |

OTHER PUBLICATIONS

Selig et al., Tetrahedron (2011), 67(47), 9204-9213.*
Ringshausen et al: "Constitutive activation of the MAPkinase p38 is critical for MMP-9 production and survival of B-CLL cells on bone marrow stromal cells" LEUKEMIA., vol. 18, No. 12, Dec. 1, 2004 (Dec. 1, 2004), pp. 1964-1970, XP055475534, US, ISSN: 0887-6924, DOI: 10.1038/sj.leu.2403544, https://dx.doi.org/10.1038/sj.leu.2403544.
Selig R et al: A frozen analogue approach to aminopyridinylimidazoles leading to novel and promising p38 MAP kinase inhibitors11 , Journal of Medicinal Chemistry, American Chemical Society, vol. 55, No. 19, Oct. 11, 2012 (Oct. 11, 2012), pp. 8429-8439, XP002753232, ISSN: 0022-2623, DOI: 10.1021/JM300852W.
International Search Report and Written Opinion for corresponding PCT application No. PCT/EP2019/057595, dated Jun. 3, 2019.

* cited by examiner

*Primary Examiner* — Niloofar Rahmani
(74) *Attorney, Agent, or Firm* — Notaro, Michalos & Zaccaria P.C.

(57) ABSTRACT

Novel 4-(1H-imidazol-5-yl)-1H-pyrrolo[2,3-b]pyridine compounds that are useful in the treatment of lymphomas, leukaemias, and solid tumors.

14 Claims, 3 Drawing Sheets

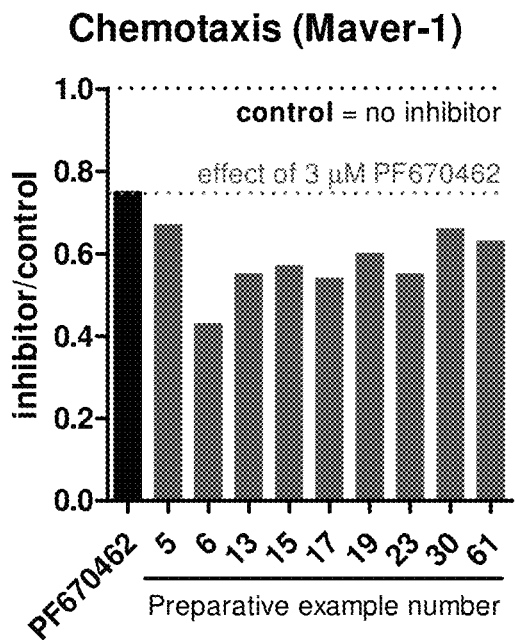
Fig. 3
Fig. 4A
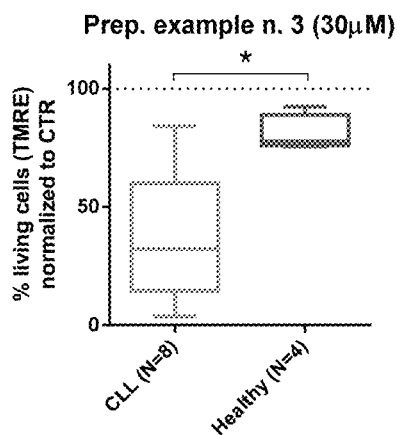
Fig. 4B
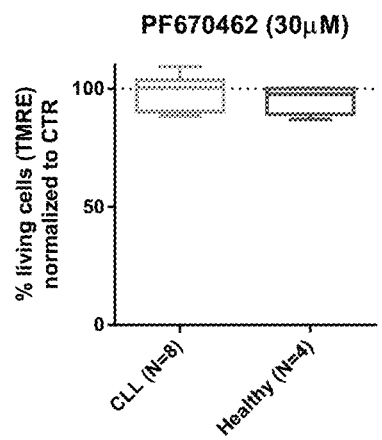

4-(1H-IMIDAZOL-5-YL)-1H-PYRROLO[2, 3-B] PYRIDINES FOR USE IN THE TREATMENT OF LEUKAEMIAS, LYMPHOMAS AND SOLID TUMORS

FIELD OF ART

The present invention relates to novel heterocyclic compounds useful in the treatment of leukaemias, lymphomas and solid tumors.

BACKGROUND ART

B-cell chronic lymphocytic leukemia (CLL) is a lymphoproliferative malignancy with highly heterogeneous disease course and unclear pathogenesis. CLL is the most common adult leukemia in western countries, however it is still considered as incurable, despite extensive effort invested in development of novel therapeutic strategies. CLL is characterized by a monoclonal expansion of dysfunctional mature B-lymphocytes that accumulate in both peripheral blood and lymphatic organs, which results in clinical complications such as hypertrophy of organs, reduced function of the immune system, anemia and others. It is believed that the disease evolves as a result of defects in apoptosis and cell signaling pathways which orchestrate interaction of the leukemic cells with their supporting microenvironment and regulate cell migration. The migration (so called homing) of leukemic cells to proliferative centers in lymphatic organs is a key process of the disease pathogenesis, because it enables interaction of the leukemic cells with their immediate environment (micro-environment). This interaction then leads to uncontrolled proliferation of tumor cells and is responsible for clinical progression of the disease. The protective tumor micro-environment also helps the leukemic cells to survive and evolve and contributes to development of tumor resistance to therapy.

Currently, no curative therapeutic strategy exists for CLL patients, which are typically treated when they develop an aggressive form of the disease with clinical symptoms. The standard treatment is a combination of chemo- and immunotherapy (such as FCR; fludarabine+cyclophosphamide and rituximab, which is a monoclonal antibody against surface receptor of B-lymphocytes) and, more recently, also novel inhibitors targeting pro-survival B cell receptor (BCR) or anti-apoptotic B-cell lymphoma 2 (BCL2) signaling, which are in different phases of clinical testing or already approved for use in various patient subgroups. Despite the fact that new treatment options have significantly enhanced patients' response to therapy, additional improvements are needed in order to prevent relapse of the disease and/or emergence of resistance. This creates a real need for new therapeutic agents which could target the disease more efficiently, with lower side effects and burden for the treated patients and/or act in combination with current therapeutic strategies to achieve final eradication of the disease.

The drugs applied in therapy of CLL are also commonly applied in case of other leukemia and lymphoma types, based on similar mechanisms of the disease pathogenesis and common signaling pathways which are disrupted. Targeting of the microenvironmental interactions, cell adhesion and cell migration mechanisms can be successfully applied also in other cancer types, such as solid tumors, whose progression and dissemination often depends on the same general mechanisms and cell signaling pathway activity.

There is a need to develop novel, more efficacious compounds which could be useful for treatment of CLL as well as other leukemias and lymphomas and other cancer types and could be prepared by practical and easy processes.

With the main focus on CLL, the present invention presents novel heterocyclic compounds for use in treatment of CLL as well as other cancer types (specified further in the document), with the structurally closest compound proposed for the treatment of CLL being inhibitor PF670462, described in WO 2014/023271. The present invention aims at providing more active compounds.

WO 2014/023271 has described the use of casein kinase I (CK1) inhibitors for treatment of CLL. In particular, tested and claimed were D4476, PF670462, IC261 and PF4800567.

The structural formula of PF670462 is

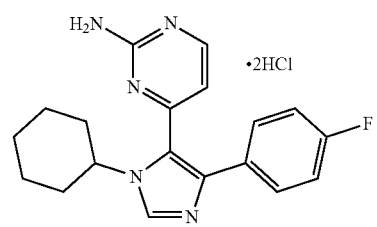 [SMILES: Nc1nccc(-c2c(-c3ccc(F)cc3)ncn2C2CCCCC2)n1]

SUMMARY OF THE INVENTION

The present invention relates to compounds of general formula I or pharmaceutically acceptable salts thereof

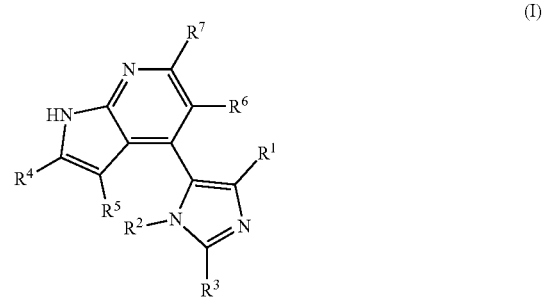

wherein:
R1 is a C6-C14 aryl, C4-C8 cycloalkyl, C3-C10 heteroaryl comprising at least one heteroatom selected from S, O, N, or C3-C7 cycloheteroalkyl comprising at least one heteratom selected from S, O, N, wherein the aryl, cycloalkyl, cycloheteroalkyl or heteroaryl may optionally be substituted by at least one substituent selected independently from C1-C4 alkyl, halogen, OH, O(C1-C4 alkyl), O(C5-C6 aryl or heteroaryl), SH, S(C1-C4 alkyl), CN, $NH_2$, NH(C1-C4 alkyl), N(C1-C4 alkyl)$_2$, $CF_3$, $C_2F_5$, $OCF_3$, $OC_2F_5$;
R2 is selected from the group consisting of
  linear or branched C1-C10 alkyl, preferably C1-C6 alkyl,
  linear or branched C1-C10 alkenyl, preferably C1-C6 alkenyl,
  C3-C8 cycloalkyl, preferably, C4-C7 cycloalkyl, wherein optionally 1-2 carbon atoms are replaced by a heteroatom selected from S, O, N,
  C3-C8 cycloalkenyl, wherein optionally 1-2 carbon atoms are replaced by a heteroatom selected from S, O, N,
  C3-C8-cycloalkyl-C1-C4-alkyl, wherein optionally 1-2 carbon atoms are replaced by a heteroatom selected from S, O, N, C6-C14 aryl,
C6-C14-aryl-C1-C4-alkyl,
C3-C10 heteroaryl comprising at least one heteroatom selected from S, O, N,
C3-C10-heteroaryl-C1-C4-alkyl comprising at least one heteroatom selected from S, O, N in the aromatic ring,
wherein each of the listed substituents can optionally be substituted by at least one substituent selected independently from C1-C4 alkyl, halogen, OH, HO—C1-C4 alkyl, O(C1-C4 alkyl), (C1-C4 alkyl)-O—C1-C4 alkyl, O(C5-C6 aryl or heteroaryl), SH, S(C1-C4 alkyl), S(C5-C6 aryl or heteroaryl), $CF_3$, $CF_3$—(C1-C4 alkyl)-, $C_2F_5$, $OCF_3$, $CF_3O$—(C1-C4 alkyl)-, $OC_2F_5$, amino ($NH_2$), $NO_2$, $N_3$, C1-C4 alkylamino, di(C1-C4 alkyl)amino, (C5-C6 aryl or heteroaryl)amino, di(C5-C6 aryl or heteroaryl) amino, $NH_2$—(C1-C4 alkyl)-, (C1-C4 alkyl)-NH—C1-C4 alkyl, (C1-C4 alkyl)$_2$-N—C1-C4-alkyl, =O, =S, CN, =N—OH, =N—O(C1-C4 alkyl), —COOH, HOOC—(C1-C4 alkyl)-, —$CONH_2$, —CONH(C1-C4 alkyl), —CON(C1-C4 alkyl)$_2$, $NH_2CO$—(C1-C4 alkyl)-, (C1-C4 alkyl)-CONH—(C1-C4 alkyl)-, (C1-C4 alkyl)$_2$N—CO—(C1-C4 alkyl)-, —COO(C1-C4 alkyl), (C1-C4 alkyl)-COO(C1-C4 alkyl), (C1-C4 alkyl)-O—CO—(C1-C4 alkyl)-, $NH_2S(O)_2$—(C1-C4 alkyl)-, (C1-C4 alkyl)-S(O)$_2$NH(C1-C4 alkyl)-, (C1-C4 alkyl)$_2$N—S(O)$_2$—(C1-C4 alkyl)-, (C1-C4 alkyl)NH—S(O)$_2$—(C1-C4 alkyl)-, —CO(C1-C4 alkyl), —CO(C5-C6 aryl or heteroaryl), (C1-C4 alkyl)-S(O)$_2$—, (C1-C4 alkyl)-S(O)—, (C1-C4 alkyl)-S(O)$_2$—NH—, (C1-C4 alkyl)-S(O)$_2$—N(C1-C4 alkyl)-, (C1-C4 alkyl)-O—CO—, (C1-C4 alkyl)-NH—CO—, (C1-C4 alkyl)$_2$N—CO—, (C1-C4 alkyl)-NH—(SO)$_2$—, (C1-C4 alkyl)$_2$N—(SO)$_2$—, (C1-C4 alkyl)-CO—NH—, (C1-C4 alkyl)-CO—N(C1-C4 alkyl)-, (C1-C4 alkyl)-OCO—NH—, (C1-C4 alkyl)-OCO—N(C1-C4 alkyl)-, (C1-C4 alkyl)-CO—NH—CO—, (C1-C4 alkyl)-CO—N(C1-C4 alkyl)-CO—, $NH_2$—CO—NH—, (C1-C4 alkyl)-NH—CO—NH—, (C1-C4 alkyl)$_2$N—CO—NH—, $NH_2$—CO—N(C1-C4 alkyl)-, (C1-C4 alkyl)-NH—CO—N(C1-C4 alkyl)-, (C1-C4 alkyl)$_2$N—CO—N(C1-C4 alkyl)-, $NH_2$—S(O)$_2$—NH—, (C1-C4 alkyl)-NH—S(O)$_2$—NH—, (C1-C4 alkyl)$_2$N—S(O)$_2$—NH—, $NH_2$—S(O)$_2$—N(C1-C4 alkyl)-, (C1-C4 alkyl)-NH—S(O)$_2$—N(C1-C4 alkyl)-, (C1-C4 alkyl)$_2$N—S(O)$_2$—N(C1-C4 alkyl)-, (C1-C4 alkyl)$_2$N—(C1-C4 alkylene)-CO—, (C1-C4 alkyl)$_2$N—(C1-C4 alkylene)-SO$_2$—, (C1-C4 alkyl)$_2$N—(C1-C4 alkylene)-SO$_2$—NH—, (C1-C4 alkyl)$_2$N—(C1-C4 alkylene)-NH—SO$_2$—;

R3 is selected from hydrogen, halogen, $CF_3$, $C_2F_5$, CN, C1-C4 alkyl, said alkyl being optionally substituted by at least one substituent selected from C1-C4 alkyl, halogen, OH, $NH_2$, NH(C1-C4 alkyl), NH(C5-C6 aryl or heteroaryl), N(C1-C4 alkyl)$_2$, N(C5-C6 aryl or heteroaryl)$_2$, O(C1-C4 alkyl), O(C5-C6 aryl or heteroaryl), SH, S(C1-C4 alkyl), S(C5-C6 aryl or heteroaryl), $OCF_3$, $OC_2F_5$, COO(C1-C4 alkyl), CONH(C1-C4 alkyl), CON(C1-C4 alkyl), $CF_3$, $C_2F_5$;

R4 is selected from hydrogen, $CF_3$, $C_2F_5$, CN, C1-C4 alkyl, optionally substituted by at least one substituent selected from C1-C4 alkyl, halogen, OH, O(C1-C4 alkyl), O(C5-C6 aryl or heteroaryl), SH, S(C1-C4 alkyl), S(C5-C6 aryl or heteroaryl), $OCF_3$, $OC_2F_5$, $CF_3$, $C_2F_5$;

R5 is selected from H, C1-C2 alkyl, halogen; preferably R5 is H;

R6 is selected from H, C1-C2 alkyl, halogen; preferably R6 is H;

R7 is selected from H, halogen, OH, O(C1-C4 alkyl), $CF_3$, $C_2F_5$, CN, $NH_2$, NH(C1-C4 alkyl), N(C1-C4 alkyl)$_2$, C1-C4 alkyl, where alkyl is optionally substituted by at least one substituent selected from C1-C4 alkyl, halogen, OH, O(C1-C4 alkyl), O(C5-C6 aryl or heteroaryl), SH, S(C1-C4 alkyl), S(C5-C6 aryl or heteroaryl), $OCF_3$, $OC_2F_5$, $CF_3$, $C_2F$; preferably R7 is H.

The compounds of formula I can be in the form of free bases or in the form of addition salts with pharmaceutically acceptable organic or inorganic acids, such as hydrochloric acid.

Halogens are selected from fluorine, chlorine, bromine and iodine.

Alkyl is a branched or linear saturated hydrocarbyl.

Alkenyl is a branched or linear hydrocarbyl comprising at least one double bond.

Cycloalkyl is a saturated hydrocarbyl comprising at least one aliphatic cycle.

Cycloalkenyl is a hydrocarbyl comprising at least one aliphatic cycle and at least one double bond in the cycle.

Aryl is a hydrocarbyl comprising at least one aromatic cycle.

Heteroaryl is a heterohydrocarbyl comprising at least one aromatic cycle comprising at least one heteroatom selected from O, S, N.

Heterocyclyl or heterocycloalkyl is a heterohydrocarbyl comprising at least one aliphatic cycle which contains at least one heteroatom selected from O, S, N in the cycle.

Cyclic structures can thus contain one or more cycles, whereas the cycles can be conjugated or connected by a C1-C3 linker.

In a preferred embodiment, R1 is a C6-C10 aryl, optionally substituted. The substituent(s) is/are preferably in meta and/or para position of the aryl ring. Preferably, the substituent is a halogen atom. More preferably, R1 is a phenyl substituted by halogen atom. Even more preferably, R1 is phenyl substituted by one or two halogens, at least one of them being fluorine. Most preferably, R1 is p-fluoro-phenyl, optionally further substituted by a fluorine or chlorine in the meta position.

In a preferred embodiment R1 is a C4-C6 heteroaryl comprising at least one, preferably one or two heteroatoms, optionally substituted. Preferably, the substituent is a halogen atom. More preferably, R1 is a pyridine substituted by halogen atom. Even more preferably, R1 is pyridyl substituted by one or two halogens, at least one of them being fluorine. Most preferably, R1 is 5-fluoropyridin-2-yl, optionally further substituted by a fluorine or chlorine.

In a preferred embodiment, R2 is selected from
C3-C8 cycloalkyl, preferably C4-C7 cycloalkyl, wherein optionally 1-2 carbon atoms are replaced by a heteroatom selected from S, O, N, and which is optionally substituted by one or more substituents selected independently from halogen, hydroxy, methoxy, ethoxy, methyl, ethyl, propyl, isopropyl, amino, methylamino, dimethylamino, methylsulfonamido, methylcarbonyl, methylaminocarbonyl, ethylsulfonamido, ethylcarbonyl, ethylaminocarbonyl, methoxycarbonyl, ethoxycarbonyl, dimethylaminoethylsulfonamido, dimethylaminoethylcarbonyl, dimethylaminopropylsulfonamido, dimethylaminopropylcarbonyl, $OCF_3$, $OC_2F_5$, $CF_3$, $C_2F_5$;

C3-C8-cycloalkyl-C1-C2-alkyl, wherein optionally 1-2 carbon atoms are replaced by a heteroatom selected from S, O, N, and which is optionally substituted by one or more substituents selected independently from halogen, hydroxy, methoxy, ethoxy, methyl, ethyl, propyl, isopropyl, amino, methylamino, dimethylamino, methylsulfonamido, methylcarbonyl, methylaminocarbonyl, ethylsulfonamido, ethylcarbonyl, ethylaminocarbonyl, methoxycarbonyl, ethoxycarbonyl, dimethylaminoethylsulfonamido, dimethylaminoethylcarbonyl, dimethylaminopropylsulfonamido, dimethylaminopropylcarbonyl, $OCF_3$, $OC_2F_5$, $CF_3$, $C_2F_5$;

C6-C14-aryl, which is optionally substituted by one or more substituents selected independently from halogen, hydroxy, methoxy, ethoxy, methyl, ethyl, propyl, isopropyl, amino, methylamino, dimethylamino, methylsulfonamido, methylcarbonyl, methylaminocarbonyl, ethylsulfonamido, ethylcarbonyl, ethylaminocarbonyl, methoxycarbonyl, ethoxycarbonyl, dimethylaminoethylsulfonamido, dimethylaminoethylcarbonyl, dimethylaminopropylsulfonamido, dimethylaminopropylcarbonyl, $OCF_3$, $OC_2F_5$, $CF_3$, $C_2F_5$;

C6-C14-aryl-C1-C2-alkyl, which is optionally substituted by one or more substituents selected independently from halogen, hydroxy, methoxy, ethoxy, methyl, ethyl, propyl, isopropyl, amino, methylamino, dimethylamino, methylsulfonamido, methylcarbonyl, methylaminocarbonyl, ethylsulfonamido, ethylcarbonyl, ethylaminocarbonyl, methoxycarbonyl, ethoxycarbonyl, dimethylaminoethylsulfonamido, dimethylaminoethylcarbonyl, dimethylaminopropylsulfonamido, dimethylaminopropylcarbonyl, $OCF_3$, $OC_2F_5$, $CF_3$, $C_2F_5$;

C3-C10-heteroaryl comprising one or two or three heteratoms selected from S, O, N in the aromatic ring, and which is optionally substituted by one or more substituents selected independently from halogen, hydroxy, methoxy, ethoxy, methyl, ethyl, propyl, isopropyl, amino, methylamino, dimethylamino, methylsulfonamido, methylcarbonyl, methylaminocarbonyl, ethylsulfonamido, ethylcarbonyl, ethylaminocarbonyl, methoxycarbonyl, ethoxycarbonyl, dimethylaminoethylsulfonamido, dimethylaminoethylcarbonyl, dimethylaminopropylsulfonamido, dimethylaminopropylcarbonyl, $OCF_3$, $OC_2F_5$, $CF_3$, $C_2F_5$;

C3-C10-heteroaryl-C1-C2-alkyl comprising one or two or three heteratoms selected from S, O, N in the aromatic ring, and which is optionally substituted by one or more substituents selected independently from halogen, hydroxy, methoxy, ethoxy, methyl, ethyl, propyl, isopropyl, amino, methylamino, dimethylamino, methylsulfonamido, methylcarbonyl, methylaminocarbonyl, ethylsulfonamido, ethylcarbonyl, ethylaminocarbonyl, methoxycarbonyl, ethoxycarbonyl, dimethylaminoethylsulfonamido, dimethylaminoethylcarbonyl, dimethylaminopropylsulfonamido, dimethylaminopropylcarbonyl, $OCF_3$, $OC_2F_5$, $CF_3$, $C_2F_5$;

C1-C6 alkyl, which is optionally substituted by one or more substituents selected independently from halogen, hydroxy, methoxy, ethoxy, amino, methylamino, dimethylamino, methylsulfonamido, methylcarbonyl, methylaminocarbonyl, ethylsulfonamido, ethylcarbonyl, ethylaminocarbonyl, methoxycarbonyl, ethoxycarbonyl, dimethylaminoethylsulfonamido, dimethylaminoethylcarbonyl, dimethylaminopropylsulfonamido, dimethylaminopropylcarbonyl, $OCF_3$, $OC_2F_5$, $CF_3$, $C_2F_5$.

In a preferred embodiment, R2 is selected from

C3-C6-heteroaryl-methyl wherein the heteroaryl comprises one heteroatom selected from O, S, N and is optionally substituted by one or more substituents selected independently from halogen, hydroxy, methoxy, ethoxy, methyl, ethyl, propyl, isopropyl, amino, methylamino, dimethylamino, methylsulfonamido, hydroxymethyl, hydroxyethyl, hydroxypropyl, methoxymethyl, methoxyethyl, methoxypropyl, dimethylaminomethyl, dimethylaminoethyl, dimethylaminopropyl, methylcarbonyl, methylaminocarbonyl, ethylsulfonamido, ethylcarbonyl, ethylaminocarbonyl, methoxycarbonyl, ethoxycarbonyl, dimethylaminoethylsulfonamido, dimethylaminoethylcarbonyl, dimethylaminopropylsulfonamido, dimethylaminopropylcarbonyl, $OCF_3$, $OC_2F_5$, $CF_3$, $C_2F_5$;

C3-C6-heteroaryl wherein the heteroaryl comprises one or two or three heteroatoms selected from O, S, N, preferably N, and is optionally substituted by one or more substituents selected independently from halogen, hydroxy, methoxy, ethoxy, methyl, ethyl, propyl, isopropyl, amino, methylamino, dimethylamino, methylsulfonamido, hydroxymethyl, hydroxyethyl, hydroxypropyl, methoxymethyl, methoxyethyl, methoxypropyl, dimethylaminomethyl, dimethylaminoethyl, dimethylaminopropyl, methylcarbonyl, methylaminocarbonyl, ethylsulfonamido, ethylcarbonyl, ethylaminocarbonyl, methoxycarbonyl, ethoxycarbonyl, dimethylaminoethylsulfonamido, dimethylaminoethylcarbonyl, dimethylaminopropylsulfonamido, dimethylaminopropylcarbonyl, $OCF_3$, $OC_2F_5$, $CF_3$, $C_2F_5$;

cyclohexyl or cyclohexylmethyl wherein the cyclohexyl ring is optionally substituted by one or more substituents selected independently from halogen, hydroxy, methoxy, ethoxy, methyl, ethyl, propyl, isopropyl, amino, methylamino, dimethylamino, methylsulfonamido, hydroxymethyl, hydroxyethyl, hydroxypropyl, methoxymethyl, methoxyethyl, methoxypropyl, dimethylaminomethyl, dimethylaminoethyl, dimethylaminopropyl, methylcarbonyl, methylaminocarbonyl, ethylsulfonamido, ethylcarbonyl, ethylaminocarbonyl, methoxycarbonyl, ethoxycarbonyl, dimethylaminoethylsulfonamido, dimethylaminoethylcarbonyl, dimethylaminopropylsulfonamido, dimethylaminopropylcarbonyl, $OCF_3$, $OC_2F_5$, $CF_3$, $C_2F_5$;

cyclopentyl or cyclopentylmethyl wherein the cyclopentyl ring is optionally substituted by one or more substituents selected independently from halogen, hydroxy, methoxy, ethoxy, methyl, ethyl, propyl, isopropyl, amino, methylamino, dimethylamino, methylsulfonamido, hydroxymethyl, hydroxyethyl, hydroxypropyl, methoxymethyl, methoxyethyl, methoxypropyl, dimethylaminomethyl, dimethylaminoethyl, dimethylaminopropyl, methylcarbonyl, methylaminocarbonyl, ethylsulfonamido, ethylcarbonyl, ethylaminocarbonyl, methoxycarbonyl, ethoxycarbonyl, dimethylaminoethylsulfonamido, dimethylaminoethylcarbonyl, dimethylaminopropylsulfonamido, dimethylaminopropylcarbonyl, $OCF_3$, $OC_2F_5$, $CF_3$, $C_2F_5$;

cyclobutyl or cyclobutylmethyl wherein the cyclobutyl ring is optionally substituted by one or more substituents selected independently from halogen, hydroxy, methoxy, ethoxy, methyl, ethyl, propyl, isopropyl, amino, methylamino, dimethylamino, methylsulfonamido, hydroxymethyl, hydroxyethyl, hydroxypropyl, methoxymethyl, methoxyethyl, methoxypropyl, dimethylaminomethyl, dimethylaminoethyl, dimethylaminopropyl, methylcarbonyl, methylaminocarbonyl, ethylsulfonamido, ethylcarbonyl, ethylaminocarbonyl, methoxycarbonyl, ethoxycarbonyl, dimethylaminoethylsulfonamido, dimethylaminoethylcarbonyl, dimethylaminopropylsulfonamido, dimethylaminopropylcarbonyl, $OCF_3$, $OC_2F_5$, $CF_3$, $C_2F_5$;

C1-C6 alkyl, substituted by halogen, OH, O(C1-C3 alkyl), OCF$_3$, OC$_2$F$_5$, CF$_3$, C$_2$F$_5$;

benzyl, optionally substituted by one or more substituents selected independently from halogen, hydroxy, methoxy, ethoxy, methyl, ethyl, propyl, isopropyl, amino, methylamino, dimethylamino, methylsulfonamido, hydroxymethyl, hydroxyethyl, hydroxypropyl, methoxymethyl, methoxyethyl, methoxypropyl, dimethylaminomethyl, dimethylaminoethyl, dimethylaminopropyl, methylcarbonyl, methylaminocarbonyl, ethylsulfonamido, ethylcarbonyl, ethylaminocarbonyl, methoxycarbonyl, ethoxycarbonyl, dimethylaminoethylsulfonamido, dimethylaminoethylcarbonyl, dimethylaminopropylsulfonamido, dimethylaminopropylcarbonyl, OCF$_3$, OC$_2$F$_5$, CF$_3$, C$_2$F$_5$;

C5-C6 cycloalkyl, wherein 1-2 carbon atoms, preferably 1 carbon atom, are replaced by a heteroatom selected from S, O, N; optionally substituted by one or more substituents selected independently from halogen, hydroxy, methoxy, ethoxy, methyl, ethyl, propyl, isopropyl, amino, methylamino, dimethylamino, methylsulfonamido, hydroxymethyl, hydroxyethyl, hydroxypropyl, methoxymethyl, methoxyethyl, methoxypropyl, dimethylaminomethyl, dimethylaminoethyl, dimethylaminopropyl, methylcarbonyl, methylaminocarbonyl, ethylsulfonamido, ethylcarbonyl, ethylaminocarbonyl, methoxycarbonyl, ethoxycarbonyl, dimethylaminoethylsulfonamido, dimethylaminoethylcarbonyl, dimethylaminopropylsulfonamido, dimethylaminopropylcarbonyl, OCF$_3$, OC$_2$F$_5$, CF$_3$, C$_2$F$_5$;

C5-C6-cycloalkyl-C1-C2-alkyl, wherein 1-2 carbon atoms, preferably 1 carbon atom, are replaced by a heteroatom selected from S, O, N; optionally substituted by one or more substituents selected independently from halogen, hydroxy, methoxy, ethoxy, methyl, ethyl, propyl, isopropyl, amino, methylamino, dimethylamino, methylsulfonamido, hydroxymethyl, hydroxyethyl, hydroxypropyl, methoxymethyl, methoxyethyl, methoxypropyl, dimethylaminomethyl, dimethylaminoethyl, dimethylaminopropyl, methylcarbonyl, methylaminocarbonyl, ethylsulfonamido, ethylcarbonyl, ethylaminocarbonyl, methoxycarbonyl, ethoxycarbonyl, dimethylaminoethylsulfonamido, dimethylaminoethylcarbonyl, dimethylaminopropylsulfonamido, dimethylaminopropylcarbonyl, OCF$_3$, OC$_2$F$_5$, CF$_3$, C$_2$F$_5$.

In a preferred embodiment, R1 is p-fluoro-phenyl or m-chloro-p-fluoro-phenyl, and R2 is cyclohexyl, cyclohexylmethyl, cyclobutyl, cyclobutylmethyl, methyl, ethyl, propyl, butyl, piperidinyl, piperidinylmethyl, tetrahydrofuryl, tetrahydrofurylmethyl, morpholinyl, morpholinylmethyl, phenyl, benzyl, thiophenyl, thiophenylmethyl, oxazolyl, oxazolylmethyl, thiazolyl, thiazolylmethyl, isothiazolyl, isothiazolylmethyl, isoxazolyl, isoxazolylmethyl, triazolyl, triazolylmethyl, pyrazolyl, pyrazolylmethyl, imidazolyl, imidazolylmethyl, pyridyl, pyridylmethyl, furyl or furanylmethyl, wherein the substituent group of R2 is optionally further substituted by one or more substituents selected independently from hydroxy, methoxy, ethoxy, methyl, ethyl, propyl, isopropyl, amino, methylamino, dimethylamino, hydroxymethyl, hydroxyethyl, hydroxypropyl, methoxymethyl, methoxyethyl, methoxypropyl, dimethylaminomethyl, dimethylaminoethyl, dimethylaminopropyl, methylsulfonamido, methylcarbonyl, methylaminocarbonyl, ethylsulfonamido, ethylcarbonyl, ethylaminocarbonyl, methoxycarbonyl, ethoxycarbonyl, dimethylaminoethylsulfonamido, dimethylaminoethylcarbonyl, dimethylaminopropylsulfonamido, dimethylaminopropylcarbonyl, OCF$_3$, OC$_2$F$_5$, CF$_3$, C$_2$F$_5$.

Preferably, R3 is selected from hydrogen, halogen (preferably iodo), methyl, ethyl, propyl, isopropyl, tert-butyl or CF$_3$. Most preferably, R3 is H, methyl or I.

In a preferred embodiment, R4 is hydrogen, halogen or C1 to C4 alkyl.

In one preferred embodiment, the present invention relates to compounds listed in Table 1 of this patent application.

Particularly preferred are the following compounds (in the form of free bases or in the form of salts with pharmaceutically acceptable acids):

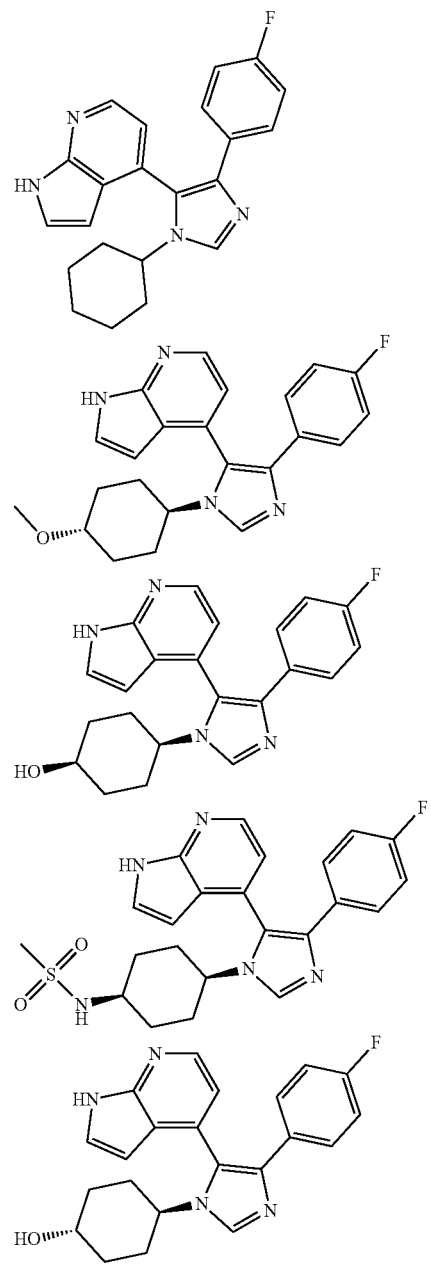

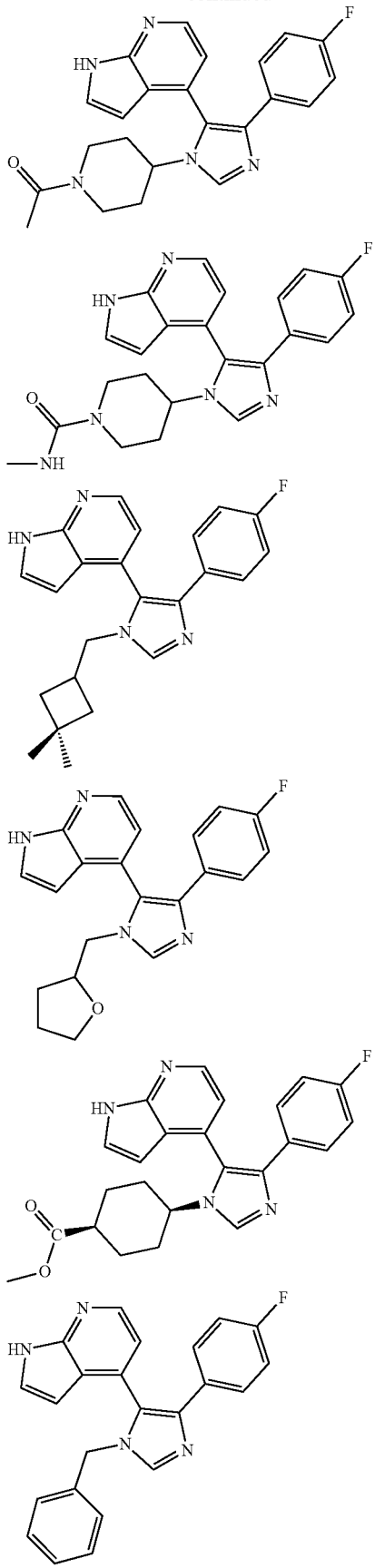
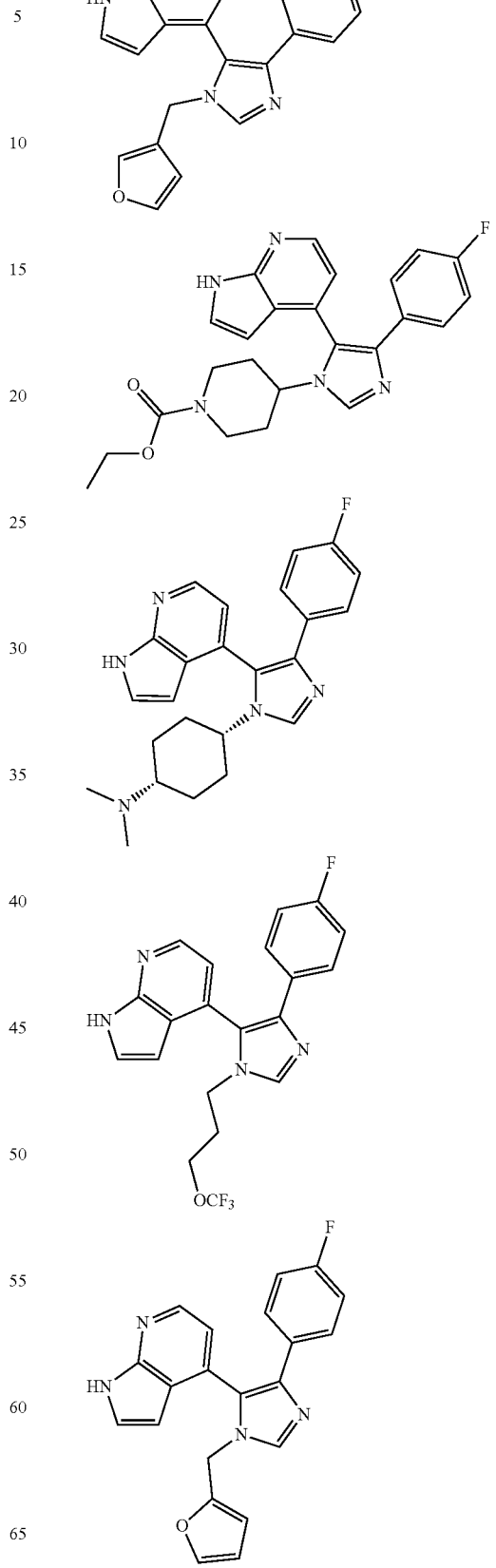

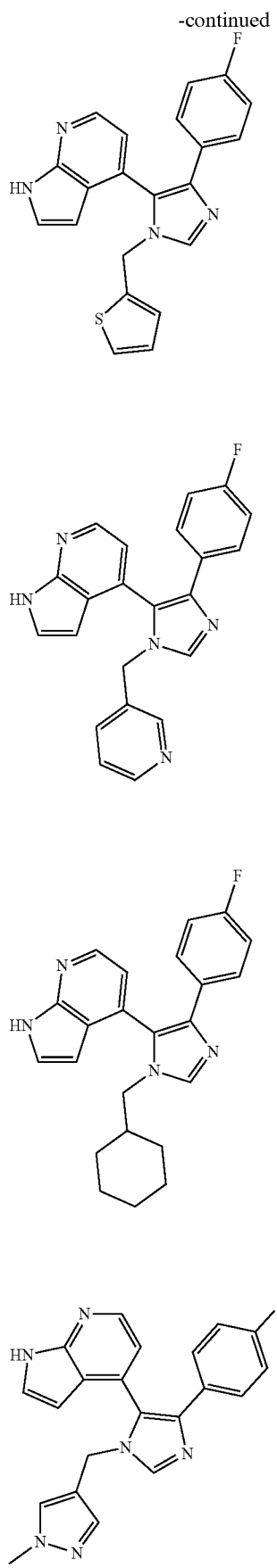
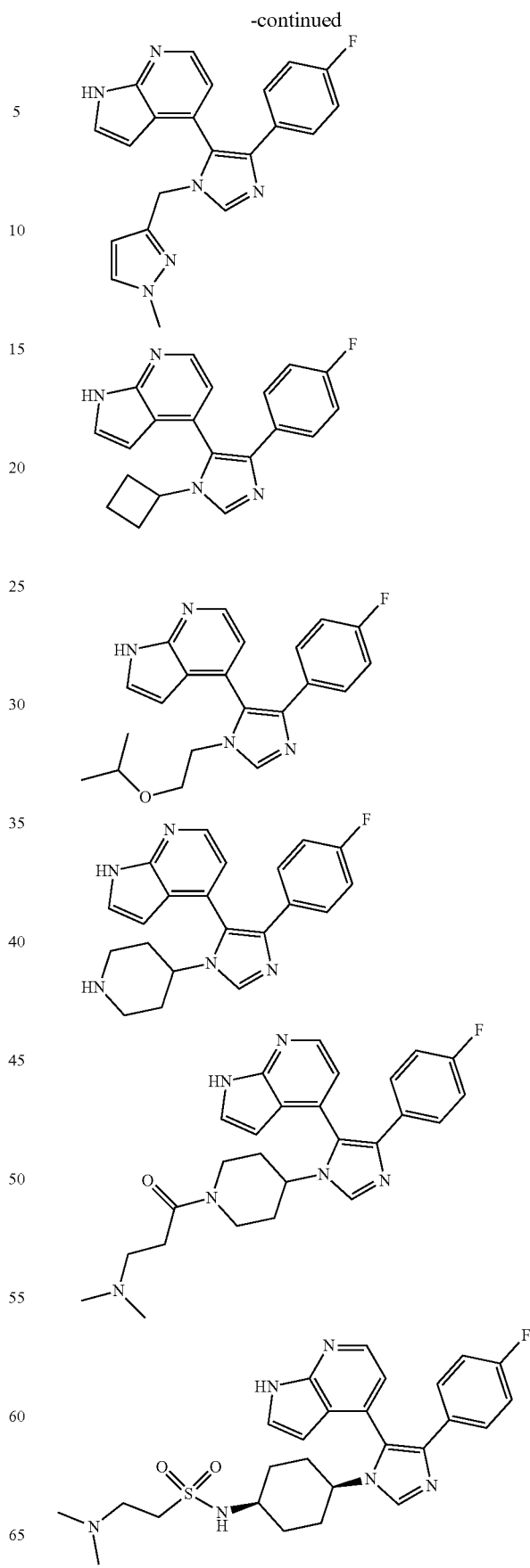

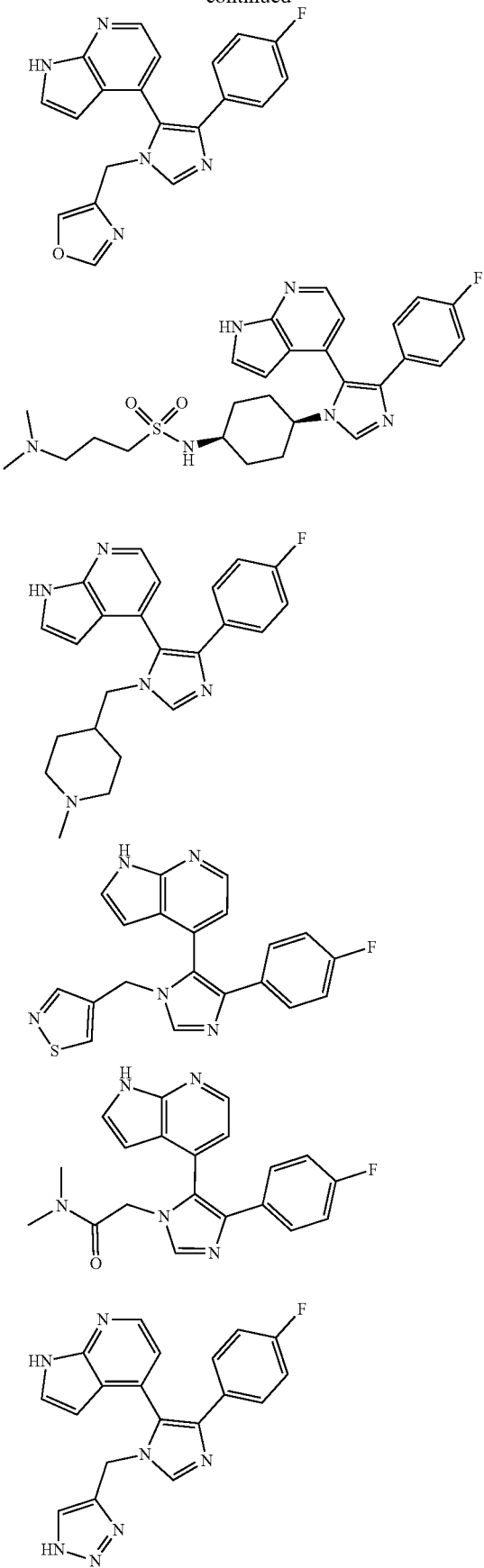
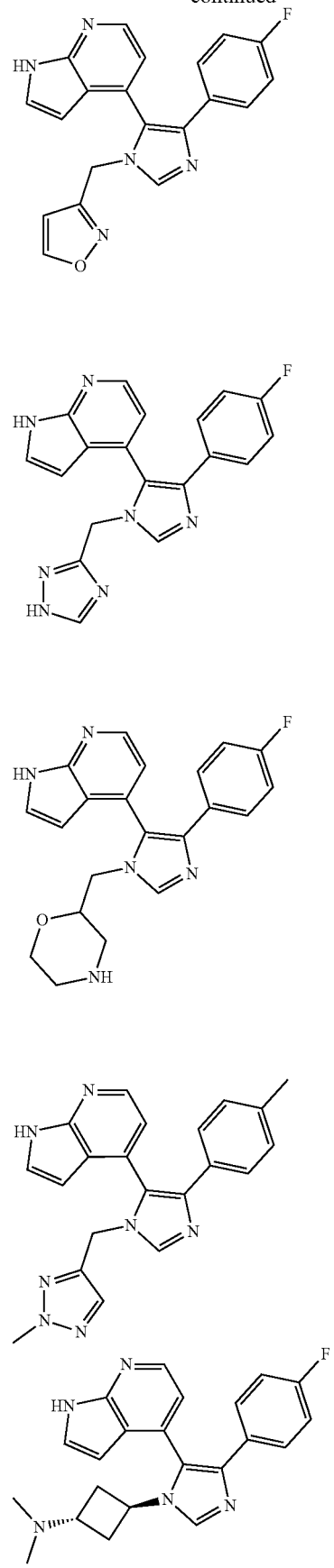

-continued
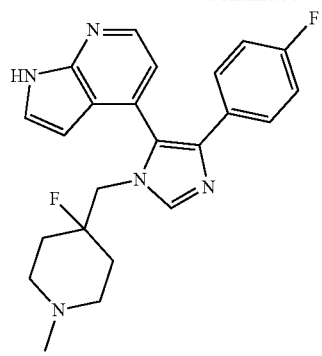
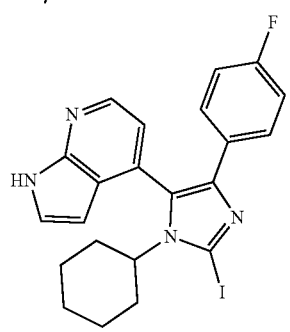
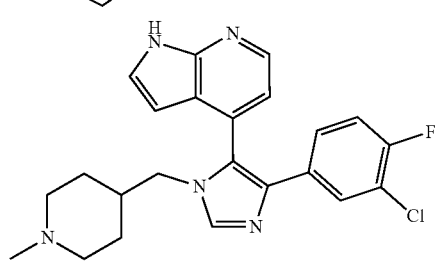
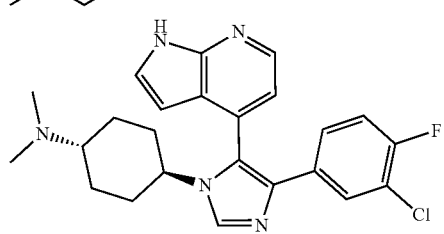
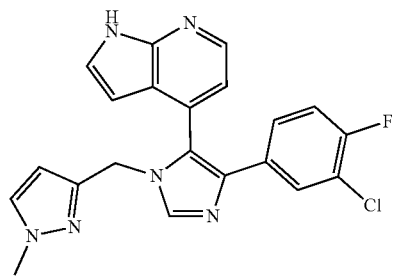
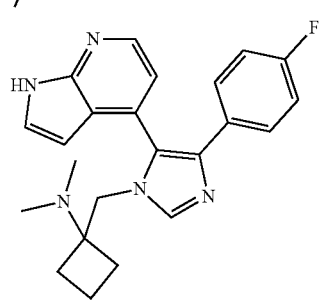
-continued
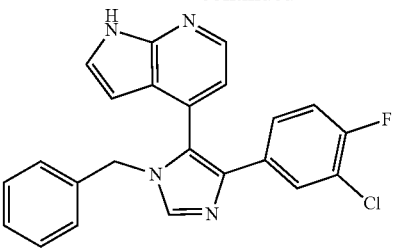
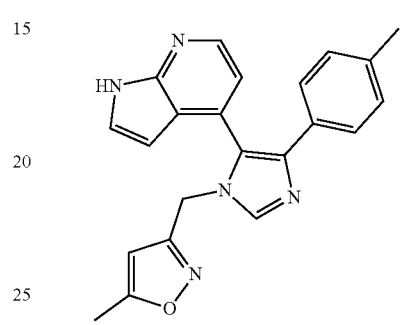
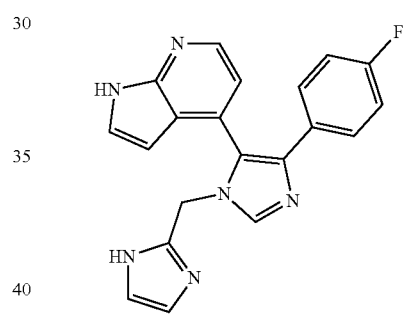
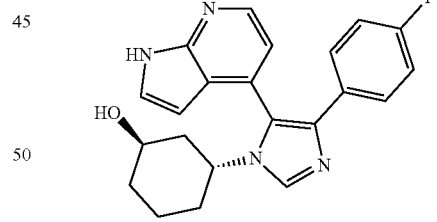
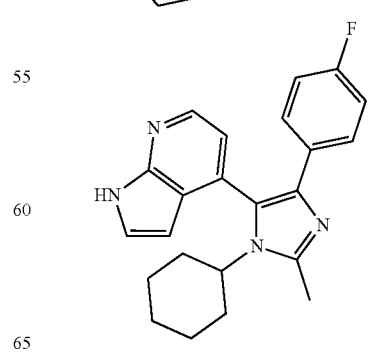

Most preferably, the compound of formula I is selected from the following:
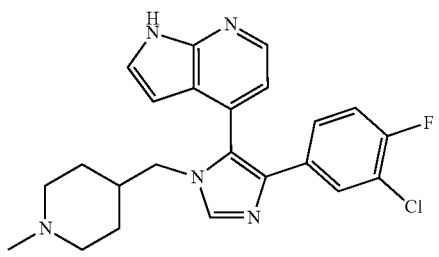
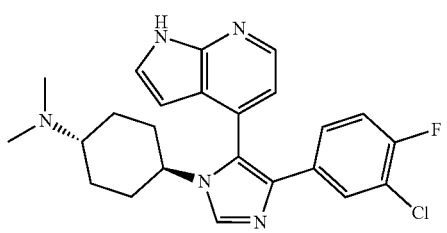
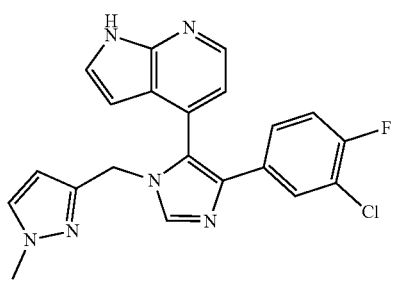
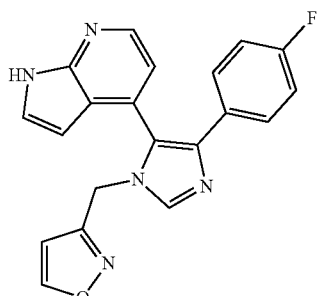
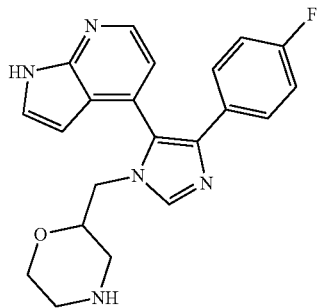
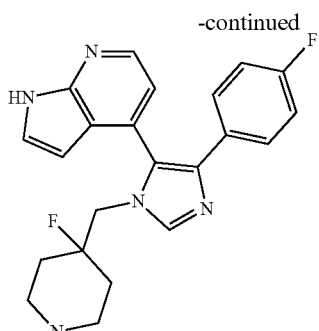
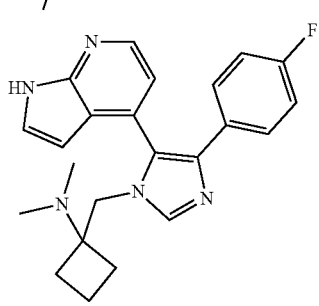
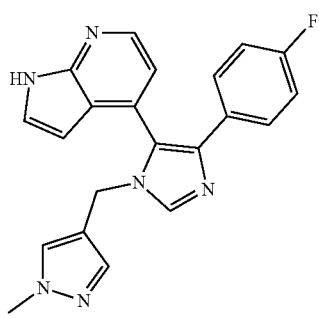
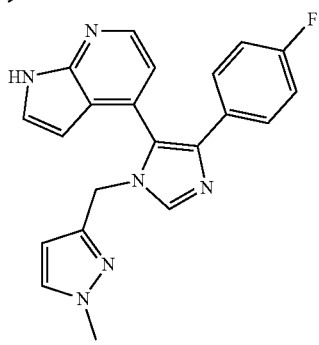
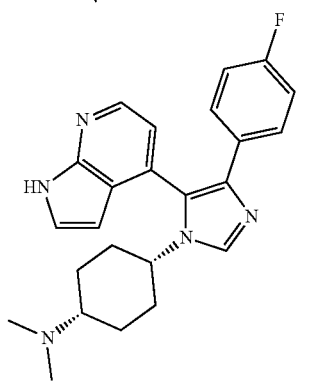

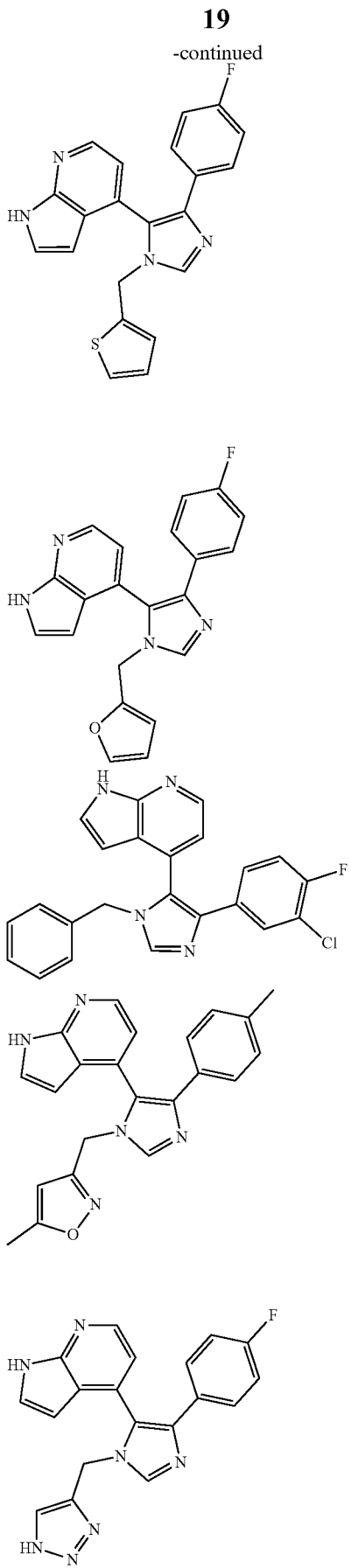

or a salt thereof, such as dihydrochloride.

The present invention further includes the compounds of formula I for use in a method of treatment of leukaemias, lymphomas and other solid tumors. The compounds of the invention have been found to decrease viability of cancer cells through induction of apoptosis and block their migration, which is one of the key processes involved in pathogenesis of several cancer types. Thus, these compounds act on cancer cells synergistically through targeting cell viability and cell migration.

The present invention also includes a method of treatment of leukaemias, lymphomas and other solid tumors, in a subject in need of such treatment, wherein at least one compound of formula I is administered to said subject. The subject is preferably a mammal, more preferably a human.

The leukaemias that can be treated by the compounds of formula I are preferably leukaemias of lymphoid origin or of myeloid origin. In particulars, the leukaemias are chronic lymphocytic leukaemia, acute lymphocytic leukaemia, chronic myeloid leukaemia, acute myeloid leukaemia. Most preferably, the leukaemia to be treated by the compound of the invention is chronic lymphocytic leukaemia.

The lymphomas that that can be treated by the compounds of formula I are preferably non-Hodgkin lymphomas, such as Burkitt lymphoma, mantle cell lymphoma, follicular lymphoma, and diffuse large B-cell lymphoma.

The solid tumors that can be treated by the compounds of formula I are preferably epithelial tumors or melanoma, in particular breast cancer, melanoma, prostate cancer, pancreatic cancer, ovarian cancer, hepatocellular carcinoma.

The present invention further provides a pharmaceutical preparation comprising at least one compound of formula I, and at least one pharmaceutically acceptable auxiliary substance. The auxiliary substances typically include solvents, fillers, binders, and other excipients.

BRIEF DESCRIPTION OF DRAWINGS

FIGS. 2C-D show the same for another 4 primary CLL samples.

FIG. 3 shows the inhibitory effects of presented compounds in a migration assay as described in Example II.3.

FIGS. 4A and 4B demonstrate selective toxicity of the compounds of formula I, represented by a preparative example 3, towards cancer cells. The tested compound (A) shows significantly higher cytotoxic effects towards cancer cells than nonmalignant controls and also higher cytotoxicity than PF670462 compound (B).

EXAMPLES OF CARRYING OUT THE INVENTION

I. Preparative Examples

Materials and Methods

Figure 1:
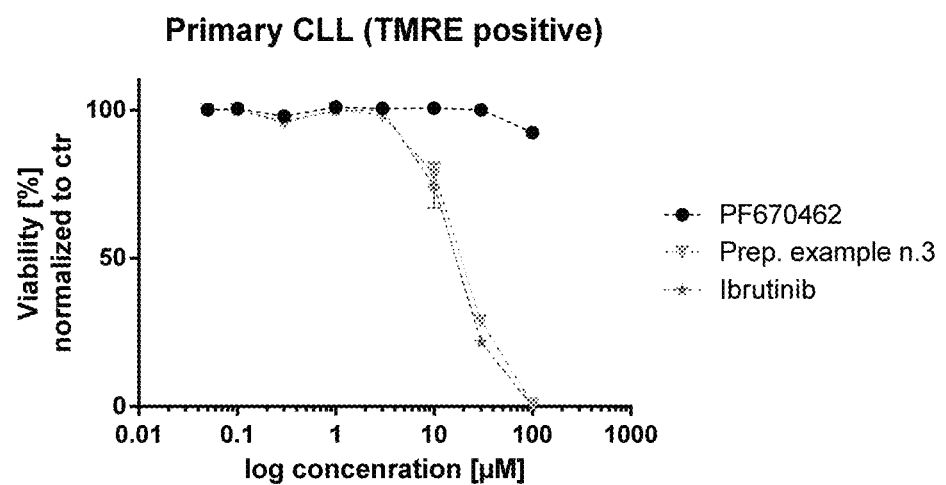
FIG. 1 shows data for viability of primary CLL cells when exposed to compound of formula I (preparatory example 3 of the invention), compared with PF670462 (structurally closest compound proposed for the treatment of CLL) and ibrutinib, a drug used in therapy of CLL, which was described to have cytotoxic effects on primary CLL cells. Compound from preparatory example 3 has similar dose-dependent cytotoxic effects to ibrutinib, while PF670462 lacks this effect.
Figure 2A:
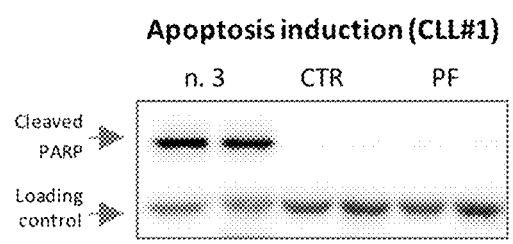
FIGS. 2A and 2C show data obtained by western blotting analysis of primary CLL cells and shows increase of cleaved PARP, a marker of apoptosis, when exposed to the compound described in preparatory example 3, but not in case of PF670462 treatment.
Figure 2B:
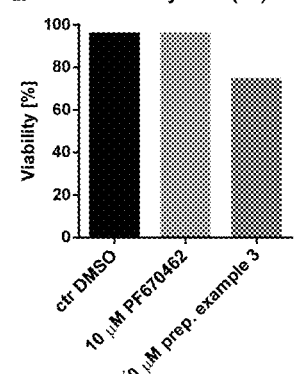
FIG. 2B shows corresponding flow cytometric analysis of the same primary sample as in 2 A and shows decrease in cell viability, corresponding to the increased PARP cleavage.
Figure 2C:
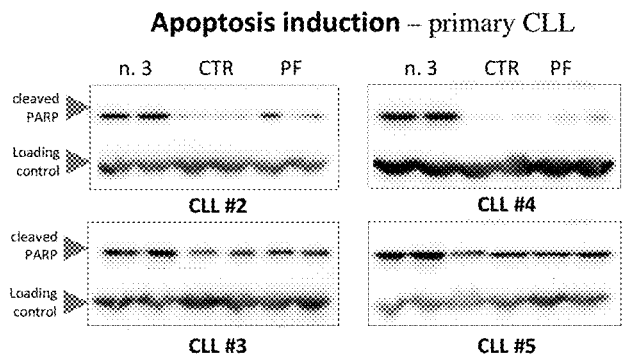
Figure 2D:
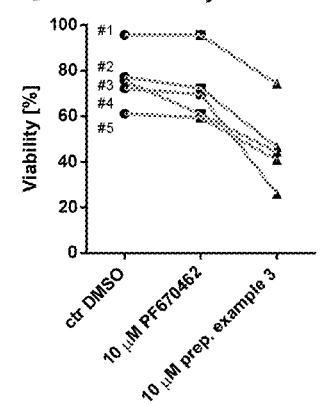

All commercially available reagents were used as supplied without further purification. The reaction solvents were purchased anhydrous and were stored under nitrogen. Unless noted otherwise, the reactions were carried out in oven-dried glassware under atmosphere of nitrogen. Column chromatography was carried out using silica gel (pore size 60 Å, 230-400 mesh particle size, 40-63 m particle size). Purification by preparative thin layer chromatography was performed using plates from Merck (PLC Silica gel 60 $F_{254}$, 1 mm). Reverse phase column chromatography was carried out using $C_{18}$-reversed phase silica gel (pore size 90 Å, 230-400 mesh particle size, 40-63 m particle size). NMR spectra were obtained in indicated deuterated solvents; chemical shifts are quoted in parts per million (δ) referenced to the appropriate deuterated solvent employed. Multiplicities are indicated by s (singlet), d (doublet), t (triplet), q (quartet), p (pentet), quin (quintet), sept (septet), m (multiplet) or (br) broad, or combinations thereof. Coupling constant values are given in Hz.

General Procedure A: Three-Component Cyclization Providing Imidazoles

To a solution of the corresponding aldehyde (1.2 eq.; unless stated otherwise) in DMF (2 mL per 0.3 mmol of aldehyde; unless stated otherwise) was added the corresponding amine (2.5 eq.; unless stated otherwise) and the resulting solution was stirred at 25° C. to form the corresponding imine. Then, the corresponding isocyano(tosyl) methyl)arene reagent (1 eq.; unless stated otherwise) and $K_2CO_3$ (1.5 eq.; unless stated otherwise*) were added and the reaction mixture was stirred at 25° C. (unless stated otherwise). The reaction was stopped after the time indicated for each particular reaction. The reaction progress was monitored by TLC.

* note: in cases when the amine was used as HCl salt, 4 eq. of $K_2CO_3$ were used A saturated aqueous solution of $NH_4Cl$ (10 mL per 1 mmol of aldehyde) was added to the reaction mixture, which was then extracted with EtOAc (2×30 mL per 1 mmol of aldehyde). The combined organic extracts were washed with $H_2O$ (2×25 mL per 1 mmol of aldehyde), dried over $MgSO_4$, filtered, and the solvent was evaporated in vacuo to provide the crude product. The residue obtained after the workup was purified using column chromatography or preparative TLC (unless stated otherwise).

General Procedure B: Suzuki Coupling with 5-bromo-1-cyclohexyl-4-(4-fluorophenyl)-1H-Imidazole To a degassed solution of 5-bromo-1-cyclohexyl-4-(4-fluorophenyl)-1H-imidazole (1 eq.) in DME/$H_2O$ (2.6+0.4 mL per 0.1 mmol of 5-bromo-1-cyclohexyl-4-(4-fluorophenyl)-1H-imidazole) was added the corresponding boronate/boronic acid (2 eq.), $K_2CO_3$ (4 eq.), methanesulfonato(tri-t-butylphosphino)(2'-amino-1,1'-biphenyl-2-yl)palladium (II) (0.1 eq; CAS:1445086-17-8) and the resulting mixture was stirred at 85° C. under nitrogen atmosphere (unless stated otherwise). The reaction progress was monitored by TLC. The reaction was stopped after the time indicated for each particular reaction. The solvent was evaporated in vacuo and the residue was purified using column chromatography or preparative TLC (unless stated otherwise).

Preparative Example 1: 4-(1-cyclohexyl-4-(3-fluorophenyl)-1H-imidazol-5-yl)-1H-pyrrolo[2,3-b]pyridine

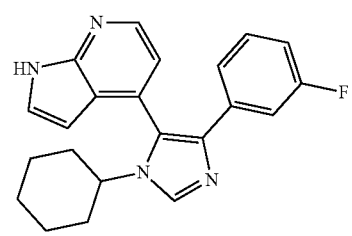 [SMILES: Fc1cccc(-c2ncn(C3CCCCC3)c2-c2ccnc3[nH]ccc23)c1]

The compound was prepared according to General procedure A using 1H-pyrrolo[2,3-b]pyridine-4-carbaldehyde, cyclohexanamine, 1-fluoro-3-(isocyano(tosyl)methyl)benzene and $K_2CO_3$. Reaction time: 200 minutes for the formation of the imine, then additional 20 hours for the cyclization step. The residue obtained after the workup was purified two times by preparative TLC (hexane/ethyl acetate, 4:3; then ethyl acetate/dichloromethane, 4:1). The product was obtained as a white solid (15 mg; 18%).

$^1$H NMR (500 MHz, $CDCl_3$) δ (ppm) 11.02 (s, 1H), 8.45 (d, J=4.86 Hz, 1H), 7.90 (s, 1H), 7.41 (d, J=3.51 Hz, 1H), 7.19-7.13 (m, 2H), 7.09-7.03 (m, 2H), 6.81-6.76 (m, 1H), 6.20 (d, J=3.49 Hz, 1H), 3.67 (tt, J=11.97, 3.71 Hz, 1H), 2.07-2.01 (m, 1H), 2.00-1.93 (m, 1H), 1.83-1.74 (m, 2H), 1.70-1.59 (m, 3H), 1.22-1.04 (m, 3H).

$^{13}$C NMR (126 MHz, $CDCl_3$) δ (ppm) 163.0 (d, J=244.13 Hz), 149.2, 143.1, 137.4 (d, J=2.68 Hz), 136.5 (d, J=8.29 Hz), 135.0, 131.5, 129.7 (d, J=8.30 Hz), 126.6, 125.2, 122.2 (d, J=2.79 Hz), 121.0, 118.0, 113.5 (d, J=6.68 Hz), 113.3 (d, J=8.24 Hz), 100.3, 55.5, 35.3, 34.5, 25.7, 25.7, 25.2.

$^{19}$F NMR (471 MHz, CDCl$_3$) δ (ppm) −110.7−−115.5 (m).
HRMS calculated for C$_{22}$H$_{22}$FN$_4$ [M+H]$^+$ 361.1823, found 361.1822.

Preparative Example 2: 4-(1-cyclohexyl-4-(2-fluorophenyl)-1H-imidazol-5-yl)-1H-pyrrolo[2,3-b]pyridine

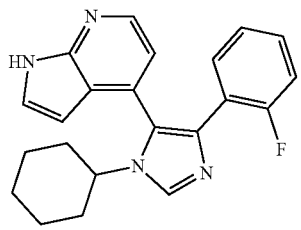 [SMILES: Fc1ccccc1-c1ncn(C2CCCCC2)c1-c1ccnc2[nH]ccc12]

The compound was prepared according to General procedure A using 1H-pyrrolo[2,3-b]pyridine-4-carbaldehyde, cyclohexanamine, 1-fluoro-2-(isocyano(tosyl)methyl)benzene and K$_2$CO$_3$. Reaction time: 210 minutes for the formation of the imine, then additional 14 hours at 25° C. plus 20 hours at 80° C. for the cyclization step. The residue obtained after the workup was purified by column chromatography (hexane/acetone, 1:1) and then by preparative TLC (ethyl acetate/dichloromethane, 4:1). The product was obtained as a colorless wax (2 mg; 2%).

$^1$H NMR (500 MHz, CDCl$_3$) δ (ppm) 9.87 (s, 1H), 8.34 (s, 1H), 8.15 (s, 1H), 7.48-7.43 (m, 1H), 7.31 (d, J=3.55 Hz, 1H), 7.21-7.14 (m, 1H), 7.07-6.97 (m, 2H), 6.91-6.81 (m, 1H), 6.16 (d, J=3.59 Hz, 1H), 3.93-3.84 (m, 1H), 2.12-2.05 (m, 1H), 2.04-1.97 (m, 1H), 1.87-1.79 (m, 2H), 1.73-1.61 (m, 3H), 1.22-1.10 (m, 3H).
$^{13}$C NMR (126 MHz, CDCl$_3$) δ (ppm) 159.8 (d, J=249.91 Hz), 148.2, 142.2, 135.2, 133.4, 131.3, 131.1 (d, J=3.09 Hz), 129.5 (d, J=8.06 Hz), 126.9, 126.4, 124.2 (d, J=3.56 Hz), 117.5, 116.0, 115.9, 100.4, 56.2, 35.3, 34.4, 25.8, 25.7, 25.2.
$^{19}$F NMR (471 MHz, CDCl$_3$) δ (ppm) −113.54.

Preparative Example 3: 4-(1-cyclohexyl-4-(4-fluorophenyl)-1H-imidazol-5-yl)-1H-pyrrolo[2,3-b]pyridine

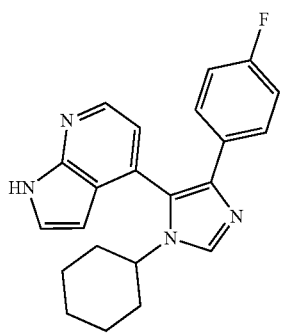 [SMILES: Fc1ccc(-c2ncn(C3CCCCC3)c2-c2ccnc3[nH]ccc23)cc1]

The compound was prepared according to General procedure A using 1H-pyrrolo[2,3-b]pyridine-4-carbaldehyde, cyclohexanamine, 1-fluoro-4-(isocyano(tosyl)methyl)benzene and K$_2$CO$_3$. Reaction time: 4.5 hours for the formation of the imine, then additional 23 hours for the cyclization step. The residue obtained after the workup was purified by three times by column chromatography (ethyl acetone/hexane, 2:3; then ethyl acetate/dichloromethane, 4:1; then acetone/dichloromethane, 3:10). The product was obtained as a white solid (1.35 g, 44%).

$^1$H NMR (500 MHz, CDCl$_3$) δ (ppm) 10.31 (s, 1H), 8.43 (d, J=4.90 Hz, 1H), 7.89 (s, 1H), 7.40-7.33 (m, 3H), 7.05 (d, J=4.88 Hz, 1H), 6.85-6.79 (m, 2H), 6.18 (d, J=3.50 Hz, 1H), 3.68 (tt, J=12.03, 3.71 Hz, 1H), 2.09-2.01 (m, 1H), 1.99-1.92 (m, 1H), 1.84-1.74 (m, 2H), 1.69-1.59 (m, 3H), 1.19-1.06 (m, 3H).
$^{13}$C NMR (126 MHz, CDCl$_3$) δ (ppm) 161.9 (d, J=245.77 Hz), 149.1, 143.3, 137.7, 134.8, 131.6, 130.1, 128.4 (d, J=7.85 Hz), 126.4, 124.4, 120.9, 118.1, 115.2 (d, J=21.38 Hz), 100.5, 55.5, 35.3, 34.5, 25.8, 25.7, 25.2.
HRMS calculated for C$_{22}$H$_{22}$FN$_4$ [M+H]$^+$ 361.1823, found 361.1827.

Preparative Example 4: 4-(1-cyclohexyl-4-(2,4-difluorophenyl)-1H-imidazol-5-yl)-1H-pyrrolo[2,3-b]pyridine

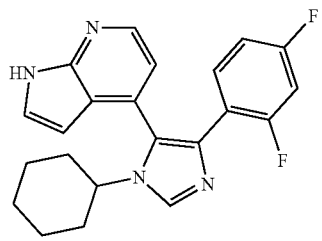 [SMILES: Fc1ccc(-c2ncn(C3CCCCC3)c2-c2ccnc3[nH]ccc23)c(F)c1]

The compound was prepared according to General procedure A using 1H-pyrrolo[2,3-b]pyridine-4-carbaldehyde, cyclohexanamine, 2,4-difluoro-1-(isocyano(tosyl)methyl) benzene and K$_2$CO$_3$. Acetonitrile was used instead of DMF. Reaction time: 3 hours for the formation of the imine, then additional 18 hours at 75° C. for the cyclization step. The residue obtained after the workup was purified two times by preparative TLC (hexane/acetone, 4:3; then ethyl acetate/dichloromethane, 4:1). The product was obtained as a colorless wax (14 mg, 15%).

$^1$H NMR (500 MHz, CDCl$_3$) δ (ppm) 10.73 (s, 1H), 8.36 (d, J=4.92 Hz, 1H), 7.96 (s, 1H), 7.44-7.35 (m, 1H), 7.32 (d, J=3.52 Hz, 1H), 6.96 (d, J=4.90 Hz, 1H), 6.77-6.71 (m, 1H), 6.63-6.58 (m, 1H), 6.14 (d, J=3.53 Hz, 1H), 3.87 (tt, J=11.96, 3.71 Hz, 1H), 2.11-2.05 (m, 1H), 2.05-1.97 (m, 1H), 1.85-1.76 (m, 2H), 1.74-1.60 (m, 3H), 1.23-1.07 (m, 3H).
$^{13}$C NMR (126 MHz, CDCl$_3$) δ (ppm) 162.3 (dd, J=248.67, 11.71 Hz), 159.9 (dd, J=252.20, 11.99 Hz), 148.9, 142.6, 135.4, 133.7, 131.9 (dd, J=9.39, 4.97 Hz), 131.3, 126.8, 126.2, 120.5, 118.7, 118.5 (dd, J=14.60, 3.70 Hz), 117.3, 111.3 (dd, J=21.31, 3.64 Hz), 104.1 (t, J=25.73 Hz), 100.2, 55.7, 35.4, 34.4, 25.8, 25.7, 25.2.
$^{19}$F NMR (471 MHz, CDCl$_3$) δ (ppm) −109.55 (d, J=7.76 Hz), −111.43 (d, J=7.45 Hz).
HRMS calculated for C$_{22}$H$_{21}$F$_2$N$_4$ [M+H]$^+$ 379.1729, found 379.1727.

Preparative Example 5: 4-(4-(3-chlorophenyl)-1-cyclohexyl-1H-imidazol-5-yl)-1H-pyrrolo[2,3-b]pyridine

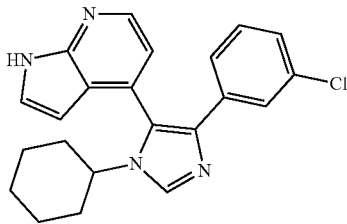 [SMILES: Brc1cccc(-c2ncn(C3CCCCC3)c2-c2ccnc3[nH]ccc23)c1]

The compound was prepared according to General procedure A using 1H-pyrrolo[2,3-b]pyridine-4-carbaldehyde, cyclohexanamine, 1-chloro-3-(isocyano(tosyl)methyl)benzene and $K_2CO_3$. Reaction time: 3 hours for the formation of the imine, then additional 18 hours for the cyclization step. The residue obtained after the workup was purified by preparative TLC (hexane/acetone, 4:3). So obtained material was 3 times triturated with dichloromethane (0.3 mL) and dried in a vacuum. The product was obtained as a white solid (16 mg, 15%).

$^1$H NMR (500 MHz, DMSO-$d_6$) δ (ppm) 11.89 (s, 1H), 8.36 (d, J=4.81 Hz, 1H), 8.13 (s, 1H), 7.50 (dd, J=3.44, 2.51 Hz, 1H), 7.40-7.34 (m, 1H), 7.15-7.05 (m, 4H), 6.03 (dd, J=3.49, 1.85 Hz, 1H), 3.60-3.49 (m, 1H), 1.98-1.90 (m, 1H), 1.82-1.64 (m, 5H), 1.55-1.49 (m, 1H), 1.17-1.02 (m, 2H), 1.00-0.90 (m, 1H).

$^{13}$C NMR (126 MHz, DMSO-$d_6$) δ (ppm) 148.7, 142.9, 135.8, 135.3, 132.8, 129.9, 129.8, 127.4, 125.7, 125.2, 125.1, 123.8, 119.6, 117.1, 98.6, 54.6, 33.9, 33.4, 25.1, 25.1, 24.5.

HRMS calculated for $C_{22}H_{22}ClN_4$ $[M+H]^+$ 377.1528, found 377.1527.

Preparative Example 6: 4-(4-(3-bromophenyl)-1-cyclohexyl-1H-imidazol-5-yl)-1H-pyrrolo[2,3-b]pyridine

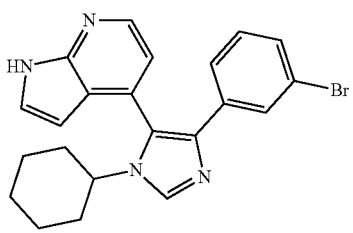

The compound was prepared according to General procedure A using 1H-pyrrolo[2,3-b]pyridine-4-carbaldehyde, cyclohexanamine, 1-bromo-3-(isocyano(tosyl)methyl)benzene and $K_2CO_3$. Reaction time: 3.5 hours for the formation of the imine, then additional 18 hours for the cyclization step. The residue obtained after the workup was purified by column chromatography (hexane/acetone/methanol, 10:10:1). So obtained material was 3 times triturated with a mixture of dichloromethane/hexane (0.5 mL+0.5 mL) and dried in a vacuum. The product was obtained as a white solid (6 mg, 6%).

$^1$H NMR (500 MHz, DMSO-$d_6$) δ (ppm) 11.89 (s, 1H), 8.36 (d, J=4.81 Hz, 1H), 8.11 (s, 1H), 7.53 (t, J=1.84 Hz, 1H), 7.50 (d, J=3.48 Hz, 1H), 7.26-7.21 (m, 1H), 7.14 (dt, J=7.95, 1.27 Hz, 1H), 7.09 (d, J=4.79 Hz, 1H), 7.04 (t, J=7.88 Hz, 1H), 6.03 (d, J=3.47 Hz, 1H), 3.59-3.50 (m, 1H), 1.97-1.91 (m, 1H), 1.83-1.63 (m, 5H), 1.57-1.50 (m, 1H), 1.18-1.03 (m, 2H), 1.00-0.92 (m, 1H).

$^{13}$C NMR (126 MHz, DMSO-$d_6$) δ (ppm) 148.7, 142.9, 137.1, 135.8, 135.2, 130.1, 129.9, 128.5, 128.1, 127.4, 125.1, 124.2, 121.5, 119.6, 117.1, 98.6, 54.6, 33.9, 33.4, 25.1, 25.1, 24.5.

HRMS calculated for $C_{22}H_{22}BrN_4$ $[M+H]^+$ 423.1004, found 423.1002.

Preparative Example 7: 4-(1-cyclohexyl-4-(2,4-dichlorophenyl)-1H-imidazol-5-yl-1H-pyrrolo[2,3-b]pyridine

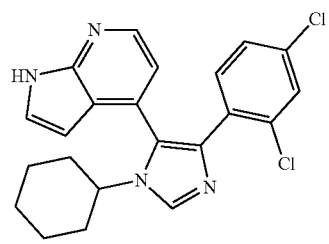 [SMILES: Clc1ccc(-c2ncn(C3CCCCC3)c2-c2ccnc3[nH]ccc23)c(Cl)c1]

To a solution of 1H-pyrrolo[2,3-b]pyridine-4-carbaldehyde (42 mg; 0.289 mmol) in tetrahydrofuran (2 mL) was added cyclohexanamine (0.067 mL; 0.600 mmol) and the resulting solution was stirred at 25° C. for 210 minutes. Then, 2,4-dichloro-1-(isocyano(tosyl)methyl)benzene (81 mg; 0.240 mmol), $Cs_2CO_3$ (117 mg; 0.360 mmol) and boron trifluoride diethyl etherate (0.088 mL; 0.720 mmol) were added. The resulting mixture was stirred at 60° C. for 16 hours and then at 70° C. for additional 7 hours. The solvent was evaporated in vacuo and The residue obtained after the workup was purified by column chromatography (hexane/acetone, 1:1) and then by preparative TLC (dichloromethane/ethyl acetate, 1:4).

The product was obtained as a colorless wax (2 mg, 2%).

$^1$H NMR (500 MHz, CDCl$_3$) δ (ppm) 9.96 (s, 1H), 8.30 (d, J=5.04 Hz, 1H), 8.27 (s, 1H), 7.34 (d, J=3.55 Hz, 1H), 7.29 (d, J=2.11 Hz, 1H), 7.23 (d, J=8.31 Hz, 1H), 7.10 (dd, J=8.33, 2.13 Hz, 1H), 6.95 (d, J=4.99 Hz, 1H), 6.18 (d, J=3.58 Hz, 1H), 3.94 (tt, J=11.92, 3.68 Hz, 1H), 2.11-2.00 (m, 2H), 1.86-1.65 (m, 5H), 1.24-1.09 (m, 3H).

$^{13}$C NMR (126 MHz, CDCl$_3$) δ (ppm) 147.5, 141.5, 135.2, 134.9, 134.6, 133.0, 130.9, 130.2, 129.9, 127.2, 127.0, 120.8, 117.4, 100.4, 56.6, 35.3, 34.3, 25.7, 25.7, 25.1.

Preparative Example 8: 4-(1-cyclohexyl-4-phenyl-1H-imidazol-5-yl-1H-pyrrolo[2,3-b]pyridine

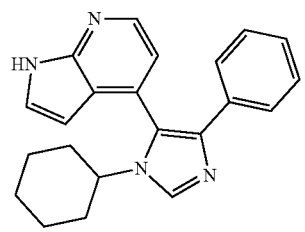 [SMILES: c1ccc(-c2ncn(C3CCCCC3)c2-c2ccnc3[nH]ccc23)cc1]

The compound was prepared according to General procedure A using 1H-pyrrolo[2,3-b]pyridine-4-carbaldehyde, cyclohexanamine, 1-((isocyano(phenyl)methyl)sulfonyl)-4-methylbenzene and K$_2$CO$_3$. Reaction time: 3 hours 20 minutes for the formation of the imine, then additional 16 hours for the cyclization step. The residue obtained after the workup was purified by preparative TLC (hexane/acetone, 10:6). So obtained material was triturated 3 times with a mixture of dichloromethane/hexane (0.25 mL+0.25 mL) and dried in a vacuum. The product was obtained as a white solid (7 mg, 9%).

$^1$H NMR (500 MHz, CDCl$_3$) δ (ppm) 9.80 (s, 1H), 8.44 (d, J=4.88 Hz, 1H), 8.23 (s, 1H), 7.46-7.40 (m, 2H), 7.38 (d, J=3.51 Hz, 1H), 7.21-7.13 (m, 3H), 7.08 (d, J=4.87 Hz, 1H), 6.19 (d, J=3.51 Hz, 1H), 3.72 (tt, J=11.95, 3.69 Hz, 1H), 2.09-2.03 (m, 1H), 2.00-1.94 (m, 1H), 1.85-1.76 (m, 2H), 1.74-1.60 (m, 3H), 1.21-1.04 (m, 3H).

$^{13}$C NMR (126 MHz, CDCl$_3$) δ (ppm) 148.9, 143.4, 134.2, 130.3, 128.6, 127.8, 126.9, 126.7, 124.9, 120.8, 118.2, 100.4, 56.3, 35.2, 34.4, 25.7, 25.6, 25.1.

HRMS calculated for C$_{22}$H$_{23}$N$_4$ [M+H]$^+$ 343.1917, found 343.1920.

Preparative Example 9: 4-(4-(4-chlorophenyl)-1-cyclohexyl-1H-imidazol-5-yl)-1H-pyrrolo[2,3-b]pyridine

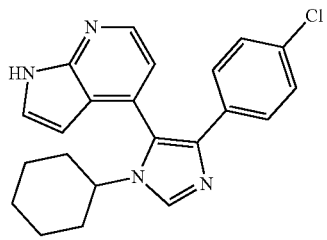 [SMILES: Brc1ccc(-c2ncn(C3CCCCC3)c2-c2ccnc3[nH]ccc23)cc1]

The compound was prepared according to General procedure A using 1H-pyrrolo[2,3-b]pyridine-4-carbaldehyde, cyclohexanamine, 1-chloro-4-(isocyano(tosyl)methyl)benzene and K$_2$CO$_3$. Reaction time: 3 hours 20 minutes for the formation of the imine, then additional 16 hours for the cyclization step. The residue obtained after the workup was purified by preparative TLC (hexane/acetone, 10:6). So obtained material was triturated 3 times with a mixture of dichloromethane/hexane (0.25 mL+0.25 mL) and dried in a vacuum. The product was obtained as a white solid (38 mg, 42%).

$^1$H NMR (500 MHz, acetone-d$_6$) δ (ppm) 10.90 (s, 1H), 8.38 (d, J=4.76 Hz, 1H), 7.95 (s, 1H), 7.52-7.49 (m, 1H), 7.42-7.38 (m, 2H), 7.14-7.10 (m, 2H), 7.09 (d, J=4.79 Hz, 1H), 6.14 (dd, J=3.49, 1.96 Hz, 1H), 3.70 (tt, J=11.80, 3.89 Hz, 1H), 2.08-2.06 (m, 1H), 1.96-1.89 (m, 1H), 1.83-1.70 (m, 4H), 1.62-1.55 (m, 1H), 1.24-1.12 (m, 2H), 1.12-1.03 (m, 1H).

$^{13}$C NMR (126 MHz, acetone-d$_6$) δ (ppm) 150.3, 144.3, 137.6, 136.1, 135.1, 132.0, 131.9, 128.8, 128.4, 127.6, 125.9, 121.1, 118.5, 100.3, 55.9, 35.4, 34.8, 26.4, 26.3, 25.8.

HRMS calculated for C$_{22}$H$_{22}$ClN$_4$ [M+H]$^+$ 377.1528, found 377.1526.

Preparative Example 10: 4-(4-(4-bromophenyl)-1-cyclohexyl-1H-imidazol-5-yl)-1H-pyrrolo[2,3-b]pyridine

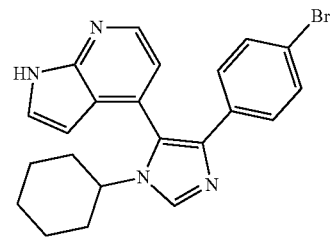

The compound was prepared according to General procedure A using 1H-pyrrolo[2,3-b]pyridine-4-carbaldehyde, cyclohexanamine, 1-bromo-4-(isocyano(tosyl)methyl)benzene and K$_2$CO$_3$. Reaction time: 3 hours 30 minutes for the formation of the imine, then additional 14 hours for the cyclization step. The residue obtained after the workup was purified two times by preparative TLC (hexane/acetone, 4:3; then dichloromethane/ethyl acetate, 1:4). The product was obtained as a white solid (11 mg, 11%).

$^1$H NMR (500 MHz, CDCl$_3$) δ (ppm) 10.53 (s, 1H), 8.44 (d, J=4.88 Hz, 1H), 7.92 (s, 1H), 7.38 (d, J=3.53 Hz, 1H), 7.29-7.22 (m, 4H), 7.05 (d, J=4.84 Hz, 1H), 6.18 (d, J=3.57 Hz, 1H), 3.67 (tt, J=12.00, 3.73 Hz, 1H), 2.08-2.01 (m, 1H), 1.98-1.92 (m, 1H), 1.84-1.73 (m, 2H), 1.70-1.59 (m, 3H), 1.21-1.02 (m, 3H).

$^{13}$C NMR (126 MHz, CDCl$_3$) δ (ppm) 149.1, 143.3, 137.3, 135.0, 132.8, 131.5, 131.4, 128.2, 126.6, 125.0, 120.8, 120.8, 118.0, 100.5, 55.6, 35.2, 34.5, 25.7, 25.7, 25.2.

HRMS calculated for C$_{22}$H$_{22}$BrN$_4$ [M+H]$^+$ 423.1004, found 423.1002.

Preparative Example 11: tert-butyl-4-(4-(4-fluorophenyl)-5-(1H-pyrrolo[2,3-b]pyridin-4-yl)-1H-imidazol-1-yl)piperidine-1-carboxylate

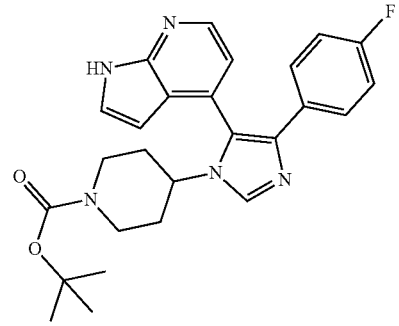 [SMILES: CC(C)(C)OC(=O)N1CCC(n2cnc(-c3ccc(F)cc3)c2-c2ccnc3[nH]ccc23)CC1]

The compound was prepared according to General procedure A using 1H-pyrrolo[2,3-b]pyridine-4-carbaldehyde, tert-butyl-4-aminopiperidine-1-carboxylate, 1-fluoro-4-(isocyano(tosyl)methyl)benzene and K$_2$CO$_3$. Reaction times: 3 hours for the formation of the imine, then additional 18 hours for the cyclization step. The residue obtained after the workup was purified by column chromatography (hexane/acetone, 10:6). So obtained material was then recrystallized from a mixture of dichloromethane/hexane (0.15 mL+0.3 mL). The product was obtained as a white solid (12 mg, 11%).

¹H NMR (500 MHz, CDCl₃) δ (ppm) 10.40 (s, 1H), 8.45 (d, J=4.88 Hz, 1H), 7.95 (s, 1H), 7.41-7.34 (m, 3H), 7.07 (d, J=4.88 Hz, 1H), 6.86-6.80 (m, 2H), 6.19 (d, J=3.53 Hz, 1H), 4.24-4.11 (m, 2H), 3.84 (tt, J=11.67, 4.38 Hz, 1H), 2.60-2.44 (m, 2H), 2.02-1.95 (m, 1H), 1.93-1.80 (m, 3H), 1.44 (s, 9H).
¹³C NMR (126 MHz, CDCl₃) δ (ppm) 162.1 (d, J=246.53 Hz), 154.5, 149.0, 143.4, 137.8, 134.7, 131.0, 129.5 (d, J=3.25 Hz), 128.4 (d, J=8.02 Hz), 126.8, 124.4, 120.8, 118.0, 115.4 (d, J=21.40 Hz), 100.3, 80.3, 54.0, 43.1, 34.0, 33.4, 28.5.
HRMS calculated for $C_{26}H_{29}FN_5O_2$ [M+H]⁺ 462.2300, found 462.2302.

Preparative Example 12: 4-(2-(4-(4-fluorophenyl)-5-(1H-pyrrolo[2,3-b]pyridin-4-yl)-1H-imidazol-1-yl)ethyl)morpholine

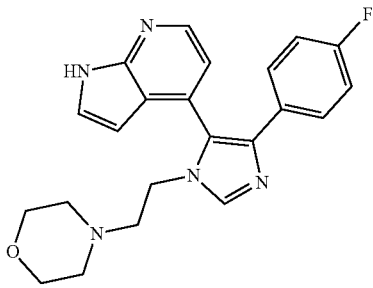 [SMILES: Fc1ccc(-c2ncn(CCN3CCOCC3)c2-c2ccnc3[nH]ccc23)cc1]

The compound was prepared according to General procedure A using 1H-pyrrolo[2,3-b]pyridine-4-carbaldehyde, 2-morpholinoethan-1-amine, 1-fluoro-4-(isocyano(tosyl)methyl)benzene and K₂CO₃. Reaction time: 3.5 hours for the formation of the imine, then additional 18 hours for the cyclization step. The residue obtained after the workup was purified by preparative TLC (methanol/acetone, 1:20). The product was obtained as a white solid (54 mg, 57%).
¹H NMR (500 MHz, CDCl₃) δ (ppm) 11.16 (s, 1H), 8.43 (d, J=4.87 Hz, 1H), 7.87 (s, 1H), 7.43-7.37 (m, 3H), 7.09 (d, J=4.87 Hz, 1H), 6.86-6.80 (m, 2H), 6.18 (d, J=3.41 Hz, 1H), 4.00-3.88 (m, 2H), 3.61-3.52 (m 4H), 2.43 (t, J=6.41 Hz, 2H), 2.29-2.20 (m 4H).
¹³C NMR (126 MHz, CDCl₃) δ (ppm) 161.9 (d, J=245.65 Hz), 149.3, 143.1, 138.6, 138.4, 131.5, 130.4 (d, J=3.17 Hz), 128.3 (d, J=7.97 Hz), 126.5, 124.7, 120.6, 117.8, 115.2 (d, J=21.44 Hz), 100.6, 66.8, 58.9, 53.6, 42.9.
¹⁹F NMR (471 MHz, CDCl₃) δ (ppm) −115.77.
HRMS calculated for $C_{22}H_{23}FN_5O$ [M+H]⁺ 392.1881, found 392.1883.

Preparative Example 13: 4-(4-(4-fluorophenyl)-1-(tetrahydro-2H-pyran-4-yl)-1H-imidazol-5-yl)-1H-pyrrolo[2,3-b]pyridine

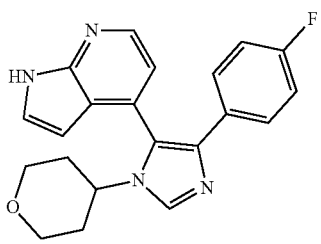 [SMILES: Fc1ccc(-c2ncn(C3CCOCC3)c2-c2ccnc3[nH]ccc23)cc1]

The compound was prepared according to General procedure A using 1H-pyrrolo[2,3-b]pyridine-4-carbaldehyde, 2-morpholinoethan-1-amine, 1-fluoro-4-(isocyano(tosyl)methyl)benzene and K₂CO₃.
Reaction time: 220 minutes for the formation of the imine, then additional 15 hours for the cyclization step. The residue obtained after the workup was purified two times by preparative TLC (dichloromethane/methanol, 9:1; then dichloromethane/methanol, 8:1). The product was obtained as a pale yellow solid (20 mg, 23%).
¹H NMR (300 MHz, CDCl₃) δ (ppm) 10.05 (s, 1H), 8.45 (d, J=4.89 Hz, 1H), 8.07 (s, 1H), 7.42-7.33 (m, 3H), 7.08 (d, J=4.92 Hz, 1H), 6.89-6.79 (m, 2H), 6.19 (d, J=3.56 Hz, 1H), 4.09-3.87 (m, 3H), 3.31-3.12 (m, 2H), 2.12-1.78 (m, 4H).
HRMS calculated for $C_{21}H_{20}FN_4O$ [M+H]⁺ 363.1616, found 363.1619.

Preparative Example 14: 4-(4-(4-fluorophenyl)-1-(1-methylpiperidin-4-yl)-1H-imidazol-5-yl)-1H-pyrrolo[2,3-b]pyridine

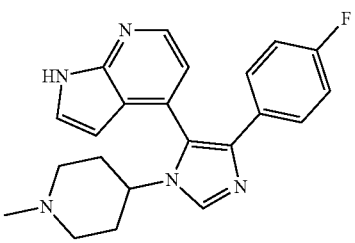 [SMILES: CN1CCC(n2cnc(-c3ccc(F)cc3)c2-c2ccnc3[nH]ccc23)CC1]

The compound was prepared according to General procedure A using 1H-pyrrolo[2,3-b]pyridine-4-carbaldehyde, 1-methylpiperidin-4-amine, 1-fluoro-4-(isocyano(tosyl)methyl)benzene and K₂CO₃.
Reaction time: 315 minutes for the formation of the imine, then additional 18 hours for the cyclization step. The residue obtained after the workup was purified two times by preparative TLC (hexane/acetone, 1:1; then dichloromethane/methanol, 12:1). So obtained material was then purified using reverse phase HPLC (acetonitrile/H₂O, gradient from 60% to 95% of acetonitrile). The product was obtained as a white solid (10 mg, 11%).
¹H NMR (500 MHz, acetone-d₆) δ (ppm) 10.90 (s, 1H), 8.37 (d, J=4.73 Hz, 1H), 7.95 (s, 1H), 7.52-7.47 (m, 1H), 7.47-7.39 (m, 2H), 7.09 (d, J=4.79 Hz, 1H), 6.91-6.83 (m, 2H), 6.14 (dd, J=3.59, 1.86 Hz, 1H), 3.68 (tt, J=11.96, 4.21 Hz, 1H), 2.84-2.75 (m, 2H), 2.12 (s, 3H), 2.01-1.91 (m, 3H), 1.84-1.74 (m, 2H), 1.72-1.65 (m, 1H).
¹³C NMR (126 MHz, acetone-d₆) δ (ppm) 162.3 (d, J=243.27 Hz), 150.3, 144.3, 138.2, 136.0, 132.7 (d, J=3.11 Hz), 131.9, 128.7 (d, J=7.91 Hz), 127.6, 125.4, 121.2, 118.6, 115.4 (d, J=21.41 Hz), 100.3, 55.6, 55.6, 54.1, 46.1, 34.6, 34.0.
¹⁹F NMR (471 MHz, acetone-d₆) δ (ppm) −118.38.
HRMS calculated for $C_{22}H_{23}FN_5$ [M+H]⁺ 376.1932, found 376.1930.

Preparative Example 15: 4-(4-(4-fluorophenyl)-1-isopentyl-1H-imidazol-5-yl)-1H-pyrrolo[2,3-b]pyridine

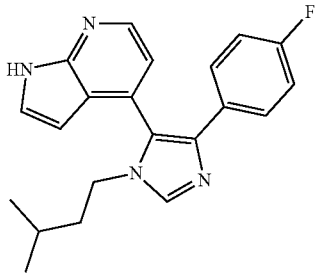 [SMILES: CC(C)CCn1cnc(-c2ccc(F)cc2)c1-c1ccnc2[nH]ccc12]

The compound was prepared according to General procedure A using 1H-pyrrolo[2,3-b]pyridine-4-carbaldehyde, 3-methylbutan-1-amine, 1-fluoro-4-(isocyano(tosyl)methyl)benzene and $K_2CO_3$. Reaction time: 3 hours 40 minutes for the formation of the imine, then additional 18 hours for the cyclization step. The residue obtained after the workup was purified two times by preparative TLC (hexane/acetone, 4:3; then dichloromethane/ethyl acetate, 1:4). The product was obtained as pale beige solid (26 mg, 31%).

$^1$H NMR (500 MHz, CDCl$_3$) δ (ppm) 10.08 (s, 1H), 8.43 (d, J=4.88 Hz, 1H), 7.98 (s, 1H), 7.44-7.36 (m, 3H), 7.09 (d, J=4.93 Hz, 1H), 6.89-6.81 (m, 2H), 6.18 (d, J=3.51 Hz, 1H), 3.95-3.80 (m, 2H), 1.46-1.36 (m, 3H), 0.70 (dd, J=17.54, 5.89 Hz, 6H).

$^{13}$C NMR (126 MHz, CDCl$_3$) δ (ppm) 162.2 (d, J=246.57 Hz), 149.0, 143.2, 137.6, 137.3, 131.0, 129.2 (d, J=2.31 Hz), 128.5 (d, J=7.96 Hz), 126.5, 124.9, 120.5, 117.9, 115.4 (d, J=21.53 Hz), 100.7, 44.6, 39.8, 25.4, 22.2.

$^{19}$F NMR (471 MHz, CDCl$_3$) δ (ppm) −114.93.

HRMS calculated for $C_{21}H_{22}FN_4$ [M+H]$^+$ 349.1823, found 349.1826.

Preparative Example 16: 4-(4-(4-fluorophenyl)-1-(tetrahydrofuran-3-yl)-1H-imidazol-5-yl)-1H-pyrrolo[2,3-b]pyridine

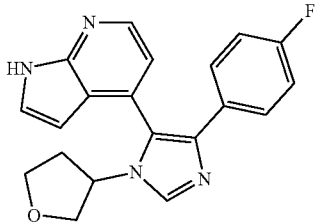 [SMILES: Fc1ccc(-c2ncn(C3CCOC3)c2-c2ccnc3[nH]ccc23)cc1]

The compound was prepared according to General procedure A using 1H-pyrrolo[2,3-b]pyridine-4-carbaldehyde, tetrahydrofuran-3-amine, 1-fluoro-4-(isocyano(tosyl)methyl)benzene and $K_2CO_3$. Reaction time: 3 hours 40 minutes for the formation of the imine, then additional 18 hours for the cyclization step. The residue obtained after the workup was purified by preparative TLC 2 times (hexane/acetone, 1:1; then dichloromethane/methanol, 12:1). The product was obtained as a colorless wax (11 mg, 13%).

$^1$H NMR (500 MHz, CDCl$_3$) δ (ppm) 10.62 (d, J=16.50 Hz, 1H), 8.44 (app t, J=4.84, 3.67 Hz, 1H), 7.96 (d, J=9.46 Hz, 1H), 7.44-7.36 (m, 3H), 7.06 (dd, J=17.25, 4.82 Hz, 1H), 6.87-6.80 (m, 2H), 6.20 (dd, J=27.42, 3.50 Hz, 1H), 4.55-4.48 (m, 1H), 4.21-4.15 (m, 1H), 4.12-4.01 (m, 1H), 3.88-3.73 (m, 2H), 2.38-2.24 (m, 1H), 2.17-2.11 (m, 1H).

$^{13}$C NMR (126 MHz, CDCl$_3$) δ (ppm) 162.0 (d, J=245.95 Hz), 149.2, 143.3 (d, J=5.54 Hz), 138.1, 135.1 (d, J=9.55 Hz), 131.2 (d, J=1.73 Hz), 129.9 (t, J=3.60 Hz), 128.4 (dd, J=7.88, 3.18 Hz), 126.6 (d, J=8.09 Hz), 124.7 (d, J=5.73 Hz), 120.8 (d, J=12.72 Hz), 118.2 (d, J=17.35 Hz), 115.3 (d, J=21.51 Hz), 100.4, 73.7, 67.3, 34.9, 29.4.

$^{19}$F NMR (471 MHz, CDCl$_3$) δ (ppm) −115.41.

HRMS calculated for $C_{20}H_{18}FN_4O$ [M+H]$^+$ 349.1459, found 349.1455.

Preparative Example 17: 4-(1-cyclobutyl-4-(4-fluorophenyl)-1H-imidazol-5-yl)-1H-pyrrolo[2,3-b]pyridine

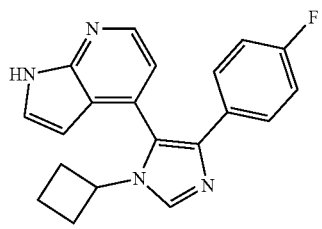 [SMILES: Fc1ccc(-c2ncn(C3CCC3)c2-c2ccnc3[nH]ccc23)cc1]

The compound was prepared according to General procedure A using 1H-pyrrolo[2,3-b]pyridine-4-carbaldehyde, cyclobutanamine, 1-fluoro-4-(isocyano(tosyl)methyl)benzene and $K_2CO_3$. Reaction time: 4 hours for the formation of the imine, then additional 14 hours for the cyclization step. The residue obtained after the workup was purified two times by preparative TLC (hexane/acetone, 3:2; then dichloromethane/ethyl acetate, 1:5). The product was obtained as a colorless wax (14 mg, 18%).

$^1$H NMR (500 MHz, CDCl$_3$) δ (ppm) 10.62 (s, 1H), 8.42 (d, J=4.88 Hz, 1H), 8.02 (s, 1H), 7.42-7.36 (m, 3H), 7.05 (d, J=4.87 Hz, 1H), 6.86-6.80 (m, 2H), 6.17 (d, J=3.48 Hz, 1H), 4.37 (p, J=8.42 Hz, 1H), 2.41-2.30 (m 2H), 2.28-2.18 (m 2H), 1.86-1.77 (m 1H), 1.71-1.61 (m, 1H).

$^{13}$C NMR (126 MHz, CDCl$_3$) δ (ppm) 162.0 (d, J=245.88 Hz), 149.1, 143.1, 138.0, 135.2, 131.4, 129.9 (d, J=3.14 Hz), 128.4 (d, J=8.01 Hz), 126.4, 124.6, 120.7, 117.9, 115.3 (d, J=21.43 Hz), 100.6, 50.2, 31.0, 15.1.

$^{19}$F NMR (471 MHz, CDCl$_3$) δ (ppm) −115.46.

HRMS calculated for $C_{20}H_{18}FN_4$ [M+H]$^+$ 333.1510, found 333.1508.

Preparative Example 18: 4-(1-cyclopentyl-4-(4-fluorophenyl)-1H-imidazol-5-yl)-1H-pyrrolo[2,3-b]pyridine

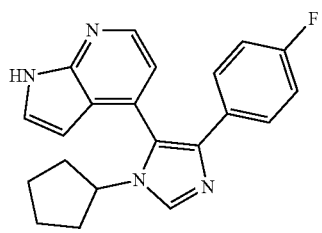

The compound was prepared according to General procedure A using 1H-pyrrolo[2,3-b]pyridine-4-carbaldehyde, cyclopentanamine, 1-fluoro-4-(isocyano(tosyl)methyl)benzene and $K_2CO_3$. Reaction time: 3.5 hours for the formation of the imine, then additional 18 hours for the cyclization step. The residue obtained after the workup was purified two times by preparative TLC (hexane/acetone, 4:3; then dichloromethane/ethyl acetate, 1:4). The product was obtained as a colorless wax (18 mg, 22%).

$^1$H NMR (500 MHz, CDCl$_3$) δ (ppm) 10.14 (s, 1H), 8.42 (d, J=4.84 Hz, 1H), 7.95 (s, 1H), 7.41-7.35 (m, 3H), 7.08 (d, J=4.86 Hz, 1H), 6.87-6.80 (m, 2H), 6.20 (d, J=3.53 Hz, 1H), 4.24 (p, J=7.08 Hz, 1H), 2.06-1.92 (m, 2H), 1.89-1.81 (m, 4H), 1.64-1.54 (m, 2H).

$^{13}$C NMR (126 MHz, CDCl$_3$) δ (ppm) 162.0 (d, J=246.24 Hz), 149.0, 143.3, 137.5, 134.6, 131.5, 129.6 (d, J=2.84 Hz), 128.4 (d, J=8.06 Hz), 126.4, 125.2, 120.9, 118.2, 115.3 (d, J=21.45 Hz), 100.6, 57.3, 34.6, 33.9, 24.19, 24.16.

$^{19}$F NMR (471 MHz, CDCl$_3$) δ (ppm) −115.31.

HRMS calculated for $C_{21}H_{20}FN_4$ [M+H]$^+$ 347.1667, found 347.1668.

Preparative Example 19: 4-(1-cycloheptyl-4-(4-fluorophenyl)-1H-imidazol-5-yl)-1H-pyrrolo[2,3-b]pyridine

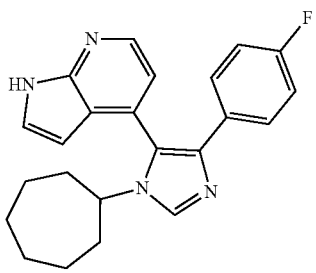 [SMILES: Fc1ccc(-c2ncn(C3CCCCCC3)c2-c2ccnc3[nH]ccc23)cc1]

The compound was prepared according to General procedure A using 1H-pyrrolo[2,3-b]pyridine-4-carbaldehyde, cycloheptanamine, 1-fluoro-4-(isocyano(tosyl)methyl)benzene and $K_2CO_3$. Reaction time: 3 hours for the formation of the imine, then additional 18 hours for the cyclization step. The residue obtained after the workup was purified two times by preparative TLC (hexane/acetone, 5:3; then dichloromethane/ethyl acetate, 1:5). The product was obtained as a colorless wax (16 mg; 18%).

$^1$H NMR (500 MHz, CDCl$_3$) δ (ppm) 10.94 (s, 1H), 8.44 (d, J=4.88 Hz, 1H), 7.89 (s, 1H), 7.41-7.35 (m, 3H), 7.05 (d, J=4.88 Hz, 1H), 6.85-6.79 (m, 2H), 6.20 (d, J=3.48 Hz, 1H), 3.88 (tt, J=10.28, 4.17 Hz, 1H), 2.09-1.98 (m, 2H), 1.96-1.82 (m, 2H), 1.74-1.64 (m, 2H), 1.57-1.47 (m, 4H), 1.31-1.18 (m, 2H).

$^{13}$C NMR (126 MHz, CDCl$_3$) δ (ppm) 161.9 (d, J=245.62 Hz), 149.3, 143.1, 137.6, 134.9, 131.7, 130.2 (d, J=3.25 Hz), 128.3 (d, J=7.83 Hz), 126.5, 124.2, 121.0, 118.1, 115.2 (d, J=21.44 Hz), 100.4, 57.4, 37.2, 36.4, 27.6, 27.5, 24.8, 24.7.

HRMS calculated for $C_{23}H_{24}FN_4$ [M+H]$^+$ 375.1980, found 375.1984.

Preparative Example 20: 4-(4-(4-fluorophenyl)-1-(2-isopropoxyethyl)-1H-imidazol-5-yl)-1H-pyrrolo[2,3-b]pyridine

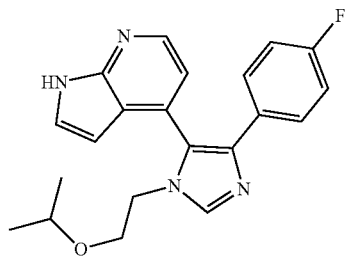 [SMILES: CC(C)OCCn1cnc(-c2ccc(F)cc2)c1-c1ccnc2[nH]ccc12]

The compound was prepared according to General procedure A using 1H-pyrrolo[2,3-b]pyridine-4-carbaldehyde, 2-isopropoxyethan-1-amine, 1-fluoro-4-(isocyano(tosyl)methyl)benzene and $K_2CO_3$. Reaction time: 4.5 hours for the formation of the imine, then additional 18 hours for the cyclization step. The residue obtained after the workup was purified by preparative TLC (dichloromethane/acetone, 1:1). So obtained material was then dissolved in dichloromethane (4 mL), hexane (1.5 mL) was added, the solvent was evaporated so that the residual volume was 2 mL, and the solution was allowed to stand at 25° C. overnight. The solid was collected by filtration and dried in a vacuum. The product was obtained as a white solid (20 mg, 23%).

$^1$H NMR (500 MHz, CDCl$_3$) δ (ppm) 9.85 (s, 1H), 8.41 (d, J=4.88 Hz, 1H), 7.90 (s, 1H), 7.43-7.37 (m, 2H), 7.34 (d, J=3.52 Hz, 1H), 7.09 (d, J=4.85 Hz, 1H), 6.86-6.81 (m, 2H), 6.19 (d, J=3.52 Hz, 1H), 4.00-3.88 (m, 2H), 3.45-3.37 (m, 3H), 1.06 (d, J=6.07 Hz, 6H).

$^{13}$C NMR (126 MHz, CDCl$_3$) δ (ppm) 161.9 (d, J=245.73 Hz), 149.1, 143.5, 138.8, 138.3, 131.4, 130.3 (d, J=3.03 Hz), 128.3 (d, J=7.88 Hz), 126.2, 124.5, 120.5, 118.2, 115.2 (d, J=21.40 Hz), 100.9, 72.5, 66.9, 46.1, 22.0.

$^{19}$F NMR (471 MHz, CDCl$_3$) δ (ppm) −115.79.

HRMS calculated for $C_{21}H_{22}FN_4O$ [M+H]$^+$ 365.1772, found 365.1776.

Preparative Example 21: 2-(4-(4-fluorophenyl-5-(1H-pyrrolo[2,3-b]pyridin-4-yl)-1H-imidazol-1-yl)-N,N-dimethylethane-1-amine

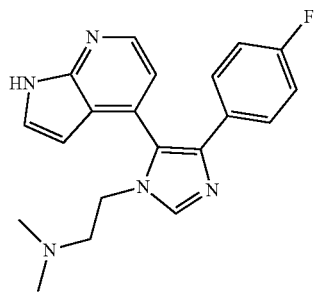 [SMILES: CN(C)CCn1cnc(-c2ccc(F)cc2)c1-c1ccnc2[nH]ccc12]

The compound was prepared according to General procedure A using 1H-pyrrolo[2,3-b]pyridine-4-carbaldehyde, N$^1$,N$^1$-dimethylethane-1,2-diamine, 1-fluoro-4-(isocyano(tosyl)methyl)benzene and $K_2CO_3$. Reaction time: 4.5 hours for the formation of the imine, then additional 18 hours for the cyclization step. The residue obtained after the workup was purified by preparative TLC (methanol/acetone, 1:20; +1% of triethylamine). The product was obtained as a white solid (58 mg, 69%).

$^1$H NMR (500 MHz, methanol-$d_4$) δ (ppm) 8.32 (d, J=4.90 Hz, 1H), 7.98 (s, 1H), 7.42 (d, J=3.51 Hz, 1H), 7.34-7.28 (m, 2H), 7.14 (d, J=4.90 Hz, 1H), 6.91-6.84 (m, 2H), 6.14 (d, J=3.50 Hz, 1H), 4.13-3.98 (m, 2H), 2.38 (td, J=6.93, 5.35 Hz, 2H), 2.03 (s, 6H).

$^{13}$C NMR (126 MHz, methanol-$d_4$) δ (ppm) 163.3 (d, J=244.89 Hz), 149.8, 143.7, 140.0, 139.4, 132.2, 131.6 (d, J=3.25 Hz), 129.6 (d, J=8.10 Hz), 128.4, 126.3, 122.0, 118.7, 115.9 (d, J=21.77 Hz), 100.7, 60.1, 45.3, 44.4.

$^{19}$F NMR (471 MHz, methanol-$d_4$) δ (ppm) −117.59.

HRMS calculated for $C_{20}H_{21}FN_5$ [M+H]$^+$ 350.1776, found 350.1779.

Preparative Example 22: 4-(1-benzyl-4-(4-fluorophenyl)-1H-imidazol-5-yl)-1H-pyrrolo[2,3-b]pyridine

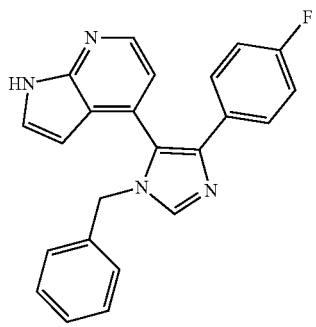 [SMILES: Fc1ccc(-c2ncn(Cc3ccccc3)c2-c2ccnc3[nH]ccc23)cc1]

The compound was prepared according to General procedure A using 1H-pyrrolo[2,3-b]pyridine-4-carbaldehyde, benzylamine, 1-fluoro-4-(isocyano(tosyl)methyl)benzene and $K_2CO_3$. Reaction time: 3 hours for the formation of the imine, then additional 23 hours for the cyclization step. The residue obtained after the workup was purified by preparative TLC (hexane/acetone, 4:3). So obtained material was then dissolved in dichloromethane (3 mL), hexane (2 mL) was added, the solvent was evaporated so that the residual volume was 1 mL, and the solution was allowed to stand at 25° C. overnight. The solid was collected by filtration and dried in a vacuum. The product was obtained as a beige solid (40 mg, 46%).

$^1$H NMR (500 MHz, CDCl$_3$) δ (ppm) 9.92 (s, 1H), 8.24 (d, J=4.92 Hz, 1H), 7.68 (s, 1H), 7.37-7.32 (m, 2H), 7.24 (d, J=3.58 Hz, 1H), 7.19-7.11 (m, 3H), 6.86 (d, J=4.93 Hz, 1H), 6.84-6.80 (m, 2H), 6.80-6.74 (m, 2H), 6.07 (d, J=3.50 Hz, 1H), 4.97 (d, J=15.42 Hz, 1H), 4.86 (d, J=15.29 Hz, 1H).

$^{13}$C NMR (126 MHz, CDCl$_3$) δ (ppm) 162.0 (d, J=245.90 Hz), 149.0, 143.2, 138.9, 138.2, 136.1, 131.2, 130.3 (d, J=3.04 Hz), 129.0, 128.3 (d, J=8.01 Hz), 128.2, 127.2, 126.2, 125.1, 120.5, 118.1, 115.2 (d, J=21.44 Hz), 100.8, 49.5.

HRMS calculated for $C_{23}H_{18}FN_4$ [M+H]$^+$ 369.1510, found 369.1512.

Preparative Example 23: 4-(4-(4-fluorophenyl)-1-(furan-3-ylmethyl)-1H-imidazol-5-yl-1H-pyrrolo[2,3-b]pyridine

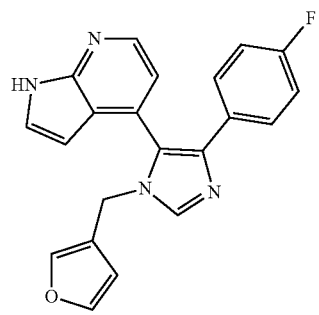 [SMILES: Fc1ccc(-c2ncn(Cc3ccoc3)c2-c2ccnc3[nH]ccc23)cc1]

The compound was prepared according to General procedure A using 1H-pyrrolo[2,3-b]pyridine-4-carbaldehyde, furan-3-ylmethanamine, 1-fluoro-4-(isocyano(tosyl)methyl)benzene and $K_2CO_3$. Reaction time: 3 hours for the formation of the imine, then additional 23 hours for the cyclization step. The residue obtained after the workup was purified by preparative TLC (hexane/acetone, 4:3).). So obtained material was then dissolved in dichloromethane (3 mL), hexane (2 mL) was added, the solvent was evaporated so that the residual volume was 1 mL, and the solution was allowed to stand at 25° C. overnight. The solid was collected by filtration and dried in a vacuum. The product was obtained as beige solid (23 mg, 27%).

$^1$H NMR (500 MHz, CDCl$_3$) δ (ppm) 9.66 (s, 1H), 8.39 (d, J=4.96 Hz, 1H), 7.80 (s, 1H), 7.43-7.38 (m, 2H), 7.35-7.32 (m, 2H), 7.07 (d, J=4.89 Hz, 1H), 6.86-6.82 (m, 2H), 6.25 (dd, J=3.33, 1.85 Hz, 1H), 6.19 (d, J=3.52 Hz, 1H), 5.97 (dd, J=3.25, 0.81 Hz, 1H), 4.97 (d, J=15.59 Hz, 1H), 4.89 (d, J=15.54 Hz, 1H).

$^{13}$C NMR (126 MHz, CDCl$_3$) δ (ppm) 162.1 (d, J=246.14 Hz), 148.8, 148.5, 143.3, 143.2, 138.6, 137.9, 131.0, 130.0 (d, J=2.70 Hz), 128.4 (d, J=8.06 Hz), 126.3, 124.7, 120.5, 118.2, 115.3 (d, J=21.56 Hz), 110.7, 109.4, 100.9, 42.4.

HRMS calculated for $C_{21}H_{16}FN_4O$[M+H]$^+$ 359.1303, found 359.1306.

Preparative Example 24: 4-(4-(4-fluorophenyl)-1-(3-methoxypropyl)-1H-imidazol-5-yl)-1H-pyrrolo[2,3-b]pyridine

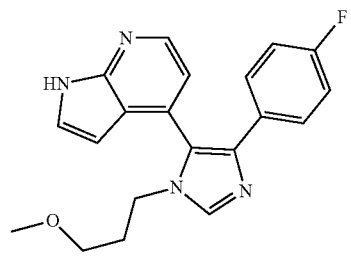 [SMILES: COCCCn1cnc(-c2ccc(F)cc2)c1-c1ccnc2[nH]ccc12]

The compound was prepared according to General procedure A using 1H-pyrrolo[2,3-b]pyridine-4-carbaldehyde, 3-methoxypropan-1-amine, 1-fluoro-4-(isocyano(tosyl)methyl)benzene and K$_2$CO$_3$. Reaction time: 2 hours for the formation of the imine, then additional 13 hours for the cyclization step. The residue obtained after the workup was purified by preparative TLC (hexane/acetone, 3:4).). So obtained material was then dissolved in dichloromethane (2 mL), hexane (2 mL) was added, the solvent was evaporated so that the residual volume was 0.5 mL, and the solution was allowed to stand at 25° C. overnight. The solid was collected by filtration and dried in a vacuum. The product was obtained as a beige solid (39 mg, 46%).

$^1$H NMR (500 MHz, CDCl$_3$) δ (ppm) 10.06 (s, 1H), 8.43 (d, J=4.89 Hz, 1H), 7.77 (s, 1H), 7.43-7.37 (m, 2H), 7.35 (d, J=3.54 Hz, 1H), 7.09 (d, J=4.88 Hz, 1H), 6.87-6.80 (m, 2H), 6.17 (d, J=3.57 Hz, 1H), 4.06-3.91 (m, 2H), 3.19 (s, 3H), 3.16 (t, J=5.79 Hz, 2H), 1.71-1.61 (m, 2H).

$^{13}$C NMR (126 MHz, CDCl$_3$) δ (ppm) 162.0 (d, J=245.82 Hz), 149.1, 143.4, 138.7, 138.2, 131.4, 130.2 (d, J=3.20 Hz), 128.3 (d, J=7.85 Hz), 126.3, 124.6, 120.4, 117.9, 115.2 (d, J=21.39 Hz), 100.8, 68.4, 58.7, 42.7, 30.8.

$^{19}$F NMR (471 MHz, CDCl$_3$) δ (ppm) −115.66.

HRMS calculated for C$_{20}$H$_{20}$FN$_4$O [M+H]$^+$ 351.1616, found 351.1619.

Preparative Example 25: 4-(4-(4-fluorophenyl)-1-methyl-1H-imidazol-5-yl-1H-pyrrolo[2,3-b]pyridine

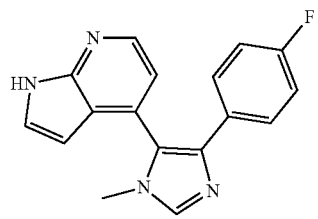 [SMILES: Cn1cnc(-c2ccc(F)cc2)c1-c1ccnc2[nH]ccc12]

The compound was prepared according to General procedure A using 1H-pyrrolo[2,3-b]pyridine-4-carbaldehyde, 2 M solution of methanamine in tetrahydrofuran, 1-fluoro-4-(isocyano(tosyl)methyl)benzene and K$_2$CO$_3$. Reaction time: 2 hours for the formation of the imine, then additional 13 hours for the cyclization step. The residue obtained after the workup was purified by column chromatography (hexane/acetone, gradient from 3:4 to 1:2). The product was obtained as a colorless wax (42 mg; 60%).

$^1$H NMR (500 MHz, CDCl$_3$) δ (ppm) 10.03 (s, 1H), 8.42 (d, J=4.87 Hz, 1H), 7.74 (s, 1H), 7.43-7.38 (m, 2H), 7.35 (d, J=3.58 Hz, 1H), 7.07 (d, J=4.85 Hz, 1H), 6.88-6.82 (m, 2H), 6.18 (d, J=3.49 Hz, 1H), 3.52 (s, 3H).

$^{13}$C NMR (126 MHz, CDCl$_3$) δ (ppm) 162.0 (d, J=245.75 Hz), 149.1, 143.4, 138.8, 138.6, 131.1, 130.4 (d, J=3.17 Hz), 128.4 (d, J=8.07 Hz), 126.1, 125.5, 120.2, 117.9, 115.3 (d, J=21.40 Hz), 100.9, 32.7.

HRMS calculated for C$_{17}$H$_{14}$FN$_4$ [M+H]$^+$ 293.1197, found 293.1199.

Preparative Example 26: 4-(4-(4-fluorophenyl)-1-((1-methylazetidin-3-yl)methyl)-1H-imidazol-5-yl)-1H-pyrrolo[2,3-b]pyridine

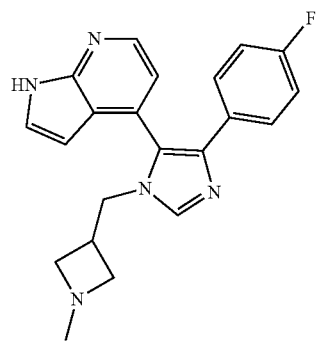 [SMILES: CN1CC(Cn2cnc(-c3ccc(F)cc3)c2-c2ccnc3[nH]ccc23)C1]

The compound was prepared according to General procedure A using 1H-pyrrolo[2,3-b]pyridine-4-carbaldehyde, (1-methylazetidin-3-yl)methanamine, 1-fluoro-4-(isocyano(tosyl)methyl)benzene and K$_2$CO$_3$. Reaction time: 3.5 hours for the formation of the imine, then additional 24 hours for the cyclization step. The residue obtained after the workup was purified by preparative TLC (dichloromethane/7 M NH$_3$ in methanol, 12:1). The product was obtained as a white solid (40 mg, 46%).

$^1$H NMR (500 MHz, acetone-d$_6$) δ (ppm) 11.00 (s, 1H), 8.37 (d, J=4.78 Hz, 1H), 7.82 (s, 1H), 7.50 (d, J=3.51 Hz, 1H), 7.46-7.41 (m, 2H), 7.11 (d, J=4.76 Hz, 1H), 6.91-6.84 (m, 2H), 6.13 (d, J=3.49 Hz, 1H), 4.15 (dd, J=14.11, 7.51 Hz, 1H), 4.05 (dd, J=14.13, 7.64 Hz, 1H), 3.05-2.98 (m, 2H), 2.72-2.66 (m, 2H), 2.41 (tt, J=7.42, 5.51 Hz, 1H), 2.07 (s, 3H).

$^{13}$C NMR (126 MHz, acetone-d$_6$) δ (ppm) 162.3 (d, J=243.32 Hz), 150.3, 144.2, 138.74, 138.72, 132.6 (d, J=3.17 Hz), 131.7, 128.8 (d, J=7.94 Hz), 127.6, 125.6, 120.9, 118.4, 115.4 (d, J=21.30 Hz), 100.4, 60.0, 49.4, 45.9, 31.9.

$^{19}$F NMR (471 MHz, acetone-d$_6$) δ (ppm) −118.23.

HRMS calculated for C$_{21}$H$_{21}$FN$_5$ [M+H]$^+$ 362.1776, found 362.1779.

Preparative Example 27: 4-(4-(4-fluorophenyl)-1-((tetrahydrofuran-2-yl)methyl)-1H-imidazol-5-yl)-1H-pyrrolo[2,3-b]pyridine

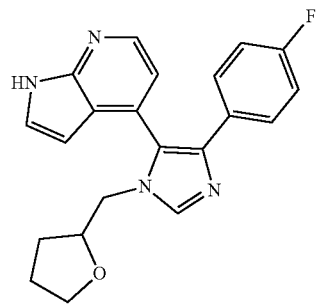 [SMILES: Fc1ccc(-c2ncn(CC3CCCO3)c2-c2ccnc3[nH]ccc23)cc1]

The compound was prepared according to General procedure A using 1H-pyrrolo[2,3-b]pyridine-4-carbaldehyde, (tetrahydrofuran-2-yl)methanamine, 1-fluoro-4-(isocyano (tosyl)methyl)benzene and K$_2$CO$_3$. Reaction time: 3.5 hours for the formation of the imine, then additional 24 hours for the cyclization step. The residue obtained after the workup was purified by preparative TLC (hexane/acetone, 7:6). So obtained material was then dissolved in dichloromethane (2 mL), hexane (1 mL) was added, the solvent was evaporated so that the residual volume was 1 mL, and the solution was allowed to stand at 25° C. overnight. The solid was collected by filtration and dried in a vacuum. The product was obtained as a white solid (35 mg, 40%).

$^1$H NMR (500 MHz, CDCl$_3$) δ (ppm) 10.33 (s, 1H), 8.42 (d, J=4.88 Hz, 1H), 7.91 (d, J=5.64 Hz, 1H), 7.42-7.33 (m, 3H), 7.08 (dd, J=11.71, 4.92 Hz, 1H), 6.88-6.80 (m, 2H), 6.19 (dd, J=6.00, 3.42 Hz, 1H), 4.00-3.81 (m, 3H), 3.79-3.74 (m, 1H), 3.73-3.65 (m, 1H), 1.81-1.66 (m, 3H), 1.34-1.25 (m, 1H).

$^{13}$C NMR (126 MHz, CDCl$_3$) δ (ppm) 161.9 (d, J=245.65 Hz), 149.2, 143.3, 138.8 (d, J=17.46 Hz), 138.3 (d, J=15.23 Hz), 131.5, 130.4 (d, J=3.13 Hz), 128.4 (d, J=7.83 Hz), 126.3, 124.9 (d, J=22.09 Hz), 120.6, 118.2 (d, J=26.88 Hz), 115.2 (d, J=21.43 Hz), 100.8 (d, J=6.25 Hz), 68.4 (d, J=3.89 Hz), 49.4, 49.2, 28.8 (d, J=7.25 Hz), 25.7 (d, J=2.52 Hz).

$^{19}$F NMR (471 MHz, CDCl$_3$) δ (ppm) −115.85.

HRMS calculated for C$_{21}$H$_{20}$FN$_4$O [M+H]$^+$ 363.1616, found 363.1620.

Preparative Example 28: 4-(4-(4-fluorophenyl)-1-(trans-4-methoxycyclohexyl)-1H-imidazol-5-yl)-1H-pyrrolo[2,3-b]pyridine

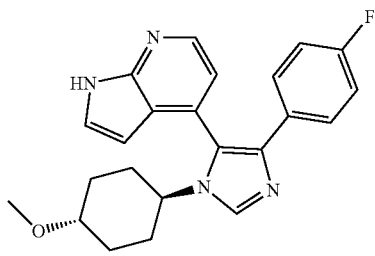 [SMILES: CO[C@H]1CC[C@H](n2cnc(-c3ccc(F)cc3)c2-c2ccnc3[nH]ccc23)CC1]

The compound was prepared according to General procedure A using 1H-pyrrolo[2,3-b]pyridine-4-carbaldehyde, trans-4-methoxycyclohexan-1-amine hydrochloride, 1-fluoro-4-(isocyano(tosyl)methyl)benzene and K$_2$CO$_3$. Reaction time: 3.5 hours for the formation of the imine, then additional 15 hours for the cyclization step. The residue obtained after the workup was purified by preparative TLC (hexane/acetone, 4:5). So obtained material was then dissolved in dichloromethane (2 mL), hexane (1.5 mL) was added, the solvent was evaporated so that the residual volume was 1.5 mL, and the solution was allowed to stand at 25° C. overnight. The solid was collected by filtration and dried in a vacuum. The product was obtained as a white solid (29 mg, 31%).

$^1$H NMR (500 MHz, CDCl$_3$) δ (ppm) 9.39 (s, 1H), 8.44 (d, J=4.88 Hz, 1H), 8.14 (s, 1H), 7.42-7.35 (m, 3H), 7.06 (d, J=4.88 Hz, 1H), 6.91-6.81 (m, 2H), 6.16 (d, J=3.58 Hz, 1H), 3.76 (tt, J=11.89, 3.73 Hz, 1H), 3.30 (s, 3H), 3.22-3.15 (m, 1H), 2.16-2.05 (m, 3H), 2.04-1.97 (m, 1H), 1.84-1.73 (m, 2H), 1.16-1.02 (m, 2H).

$^{13}$C NMR (126 MHz, CDCl$_3$) δ (ppm) 162.1 (d, J=247.58 Hz), 154.5, 148.8, 143.6, 136.7, 134.3, 128.6 (d, J=8.03 Hz), 126.6, 124.7, 120.5, 118.1, 115.6 (d, J=21.71 Hz), 100.4, 77.7, 56.2, 55.3, 32.7, 32.1, 30.8, 30.8.

HRMS calculated for C$_{23}$H$_{24}$FN$_4$O[M+H]$^+$ 391.1929, found 391.1932.

Preparative Example 29: 4-(1-((3,3-dimethylcyclobutyl)methyl)-4-(4-fluorophenyl)-1H-imidazol-5-yl)-1H-pyrrolo[2,3-b]pyridine

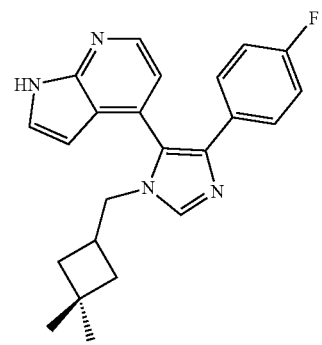

The compound was prepared according to General procedure A using 1H-pyrrolo[2,3-b]pyridine-4-carbaldehyde, (3,3-dimethylcyclobutyl)methanamine hydrochloride, 1-fluoro-4-(isocyano(tosyl)methyl)benzene and K$_2$CO$_3$. Reaction time: 3.5 hours for the formation of the imine, then additional 15 hours for the cyclization step. The residue obtained after the workup was purified by two times preparative TLC (dichloromethane/ethyl acetate, 1:4; then hexane/acetone, 2:1). The product was obtained as a colorless wax (7 mg, 8%).

$^1$H NMR (500 MHz, CDCl$_3$) δ (ppm) 10.08 (s, 1H), 8.42 (d, J=4.88 Hz, 1H), 7.72 (s, 1H), 7.40-7.34 (m, 3H), 7.06 (d, J=4.88 Hz, 1H), 6.86-6.80 (m, 2H), 6.18 (d, J=3.54 Hz, 1H), 3.86-3.72 (m, 2H), 2.37 (hept, J=8.20 Hz, 1H), 1.77-1.70 (m, 2H), 1.39-1.32 (m, 2H), 1.03 (s, 3H), 0.95 (s, 3H).

$^{13}$C NMR (126 MHz, CDCl$_3$) δ (ppm) 161.9 (d, J=245.71 Hz), 149.1, 143.3, 138.4, 137.3, 131.6, 130.3 (d, J=3.17 Hz), 128.3 (d, J=8.01 Hz), 126.2, 124.7, 120.6, 118.1, 115.2 (d, J=21.37 Hz), 100.8, 52.0, 39.0, 31.7, 31.1, 29.0, 28.5.

$^{19}$F NMR (471 MHz, CDCl$_3$) δ (ppm) −115.80.

HRMS calculated for C$_{23}$H$_{24}$FN$_4$ [M+H]$^+$ 375.1980, found 375.1984.

Preparative Example 30: 4-(4-(4-fluorophenyl)-1-(2-methylallyl)-1H-imidazol-5-yl)-1H-pyrrolo[2,3-b]pyridine

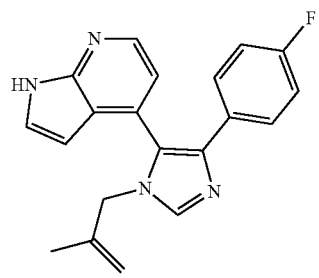 [SMILES: C=C(C)Cn1cnc(-c2ccc(F)cc2)c1-c1ccnc2[nH]ccc12]

The compound was prepared according to General procedure A using 1H-pyrrolo[2,3-b]pyridine-4-carbaldehyde, 2-methylprop-2-en-1-amine, 1-fluoro-4-(isocyano(tosyl)

methyl)benzene and K₂CO₃. Reaction time: 3 hours 15 minutes for the formation of the imine, then additional 16 hours for the cyclization step. The residue obtained after the workup was purified two times by preparative TLC (hexane/acetone, 8:5; then dichloromethane/ethyl acetate, 1:4). The product was obtained as a white solid (23 mg, 46%).

$^{1}$H NMR (500 MHz, CDCl₃) δ (ppm) 11.00 (s, 1H), 8.40 (d, J=4.88 Hz, 1H), 7.72 (s, 1H), 7.45-7.39 (m, 2H), 7.35 (d, J=3.98 Hz, 1H), 7.08 (d, J=4.90 Hz, 1H), 6.86-6.81 (m, 2H), 6.15 (d, J=3.48 Hz, 1H), 4.85-4.80 (m, 1H), 4.58-4.53 (m, 1H), 4.44-4.23 (m, 2H), 1.56 (s, 3H).

$^{13}$C NMR (126 MHz, CDCl₃) δ (ppm) 161.9 (d, J=245.60 Hz), 149.3, 142.9, 140.6, 138.7, 138.4, 131.3, 130.5 (d, J=3.17 Hz), 128.3 (d, J=8.02 Hz), 126.3, 125.2, 120.6, 117.7, 115.2 (d, J=21.42 Hz), 113.6, 100.7, 51.3, 19.9.

$^{19}$F NMR (471 MHz, CDCl₃) δ (ppm) −115.83.

HRMS calculated for $C_{20}H_1FN_4$ [M+H]⁺ 333.1510, found 333.1513.

Preparative Example 31: cis-4-(4-(4-fluorophenyl)-5-(1H-pyrrolo[2,3-b]pyridin-4-yl-1H-imidazol-1-yl)cyclohexan-1-ol

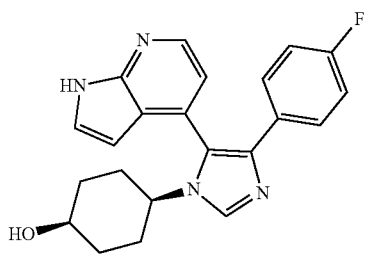 [SMILES: O[C@H]1CC[C@@H](n2cnc(-c3ccc(F)cc3)c2-c2ccnc3[nH]ccc23)CC1]

The compound was prepared according to General procedure A using 1H-pyrrolo[2,3-b]pyridine-4-carbaldehyde, cis-4-aminocyclohexan-1-ol hydrochloride, 1-fluoro-4-(isocyano(tosyl)methyl)benzene and K₂CO₃. Reaction time: 4 hours for the formation of the imine, then additional 19 hours for the cyclization step. The residue obtained after the workup was purified two times by preparative TLC (acetone; then dichloromethane/methanol, 15:1). The product was obtained as a white solid (15 mg, 17%).

$^{1}$H NMR (500 MHz, methanol-d₄) δ (ppm) 8.31 (d, J=4.94 Hz, 1H), 8.05 (s, 1H), 7.41 (d, J=3.51 Hz, 1H), 7.31-7.24 (m 2H), 7.09 (d, J=4.97 Hz, 1H), 6.88-6.82 (m 2H), 6.13 (d, J=3.50 Hz, 1H), 3.88 (p, J=2.94 Hz, 1H), 3.78 (tt, J=12.12, 3.67 Hz, 1H), 2.23-2.11 (m, 2H), 1.86-1.75 (m, 3H), 1.74-1.67 (m, 1H), 1.45-1.37 (m, 1H), 1.36-1.28 (m, 1H).

$^{13}$C NMR (126 MHz, methanol-d₄) δ (ppm) 163.2 (d, J=244.81 Hz), 149.8, 143.7, 138.8, 136.6, 132.4, 131.6 (d, J=3.24 Hz), 129.6 (d, J=8.02 Hz), 128.3, 126.1, 122.3, 118.8, 115.9 (d, J=21.62 Hz), 100.5, 64.9, 56.3, 32.59, 32.56, 29.3, 28.8.

$^{19}$F NMR (471 MHz, methanol-d₄) δ (ppm) −117.74.

HRMS calculated for $C_{22}H_{22}FN_4O$ [M+H]⁺ 377.1772, found 377.1775.

Preparative Example 32: trans-4-(4-(4-fluorophenyl)-5-(1H-pyrrolo[2,3-b]pyridin-4-yl)-1H-imidazol-1-yl)cyclohexan-1-ol

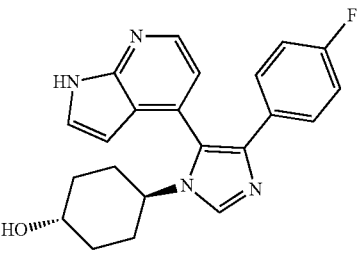 [SMILES: O[C@H]1CC[C@H](n2cnc(-c3ccc(F)cc3)c2-c2ccnc3[nH]ccc23)CC1]

The compound was prepared according to General procedure A using 1H-pyrrolo[2,3-b]pyridine-4-carbaldehyde, trans-4-aminocyclohexan-1-ol hydrochloride, 1-fluoro-4-(isocyano(tosyl)methyl)benzene and K₂CO₃. Reaction time: 4 hours for the formation of the imine, then additional 19 hours for the cyclization step. The residue obtained after the workup was purified by preparative TLC (acetone). So obtained material was then dissolved in methanol (3 mL), dichloromethane (3 mL) was added, the solvent was evaporated so that the residual volume was 0.5 mL, and the solution was allowed to stand at 25° C. overnight. The solid was collected by filtration and dried in a vacuum. The product was obtained as a white solid (17 mg, 31%).

$^{1}$H NMR (500 MHz, methanol-d₄) δ (ppm) 8.32 (d, J=4.88 Hz, 1H), 8.04 (s, 1H), 7.42 (d, J=3.52 Hz, 1H), 7.29-7.25 (m, 2H), 7.09 (d, J=4.89 Hz, 1H), 6.88-6.83 (m, 2H), 6.12 (d, J=3.51 Hz, 1H), 3.75 (tt, J=11.60, 4.16 Hz, 1H), 3.59 (tt, J=11.01, 4.04 Hz, 1H), 2.08-2.03 (m, 1H), 2.00-1.86 (m, 5H), 1.21-1.13 (m, 1H), 1.13-1.03 (m, 1H).

$^{13}$C NMR (126 MHz, methanol-d₄) δ (ppm) 163.2 (d, J=244.83 Hz), 149.8, 143.7, 138.9, 136.6, 132.3, 131.6 (d, J=3.20 Hz), 129.6 (d, J=7.85 Hz), 128.4, 126.2, 122.3, 118.8, 115.9 (d, J=21.76 Hz), 100.4, 69.8, 56.1, 35.08, 35.86, 33.3, 32.9.

$^{19}$F NMR (471 MHz, methanol-d₄) δ (ppm) −117.68.

HRMS calculated for $C_{22}H_{22}FN_4O$ [M+H]⁺ 377.1772, found 377.1774.

Preparative Example 33: Methyl cis-4-(4-(4-fluorophenyl)-5-(1H-pyrrolo[2,3-b]pyridin-4-yl)-1H-imidazol-1-yl)cyclohexane-1-carboxylate

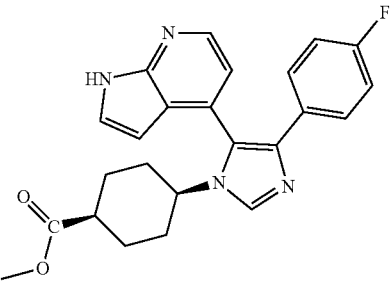 [SMILES: COC(=O)[C@H]1CC[C@@H](n2cnc(-c3ccc(F)cc3)c2-c2ccnc3[nH]ccc23)CC1]

The compound was prepared according to General procedure A using 1H-pyrrolo[2,3-b]pyridine-4-carbaldehyde, methyl cis-4-aminocyclohexane-1-carboxylate hydrochloride, 1-fluoro-4-(isocyano(tosyl)methyl)benzene and K$_2$CO$_3$. Reaction time: 1 hour 15 minutes for the formation of the imine, then additional 16 hours for the cyclization step. The residue obtained after the workup was purified two times by preparative TLC (acetone/hexane, 5:4; then ethyl acetate/acetone, 10:1). The product was obtained as a colorless wax (14 mg, 14%).

$^1$H NMR (500 MHz, methanol-d$_4$) δ (ppm) 8.31 (d, J=4.92 Hz, 1H), 7.98 (s, 1H), 7.41 (d, J=3.51 Hz, 1H), 7.30-7.24 (m, 2H), 7.08 (d, J=4.91 Hz, 1H), 6.90-6.80 (m, 2H), 6.12 (d, J=3.51 Hz, 1H), 3.81 (tt, J=11.61, 4.14 Hz, 1H), 3.70 (s, 3H), 2.60 (tt, J=5.21, 2.68 Hz, 1H), 2.23-2.10 (m, 2H), 1.95-1.77 (m, 4H), 1.49-1.41 (m, 1H), 1.41-1.32 (m, 1H).

$^{13}$C NMR (126 MHz, methanol-d$_4$) δ (ppm) 176.3, 163.2 (d, J=244.78 Hz), 149.8, 143.7, 138.9, 136.7, 132.4, 131.6 (d, J=3.19 Hz), 129.6 (d, J=8.02 Hz), 128.4, 126.0, 122.4, 118.9, 115.9 (d, J=21.58 Hz), 100.5, 56.4, 52.2, 39.0, 31.9, 31.4, 27.41, 27.38.

$^{19}$F NMR (471 MHz, methanol-d$_4$) δ (ppm) −117.69.

HRMS calculated for C$_{24}$H$_{24}$FN$_4$O$_2$ [M+H]$^+$ 419.1878, found 419.1880.

Preparative Example 34: Methyl trans-4-(4-(4-fluorophenyl)-5-(1H-pyrrolo[2,3-b]pyridin-4-yl)-1H-imidazol-1-yl)cyclohexane-1-carboxylate

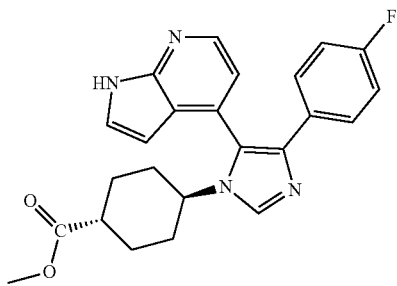 [SMILES: COC(=O)[C@H]1CC[C@H](n2cnc(-c3ccc(F)cc3)c2-c2ccnc3[nH]ccc23)CC1]

The compound was prepared according to General procedure A using 1H-pyrrolo[2,3-b]pyridine-4-carbaldehyde, methyl trans-4-aminocyclohexane-1-carboxylate hydrochloride, 1-fluoro-4-(isocyano(tosyl)methyl)benzene and K$_2$CO$_3$. Reaction time: 1 hour 15 minutes for the formation of the imine, then additional 16 hours for the cyclization step. The residue obtained after the workup was purified two times by preparative TLC (acetone/hexane, 5:4; then ethyl acetate/acetone, 10:1). The product was obtained as a colorless wax (9 mg, 9%).

$^1$H NMR (500 MHz, methanol-d$_4$) δ (ppm) 8.40-8.31 (m, 2H), 7.44 (d, J=3.54 Hz, 1H), 7.32-7.26 (m, 2H), 7.13 (d, J=4.95 Hz, 1H), 6.94-6.88 (m, 2H), 6.14 (d, J=3.51 Hz, 1H), 3.82 (tt, J=12.20, 3.63 Hz, 1H), 3.61 (s, 3H), 2.40 (tt, J=12.29, 3.43 Hz, 1H), 2.17-2.12 (m, 1H), 2.09-1.97 (m, 3H), 1.93-1.83 (m, 2H), 1.28-1.16 (m, 2H).

$^{13}$C NMR (126 MHz, methanol-d$_4$) δ (ppm) 176.9, 164.6 (d, J=246.14 Hz), 149.8, 143.8, 136.4, 131.1, 129.9 (d, J=8.19 Hz), 128.7, 126.5, 122.2, 118.8, 116.2 (d, J=22.06 Hz), 100.3, 56.6, 52.2, 42.9, 34.1, 33.7, 29.13, 29.11.

HRMS calculated for C$_{24}$H$_{24}$FN$_4$O$_2$ [M+H]$^+$ 419.1878, found 419.1880.

Preparative Example 35: 4-(1-(4,4-difluorocyclohexyl)-4-(4-fluorophenyl)-1H-imidazol-5-yl)-1H-pyrrolo[2,3-b]pyridine

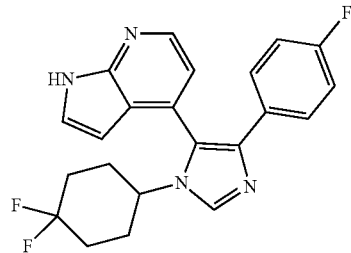 [SMILES: Fc1ccc(-c2ncn(C3CCC(F)(F)CC3)c2-c2ccnc3[nH]ccc23)cc1]

The compound was prepared according to General procedure A using 1H-pyrrolo[2,3-b]pyridine-4-carbaldehyde, 4,4-difluorocyclohexan-1-amine hydrochloride, 1-fluoro-4-(isocyano(tosyl)methyl)benzene and K$_2$CO$_3$. Reaction time: 2 hours for the formation of the imine, then additional 14 hours for the cyclization step. The residue obtained after the workup was purified three times by preparative TLC (acetone/hexane, 2:3; then ethyl acetate/dichloromethane, 4:1; then acetone/hexane, 1:1). The product was obtained as a colorless wax (12 mg, 13%).

$^1$H NMR (500 MHz, CDCl$_3$) δ (ppm) 10.66 (s, 1H), 8.45 (d, J=4.88 Hz, 1H), 7.84 (s, 1H), 7.40 (d, J=3.53 Hz, 1H), 7.38-7.33 (m, 2H), 7.06 (d, J=4.88 Hz, 1H), 6.86-6.79 (m, 2H), 6.19 (d, J=3.46 Hz, 1H), 3.86-3.76 (m, 1H), 2.21-1.976 (m, 7H), 1.73-1.51 (m, 2H).

$^{13}$C NMR (126 MHz, CDCl$_3$) δ (ppm) 161.8 (d, J=245.99 Hz), 149.1, 143.2, 138.4, 134.6, 131.3, 130.1 (d, J=3.20 Hz), 128.2 (d, J=7.91 Hz), 126.5, 124.2, 121.5 (dd, J=243.78, 239.80 Hz), 120.7, 117.8, 115.1 (d, J=21.39 Hz), 100.1, 52.9, 32.8 (td, J=25.17, 8.90 Hz), 30.5 (d, J=10.32 Hz), 29.9 (d, J=10.29 Hz).

$^{19}$F NMR (471 MHz, CDCl$_3$) δ (ppm) −94.72 (d, J=240.75 Hz), −102.52 (d, J=240.25 Hz), −115.62.

HRMS calculated for C$_{22}$H$_{20}$F$_3$N$_4$ [M+H]$^+$ 397.1635, found 397.1634.

Preparative Example 36: 4-(4-(4-fluorophenyl-1-(trans-4-(trifluoromethylcyclohexyl-1H-imidazol-5-yl)-1H-pyrrolo[2,3-b]pyridine

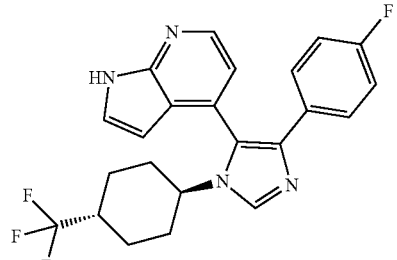

The compound was prepared according to General procedure A using 1H-pyrrolo[2,3-b]pyridine-4-carbaldehyde, trans-4-(trifluoromethyl)cyclohexan-1-amine hydrochloride, 1-fluoro-4-(isocyano(tosyl)methyl)benzene and K$_2$CO$_3$. Reaction time: 2 hours for the formation of the imine, then additional 14 hours for the cyclization step. The residue obtained after the workup was purified two times by preparative TLC (acetone/hexane, 2:3; then ethyl acetate/dichloromethane, 4:1). The product was obtained as a pale green wax (4 mg, 4%).

$^1$H NMR (500 MHz, CDCl$_3$) δ (ppm) 9.83 (s, 1H), 8.45 (s, 1H), 7.91 (s, 1H), 7.42-7.32 (m, 3H), 7.05 (d, J=4.73 Hz, 1H), 6.88-6.78 (m, 2H), 6.18 (d, J=2.46 Hz, 1H), 3.71 (tt, J=11.84, 3.44 Hz, 1H), 2.20-1.95 (m, 7H), 1.77 (pd, J=12.89, 3.61 Hz, 2H).

$^{13}$C NMR (126 MHz, CDCl$_3$) δ (ppm) 162.0 (d, J=246.17 Hz), 149.0, 143.6, 138.0, 134.6, 131.2, 129.9 (d, J=3.08 Hz), 128.4 (d, J=8.04 Hz), 126.5, 126.1, 124.4, 120.8, 118.1, 115.2, 100.4, 54.4, 41.0 (q, J=27.05 Hz), 32.9 (d, J=82.21 Hz), 24.4 (d, J=7.12 Hz).

$^{19}$F NMR (471 MHz, CDCl$_3$) δ (ppm) −73.63, −115.38.

HRMS calculated for C$_{23}$H$_{21}$F$_4$N$_4$ [M+H]$^+$ 429.1697, found 429.1694.

Preparative Example 37: 4-(4-(4-fluorophenyl)-1-(piperidin-4-yl)-1H-imidazol-5-yl)-1H-pyrrolo[2,3-b]pyridine

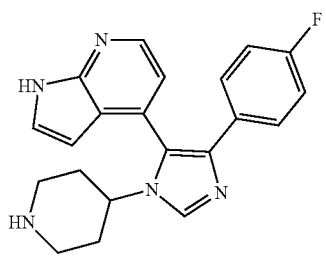 [SMILES: Fc1ccc(-c2ncn(C3CCNCC3)c2-c2ccnc3[nH]ccc23)cc1]

To a solution of tert-butyl 4-(4-(4-fluorophenyl)-5-(1H-pyrrolo[2,3-b]pyridin-4-yl)-1H-imidazol-1-yl)piperidine-1-carboxylate (53 mg, 0.115 mmol) in dichloromethane (2 mL) was added TFA (0.2 mL). The resulting mixture was stirred at 25° C. for 2 hours. Then, a saturated aqueous solution of NaHCO$_3$ (1.5 mL) was added to the mixture and the solvents were evaporated in vacuo. The residue obtained after the workup was purified by column chromatography (dichloromethane/7 M NH$_3$ in methanol, 8:1). The product was obtained as a colorless wax (16 mg, 38%).

$^1$H NMR (500 MHz, methanol-d$_4$) δ (ppm) 8.32 (d, J=4.96 Hz, 1H), 8.06 (s, 1H), 7.41 (d, J=3.51 Hz, 1H), 7.30-7.25 (m 2H), 7.09 (d, J=4.96 Hz, 1H), 6.88-6.83 (m 2H), 6.12 (d, J=3.51 Hz, 1H), 3.87 (ddd, J=16.11, 10.58, 4.44 Hz, 1H), 3.11-2.98 (m, 2H), 2.44 (td, J=12.63, 2.74 Hz, 1H), 2.40-2.31 (m, 1H), 2.06-1.96 (m, 1H), 1.96-1.84 (m, 3H).

$^{13}$C NMR (126 MHz, methanol-d$_4$) δ (ppm) 163.2 (d, J=245.04 Hz), 149.8, 143.8, 139.0, 136.7, 132.2, 131.5 (d, J=3.21 Hz), 129.6 (d, J=8.11 Hz), 128.4, 126.0, 122.3, 118.8, 115.9 (d, J=21.78 Hz), 100.4, 55.1, 46.2, 46.2, 35.3, 34.9.

$^{19}$F NMR (471 MHz, methanol-d$_4$) δ (ppm) −117.59.

HRMS calculated for C$_{21}$H$_{21}$FN$_5$ [M+H]$^+$ 362.1776, found 362.1774.

Preparative Example 38: 2-methyl-4-(4,4,5,5-tetramethyl-1,3,2-dioxaborolan-2-yl)-1H-pyrrolo[2,3-b]pyridine

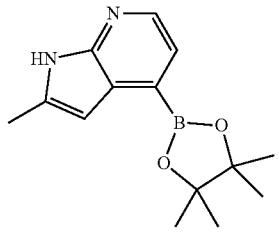

To a degassed solution of 4-bromo-2-methyl-1H-pyrrolo[2,3-b]pyridine (122 mg; 0.578 mmol) in dioxane (3.0 mL) were added potassium acetate (141 mg; 1.45 mmol), 4,4,4',4',5,5,5',5'-octamethyl-2,2'-bis(1,3,2-dioxaborolane) (293 mg; 1.156 mmol), (2-dicyclohexylphosphino-2',6'-dimethoxybiphenyl) [2-(2'-amino-1,1'-biphenyl)]palladium(II) methanesulfonate (18 mg; 0.023 mmol; CAS: 1445085-82-4) and the mixture was stirred at 90° C. for 3.5 hours. The solvent was evaporated in vacuo and the residue was purified by column chromatography (dichloromethane/methanol, 10:1). The product was obtained as a gray solid (57 mg, 75% yield; ca. 70% purity).

$^1$H NMR (500 MHz, CDCl$_3$) δ (ppm) 10.45 (s, 1H), 8.19 (d, J=4.89 Hz, 1H), 7.43 (d, J=4.78 Hz, 1H), 6.60 (s, 1H), 2.55 (s, 3H), 1.40 (s, 12H).

$^{13}$C NMR (126 MHz, CDCl$_3$) δ (ppm) 148.7, 148.0, 139.2, 137.7, 127.1, 121.6, 100.7, 84.2, 25.1, 14.3.

HRMS calculated for C$_{14}$H$_{20}$BN$_2$O$_2$ [M+H]$^+$ 259.1615, found 259.1613.

Preparative Example 39: 4-(1-cyclohexyl-4-(4-fluorophenyl)-1H-imidazol-5-yl)-2-methyl-1H-pyrrolo[2,3-b]pyridine

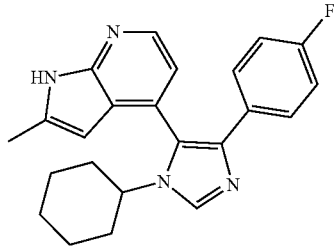 [SMILES: Cc1cc2c(-c3c(-c4ccc(F)cc4)ncn3C3CCCCC3)ccnc2[nH]1]

The compound was prepared according to General procedure B using 2-methyl-4-(4,4,5,5-tetramethyl-1,3,2-dioxaborolan-2-yl)-1H-pyrrolo[2,3-b]pyridine. Reaction temperature: 100° C. Reaction time: 16 hours. The residue obtained after the workup was purified two times by preparative TLC (hexane/acetone, 2:1; then ethyl acetate/dichloromethane, 4:1). The product was obtained as a white solid (10 mg, 29%).

$^1$H NMR (500 MHz, CDCl$_3$) δ (ppm) 10.90 (s, 1H), 8.30 (d, J=4.92 Hz, 1H), 7.88 (s, 1H), 7.41-7.35 (m, 2H), 6.98 (d, J=4.94 Hz, 1H), 6.86-6.80 (m, 2H), 5.88 (s, 1H), 3.66 (tt, J=12.03, 3.73 Hz, 1H), 2.51 (s, 3H), 2.07-2.01 (m, 1H), 2.00-1.95 (m, 1H), 1.82-1.75 (m, 2H), 1.72-1.59 (m, 3H), 1.21-1.06 (m, 3H).

$^{13}$C NMR (126 MHz, CDCl$_3$) δ (ppm) 161.9 (d, J=245.59 Hz), 149.5, 141.3, 138.2, 137.3, 134.6, 130.2 (d, J=3.16 Hz), 130.0, 128.2 (d, J=7.85 Hz), 124.7, 122.7, 117.9, 115.2 (d, J=21.40 Hz), 98.0, 55.4, 35.3, 34.4, 25.8, 25.7, 25.2, 14.4.

HRMS calculated for C$_{23}$H$_{24}$FN$_4$ [M+H]$^+$ 375.1980, found 375.1980.

Preparative Example 40:
N-(thiophen-3-yl(tosyl)methyl)formamide

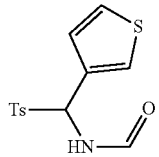

To a solution of 4-methylbenzenesulfinic acid (668 mg; 4.28 mmol) in toluene/acetonitrile (2+2 mL) were added formamide (0.283 mL; 7.12 mmol), thiophene-3-carbaldehyde (0.250 mL; 2.85 mmol) and trimethylsilylchloride (0.398 mL; 3.14 mmol) and the mixture was stirred at 50° C. for 5 hours. Hexane (1 mL), diethylether (2 mL) and H$_2$O (7 mL) were added and the resulting mixture was stirred at 0° C. for 10 minutes. The precipitate was collected by filtration, washed with diethylether (1 mL) and hexane (1 mL) and dried in a vacuum. The product was obtained as a white solid (124 mg, 15%).

$^1$H NMR (300 MHz, DMSO-d$_6$) δ (ppm) 9.63 (d, J=10.40 Hz, 1H), 7.97 (d, J=1.31 Hz, 1H), 7.73-7.63 (m, 3H), 7.59 (dd, J=4.96, 2.99 Hz, 1H), 7.44-7.39 (m, 2H), 7.27 (dd, J=5.04, 1.28 Hz, 1H), 6.49 (d, J=10.41 Hz, 1H), 2.41 (s, 3H).

Preparative Example 41:
3-(isocyano(tosyl)methyl)thiophene

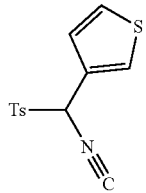

To a cold solution (0° C.) of N-(thiophen-3-yl(tosyl)methyl)formamide (71 mg; 0.240 mmol) in tetrahydrofuran (2.5 mL) was added trimethylamine (0.167 mL; 1.20 mmol), followed by dropwise addition of POCl$_3$ (0.025 mL; 0.264 mmol) and the resulting mixture was stirred at 0° C. for 1 hour. A saturated aqueous solution of NaHCO$_3$ (0.5 mL), a saturated aqueous solution of NH$_4$Cl (20 mL) and ethyl acetate (20 mL) were added to the mixture, the layers were separated, and the aqueous part was washed with ethyl acetate (2×20 mL). Organic extracts were combined, dried over MgSO$_4$, filtered, and the solvent was evaporated in vacuo. The residue obtained after the workup was purified by column chromatography (hexane/acetone, 3:1). The product was obtained as a white solid (40 mg, 60%).

$^1$H NMR (500 MHz, acetone-d$_6$) δ (ppm) 7.69-7.65 (m, 2H), 7.62-7.54 (m, 2H), 7.51-7.47 (m, 2H), 7.16 (dd, J=4.84, 1.56 Hz, 1H), 6.52 (s, 1H).

$^{13}$C NMR (126 MHz, acetone-d$_6$) δ (ppm) 166.2, 147.5, 132.2, 131.0, 130.7, 129.0, 128.6, 128.1, 127.8, 72.7, 21.7.

Preparative Example 42: 4-(1-cyclohexyl-4-(thiophen-3-yl)-1H-imidazol-5-yl)-1H-pyrrolo[2,3-b]pyridine

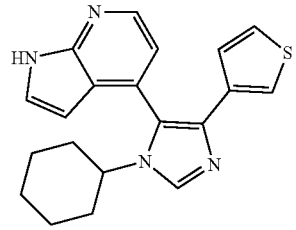 [SMILES: c1cc(-c2c(-c3ccsc3)ncn2C2CCCCC2)c2cc[nH]c2n1]

The compound was prepared according to General procedure A using 1H-pyrrolo[2,3-b]pyridine-4-carbaldehyde, cyclohexanamine, 3-(isocyano(tosyl)methyl)thiophene and K$_2$CO$_3$. Reaction time: 140 minutes for the formation of the imine, then additional 15 hours for the cyclization step. The residue obtained after the workup was purified two times by preparative TLC 2 times (acetone/hexane, 2:3; then ethyl acetate/dichloromethane, 5:1). The product was obtained as a white solid (4 mg; 10%).

$^1$H NMR (500 MHz, CDCl$_3$) δ (ppm) 10.08 (s, 1H), 8.44 (d, J=4.88 Hz, 1H), 7.80 (s, 1H), 7.37 (dd, J=3.62, 1.88 Hz, 1H), 7.15 (dd, J=3.03, 1.26 Hz, 1H), 7.14-7.06 (m, 2H), 6.99 (dd, J=5.11, 1.25 Hz, 1H), 6.24 (dd, J=3.66, 1.48 Hz, 1H), 3.65 (tt, J=12.02, 3.77 Hz, 1H), 2.08-2.01 (m, 1H), 1.97-1.92 (m, 1H), 1.82-1.72 (m, 2H), 1.69-1.59 (m, 3H), 1.20-1.06 (m, 3H).

$^{13}$C NMR (126 MHz, CDCl$_3$) δ (ppm) 149.1, 143.4, 135.5, 135.4, 134.6, 131.8, 126.5, 126.2, 125.0, 124.0, 121.0, 120.3, 118.3, 100.7, 55.4, 35.2, 34.5, 25.8, 25.7, 25.2.

HRMS calculated for C$_{20}$H$_{21}$N$_4$S[M+H]$^+$ 349.1481, found 349.1479.

Preparative Example 43:
3-(isocyano(tosyl)methyl)pyridine

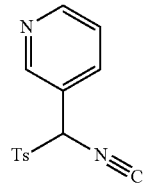

To a cold solution (−78° C.) of 3-(isocyanomethyl)pyridine (146 mg; 1.236 mmol) in tetrahydrofuran (5.0 mL) was added dropwise 2.5 M solution of n-BuLi in hexane (0.734 mL). After 5 minutes of stirring at −78° C., a solution of 4-methylbenzenesulfonyl fluoride (378 mg; 2.17 mmol) in tetrahydrofuran (2 mL) was added dropwise. The mixture was removed from cooling bath and stirred at 25° C. for 60 minutes. A saturated aqueous solution of NH$_4$Cl (20 mL) and ethyl acetate (20 mL) were added to the mixture, the layers were separated, and the aqueous part was washed with ethyl acetate (2×15 mL). Organic extracts were combined, dried over MgSO$_4$, filtered, and the solvent was evaporated in vacuo. The residue obtained after the workup was purified by column chromatography (hexane/ethyl acetate, 1:2). The product was obtained as a brown wax (42 mg, 9%).

$^1$H NMR (500 MHz, acetone-d$_6$) δ (ppm) 8.72 (dd, J=4.79, 1.62 Hz, 1H), 8.61 (dd, J=2.34, 1.15 Hz, 1H), 7.87-7.83 (m, 1H), 7.76-7.73 (m, 2H), 7.56-7.52 (m, 3H), 6.59 (s, 1H), 2.50 (s, 3H).

$^{13}$C NMR (126 MHz, acetone-d$_6$) δ (ppm) 167.4, 152.5, 150.5, 148.0, 136.8, 131.9, 131.1, 131.0, 124.7, 124.5, 74.3, 21.7.

Preparative Example 44: 4-(~cyclohexyl-4-(pyridin-3-yl)-1H-imidazol-5-yl-1H-pyrrolo[2,3-b]pyridine

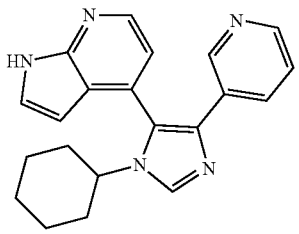 [SMILES: c1cncc(-c2ncn(C3CCCCC3)c2-c2ccnc3[nH]ccc23)c1]

The compound was prepared according to General procedure A using 1H-pyrrolo[2,3-b]pyridine-4-carbaldehyde, cyclohexanamine, 3-(isocyano(tosyl)methyl)pyridine (30 mg; 0.110 mmol) and K$_2$CO$_3$.

Reaction time: 165 minutes for the formation of the imine, then additional 18 hours at 25° C. plus 2 hours at 50° C. for the cyclization step. The residue obtained after the workup was purified two times by preparative TLC (ethyl acetate/methanol, 20:1; then ethyl acetone/dichloromethane, 3:2). The product was obtained as a white solid (3.5 mg; 9%).

$^1$H NMR (500 MHz, acetone-d$_6$) δ (ppm) 10.93 (s, 1H), 8.56 (d, J=2.19 Hz, 1H), 8.39 (d, J=4.76 Hz, 1H), 8.25 (dd, J=4.73, 1.68 Hz, 1H), 8.00 (s, 1H), 7.70 (dt, J=7.95, 2.00 Hz, 1H), 7.51 (d, J=3.51 Hz, 1H), 7.14-7.08 (m, 2H), 6.15 (d, J=3.43 Hz, 1H), 3.74 (tt, J=11.97, 3.91 Hz, 1H), 2.04-1.87 (m, 2H), 1.86-1.70 (m, 4H), 1.62-1.56 (m, 1H), 1.24-1.15 (m, 2H), 1.14-1.03 (m, 1H).

$^{13}$C NMR (126 MHz, acetone-d$_6$) δ (ppm) 150.3, 148.3, 147.9, 144.3, 136.5, 136.1, 133.5, 131.9, 131.6, 127.7, 126.4, 123.8, 121.1, 118.5, 100.2, 55.9, 35.4, 34.9, 26.4, 26.3, 25.8.

HRMS calculated for C$_{21}$H$_{22}$N$_5$ [M+H]$^+$ 344.1870, found 344.1868.

Preparative Example 45: 4-(4-fluorophenyl)-1-phenyl-1H-imidazole

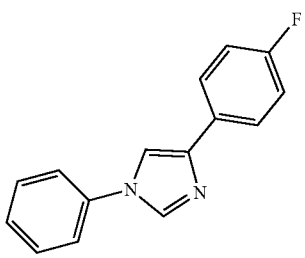 [SMILES: Fc1ccc(-c2cn(-c3ccccc3)cn2)cc1]

To a solution of 4-(4-fluorophenyl)-1H-imidazole (440 mg; 2.71 mmol) in dichloromethane (8 mL) were added triethylamine (0.8 mL), phenylboronic acid (496 mg; 4.07 mmol), copper(II) acetate (74 mg; 0.407 mmol) and the resulting mixture was stirred at 25° C. for 16 hours under oxygen atmosphere. The solvent was evaporated in vacuo and the residue was purified by column chromatography (ethyl acetate/hexane, 1:1). The product was obtained as a white solid (500 mg, 77%).

$^1$H NMR (500 MHz, CDCl$_3$) δ (ppm) 7.92 (d, J=1.36 Hz, 1H), 7.83-7.79 (m, 2H), 7.54-7.49 (m, 3H), 7.47-7.43 (m, 2H), 7.43-7.38 (m, 1H), 7.12-7.07 (m, 2H).

$^{13}$C NMR (126 MHz, CDCl$_3$) δ (ppm) 162.4 (d, J=245.97 Hz), 142.3, 137.3, 135.8, 130.2, 129.8 (d, J=3.18 Hz), 127.9, 126.8 (d, J=7.98 Hz), 121.6, 115.7 (d, J=21.48 Hz), 113.7.

$^{19}$F NMR (471 MHz, CDCl$_3$) δ (ppm) −115.15.

HRMS calculated for C$_{15}$H$_{12}$FN$_2$ [M+H]$^+$ 239.0979, found 239.0981.

Preparative Example 46: 5-bromo-4-(4-fluorophenyl-1-phenyl-1H-imidazole

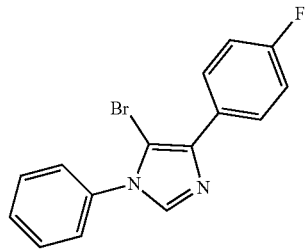 [SMILES: Fc1ccc(-c2ncn(-c3ccccc3)c2Br)cc1]

To a cold solution (0° C.) of 4-(4-fluorophenyl)-1-phenyl-1H-imidazole (500 mg; 2.10 mmol) in dichloromethane (6 mL) was added N-bromosuccinimide (392 mg; 2.20 mmol) and the resulting mixture was stirred at 0° C. for 75 minutes. The solvent was evaporated in vacuo and the residue was purified by column chromatography (ethyl acetate/hexane, 1:1). The product was obtained as a beige solid (473 mg, 78%).

$^1$H NMR (500 MHz, CDCl$_3$) δ (ppm) 8.05-7.96 (m, 2H), 7.85 (s, 1H), 7.58-7.50 (m, 3H), 7.44-7.38 (m, 2H), 7.17-7.11 (m, 2H).

$^{13}$C NMR (126 MHz, CDCl$_3$) δ (ppm) 162.5 (d, J=247.19 Hz), 138.6, 138.0, 135.5, 129.7, 129.6, 128.8 (d, J=8.13 Hz), 126.8, 115.5 (d, J=21.67 Hz), 100.8.

HRMS calculated for C$_{15}$H$_{11}$BrFN$_2$ [M+H]$^+$ 317.0084, found 317.0086.

Preparative Example 47: 4-(4-(4-fluorophenyl-1-phenyl-1H-imidazol-5-yl)-1H-pyrrolo[2,3-b]pyridine

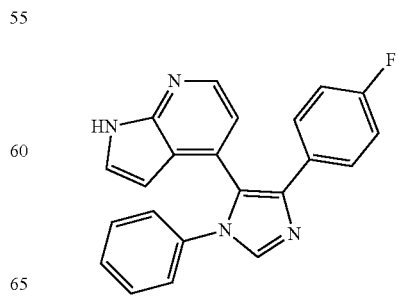

To a degassed solution of 5-bromo-4-(4-fluorophenyl)-1-phenyl-1H-imidazole (31.0 mg; 0.098 mmol) in dioxane/H₂O (2.1 mL+0.3 mL) were added 4-(4,4,5,5-tetramethyl-1,3,2-dioxaborolan-2-yl)-1H-pyrrolo[2,3-b]pyridine (35.8 mg; 0.147 mmol), potassium tert-butoxide (44.0 mg; 0.392 mmol), methanesulfonato(tri-t-butylphosphino)(2'-amino-1,1'-biphenyl-2-yl)palladium(II) (3.4 mg; 5.88 μmol; CAS: 1445086-17-8) and the resulting mixture was stirred for 15 hours at reflux. The solvent was evaporated and the residue was purified by preparative TLC (acetone/hexane, 1:1). The product was obtained as a white solid (2 mg, 6%).

¹H NMR (500 MHz, methanol-d₄) δ (ppm) 8.21 (s, 1H), 8.10 (d, J=4.98 Hz, 1H), 7.40-7.35 (m, 2H), 7.34-7.29 (m, 3H), 7.27 (d, J=3.52 Hz, 1H), 7.23-7.18 (m, 2H), 6.97-6.91 (m, 2H), 6.86 (d, J=4.99 Hz, 1H), 6.01 (d, J=3.51 Hz, 1H).

¹³C NMR (126 MHz, methanol-d₄) δ (ppm) 163.6 (d, J=245.72 Hz), 149.5, 143.1, 139.8, 139.8, 137.3, 131.5, 130.8 (d, J=3.11 Hz), 130.5, 130.2 (d, J=8.15 Hz), 129.7, 128.0, 127.0, 126.6, 121.8, 118.9, 116.1 (d, J=21.87 Hz), 101.0.

¹⁹F NMR (471 MHz, methanol-d₄) δ (ppm) −116.71.

HRMS calculated for $C_{22}H_{16}FN_4$ [M+H]⁺ 355.1354, found 355.1350.

Preparative Example 48:
3-4-4-fluorophenyl)-1H-imidazol-1-yl)pyridine

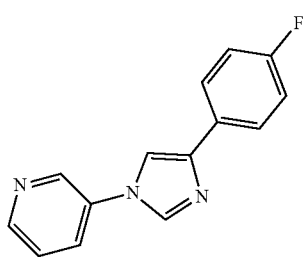 [SMILES: Fc1ccc(-c2cn(-c3cccnc3)cn2)cc1]

To a solution of 4-(4-fluorophenyl)-1H-imidazole (96 mg; 0.592 mmol) in dichloromethane (2.0 mL) were added triethylamine (0.20 mL), 3-(4,4,5,5-tetramethyl-1,3,2-dioxaborolan-2-yl)pyridine (182 mg; 0.888 mmol), DMAP (108 mg; 0.888 mmol), copper(II) acetate (118 mg; 0.651 mmol) and the resulting mixture was stirred at 25° C. for 17 hours. The solvent was evaporated and the residue was purified by column chromatography (dichloromethane/methanol, 12:1). The product was obtained as a white solid (152 mg, 81%).

¹H NMR (500 MHz, CDCl₃) δ (ppm) 9.16-8.62 (br m, 2H), 7.95 (s, 1H), 7.85-7.75 (m, 3H), 7.62-7.45 (br m, 2H), 7.13-7.07 (m, 2H).

¹³C NMR (126 MHz, CDCl₃) δ (ppm) 162.5 (d, J=246.29 Hz), 148.94, 148.91, 142.8, 135.7, 129.5 (d, J=2.54 Hz), 128.8, 126.9 (d, J=7.98 Hz), 124.9, 115.8 (d, J=21.59 Hz), 113.5.

¹⁹F NMR (471 MHz, CDCl₃) δ (ppm) −114.69.

HRMS calculated for $C_{14}H_{11}FN_3$ [M+H]⁺ 240.0932, found 240.0930.

Preparative Example 49: 3-(5-bromo-4-(4-fluorophenyl)-1H-imidazol-1-yl)pyridine

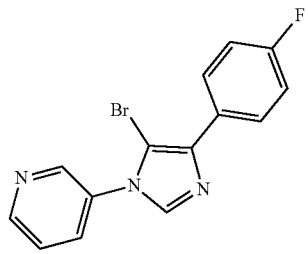 [SMILES: Fc1ccc(-c2ncn(-c3cccnc3)c2Br)cc1]

To a cold solution (0° C.) of 3-(4-(4-fluorophenyl)-1H-imidazol-1-yl)pyridine (73 mg; 0.305 mmol) in dichloromethane (2 mL) was added N-bromosuccinimide (57 mg; 0.320 mmol) and the resulting mixture was stirred at 0° C. for 3 hours. The solvent was evaporated and the residue was purified by column chromatography (dichloromethane/acetone, 3:1). The product was obtained as a white solid (36 mg, 87%).

¹H NMR (500 MHz, methanol-d₄) δ (ppm) 8.77-8.73 (m, 2H), 8.15 (s, 1H), 8.04 (ddd, J=8.18, 2.52, 1.45 Hz, 1H), 7.96-7.91 (m, 2H), 7.68 (dd, J=8.10, 4.88 Hz, 1H), 7.22-7.17 (m, 2H).

¹³C NMR (126 MHz, methanol-d₄) δ (ppm) 163.9 (d, J=246.19 Hz), 151.2, 148.3, 140.4, 140.3, 136.5, 134.1, 130.2 (d, J=8.19 Hz), 130.1 (d, J=3.20 Hz), 125.8, 116.3 (d, J=21.90 Hz), 102.0.

¹⁹F NMR (471 MHz, methanol-d₄) δ (ppm) −115.98.

HRMS calculated for $C_{14}H_{10}BrFN_3$ [M+H]⁺ 318.0037, found 318.0036.

Preparative Example 50: 4-(4-(4-fluorophenyl)-1-(pyridin-3-yl)-1H-imidazol-5-yl)-1H-pyrrolo[2,3-b]pyridine

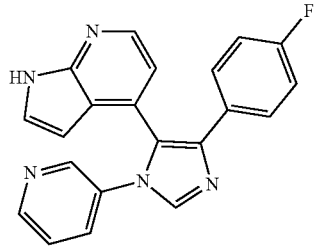 [SMILES: Fc1ccc(-c2ncn(-c3cccnc3)c2-c2ccnc3[nH]ccc23)cc1]

To a degassed solution of 3-(5-bromo-4-(4-fluorophenyl)-1H-imidazol-1-yl)pyridine (31.0 mg; 0.097 mmol) in dimethoxyethane/H₂O (1.8 mL+0.30 mL) were added 4-(4,4,5,5-tetramethyl-1,3,2-dioxaborolan-2-yl)-1H-pyrrolo[2,3-b]pyridine (36.0 mg; 0.146 mmol), sodium methoxide (21.0 mg; 0.388 mmol), methanesulfonato(tri-t-butylphosphino)(2'-amino-1,1'-biphenyl-2-yl)palladium(II) (5.50 mg; 9.70 μmol; CAS:1445086-17-8) and the resulting mixture was stirred at reflux for 6 hours. The solvent was evaporated and the residue was purified by preparative TLC (acetone/dichloromethane, 1:1).

The product was obtained as a yellow solid (13 mg, 38%).

¹H NMR (500 MHz, acetone-d₆) δ (ppm) 10.81 (s, 1H), 8.50 (d, J=2.58 Hz, 1H), 8.47 (dd, J=4.83, 1.50 Hz, 1H), 8.21

(d, J=4.81 Hz, 1H), 8.09 (s, 1H), 7.62 (ddd, J=8.14, 2.61, 1.50 Hz, 1H), 7.55-7.50 (m, 2H), 7.39 (dd, J=3.46, 2.39 Hz, 1H), 7.31 (dd, J=8.13, 4.70 Hz, 1H), 6.98-6.93 (m, 3H), 6.09 (dd, J=3.52, 1.85 Hz, 1H).

$^{13}$C NMR (126 MHz, acetone-$d_6$) δ (ppm) 162.7 (d, J=244.01 Hz), 150.1, 149.9, 147.1, 143.9, 139.9, 139.4, 134.2, 133.5, 131.9 (d, J=3.17 Hz), 130.6, 129.3 (d, J=8.03 Hz), 127.5, 126.1, 124.6, 120.6, 118.7, 115.7 (d, J=21.47 Hz), 100.6.

$^{19}$F NMR (471 MHz, acetone-$d_6$) δ (ppm) −117.34.

HRMS calculated for $C_{21}H_{15}FN_5$ [M+H]$^+$ 356.1306, found 356.1304.

Preparative Example 51:
5-bromo-4-(4-fluorophenyl)-1H-imidazole

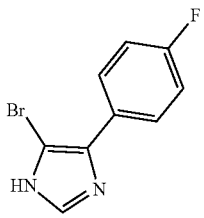 [SMILES: Fc1ccc(-c2nc[nH]c2Br)cc1]

To a cold solution (0° C.) of 4-(4-fluorophenyl)-1H-imidazole (106 mg; 0.654 mmol) in dichloromethane/tetrahydrofuran (3 mL+3 mL) was added N-bromosuccinimide (122 mg; 0.687 mmol) and the resulting mixture was stirred at 0° C. for 75 minutes. The solvent was evaporated and the residue was purified by column chromatography (ethyl acetate/methanol, 100:1). The product was obtained as a white solid (138 mg, 87%).

$^1$H NMR (500 MHz, methanol-$d_4$) δ (ppm) 7.80-7.60 (m, 3H), 7.25-7.15 (m, 2H).

$^{13}$C NMR (126 MHz, methanol-$d_4$) δ (ppm) 163.8 (d, J=246.74 Hz), 136.9, 130.0 (d, J=8.30 Hz), 128.4, 116.6 (d, J=21.91 Hz), 112.3.

$^{19}$F NMR (471 MHz, methanol-$d_4$) δ (ppm) −115.57.

HRMS calculated for $C_9H_7BrFN_2$ [M+H]$^+$ 240.9771, found 240.9774.

Preparative Example 52: 5-bromo-4-(4-fluorophenyl)-1-(thiophen-3-yl)-1H-imidazole

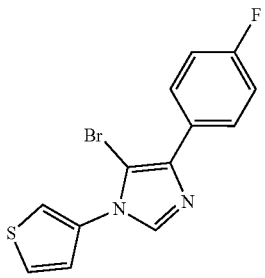 [SMILES: Fc1ccc(-c2ncn(-c3ccsc3)c2Br)cc1]

To a solution of 5-bromo-4-(4-fluorophenyl)-1H-imidazole (236 mg; 0.979 mmol) in acetonitrile (10 mL) were added triethylamine (1.0 mL), thiophen-3-ylboronic acid (150 mg; 1.17 mmol), DMAP (179 mg; 1.47 mmol), copper (II) acetate (196 mg; 1.08 mmol) and the resulting mixture was stirred at 40° C. for 6 hours. Then, additional thiophen-3-ylboronic acid (150 mg; 1.17 mmol) was added and the mixture was stirred for additional 16 hours. The solvent was evaporated and the residue was purified by column chromatography (toluene/acetone, 15:1) a then by preparative TLC (toluene/acetone, 20:1). The product was obtained as colorless wax (68 mg, 22%).

$^1$H NMR (500 MHz, CDCl$_3$) δ (ppm) 8.03-7.95 (m, 2H), 7.84 (s, 1H), 7.48 (dd, J=5.09, 3.21 Hz, 1H), 7.43 (dd, J=3.24, 1.43 Hz, 1H), 7.19 (dd, J=5.17, 1.44 Hz, 1H), 7.16-7.10 (m, 2H).

$^{13}$C NMR (126 MHz, CDCl$_3$) δ (ppm) 162.5 (d, J=247.42 Hz), 138.6, 138.2, 133.5, 128.9 (d, J=3.40 Hz), 128.8 (d, J=8.17 Hz), 126.7, 125.2, 121.1, 115.5 (d, J=21.54 Hz), 100.8.

HRMS calculated for $C_{13}H_9BrFN_2S$[M+H]$^+$ 324.9656, found 324.9654.

Preparative Example 53: (4-chloro-1H-pyrrolo[2,3-b]pyridin-2-yl)methanol

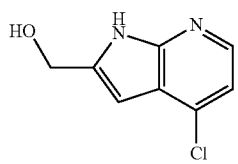 [SMILES: OCc1cc2c(Cl)ccnc2[nH]1]

To a cold solution (−65° C.) of methyl 4-chloro-1H-pyrrolo[2,3-b]pyridine-2-carboxylate (1.11 g; 5.28 mmol) in tetrahydrofuran (16 mL) was added 1 M solution of LiAlH$_4$ in tetrahydrofuran (6.86 mL; 6.86 mmol) and the resulting mixture was stirred at −65° C. for 90 minutes and then at 25° C. for 30 minutes. A saturated aqueous solution of NH$_4$Cl and H$_2$O (50+50 mL) were added and the mixture was extracted with ethyl acetate (3×60 mL). The combined organic extracts were dried over MgSO$_4$, filtered, and the solvent was evaporated in vacuo. The residue was purified by column chromatography (ethyl acetate/methanol; 33:1). The product was obtained as a white solid (0.850 g, 88%).

$^1$H NMR (500 MHz, methanol-$d_4$) δ (ppm) 8.06 (d, J=5.29 Hz, 1H), 7.11 (d, J=5.30 Hz, 1H), 6.47 (s, 1H), 4.76 (d, J=0.82 Hz, 2H).

$^{13}$C NMR (126 MHz, methanol-$d_4$) δ (ppm) 150.4, 143.4, 142.8, 136.6, 121.6, 116.7, 97.1, 58.5.

HRMS calculated for $C_8H_8ClN_2O$[M+H]$^+$ 183.0320, found 183.0323.

Preparative Example 54: (4-vinyl-1H-pyrrolo[2,3-b]pyridin-2-yl)methanol

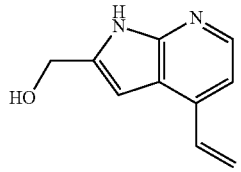

To a degassed solution of (4-chloro-1H-pyrrolo[2,3-b]pyridin-2-yl)methanol (840 mg; 4.60 mmol) in dimethoxyethane/H$_2$O (12 mL+4.0 mL) were added potassium trifluoro(vinyl)borate (1.05 g; 7.82 mmol), cesium carbonate (5.99 g; 18.4 mmol), bis(di-tert-butyl(4-dimethylaminophenyl)

phosphine)dichloropalladium(II) (98 mg; 0.138 mmol; CAS:887919-35-9) and the resulting mixture was stirred at reflux for 5 hours. The solvent was evaporated and the residue was purified by column chromatography (methanol/dichloromethane, gradient from 1:15 to 1:10). The product was obtained as a yellow solid (763 mg, 95%).

$^1$H NMR (500 MHz, acetone-d$_6$) δ (ppm) 10.92 (s, 1H), 8.17 (d, J=4.96 Hz, 1H), 7.13 (d, J=5.02 Hz, 1H), 7.09 (dd, J=17.71, 11.13 Hz, 1H), 6.60 (s, 1H), 6.12 (dd, J=17.75, 1.10 Hz, 1H), 5.56 (dd, J=11.13, 1.11 Hz, 1H), 4.83 (d, J=3.35 Hz, 2H), 4.36 (app s, 1H).

$^{13}$C NMR (126 MHz, acetone-d$_6$) δ (ppm) 151.1, 143.3, 142.2, 137.1, 135.2, 119.2, 118.7, 113.1, 96.9, 58.6.

HRMS calculated for C$_{10}$H$_{11}$N$_2$O[M+H]$^+$ 175.0866, found 175.0864.

Preparative Example 55: 2-(hydroxymethyl-1H-pyrrolo[2,3-b]pyridine-4-carbaldehyde

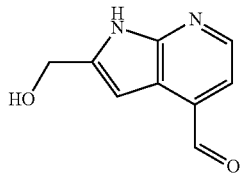

To a cold solution (0° C.) of (4-vinyl-1H-pyrrolo[2,3-b]pyridin-2-yl)methanol (750 mg; 4.31 mmol) in dioxane/H$_2$O (18+6 mL) were added 2,6-lutidine (1.00 mL; 924 mg; 8.62 mmol), NaIO$_4$ (3.62 g; 17.2 mmol), K$_2$OsO$_4$.2H$_2$O (48 mg; 0.129 mmol) and the resulting mixture was stirred at 25° C. for 9 hours. A solution of Na$_2$S$_2$O$_3$ (2.6 g) in H$_2$O (100 mL) was added and the resulting mixture was extracted with ethyl acetate (3×70 mL). The combined organic extracts were dried over MgSO$_4$, filtered, and the solvent was evaporated in vacuo. The residue was purified by column chromatography (acetone/dichloromethane; gradient from 1:2 to 1:0). The product was obtained as a yellow solid (272 mg, 36%).

$^1$H NMR (500 MHz, acetone-d$_6$) δ (ppm) 11.10 (s, 1H), 10.37 (s, 1H), 8.45 (d, J=4.79 Hz, 1H), 7.55 (d, J=4.81 Hz, 1H), 7.00 (s, 1H), 4.89 (d, J=5.94 Hz, 2H), 4.50 (t, J=5.89 Hz, 1H).

$^{13}$C NMR (126 MHz, acetone-d$_6$) δ (ppm) 193.9, 151.9, 146.4, 143.3, 133.5, 118.7, 118.2, 98.2, 58.6.

HRMS calculated for C$_9$H$_9$N$_2$O$_2$ [M+H]$^+$ 177.0659, found 177.0655.

Preparative Example 56: (4-(1-cyclohexyl-4-(4-fluorophenyl)-1H-imidazol-5-yl)-1H-pyrrolo[2,3-b]pyridin-2-yl)methanol

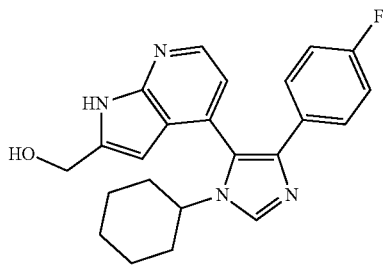 [SMILES: OCc1cc2c(-c3c(-c4ccc(F)cc4)ncn3C3CCCCC3)ccnc2[nH]1]

To a solution of 2-(hydroxymethyl)-1H-pyrrolo[2,3-b]pyridine-4-carbaldehyde (97 mg; 0.551 mmol) in acetonitrile (8 mL) was added cyclohexaneamine (0.189 mL; 163 mg; 1.65 mmol) and the resulting mixture was stirred at 25° C. for 4 hours. Then, 1-fluoro-4-(isocyano(tosyl)methyl)benzene (159 mg; 0.551 mmol) and cesium carbonate (269 mg; 0.827 mmol) were added and the resulting mixture was stirred at 50° C. for 16 hours. Then methanol (6 mL) and additional 1-fluoro-4-(isocyano(tosyl)methyl)benzene (159 mg; 0.551 mmol) were added and the resulting mixture was stirred at 60° C. for additional 8 hours. The solvent was evaporated and the residue was purified by column chromatography (ethyl acetate/methanol, 20:1). So obtained material was then recrystallized from a hot solution of dichloromethane/ethyl acetate (1 mL+1 mL) and washed 2 times with a solution of hexane/ethyl acetate (0.15 mL+0.15 mL) and then washed with a solution of acetone/chloroform (0.5 mL+0.5 mL) and dried in a vacuum. The product was obtained as a pale yellow solid (68 mg, 32%).

$^1$H NMR (500 MHz, methanol-d$_4$) δ (ppm) 8.27 (d, J=4.92 Hz, 1H), 8.02 (s, 1H), 7.31-7.26 (m, 2H), 7.05 (d, J=4.97 Hz, 1H), 6.87-6.82 (m, 2H), 6.04 (app t, J=0.90 Hz, 1H), 4.70 (d, J=0.92 Hz, 2H), 3.70 (tt, J=11.85, 3.78 Hz, 1H), 2.07-2.02 (m, 1H), 1.96-1.90 (m, 1H), 1.82-1.69 (m, 4H), 1.64-1.59 (m, 1H), 1.26-1.05 (m, 3H).

$^{13}$C NMR (126 MHz, methanol-d$_4$) δ (ppm) 163.2 (d, J=244.68 Hz), 150.2, 143.5, 143.3, 138.6, 136.6, 132.1, 131.7 (d, J=3.18 Hz), 129.5 (d, J=7.86 Hz), 126.0, 123.0, 119.0, 115.9 (d, J=21.76 Hz), 97.9, 58.5, 56.9, 35.7, 35.1, 26.7, 26.6, 26.1.

$^{19}$F NMR (471 MHz, methanol-d$_4$) δ (ppm) −117.83.

HRMS calculated for C$_{23}$H$_{24}$FN$_4$O [M+H]$^+$ 391.1929, found 391.1932.

Preparative Example 57: 4-chloro-2-(methoxymethyl-1H-pyrrolo[2,3-b]pyridine

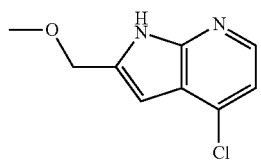

To a cold solution (0° C.) of (4-chloro-1H-pyrrolo[2,3-b]pyridin-2-yl)methanol (930 mg; 5.09 mmol) in tetrahydrofuran (25 mL) was added PBr$_3$ (0.958 mL; 2.76 g; 10.2 mmol) the resulting mixture was stirred for 12 hours while being allowed to warm to 25° C. Then, the mixture was cooled to 0° C. and methanol (12 mL) followed by a suspension of sodium methoxide (2.43 g; 45.0 mmol) in methanol (32 mL) were added and the resulting mixture was stirred at 25° C. for 5 hours. Then, additional suspension of sodium methoxide (270 mg; 5.09 mmol) in methanol (12 mL) was added and the resulting mixture was stirred at 25° C. for additional 19 hours. A saturated aqueous solution of NH$_4$Cl (6 mL) was added and all solvents were evaporated in vacuo. The residue was purified by column chromatography (ethyl acetate). The product was obtained as a white solid (568 mg, 57%).

$^1$H NMR (500 MHz, acetone-d$_6$) δ (ppm) 11.16 (s, 1H), 8.16 (d, J=5.18 Hz, 1H), 7.13 (d, J=5.20 Hz, 1H), 6.51 (s, 1H), 4.65 (s, 2H), 3.37 (s, 3H).

$^{13}$C NMR (126 MHz, acetone-d$_6$) δ (ppm) 144.2, 139.0, 135.2, 120.3, 116.5, 116.4, 98.3, 67.9, 58.2.

HRMS calculated for C$_9$H$_{10}$ClN$_2$O[M+H]$^+$ 197.0476, found 197.0478.

Preparative Example 58: 2-(methoxymethyl)-4-vinyl-1H-pyrrolo[2,3-b]pyridine

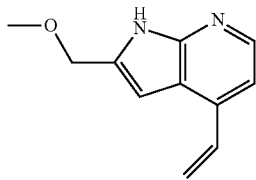

To a degassed solution of 4-chloro-2-(methoxymethyl)-1H-pyrrolo[2,3-b]pyridine (548 mg; 2.79 mmol) in dioxane/H$_2$O (12 mL+4.0 mL) were added potassium trifluoro(vinyl)borate (746 mg; 5.57 mmol), cesium carbonate (3.64 g; 11.2 mmol), bis(di-tert-butyl(4-dimethylaminophenyl)phosphine) dichloropalladium(II) (98 mg; 0.138 mmol; CAS: 887919-35-9) and the resulting mixture was stirred at reflux for 2 hours. The solvent was evaporated and the residue was purified by column chromatography (ethyl acetate). The product was obtained as a yellow solid (290 mg, 55%).

$^1$H NMR (500 MHz, CDCl$_3$) δ (ppm) 11.69 (s, 1H), 8.31 (d, J=5.08 Hz, 1H), 7.14 (d, J=5.11 Hz, 1H), 7.04 (dd, J=17.67, 11.03 Hz, 1H), 6.59 (s, 1H), 6.10 (dd, J=17.69, 0.94 Hz, 1H), 5.60 (dd, J=11.04, 0.91 Hz, 1H), 4.72 (s, 2H), 3.44 (s, 3H).

$^{13}$C NMR (126 MHz, CDCl$_3$) δ (ppm) 150.1, 142.4, 137.7, 136.9, 134.0, 119.1, 118.9, 112.7, 98.3, 68.1, 58.2.

HRMS calculated for C$_{11}$H$_{13}$N$_2$O[M+H]$^+$ 189.1022, found 189.1019.

Preparative Example 59: 2-(methoxymethyl)-1H-pyrrolo[2,3-b]pyridine-4-carbaldehyde

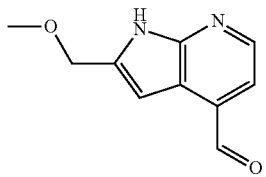

To a solution of 2-(methoxymethyl)-4-vinyl-1H-pyrrolo[2,3-b]pyridine (277 mg; 1.47 mmol) in dioxane/H$_2$O (6+2 mL) were added 2,6-lutidine (0.342 mL; 315 mg; 2.94 mmol), NaIO$_4$ (1.26 g; 5.88 mmol) and K$_2$OsO$_4$·2H$_2$O (13.5 mg; 0.037 mmol), and the resulting mixture was stirred at 25° C. for 15 hours. A solution of Na$_2$S$_2$O$_3$ (1.0 g) in H$_2$O (60 mL) was added and the resulting mixture was extracted with ethyl acetate (3×40 mL). The combined organic extracts were dried over MgSO$_4$, filtered, and the solvent was evaporated in vacuo. The residue was purified by column chromatography (hexane/ethyl acetate; 1:1). The crude product (272 mg; ca. 60% purity) was used without further purification in the next step.

$^1$H NMR (500 MHz, CDCl$_3$) δ (ppm) 11.15 (s, 1H), 10.35 (s, 1H), 8.56 (d, J=4.95 Hz, 1H), 7.51 (d, J=4.86 Hz, 1H), 7.07 (s, 1H), 4.77 (s, 2H), 3.47 (s, 3H).

$^{13}$C NMR (126 MHz, CDCl$_3$) δ (ppm) 192.8 (d, J=4.95 Hz), 150.9, 142.7, 141.2, 133.2, 118.4, 118.0, 99.6, 68.0, 58.5.

HRMS calculated for C$_{10}$H$_{11}$N$_2$O$_2$ [M+H]$^+$ 191.0815, found 191.0817.

Preparative Example 60: 4-(1-cyclohexyl-4-(4-fluorophenyl)-1H-imidazol-5-yl)-2-(methoxymethyl)-1H-pyrrolo[2,3-b]pyridine

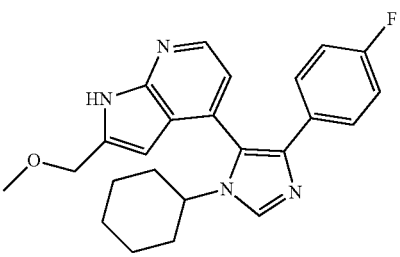 [SMILES: COCc1cc2c(-c3c(-c4ccc(F)cc4)ncn3C3CCCCC3)ccnc2[nH]1]

The compound was prepared according to General procedure A using 2-(methoxymethyl)-1H-pyrrolo[2,3-b]pyridine-4-carbaldehyde, cyclohexaneamine, 1-fluoro-4-(isocyano(tosyl)methyl) benzene and K$_2$CO$_3$. Reaction time: 4 hours for the formation of the imine, then additional 14 hours for the cyclization step. The residue obtained after the workup was purified by column chromatography (hexane/acetone; 1:1) and then two times by preparative TLC (hexane/acetone; 1:1; then ethyl acetate/toluene, 2:1). The product was obtained as a white solid (7 mg; 3%).

$^1$H NMR (500 MHz, CDCl$_3$) δ (ppm) 11.05 (s, 1H), 8.43 (d, J=4.88 Hz, 1H), 7.81 (s, 1H), 7.39-7.34 (m, 2H), 7.04 (d, J=4.90 Hz, 1H), 6.84-6.78 (m, 2H), 6.05 (s, 1H), 4.67-4.55 (m, 2H), 3.67 (tt, J=11.97, 3.75 Hz, 1H), 3.39 (s, 3H), 2.09-2.04 (m, 1H), 1.96-1.91 (m, 1H), 1.83-1.73 (m, 2H), 1.69-1.61 (m, 3H), 1.21-1.13 (m, 2H), 1.12-1.03 (m, 1H).

$^{13}$C NMR (126 MHz, CDCl$_3$) δ (ppm) 161.8 (d, J=245.41 Hz), 149.7, 143.1, 137.9, 137.6, 134.9, 131.5, 130.6 (d, J=3.08 Hz), 128.2 (d, J=7.81 Hz), 124.4, 121.4, 118.0, 115.1 (d, J=21.35 Hz), 99.0, 68.0, 58.3, 55.3, 35.2, 34.6, 25.8, 25.7, 25.2.

$^{19}$F NMR (471 MHz, CDCl$_3$) δ (ppm) −116.20.

HRMS calculated for C$_{24}$H$_{26}$FN$_4$O [M+H]$^+$ 405.2085, found 405.2087.

Preparative Example 61: 4-(1-cyclohexyl-4-(4-fluorophenyl)-2-methyl-1H-imidazol-5-yl)-1H-pyrrolo[2,3-b]pyridine

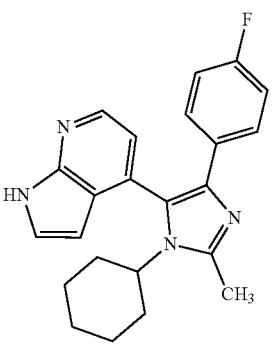 [SMILES: Cc1nc(-c2ccc(F)cc2)c(-c2ccnc3[nH]ccc23)n1C1CCCCC1]

To a cold solution (−78° C.) of 4-(1-cyclohexyl-4-(4-fluorophenyl)-1H-imidazol-5-yl)-1H-pyrrolo[2,3-b]pyridine (215 mg; 0.596 mmol) in tetrahydrofuran (13 mL) were added 1,2-bis(dimethylamino)ethane (0.268 mL; 208 mg; 1.79 mmol), then dropwise 2.5 M solution of n-BuLi in hexane (0.596 mL; 1.49 mmol) and the resulting mixture was stirred at −78° C. for 70 minutes. Then, a solution of iodomethane (127 mg; 0.894) in tetrahydrofuran (3 mL) was added and the resulting mixture was stirred at −78° C. for 40 minutes and then at 25° C. for 30 minutes. A saturated aqueous solution of NH$_4$Cl (20 mL) was added and the mixture was extracted with ethyl acetate (2×25 mL). The combined organic extracts were dried over MgSO$_4$, filtered, and the solvent was evaporated in vacuo. The residue was purified by column chromatography (ethyl acetate). So obtained material was purified using reverse phase HPLC (acetonitrile/H$_2$O, gradient from 60% to 95% of acetonitrile; stationary phase: NUCLEODUR© C18 HTec, 5 μm, length: 250 mm, diameter: 21 mm). The product was obtained as a white solid (12.5 mg; 6%).

$^1$H NMR (500 MHz, CDCl$_3$) δ (ppm) 9.86 (s, 1H), 8.41 (s, 1H), 7.37-7.27 (m, 3H), 7.06-6.98 (m, 1H), 6.83-6.75 (m, 2H), 6.22 (d, J=3.49 Hz, 1H), 3.78-3.67 (m, 1H), 2.73 (s, 3H), 1.93-1.83 (m, 3H), 1.80-1.71 (m, 3H), 1.62-1.56 (m, 1H), 1.13-0.96 (m, 3H).

$^{13}$C NMR (126 MHz, CDCl$_3$) δ (ppm) 161.9 (d, J=245.96 Hz), 148.9, 144.8, 143.3, 135.5, 132.2, 129.5, 128.3 (d, J=7.88 Hz), 126.3, 125.0, 121.5, 118.8, 115.2 (d, J=21.38 Hz), 100.7, 57.3, 32.3, 26.2, 26.1, 25.2.

HRMS calculated for C$_{23}$H$_{24}$FN$_4$ [M+H]$^+$ 375.1980, found 375.1982.

Preparative Example 62:
1-cyclohexyl-4,5-diiodo-1H-imidazole

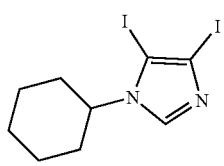 [SMILES: Ic1ncn(C2CCCCC2)c1I]

To a solution of 1-cyclohexyl-1H-imidazole (1.845 g; 12.28 mmol) in DMF (30 mL) was added N-iodosuccinimide (6.079 g; 27.0 mmol) and the resulting mixture was stirred at 85° C. for 15 hours. A solution of Na$_2$S$_2$O$_3$ (2.5 g) in H$_2$O (100 mL) and ethyl acetate (150 mL) were added, the layers were separated and the organic phase was washed with H$_2$O (3×100 mL). The combined organic extracts were dried over MgSO$_4$, filtered, and the solvent was evaporated in vacuo. The residue was purified by column chromatography (hexane/ethyl acetate; 3:1). The product was obtained as a yellow wax (2.36 g; 48%).

$^1$H NMR (500 MHz, CDCl$_3$) δ (ppm) 7.64 (s, 1H), 3.92 (tt, J=11.90, 3.68 Hz, 1H), 2.14-2.08 (m, 2H), 1.96-1.90 (m, 2H), 1.81-1.75 (m, 1H), 1.61-1.52 (m, 2H), 1.49-1.40 (m, 2H), 1.30-1.20 (m, 1H).

$^{13}$C NMR (126 MHz, CDCl$_3$) δ (ppm) 138.4, 95.7, 82.4, 60.5, 34.1, 25.7, 25.3.

HRMS calculated for C$_9$H$_{13}$I$_2$N$_2$ [M+H]$^+$ 402.9163, found 402.9164.

Preparative Example 63:
1-cyclohexyl-4-iodo-1H-imidazole

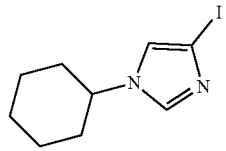 [SMILES: Ic1cn(C2CCCCC2)cn1]

To a cold solution (0° C.) of 1-cyclohexyl-4,5-diiodo-1H-imidazole (2.84 g; 7.06 mmol) in tetrahydrofuran (20 mL) was added dropwise 3 M solution of MeMgCl in tetrahydrofuran (2.59 mL; 7.77 mmol) and the resulting mixture was stirred at 0° C. for 45 minutes. A saturated aqueous solution of NH$_4$Cl (30 mL) was added and the mixture was extracted with dichloromethane (3×100 mL). The combined organic extracts were dried over MgSO$_4$, filtered, and the solvent was evaporated in vacuo. The residue was purified by column chromatography (ethyl acetate/hexane; 2:3). The product was obtained as a yellow wax (1.67 g, 86%).

$^1$H NMR (500 MHz, CDCl$_3$) δ (ppm) 7.45 (d, J=1.53 Hz, 1H), 7.03 (d, J=1.52 Hz, 1H), 3.89 (tt, J=11.77, 3.84 Hz, 1H), 2.12-2.06 (m, 2H), 1.92-1.86 (m, 2H), 1.77-1.72 (m, 1H), 1.55-1.63 (m, 2H), 1.44-1.35 (m, 2H), 1.26-1.18 (m, 1H).

$^{13}$C NMR (126 MHz, CDCl$_3$) δ (ppm) 137.0, 122.9, 81.2, 57.5, 34.4, 25.4, 25.2.

HRMS calculated for C$_9$H$_{14}$IN$_2$ [M+H]$^+$ 277.0196, found 277.0198.

Preparative Example 64: 4-(cyclohex-1-en-1-yl)-1-cyclohexyl-1H-imidazole

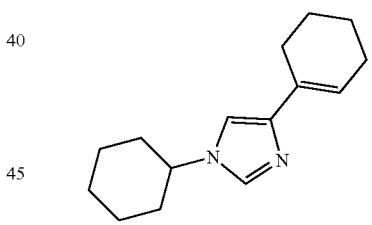

To a degassed solution of 1-cyclohexyl-4-iodo-1H-imidazole (980 mg; 3.55 mmol) in 1-butanol/H$_2$O (8.0 mL+1.60 mL) were added potassium cyclohex-1-en-1-yltrifluoroborate (689 mg; 3.66 mmol), K$_3$PO$_4$ (2.64 g; 12.4 mmol), (2-dicyclohexylphosphino-2',6'-dimethoxybiphenyl) [2-(2'-amino-1,1'-biphenyl)]palladium(II) methanesulfonate (55 mg; 0.071 mmol; CAS:1445085-82-4), 2-dicyclohexylphosphino-2',6'-dimethoxybiphenyl (73 mg, 0.178 mmol; CAS: 657408-07-6) and the resulting mixture was stirred at 80° C. for 5 hours. The solvent was evaporated in vacuo and the residue was purified by column chromatography (ethyl acetate). The product was obtained as a yellow wax (307 mg, 38%).

$^1$H NMR (500 MHz, CDCl$_3$) δ (ppm) 7.55 (d, J=1.33 Hz, 1H), 6.82 (d, J=1.25 Hz, 1H), 6.45 (tt, J=3.88, 1.73 Hz, 1H), 3.86 (tt, J=11.82, 3.85 Hz, 1H), 2.33-2.27 (m, 2H), 2.21-2.16 (m, 2H), 2.13-2.07 (m, 2H), 1.93-1.86 (m, 2H), 1.77-1.71 (m, 3H), 1.67-1.60 (m, 4H), 1.45-1.35 (m, 2H), 1.28-1.19 (m, 1H).

$^{13}$C NMR (126 MHz, CDCl$_3$) δ (ppm) 143.1, 135.0, 129.5, 122.1, 111.8, 57.1, 34.5, 26.2, 25.5, 25.4, 25.4, 22.8, 22.6.

HRMS calculated for C$_{15}$H$_{23}$N$_2$ [M+H]$^+$ 231.1856, found 231.1855.

Preparative Example 65:
1,4-dicyclohexyl-1H-imidazole

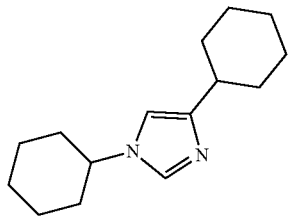 [SMILES: c1nc(C2CCCCC2)cn1C1CCCCC1]

To a solution of 4-(cyclohex-1-en-1-yl)-1-cyclohexyl-1H-imidazole (298 mg; 1.29 mmol) in ethanol (10 mL) was added Pd(OH)$_2$/C (60 mg; 10-20% Pd basis) and the resulting mixture was stirred in a hydrogenator under hydrogen atmosphere (70 bar) at 50° C. for 18 hours. The solvent was evaporated in vacuo and the residue was purified by column chromatography (ethyl acetate). The product was obtained as a yellow wax (194 mg, 65%).

$^1$H NMR (500 MHz, CDCl$_3$) δ (ppm) 7.44 (d, J=1.39 Hz, 1H), 6.62 (s, 1H), 3.82 (tt, J=11.82, 3.87 Hz, 1H), 2.52 (tt, J=11.16, 3.62 Hz, 1H), 2.12-2.06 (m, 2H), 2.05-1.98 (m, 2H), 1.91-1.85 (m, 2H), 1.82-1.66 (m, 4H), 1.64-1.55 (m, 2H), 1.42-1.31 (m, 6H), 1.28-1.18 (m, 2H).

$^{13}$C NMR (126 MHz, CDCl$_3$) δ (ppm) 148.2, 134.2, 111.5, 56.9, 37.7, 34.5, 33.2, 26.6, 26.5, 25.6, 25.4.

HRMS calculated for C$_{15}$H$_{25}$N$_2$ [M+H]$^+$ 233.2012, found 233.2013.

Preparative Example 66:
5-bromo-1,4-dicyclohexyl-1H-imidazole

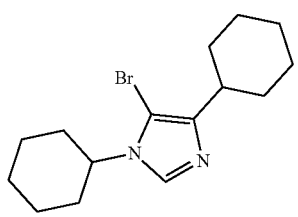 [SMILES: Brc1c(C2CCCCC2)ncn1C1CCCCC1]

To a cold solution (–3° C.) of 1,4-dicyclohexyl-1H-imidazole (194 mg; 0.835 mmol) in dichloromethane (5 mL) was added N-bromosuccinimide (156 mg; 0.877 mmol) and the resulting mixture was stirred at –3° C. for 105 minutes. The solvent was evaporated and the residue was purified by column chromatography (ethyl acetate/hexane, 1:1). The product was obtained as a pale yellow solid (145 mg, 56%).

$^1$H NMR (500 MHz, CDCl$_3$) δ (ppm) 7.68 (s, 1H), 3.95 (tt, J=11.94, 3.66 Hz, 1H), 2.63 (tt, J=11.83, 3.81 Hz, 1H), 2.16-2.09 (m, 2H), 1.96-1.90 (m, 2H), 1.86-1.80 (m, 2H), 1.79-1.65 (m, 6H), 1.63-1.53 (m, 2H), 1.46-1.25 (m, 6H).

$^{13}$C NMR (126 MHz, CDCl$_3$) δ (ppm) 143.3, 134.1, 99.2, 57.0, 36.8, 33.8, 31.8, 26.7, 26.0, 25.7, 25.3.

HRMS calculated for C$_{15}$H$_{24}$BrN$_2$ [M+H]$^+$ 311.1117, found 311.1119.

Preparative Example 67:4-(1,4-dicyclohexyl-1H-imidazol-5-yl)-1H-pyrrolo[2,3-b]pyridine

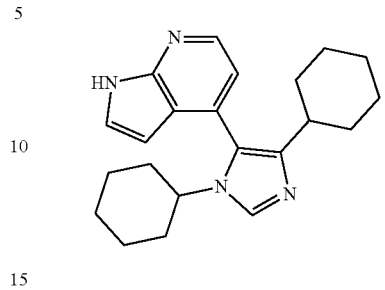

To a degassed solution of 5-bromo-1,4-dicyclohexyl-1H-imidazole (58.0 mg; 0.186 mmol) in dimethoxyethane/H$_2$O (3.0 mL+0.43 mL) were added 4-(4,4,5,5-tetramethyl-1,3,2-dioxaborolan-2-yl)-1H-pyrrolo[2,3-b]pyridine (68.0 mg; 0.280 mmol), K$_3$PO$_4$ (138 mg; 0.651 mmol), 2-dicyclohexylphosphino-2',6'-dimethoxybiphenyl (3.80 mg; 0.0093 mmol), (2-dicyclohexylphosphino-2',6'-dimethoxybiphenyl)[2-(2'-amino-1,1'-biphenyl)]palladium(II) methanesulfonate (4.40 mg; 5.58 µmol; CAS:1445085-82-4) and the resulting mixture was stirred at reflux for 4.5 hours. The solvent was evaporated and the residue was purified by column chromatography (ethyl acetate/methanol, gradient from 1:0 to 30:1). So obtained material was purified two times by preparative TLC (acetone/hexane, 1:1; then dichloromethane/methanol, 35:1). The product was obtained as a pale yellow wax (4 mg; 4%).

$^1$H NMR (500 MHz, CDCl$_3$) δ (ppm) 9.53 (s, 1H), 8.68 (s, 1H), 8.49 (d, J=4.82 Hz, 1H), 7.51 (d, J=3.55 Hz, 1H), 7.02 (d, J=4.79 Hz, 1H), 6.20 (d, J=3.51 Hz, 1H), 3.75 (tt, J=12.09, 3.71 Hz, 1H), 2.55-2.44 (m, 1H), 2.05-1.99 (m, 1H), 1.98-1.93 (m, 1H), 1.85-1.55 (m, 16H), 1.15-1.06 (m, 2H).

HRMS calculated for C$_{22}$H$_{29}$N$_4$ [M+H]$^+$ 349.2387, found 349.2390.

Preparative Example 68: 1-(4-(4-(4-fluorophenyl)-5-(1H-pyrrolo[2,3-b]pyridin-4-yl)-1H-imidazol-1-yl)piperidin-1-yl)ethan-1-one

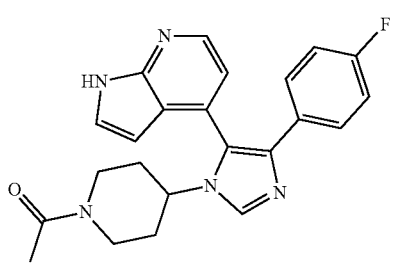 [SMILES: CC(=O)N1CCC(n2cnc(-c3ccc(F)cc3)c2-c2ccnc3[nH]ccc23)CC1]

To a solution of 4-(4-(4-fluorophenyl)-1-(piperidin-4-yl)-1H-imidazol-5-yl)-1H-pyrrolo[2,3-b]pyridine (22.5 mg; 0.0623 mmol) in acetonitrile (2 mL) was added pyridine (24.6 mg; 0.312 mmol), followed by acetic anhydride (0.0065 mL; 7.0 mg; 0.0685 mmol) and the resulting mixture was stirred at 25° C. for 45 minutes. Then, methanol (2 mL) was added and the solvent was evaporated in vacuo.

The residue was purified by preparative TLC (acetone/methanol, 20:1). The product was obtained as a white solid (17 mg, 68%).

$^{1}$H NMR (500 MHz, methanol-$d_4$) δ (ppm) 8.33 (app t, J=4.58 Hz, 1H), 8.09 (s, 1H), 7.42 (dd, J=6.03, 3.49 Hz, 1H), 7.31-7.25 (m, 2H), 7.12 (dd, J=9.43, 4.94 Hz, 1H), 6.89-6.82 (m, 2H), 6.13 (dd, J=10.83, 3.51 Hz, 1H), 4.64-4.53 (m, 1H), 4.06-3.97 (m, 1H), 3.98-3.87 (m, 1H), 3.03-2.86 (m, 1H), 2.52-2.34 (m, 1H), 2.08 (d, J=6.76 Hz, 4H), 2.05-1.96 (m, 1H), 1.96-1.85 (m, 2H).

$^{13}$C NMR (126 MHz, methanol-$d_4$) δ (ppm) 171.5, 163.3 (d, J=245.02 Hz), 149.8, 143.8 (d, J=5.36 Hz), 139.0 (d, J=2.63 Hz), 136.8, 132.1, 131.5 (d, J=3.22 Hz), 129.6 (d, J=8.04 Hz), 128.5 (d, J=9.41 Hz), 126.0, 122.3 (d, J=3.97 Hz), 118.9, 115.9 (d, J=21.75 Hz), 100.4, 54.9, 46.6, 41.8, 34.8, 34.4, 34.1, 33.8, 21.1.

$^{19}$F NMR (471 MHz, methanol-$d_4$) δ (ppm) −117.50.

HRMS calculated for $C_{23}H_{23}FN_5O[M+H]^+$ 404.1881, found 404.1884.

Preparative Example 69: 4-(4-(4-fluorophenyl-1-(1-(methylsulfonyl)piperidin-4-yl)-1H-imidazol-5-yl)-1H-pyrrolo[2,3-b]pyridine

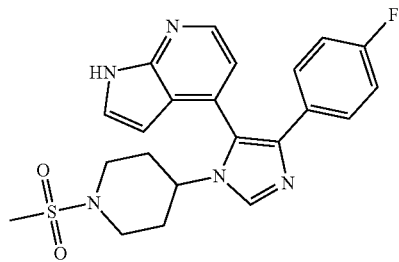 [SMILES: CS(=O)(=O)N1CCC(n2cnc(-c3ccc(F)cc3)c2-c2ccnc3[nH]ccc23)CC1]

To a solution of 4-(4-(4-fluorophenyl)-1-(piperidin-4-yl)-1H-imidazol-5-yl)-1H-pyrrolo[2,3-b]pyridine (22.5 mg; 0.0623 mmol) in acetonitrile (2 mL) was added pyridine (24.6 mg; 0.312 mmol), then methanesulfonyl chloride (0.0053 mL; 7.8 mg; 0.0685 mmol) and the resulting mixture was stirred at 25° C. for 45 minutes. Then, additional methanesulfonyl chloride (0.0030 mL; 4.4 mg; 0.0384 mmol) was added and the resulting mixture was stirred for additional 50 minutes. Then, methanol (2 mL) was added and the solvent was evaporated in vacuo. The residue was purified by preparative TLC (acetone/dichloromethane, 3:2). The product was obtained as a white solid (17 mg, 68%).

$^{1}$H NMR (500 MHz, methanol-$d_4$) δ (ppm) 8.33 (d, J=4.94 Hz, 1H), 8.13 (s, 1H), 7.42 (d, J=3.51 Hz, 1H), 7.33-7.25 (m, 2H), 7.12 (d, J=4.91 Hz, 1H), 6.92-6.82 (m, 2H), 6.14 (d, J=3.48 Hz, 1H), 3.90 (tt, J=11.77, 4.42 Hz, 1H), 3.82-3.70 (m, 2H), 2.76 (s, 3H), 2.71-2.63 (m, 1H), 2.62-2.54 (m, 1H), 2.17-2.06 (m, 3H), 2.03-1.97 (m, 1H).

$^{13}$C NMR (126 MHz, methanol-$d_4$) δ (ppm) 163.3 (d, J=244.92 Hz), 149.8, 143.8, 139.1, 136.9, 132.0, 131.4 (d, J=3.19 Hz), 129.6 (d, J=8.09 Hz), 128.5, 126.0, 122.4, 118.9, 115.9 (d, J=21.79 Hz), 100.4, 54.5, 46.32, 46.29, 35.1, 34.2, 33.8.

$^{19}$F NMR (471 MHz, methanol-$d_4$) δ (ppm) −117.50.

HRMS calculated for $C_{22}H_{23}FN_5O_2S[M+H]^+$ 440.1551, found 440.1554.

Preparative Example 70: Ethyl 4-(4-(4-fluorophenyl)-5-(1H-pyrrolo[2,3-b]pyridin-4-yl)-1H-imidazol-1-yl)piperidine-1-carboxylate

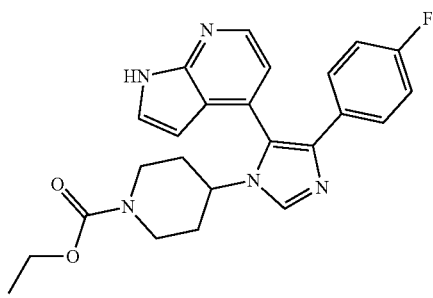 [SMILES: CCOC(=O)N1CCC(n2cnc(-c3ccc(F)cc3)c2-c2ccnc3[nH]ccc23)CC1]

To a cold solution (−25° C.) of 4-(4-(4-fluorophenyl)-1-(piperidin-4-yl)-1H-imidazol-5-yl)-1H-pyrrolo[2,3-b]pyridine (20.0 mg; 0.055 mmol) in acetonitrile (1.5 mL) was added pyridine (22 mg; 0.278 mmol), then 4-nitrophenyl chloroformate (12.5 mg; 0.061 mmol) and the resulting mixture was stirred for 90 minutes while being allowed to warm to 25° C. Then, ethanol (5 mL) and 1 M solution of NaHMDS in tetrahydrofuran (0.066 mL; 0.066 mmol) were added and the resulting mixture was stirred at 50° C. for 20 hours. Then, additional 1 M solution of NaHMDS in tetrahydrofuran (0.066 mL) was added and the resulting mixture was stirred at 50° C. for additional 4 hours. A saturated aqueous solution of NH$_4$Cl (1 mL) was added and the solvent was evaporated in vacuo. The residue was purified by column chromatography (ethyl acetate/acetone, 10:1) and then by preparative TLC (ethyl acetate/acetone, 6:1).

The product was obtained as a white solid (6 mg, 26%).

$^{1}$H NMR (500 MHz, acetone-$d_6$) δ (ppm) 10.92 (s, 1H), 8.37 (d, J=4.81 Hz, 1H), 8.01 (s, 1H), 7.50 (dd, J=3.54, 2.28 Hz, 1H), 7.45-7.39 (m, 2H), 7.11 (d, J=4.78 Hz, 1H), 6.90-6.84 (m, 2H), 6.15 (dd, J=3.52, 1.81 Hz, 1H), 4.22-4.08 (m, 2H), 4.06 (q, J=7.06 Hz, 2H), 3.95 (tt, J=11.81, 4.17 Hz, 1H), 2.78-2.54 (m, 3H), 1.98-1.88 (m, 3H), 1.19 (t, J=7.10 Hz, 3H).

$^{13}$C NMR (126 MHz, acetone-$d_6$) δ (ppm) 162.3 (d, J=243.15 Hz), 155.6, 150.2, 144.3, 138.2, 136.1, 132.6 (d, J=3.14 Hz), 131.7, 128.7 (d, J=7.91 Hz), 127.6, 125.3, 121.2, 118.6, 115.4 (d, J=21.44 Hz), 100.3, 61.7, 54.1, 43.80, 43.76, 34.3, 33.8, 15.0.

$^{19}$F NMR (471 MHz, acetone-$d_6$) δ (ppm) −118.30.

HRMS calculated for $C_{24}H_{25}FN_5O_2$ $[M+H]^+$ 434.1987, found 434.1990.

Preparative Example 71: 4-(4-(4-fluorophenyl)-5-(1H-pyrrolo[2,3-b]pyridin-4-yl)-1H-imidazol-1-yl)-N-methylpiperidine-1-carboxamide

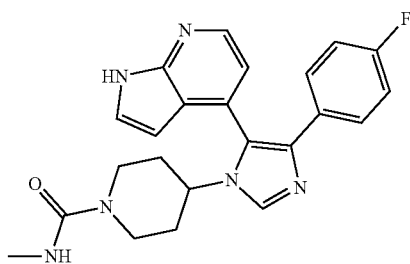 [SMILES: CNC(=O)N1CCC(n2cnc(-c3ccc(F)cc3)c2-c2ccnc3[nH]ccc23)CC1]

To a cold solution (−25° C.) of 4-(4-(4-fluorophenyl)-1-(piperidin-4-yl)-1H-imidazol-5-yl)-1H-pyrrolo[2,3-b]pyridine (20.0 mg; 0.055 mmol) in acetonitrile (1.5 mL) was added pyridine (22 mg; 0.278 mmol), then 4-nitrophenyl chloroformate (12.5 mg; 0.061 mmol) and the resulting mixture was stirred for 90 minutes while being allowed to warm to 25° C. The precipitate was filtered off and the filtrate was concentrated to dryness in vacuo. So obtained material was dissolved in 2.0 M solution of methylamine in THF (3 mL) and the resulting mixture was stirrred under nitrogen atmosphere at 25° C. for 18 hours and then at 50° C. for additional 3 hours. Then the solvent was evaporated and the residue was purified by preparative TLC (dichloromethane/acetone/methanol, 10:10:1). The product was obtained as a white solid (7 mg, 30%).

$^1$H NMR (500 MHz, acetone-$d_6$) δ (ppm) 10.93 (s, 1H), 8.37 (d, J=4.73 Hz, 1H), 7.99 (s, 1H), 7.50 (dd, J=3.49, 2.00 Hz, 1H), 7.46-7.37 (m, 2H), 7.10 (d, J=4.78 Hz, 1H), 6.91-6.83 (m, 2H), 6.15 (dd, J=3.50, 1.55 Hz, 1H), 5.77 (app d, J=5.29 Hz, 1H), 4.13-4.03 (m, 2H), 3.92 (tt, J=11.80, 4.23 Hz, 1H), 2.66 (d, J=4.52 Hz, 3H), 2.63-2.57 (m, 1H), 2.55-2.48 (m, 1H), 2.03-1.97 (m, 1H), 1.94-1.84 (m, 3H).

$^{13}$C NMR (126 MHz, acetone-$d_6$) δ (ppm) 162.3 (d, J=243.32 Hz), 158.5, 150.3, 144.3, 138.1, 136.1, 132.6 (d, J=3.11 Hz), 131.8, 128.7 (d, J=7.80 Hz), 127.6, 125.3, 121.2, 118.6, 115.4 (d, J=21.52 Hz), 100.3, 54.4, 43.9, 43.9, 34.4, 34.0, 27.7.

$^{19}$F NMR (471 MHz, acetone-$d_6$) δ (ppm) −118.33.

HRMS calculated for $C_{23}H_{24}FN_6O[M+H]^+$ 419.1990, found 419.1993.

Preparative Example 72: tert-butyl (cis-4-(4-(4-fluorophenyl)-5-(1H-pyrrolo[2,3-b]pyridin-4-yl)-1H-imidazol-1-yl) cyclo hexyl)carbamate

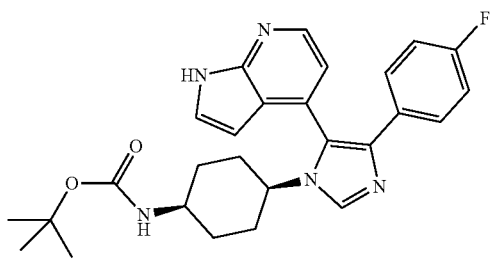 [SMILES: CC(C)(C)OC(=O)N[C@H]1CC[C@@H](n2cnc(-c3ccc(F)cc3)c2-c2ccnc3[nH]ccc23)CC1]

The compound was prepared according to General procedure A using 1H-pyrrolo[2,3-b]pyridine-4-carbaldehyde, tert-butyl (cis-4-aminocyclohexyl)carbamate, 1-fluoro-4-(isocyano(tosyl)methyl)benzene and $K_2CO_3$. Reaction times: 3 hours 15 minutes for the formation of the imine, then additional 14 hours for the cyclization step. The residue obtained after the workup was purified by column chromatography (hexane/acetone, 5:4). The product was obtained as a white solid (148 mg, 37%, ca. 80% purity).

$^1$H NMR (500 MHz, CDCl$_3$) δ (ppm) 10.31 (s, 1H), 8.35 (d, J=4.79 Hz, 1H), 7.95 (br s, 1H), 7.34-7.24 (m, 3H), 6.98 (d, J=4.85 Hz, 1H), 6.77 (t, J=8.75 Hz, 2H), 6.11 (d, J=3.50 Hz, 1H), 4.87 (br s, 1H), 3.73-3.67 (m, 2H), 3.62-3.56 (m, 1H), 3.37-3.29 (m, 1H), 1.87-1.72 (m, 4H), 1.70-1.63 (m, 2H), 1.39 (s, 9H).

HRMS calculated for C27H31FN5O2 [M+H]$^+$ 476.2456, found 476.2459.

Preparative Example 73: cis-4-(4-(4-fluorophenyl)-5-(1H-pyrrolo[2,3-b]pyridin-4-yl)-1H-imidazol-1-yl) cyclohexan-1-amine

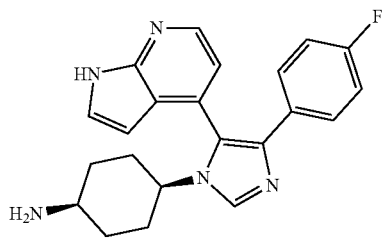 [SMILES: N[C@H]1CC[C@@H](n2cnc(-c3ccc(F)cc3)c2-c2ccnc3[nH]ccc23)CC1]

To a solution of tert-butyl(cis-4-(4-(4-fluorophenyl)-5-(1H-pyrrolo[2,3-b]pyridin-4-yl)-1H-imidazol-1-yl)cyclohexyl)carbamate (600 mg, 1.262 mmol) in dichloromethane (15 mL) was added TFA (1.5 mL) and the resulting mixture was stirred at 25° C. for 16 hours. A saturated aqueous solution of NaHCO$_3$ (30 mL) was added and the mixture was extracted with ethyl acetate (2×100 mL). The combined organic extracts were dried over MgSO$_4$, filtered, and the solvent was evaporated in vacuo. The residue was purified by column chromatography (dichloromethane/7 M NH$_3$ in methanol, 10:1). The product was obtained as a white solid (290 mg, 61%).

$^1$H NMR (500 MHz, methanol-$d_4$) δ (ppm) 8.31 (d, J=4.95 Hz, 1H), 8.16 (s, 1H), 7.41 (d, J=3.51 Hz, 1H), 7.30-7.26 (m, 2H), 7.08 (d, J=4.91 Hz, 1H), 6.88-6.84 (m, 2H), 6.12 (d, J=3.54 Hz, 1H), 3.76 (tt, J=11.66, 3.93 Hz, 1H), 3.05 (t, J=3.40 Hz, 1H), 2.16-2.07 (m, 2H), 1.87-1.81 (m, 1H), 1.74-1.65 (m, 3H), 1.54-1.46 (m, 1H), 1.44-1.38 (m, 1H).

$^{13}$C NMR (126 MHz, methanol-$d_4$) δ (ppm) 163.2 (d, J=245.02 Hz), 149.8, 143.7, 138.7, 137.0, 132.4, 131.6 (d, J=3.25 Hz), 129.6 (d, J=8.09 Hz), 128.3, 126.0, 122.3, 118.8, 115.9 (d, J=21.80 Hz), 100.4, 56.1, 48.5, 32.3, 32.2, 29.1, 28.6.

HRMS calculated for $C_{22}H_{23}FN_5$ $[M+H]^+$ 376.1932, found 376.1934.

Preparative Example 74: N-(cis-4-(4-(4-fluorophenyl)-5-(1H-pyrrolo[2,3-b]pyridin-4-yl)-1H-imidazol-1-yl)cyclohexyl)methanesulfonamide

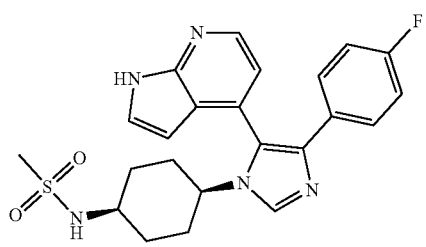 [SMILES: CS(=O)(=O)N[C@H]1CC[C@@H](n2cnc(-c3ccc(F)cc3)c2-c2ccnc3[nH]ccc23)CC1]

To a cold solution (0° C.) of cis-4-(4-(4-fluorophenyl)-5-(1H-pyrrolo[2,3-b]pyridin-4-yl)-1H-imidazol-1-yl)cyclohexan-1-amine (290 mg; 0.772 mmol) in dichloromethane (20 mL) and THF (4.0 mL) was added triethylamine (0.332 mL; 234 mg; 2.32 mmol), then methanesulfonyl chloride (0.065 mL; 97 mg; 0.849 mmol) and the resulting mixture was stirred at 0° C. for 20 minutes.

Then, aqueous saturated solution of NaHCO$_3$ (25 mL) was added and the mixture was extracted with CH$_2$C2 (2×100 mL). The organic extracts were dried over MgSO$_4$, filtered, and the solvent was evaporated in vacuo. The residue was purified by column chromatography (acetone/hexane, 1:1). The product was obtained as a white solid (200 mg, 57%).

$^1$H NMR (500 MHz, acetone-d$_6$) δ (ppm) 10.90 (s, 1H), 8.37 (d, J=4.81 Hz, 1H), 8.01 (s, 1H), 7.50 (dd, J=3.53, 2.37 Hz, 1H), 7.48-7.38 (m, 2H), 7.09 (d, J=4.77 Hz, 1H), 6.93-6.82 (m, 2H), 6.20 (app d, J=7.38 Hz, 1H), 6.15 (dd, J=3.51, 1.83 Hz, 1H), 3.78 (tt, J=11.86, 3.80 Hz, 1H), 3.64 (tt, J=6.24, 2.90 Hz, 1H), 2.93 (s, 3H), 2.26-2.15 (m, 2H), 1.96-1.89 (m, 3H), 1.86-1.80 (m, 1H), 1.62-1.53 (m, 1H), 1.52-1.44 (m, 1H).

$^{13}$C NMR (126 MHz, acetone-d$_6$) δ (ppm) 162.2 (d, J=243.18 Hz), 150.2, 144.3, 137.9, 136.1, 132.7 (d, J=3.15 Hz), 131.9, 128.7 (d, J=7.76 Hz), 127.5, 125.3, 121.2, 118.6, 115.4 (d, J=21.46 Hz), 100.3, 54.7, 48.4, 41.1, 31.4, 31.3, 30.4, 28.9.

$^{19}$F NMR (471 MHz, acetone-d$_6$) δ (ppm) −118.39.

HRMS calculated for C$_{23}$H$_{25}$FN$_5$O$_2$S [M+H]$^+$ 454.1708, found 454.1705.

Preparative Example 75: N-(cis-4-(4-(4-fluorophenyl)-5-(1H-pyrrolo[2,3-b]pyridin-4-yl)-1H-imidazol-1-yl)cyclohexyl)acetamide

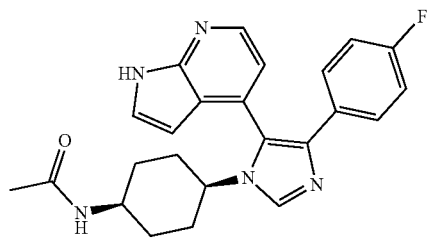 [SMILES: CC(=O)N[C@H]1CC[C@@H](n2cnc(-c3ccc(F)cc3)c2-c2ccnc3[nH]ccc23)CC1]

To a cold solution (−25° C.) of cis-4-(4-(4-fluorophenyl)-5-(1H-pyrrolo[2,3-b]pyridin-4-yl)-1H-imidazol-1-yl)cyclohexan-1-amine (22.0 mg; 0.0586 mmol) in acetonitrile (2 mL) was added pyridine (0.0234 mL; 23.0 mg; 0.293 mmol), then acetic anhydride (0.0066 mL; 7.2 mg; 0.070 mmol) the resulting mixture was stirred at 25° C. for 150 minutes. Methanol (3 mL) was added and the solvents were evaporated in vacuo.

The residue obtained after the workup was purified by preparative TLC (acetone/methanol, 15:1). The product was obtained as a white solid (16 mg, 65%).

$^1$H NMR (500 MHz, methanol-d$_4$) δ (ppm) 8.32 (d, J=4.95 Hz, 1H), 8.09 (s, 1H), 7.42 (d, J=3.51 Hz, 1H), 7.33-7.25 (m, 2H), 7.09 (d, J=4.95 Hz, 1H), 6.91-6.83 (m, 2H), 6.12 (d, J=3.52 Hz, 1H), 3.96 (t, J=3.21 Hz, 1H), 3.81 (tt, J=11.59, 3.83 Hz, 1H), 2.08-1.98 (m, 2H), 2.00 (s, 3H), 1.95-1.90 (m, 1H), 1.86-1.75 (m, 3H), 1.52-1.44 (m, 1H), 1.44-1.35 (m, 1H).

$^{13}$C NMR (126 MHz, methanol-d$_4$) δ (ppm) 172.8, 163.3 (d, J=244.97 Hz), 149.8, 143.8, 138.8, 136.7, 132.3, 131.6 (d, J=2.08 Hz), 129.6 (d, J=7.78 Hz), 128.4, 126.1, 122.3, 118.8, 115.9 (d, J=21.74 Hz), 100.4, 55.9, 44.6, 30.04, 30.01, 29.95, 29.5, 22.7.

$^{19}$F NMR (471 MHz, methanol-d$_4$) δ (ppm) −117.67.

HRMS calculated for C$_{24}$H$_{25}$FN$_5$O[M+H]$^+$ 418.2038, found 418.2035.

Preparative Example 76: tert-butyl (trans-4-(4-(4-fluorophenyl)-5-(1H-pyrrolo[2,3-b]pyridin-4-yl-1H-imidazol-1-yl)cyclohexyl)carbamate

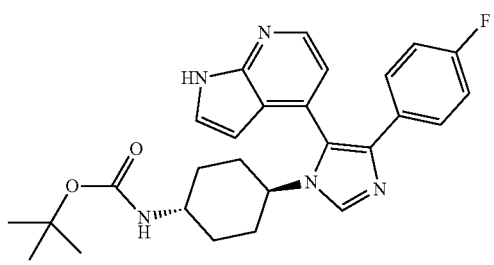 [SMILES: CC(C)(C)OC(=O)N[C@H]1CC[C@H](n2cnc(-c3ccc(F)cc3)c2-c2ccnc3[nH]ccc23)CC1]

The compound was prepared according to General procedure A using 1H-pyrrolo[2,3-b]pyridine-4-carbaldehyde, tert-butyl (trans-4-aminocyclohexyl)carbamate, 1-fluoro-4-(isocyano(tosyl)methyl) benzene and K$_2$CO$_3$. Reaction times: 3 hours 15 minutes for the formation of the imine, then additional 14 hours for the cyclization step. The residue obtained after the workup was purified by column chromatography (hexane/acetone, 5:4). The product was obtained as a white solid (131 mg, 33%, ca. 80% purity).

$^1$H NMR (500 MHz, CDCl$_3$) δ (ppm) 10.33 (s, 1H), 8.41 (d, J=4.83 Hz, 1H), 7.84 (s, 1H), 7.42-7.29 (m, 3H), 7.04 (d, J=4.87 Hz, 1H), 6.88-6.77 (m, 2H), 6.16 (d, J=3.51 Hz, 1H), 4.32 (br s, 1H), 3.69 (tt, J=12.05, 3.62 Hz, 1H), 3.52-3.35 (m, 1H), 2.10-1.95 (m, 4H), 1.87-1.74 (m, 2H), 1.41 (s, 9H), 1.09-0.92 (m, 2H).

$^{13}$C NMR (126 MHz, CDCl$_3$) δ (ppm) 162.7, 161.9 (d, J=245.76 Hz), 149.1, 143.3, 138.1, 134.7, 131.5, 130.2 (d, J=3.08 Hz), 128.3 (d, J=8.00 Hz), 126.5, 124.4, 120.8, 118.0, 115.2 (d, J=21.37 Hz), 100.4, 79.7, 54.5, 48.8, 33.6, 32.9, 32.4, 32.3, 28.5.

HRMS calculated for C27H$_{31}$FN$_5$O$_2$ [M+H]$^+$ 476.2456, found 476.2458.

Preparative Example 77: trans-4-(4-(4-fluorophenyl-5-(1H-pyrrolo[2,3-b]pyridin-4-yl-1H-imidazol-1-yl) cyclohexan-1-amine

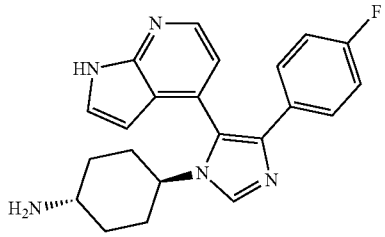 [SMILES: N[C@H]1CC[C@H](n2cnc(-c3ccc(F)cc3)c2-c2ccnc3[nH]ccc23)CC1]

To a solution of tert-butyl (trans-4-(4-(4-fluorophenyl)-5-(1H-pyrrolo[2,3-b]pyridin-4-yl)-1H-imidazol-1-yl)cyclohexyl)carbamate (121 mg, 0.254 mmol) in dichloromethane (4 mL) was added TFA (0.4 mL) and the resulting mixture was stirred at 25° C. for 1 hour. Saturated aqueous solution of NaHCO$_3$ (10 mL) was added and the mixture was extracted with dichloromethane (20 mL) and then with ethyl acetate (4×20 mL). The combined organic extracts were dried over MgSO$_4$, filtered, and the solvent was evaporated in vacuo. The residue was purified by column chromatography (dichloromethane/7 M $NH_3$ in methanol, 10:1). The product was obtained as a white solid (54 mg, 56%).

$^1$H NMR (500 MHz, methanol-$d_4$) δ (ppm) 8.32 (d, J=4.99 Hz, 1H), 8.04 (s, 1H), 7.42 (d, J=3.51 Hz, 1H), 7.30-7.25 (m, 2H), 7.08 (d, J=4.92 Hz, 1H), 6.88-6.83 (m, 2H), 6.13 (d, J=3.50 Hz, 1H), 3.79-3.69 (m, 1H), 2.71 (tt, J=11.28, 3.84 Hz, 1H), 2.07-2.02 (m, 1H), 2.00-1.85 (m, 5H), 1.11-0.96 (m, 2H).

$^{13}$C NMR (126 MHz, methanol-$d_4$) δ (ppm) 163.2 (d, J=244.83 Hz), 149.8, 143.7, 138.8, 136.6, 132.4, 131.6 (d, J=3.25 Hz), 129.6 (d, J=8.07 Hz), 128.4, 126.1, 122.3, 118.8, 115.9 (d, J=21.74 Hz), 100.4, 56.2, 50.2, 35.2, 35.2, 34.0, 33.5.

HRMS calculated for $C_{22}H_{23}FN_5$ $[M+H]^+$ 376.1932, found 376.1935.

Preparative Example 78: N-(trans-4-(4-(4-fluorophenyl)-5-(1H-pyrrolo[2,3-b]pyridin-4-yl)-1H-imidazol-1-yl)cyclohexyl)acetamide

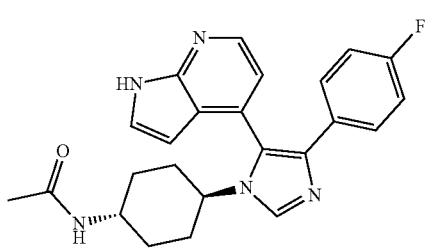 [SMILES: CC(=O)N[C@H]1CC[C@H](n2cnc(-c3ccc(F)cc3)c2-c2ccnc3[nH]ccc23)CC1]

To a solution of trans-4-(4-(4-fluorophenyl)-5-(1H-pyrrolo[2,3-b]pyridin-4-yl)-1H-imidazol-1-yl)cyclohexan-1-amine (20.0 mg; 0.0533 mmol) in acetonitrile (2 mL) was added pyridine (0.0215 mL; 21.0 mg; 0.266 mmol), then acetic anhydride (0.0055 mL; 6.0 mg; 0.0586 mmol) and the resulting mixture was stirred at 25° C. for 45 minutes. Methanol (2 mL) was added and the solvent was evaporated in vacuo. The residue was purified by preparative TLC (acetone/methanol, 20:1). The product was obtained as a white solid (12 mg, 54%).

$^1$H NMR (500 MHz, methanol-$d_4$) δ (ppm) 8.32 (d, J=4.96 Hz, 1H), 8.08 (s, 1H), 7.42 (d, J=3.55 Hz, 1H), 7.30-7.24 (m, 2H), 7.09 (d, J=4.90 Hz, 1H), 6.89-6.83 (m, 2H), 6.13 (d, J=3.50 Hz, 1H), 3.79-3.73 (m, 1H), 3.68 (tt, J=11.72, 3.83 Hz, 1H), 2.11-2.05 (m, 1H), 1.99-1.87 (m, 5H), 1.86 (s, 3H), 1.17-1.07 (m, 1H), 1.07-1.02 (m, 1H).

$^{13}$C NMR (126 MHz, methanol-$d_4$) δ (ppm) 172.5, 163.2 (d, J=245.06 Hz), 149.8, 143.7, 138.9, 136.7, 132.4, 131.6 (d, J=3.19 Hz), 129.6 (d, J=8.01 Hz), 128.4, 126.1, 122.4, 118.8, 115.9 (d, J=21.79 Hz), 100.4, 56.0, 33.9, 33.5, 32.4, 32.3, 30.7, 22.6.

$^{19}$F NMR (471 MHz, methanol-$d_4$) δ (ppm) -117.71.

HRMS calculated for $C_{24}H_{25}FN_5O[M+H]^+$ 418.2038, found 418.2035.

Preparative Example 79: N-(trans-4-(4-(4-fluorophenyl)-5-(1H-pyrrolo[2,3-b]pyridin-4-yl)-1H-imidazol-1-yl)cyclohexyl)methanesulfonamide

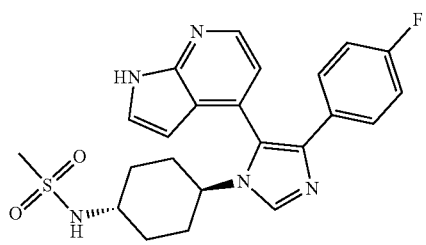 [SMILES: CS(=O)(=O)N[C@H]1CC[C@H](n2cnc(-c3ccc(F)cc3)c2-c2ccnc3[nH]ccc23)CC1]

To a solution of trans-4-(4-(4-fluorophenyl)-5-(1H-pyrrolo[2,3-b]pyridin-4-yl)-1H-imidazol-1-yl)cyclohexan-1-amine (20.0 mg; 0.0533 mmol) in acetonitrile (2 mL) was added pyridine (0.0215 mL; 21.0 mg; 0.266 mmol), then methanesulfonyl chloride (0.0045 mL; 6.7 mg; 0.0585 mmol) and the resulting mixture was stirred at 25° C. for 45 minutes. Then, additional methanesulfonyl chloride (0.0030 mL; 4.4 mg; 0.0384 mmol) was added and the resulting mixture was stirred for additional 50 minutes. Methanol (2 mL) was added and the solvents were evaporated in vacuo. The residue was purified by preparative TLC (acetone/dichloromethane, 3:2). The product was obtained as a white solid (6 mg, 25%).

$^1$H NMR (500 MHz, acetone-$d_6$) δ (ppm) 10.89 (br s, 1H), 8.37 (d, J=4.80 Hz, 1H), 7.96 (s, 1H), 7.50 (dd, J=3.50, 1.78 Hz, 1H), 7.46-7.38 (m, 2H), 7.09 (d, J=4.78 Hz, 1H), 6.90-6.83 (m, 2H), 6.15 (dd, J=3.54, 1.71 Hz, 1H), 5.83 (d, J=7.69 Hz, 1H), 3.73 (tt, J=11.73, 3.96 Hz, 1H), 3.38-3.29 (m, 1H), 2.89 (s, 3H), 2.13-2.07 (m, 3H), 2.03-1.92 (m, 3H), 1.33-1.18 (m, 2H).

$^{13}$C NMR (126 MHz, acetone-$d_6$) δ (ppm) 161.3, 150.3, 144.3, 138.1, 135.8, 132.7 (d, J=3.16 Hz), 131.9, 128.7 (d, J=8.02 Hz), 127.6, 125.4, 121.2, 118.6, 115.4 (d, J=21.38 Hz), 100.3, 54.7, 52.4, 41.6, 33.9, 33.8, 33.8, 33.3.

$^{19}$F NMR (471 MHz, acetone-$d_6$) δ (ppm) -118.38.

HRMS calculated for $C_{23}H_{25}FN_5O_2S[M+H]^+$ 454.1708, found 454.1711.

Preparative Example 80: 4-(4-(4-fluorophenyl-1-(3-(trifluoromethoxy)propyl)-1H-imidazol-5-yl)-1H-pyrrolo[2,3-b]pyridine

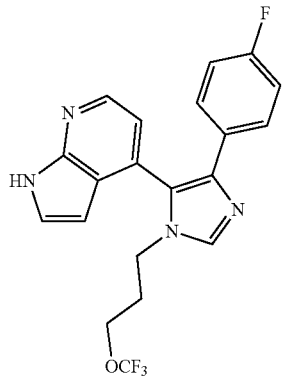 [SMILES: Fc1ccc(-c2ncn(CCCOC(F)(F)F)c2-c2ccnc3[nH]ccc23)cc1]

The compound was prepared according to General procedure A using 1H-pyrrolo[2,3-b]pyridine-4-carbaldehyde, 3-(trifluoromethoxy)propylamine hydrochloride, 1-fluoro-4-(isocyano(tosyl)methyl) benzene and K$_2$CO$_3$. Reaction time: 3 hours for the formation of the imine, then additional 14 hours for the cyclization step. The residue obtained after the workup was purified by column chromatography (hexane/acetone, 1:1) and then by recrystallization from a mixture of dichloromethane/hexane (4:10). The product was obtained as a white solid (40 mg, 30%).

$^1$H NMR (500 MHz, CDCl$_3$) δ (ppm) 10.22 (s, 1H), 8.45 (s, 1H), 7.79 (s, 1H), 7.43-7.34 (m, 3H), 7.09 (d, J=4.77 Hz, 1H), 6.84 (t, J=8.76 Hz, 2H), 6.18 (d, J=3.54 Hz, 1H), 4.14-3.95 (m, 2H), 3.78 (t, J=5.80 Hz, 2H), 1.87-1.70 (m, 2H).

$^{13}$C NMR (126 MHz, CDCl$_3$) δ (ppm) 162.0 (d, J=246.10 Hz), 149.1, 143.4, 139.3, 138.1, 131.1, 130.1 (d, J=3.14 Hz), 128.4 (d, J=7.91 Hz), 126.5, 124.5, 121.5 (q, J=255.12 Hz), 120.4, 117.8, 115.3 (d, J=21.46 Hz), 100.5, 63.5 (q, J=3.26 Hz), 42.0, 30.0.

$^{19}$F NMR (471 MHz, CDCl$_3$) δ (ppm) −61.05, −115.41.

HRMS calculated for C$_{20}$H$_{17}$F$_4$N$_4$O [M+H]$^+$ 405.1333, found 405.1335.

Preparative Example 81: 4-(4-(4-fluorophenyl)-1-(furan-2-ylmethyl)-1H-imidazol-5-yl)-1H-pyrrolo[2,3-b]pyridine

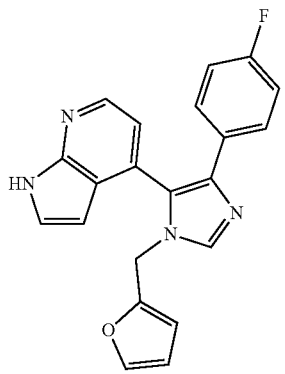 [SMILES: Fc1ccc(-c2ncn(Cc3ccco3)c2-c2ccnc3[nH]ccc23)cc1]

The compound was prepared according to General procedure A using 1H-pyrrolo[2,3-b]pyridine-4-carbaldehyde, 2-aminomethylfuran, 1-fluoro-4-(isocyano(tosyl)methyl) benzene and K$_2$CO$_3$ (3 eq.). Reaction time: 3 hours for the formation of the imine, then additional 14 hours for the cyclization step. The residue obtained after the workup was purified by preparative TLC (hexane/acetone, 1:1). The product was obtained as a white solid (15 mg, 15%).

$^1$H NMR (500 MHz, acetone-d$_6$) δ (ppm) 10.88 (s, 1H), 8.35 (s, 1H), 7.84 (s, 1H), 7.51-7.43 (m, 3H), 7.42-7.37 (m, 1H), 7.07 (d, J=4.68 Hz, 1H), 6.93-6.85 (m, 2H), 6.26 (dd, J=3.24, 1.86 Hz, 1H), 6.11 (dd, J=3.60, 1.78 Hz, 1H), 6.01-5.94 (m, 1H), 5.17 (d, J=16.02 Hz, 1H), 5.02 (d, J=15.80 Hz, 1H).

$^{13}$C NMR (126 MHz, acetone-d$_6$) δ (ppm) 162.4 (d, J=243.32 Hz), 150.7, 150.3, 144.1, 143.8, 139.0, 132.5 (d, J=3.15 Hz), 131.2, 128.9 (d, J=7.83 Hz), 127.4, 127.3, 125.8, 120.8, 118.5, 115.5 (d, J=21.46 Hz), 111.3, 109.4, 100.6, 42.6.

HRMS calculated for C$_{21}$H$_{16}$FN$_4$O [M+H]$^+$ 359.1303, found 359.1301.

Preparative Example 82: 4-(4-(4-fluorophenyl)-1-(pyridin-3-ylmethyl)-1H-imidazol-5-yl)-1H-pyrrolo[2,3-b]pyridine

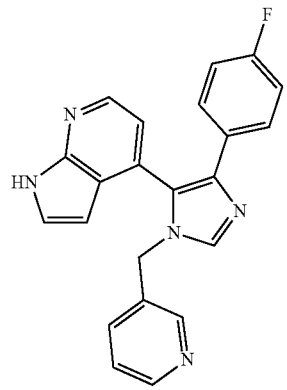 [SMILES: Fc1ccc(-c2ncn(Cc3cccnc3)c2-c2ccnc3[nH]ccc23)cc1]

The compound was prepared according to Genera procedure A using 1H-pyrrolo[2,3-b]pyridine-4-carbaldehyde, 3-(aminomethyl)pyridine, 1-fluoro-4-(isocyano(tosyl)methyl)benzene and K$_2$CO$_3$ (3 eq.). Reaction time: 3 hours for the formation of the imine, then additional 14 hours for the cyclization step. The residue obtained after the workup was purified by preparative TLC (acetone). The product was obtained as an off-white solid (20 mg, 19%).

$^1$H NMR (500 MHz, CDCl$_3$) δ (ppm) 9.63 (s, 1H), 8.45 (d, J=4.49 Hz, 1H), 8.33 (d, J=4.89 Hz, 1H), 8.13 (s, 1H), 7.80 (s, 1H), 7.43-7.38 (m, 2H), 7.31 (d, J=3.55 Hz, 1H), 7.17-7.11 (m, 2H), 6.93 (d, J=4.85 Hz, 1H), 6.87-6.81 (m, 2H), 6.11 (d, J=3.51 Hz, 1H), 5.12-4.94 (m, 2H).

$^{13}$C NMR (126 MHz, CDCl$_3$) δ (ppm) 162.1 (d, J=246.24 Hz), 149.7, 148.9, 148.6, 143.4, 139.4, 138.1, 134.7, 131.7, 130.9, 130.0 (d, J=3.19 Hz), 128.3 (d, J=7.89 Hz), 126.4, 124.8, 123.7, 120.4, 118.0, 115.3 (d, J=21.57 Hz), 100.6, 47.2.

HRMS calculated for C$_{22}$H$_{17}$FN$_5$ [M+H]$^+$ 370.1463, found 370.1461.

Preparative Example 83: 4-(4-(4-fluorophenyl)-1-(pyridin-4-ylmethyl)-1H-imidazol-5-yl)-1H-pyrrolo[2,3-b]pyridine

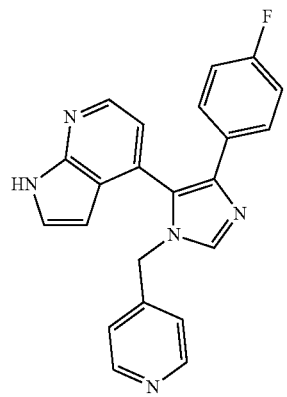 [SMILES: Fc1ccc(-c2ncn(Cc3ccncc3)c2-c2ccnc3[nH]ccc23)cc1]

The compound was prepared according to General procedure A using 1H-pyrrolo[2,3-b]pyridine-4-carbaldehyde, 4-(aminomethyl)pyridine, 1-fluoro-4-(isocyano(tosyl) methyl)benzene and $K_2CO_3$ (3 eq.). Reaction time: 3 hours for the formation of the imine, then additional 14 hours for the cyclization step. The residue obtained after the workup was purified two times by preparative TLC (acetone, then dichloromethane/methanol, 10:1). The product was obtained as a white solid (23 mg, 22%).

$^1$H NMR (500 MHz, CDCl$_3$) δ (ppm) 9.61 (s, 1H), 8.45 (s, 2H), 8.31 (s, 1H), 7.82 (s, 1H), 7.46-7.40 (m, 2H), 7.28 (d, J=3.57 Hz, 1H), 6.90 (d, J=4.88 Hz, 1H), 6.88-6.83 (m, 2H), 6.76 (d, J=4.95 Hz, 2H), 6.08 (d, J=3.53 Hz, 1H), 5.08 (d, J=16.02 Hz, 1H), 4.98 (d, J=16.31 Hz, 1H).

$^{13}$C NMR (126 MHz, CDCl$_3$) δ (ppm) 162.1 (d, J=246.50 Hz), 150.3, 148.8, 145.3, 143.3, 139.5, 138.4, 130.7, 130.0 (d, J=3.48 Hz), 128.3 (d, J=7.83 Hz), 126.4, 124.9, 121.5, 120.3, 117.9, 115.3 (d, J=21.66 Hz), 100.6, 48.3.

HRMS calculated for $C_{22}H_{17}FN_5$ [M+H]$^+$ 370.1463, found 370.1466.

Preparative Example 84: 4-(4-(4-fluorophenyl)-1-(thiophen-2-ylmethyl)-1H-imidazol-5-yl)-1H-pyrrolo[2,3-b]pyridine

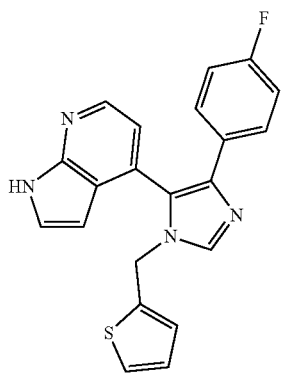 [SMILES: Fc1ccc(-c2ncn(Cc3cccs3)c2-c2ccnc3[nH]ccc23)cc1]

The compound was prepared according to General procedure A using 1H-pyrrolo[2,3-b]pyridine-4-carbaldehyde, 2-(aminomethyl)thiophene, 1-fluoro-4-(isocyano(tosyl) methyl)benzene and $K_2CO_3$ (3 eq.). Reaction time: 3 hours for the formation of the imine, then additional 14 hours for the cyclization step. The residue obtained after the workup was purified by column chromatography (hexane/acetone, 1:1). The obtained solid was triturated with hexane (5 mL) and dried in a vacuum. The product was obtained as a pale yellow solid (35 mg, 33%).

$^1$H NMR (500 MHz, CDCl$_3$) δ (ppm) 10.26 (s, 1H), 8.40 (s, 1H), 7.79 (s, 1H), 7.45-7.38 (m, 2H), 7.35 (d, J=3.53 Hz, 1H), 7.18 (dd, J=5.14, 1.20 Hz, 1H), 7.04 (d, J=4.72 Hz, 1H), 6.92-6.75 (m, 3H), 6.66-6.62 (m, 1H), 6.18 (d, J=3.55 Hz, 1H), 5.19 (d, J=15.66 Hz, 1H), 5.10 (d, J=15.63 Hz, 1H).

$^{13}$C NMR (126 MHz, CDCl$_3$) δ (ppm) 162.0 (d, J=245.79 Hz), 149.1, 143.3, 139.0, 138.3, 137.9, 131.1, 130.3 (d, J=3.13 Hz), 128.4 (d, J=7.96 Hz), 127.1, 126.9, 126.3, 126.3, 124.7, 120.6, 118.1, 115.2 (d, J=21.44 Hz), 100.8, 44.3.

HRMS calculated for $C_{21}H_{16}FN_4S$[M+H]$^+$ 375.1074, found 375.1075.

Preparative Example 85: 4-(4-(4-fluorophenyl)-1-(4-(trifluoromethoxy)benzyl-1H-imidazol-5-yl)-1H-pyrrolo[2,3-b]pyridine

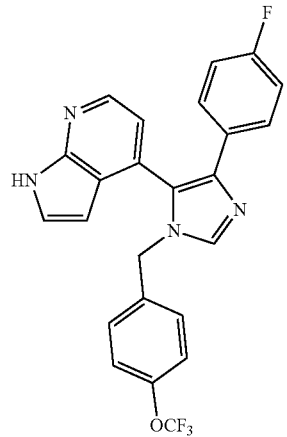 [SMILES: Fc1ccc(-c2ncn(Cc3ccc(OC(F)(F)F)cc3)c2-c2ccnc3[nH]ccc23)cc1]

The compound was prepared according to General procedure A using 1H-pyrrolo[2,3-b]pyridine-4-carbaldehyde, 4-(trifluoromethoxy)benzylamine, 1-fluoro-4-(isocyano(tosyl)methyl)benzene and $K_2CO_3$ (3 eq.). Reaction time: 3 hours for the formation of the imine, then additional 14 hours for the cyclization step. The residue obtained after the workup was purified by column chromatography (hexane/acetone, 1:1). The obtained solid was triturated with hexane (5 mL) and dried in a vacuum. The product was obtained as a pale yellow solid (45 mg, 35%).

$^1$H NMR (500 MHz, CDCl$_3$) δ (ppm) 10.03 (s, 1H), 8.31 (d, J=4.91 Hz, 1H), 7.78 (s, 1H), 7.43-7.39 (m, 2H), 7.29 (d, J=3.58 Hz, 1H), 7.03-6.99 (m, 2H), 6.91 (d, J=4.85 Hz, 1H), 6.89-6.80 (m, 4H), 6.07 (d, J=3.53 Hz, 1H), 5.04 (d, J=15.44 Hz, 1H), 4.96 (d, J=14.68 Hz, 1H).

$^{13}$C NMR (126 MHz, CDCl$_3$) δ (ppm) 162.0 (d, J=245.99 Hz), 149.0, 143.3, 139.3, 138.2, 134.9, 131.1, 130.2 (d, J=3.30 Hz), 128.6, 128.3 (d, J=7.97 Hz), 126.3, 124.9, 121.4, 120.5, 119.5, 117.9, 115.3 (d, J=21.51 Hz), 100.6, 48.9.

HRMS calculated for $C_{24}H_{17}F_4N_4O$ [M+H]$^+$ 453.1333, found 453.1335.

Preparative Example 86: 4-(1-((1r,4r)-1-azabicyclo [2.2.1]heptan-4-yl)-4-(4-fluorophenyl)-1H-imidazol-5-yl)-1H-pyrrolo[2,3-b]pyridine

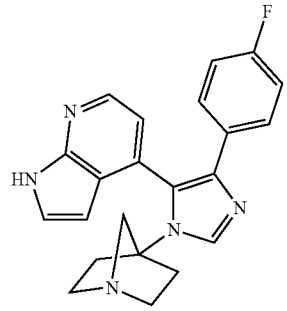 [SMILES: Fc1ccc(-c2ncn(C34CCN(CC3)C4)c2-c2ccnc3[nH]ccc23)cc1]

The compound was prepared according to General procedure A using 1H-pyrrolo[2,3-b]pyridine-4-carbaldehyde, 1-azabicyclo[2.2.1]heptan-4-amine dihydrochloride, 1-fluoro-4-(isocyano(tosyl)methyl) benzene and $K_2CO_3$ (4 eq.). Reaction time: 3 hours for the formation of the imine, then additional 14 hours for the cyclization step. The residue obtained after the workup was purified two times by preparative TLC (dichloromethane/methanol/7.0 M $NH_3$ in methanol, 9/1/0.02; then acetone/methanol/7.0 M $NH_3$ in methanol, 9:1:0.03). The product was obtained as a white solid (15 mg, 14%).

$^1$H NMR (500 MHz, acetone-$d_6$) δ (ppm) 10.92 (s, 1H), 8.37 (d, J=4.74 Hz, 1H), 7.81 (s, 1H), 7.51 (d, J=3.51 Hz, 1H), 7.41-7.36 (m, 2H), 7.16 (d, J=4.79 Hz, 1H), 6.86-6.79 (m, 2H), 6.17 (d, J=3.51 Hz, 1H), 2.99-2.84 (m, 2H), 2.82-2.72 (m, 2H), 2.60-2.45 (m, 2H), 1.97-1.87 (m, 1H), 1.80-1.69 (m, 1H), 1.69-1.60 (m, 1H), 1.29-1.26 (m, 1H).

$^{13}$C NMR (126 MHz, acetone-$d_6$) δ (ppm) 162.2 (d, J=243.02 Hz), 150.0, 143.9, 139.1, 137.4, 133.7, 132.6 (d, J=3.15 Hz), 128.5 (d, J=7.83 Hz), 127.6, 127.5, 126.2, 122.5, 120.2, 115.4 (d, J=21.33 Hz), 100.7, 69.6, 63.1, 55.9 (d, J=9.88 Hz), 38.0, 37.5.

HRMS calculated for $C_{22}H_{21}FN_5$ [M+H]$^+$ 374.1776, found 374.1781.

Preparative Example 87: 4-(4-(4-fluorophenyl)-1-phenethyl-1H-imidazol-5-yl)-1H-pyrrolo[2,3-b]pyridine

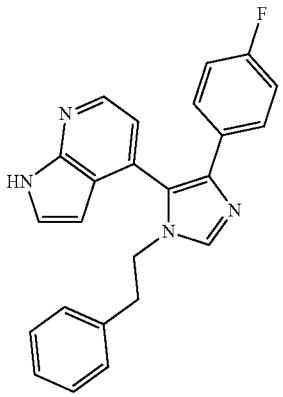 [SMILES: Fc1ccc(-c2ncn(CCc3ccccc3)c2-c2ccnc3[nH]ccc23)cc1]

The compound was prepared according to General procedure A using 1H-pyrrolo[2,3-b]pyridine-4-carbaldehyde, 2-phenylethylamine, 1-fluoro-4-(isocyano(tosyl)methyl) benzene and $K_2CO_3$ (3 eq.). Reaction time: 3 hours for the formation of the imine, then additional 14 hours for the cyclization step. The residue obtained after the workup was purified by column chromatography (hexane/acetone, 3:2). The obtained solid was triturated with a mixture of dichloromethane/hexane (3 mL+3 mL) and dried in a vacuum. The product was obtained as a white solid (70 mg, 64%).

$^1$H NMR (500 MHz, CDCl$_3$) δ (ppm) 10.40 (s, 1H), 8.43 (d, J=4.86 Hz, 1H), 7.56 (s, 1H), 7.44-7.35 (m, 3H), 7.25-7.14 (m, 3H), 6.99 (d, J=4.79 Hz, 1H), 6.94-6.78 (m, 4H), 6.20 (d, J=3.45 Hz, 1H), 4.19-3.95 (m, 2H), 2.75 (t, J=7.13 Hz, 2H).

$^{13}$C NMR (126 MHz, CDCl$_3$) δ (ppm) 161.9 (d, J=245.79 Hz), 149.2, 143.3, 138.8, 137.9, 137.2, 131.5, 130.3 (d, J=3.21 Hz), 128.9, 128.7, 128.3 (d, J=7.89 Hz), 127.1, 126.4, 124.6, 120.5, 117.9, 115.2 (d, J=21.44 Hz), 100.8, 47.4, 37.6.

HRMS calculated for $C_{24}H_{20}FN_4$ [M+H]$^+$ 383.1667, found 383.1670.

Preparative Example 88: 4-(1-(cyclohexylmethyl)-4-(4-fluorophenyl)-1H-imidazol-5-yl)-1H-pyrrolo[2,3-b]pyridine

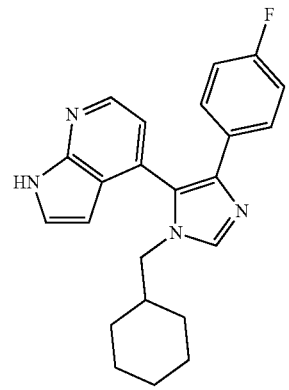 [SMILES: Fc1ccc(-c2ncn(CC3CCCCC3)c2-c2ccnc3[nH]ccc23)cc1]

The compound was prepared according to General procedure A using 1H-pyrrolo[2,3-b]pyridine-4-carbaldehyde, cyclohexanemethylamine, 1-fluoro-4-(isocyano(tosyl) methyl)benzene and $K_2CO_3$ (3 eq.). Reaction time: 3 hours for the formation of the imine, then additional 14 hours for the cyclization step. The residue obtained after the workup was purified by column chromatography (hexane/acetone, 3:2) and then by recrystallization from a mixture of diethyl ether/hexane (2:7). The product was obtained as a white solid (30 mg, 28%).

$^1$H NMR (500 MHz, CDCl$_3$) δ (ppm) 10.36 (s, 1H), 8.43 (s, 1H), 7.73 (s, 1H), 7.43-7.34 (m, 3H), 7.08 (d, J=4.66 Hz, 1H), 6.83 (t, J=8.61 Hz, 2H), 6.18 (d, J=3.47 Hz, 1H), 3.77-3.59 (m, 2H), 1.63-1.51 (m, 3H), 1.47-1.31 (m, 3H), 1.08-0.96 (m, 3H), 0.77-0.64 (m, 2H).

$^{13}$C NMR (126 MHz, CDCl$_3$) δ (ppm) 161.9 (d, J=245.69 Hz), 149.1, 143.2, 138.4, 138.3, 131.7, 130.3, 128.3 (d, J=7.88 Hz), 126.3, 125.0, 120.6, 118.0, 115.2 (d, J=21.44 Hz), 100.8, 52.1, 39.0, 30.5 (d, J=7.77 Hz), 26.2, 25.6.

HRMS calculated for $C_{23}H_{24}FN_4$ [M+H]$^+$ 375.1980, found 375.1982.

Preparative Example 89: (1s,3s)-3-((4-(4-fluorophenyl-5-(1H-pyrrolo[2,3-b]pyridin-4-yl-1H-imidazol-1-yl)methyl)-N,N-dimethylcyclobutan-1-amine

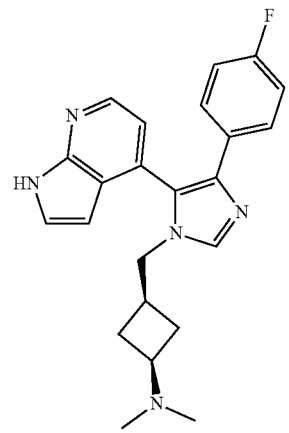 [SMILES: CN(C)[C@H]1C[C@@H](Cn2cnc(-c3ccc(F)cc3)c2-c2ccnc3[nH]ccc23)C1]

The compound was prepared according to General procedure A using 1H-pyrrolo[2,3-b]pyridine-4-carbaldehyde, cis-3-(aminomethyl)-N,N-dimethylcyclobutan-1-amine (CAS: 1909287-66-6), 1-fluoro-4-(isocyano(tosyl)methyl)benzene and $K_2CO_3$ (3 eq.). Reaction time: 3 hours for the formation of the imine, then additional 14 hours for the cyclization step. The residue obtained after the workup was purified by preparative TLC (dichloromethane/methanol/7.0 M $NH_3$ in methanol, 9:1:0.5) and then by recrystallization from a mixture of diethylether/hexane (4:7). The product was obtained as a white solid (75 mg, 68%).

$^1$H NMR (500 MHz, $CDCl_3$) δ (ppm) 11.18 (s, 1H), 8.41 (d, J=4.88 Hz, 1H), 7.68 (s, 1H), 7.44-7.35 (m, 3H), 7.05 (d, J=4.88 Hz, 1H), 6.87-6.78 (m, 2H), 6.17 (dd, J=3.50, 1.62 Hz, 1H), 3.92-3.75 (m, 2H), 2.40-2.32 (m, 1H), 2.10-2.03 (m, 3H), 2.02 (s, 6H), 1.46-1.33 (m, 2H).

$^{13}$C NMR (126 MHz, $CDCl_3$) δ (ppm) 161.8 (d, J=245.42 Hz), 149.4, 143.1, 138.8, 137.6, 131.6, 130.6 (d, J=3.18 Hz), 128.3 (d, J=7.93 Hz), 126.4, 124.6, 120.6, 117.8, 115.1 (d, J=21.40 Hz), 100.5, 57.4, 51.5, 41.7, 32.4, 28.0.

HRMS calculated for $C_{23}H_{25}FN_5$ [M+H]$^+$ 390.2089, found 390.2084.

Preparative Example 90: (1s,4s)-4-(4-(4-fluorophenyl-5-(1H-pyrrolo[2,3-b]pyridin-4-yl)-1H-imidazol-1-yl)-N,N-dimethylcyclohexan-1-amine

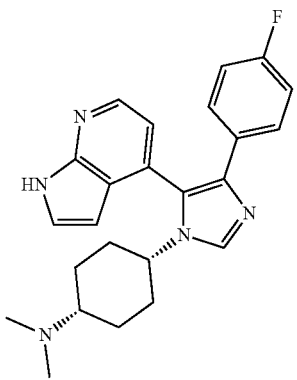 [SMILES: CN(C)[C@H]1CC[C@@H](n2cnc(-c3ccc(F)cc3)c2-c2ccnc3[nH]ccc23)CC1]

The compound was prepared according to General procedure A using 1H-pyrrolo[2,3-b]pyridine-4-carbaldehyde, cis-$N_1,N_1$-dimethylcyclohexane-1,4-diamine dihydrochloride (CAS: 1031289-75-4), 1-fluoro-4-(isocyano(tosyl)methyl)benzene and $K_2CO_3$ (3 eq.). Reaction time: 3 hours for the formation of the imine, then additional 14 hours for the cyclization step. The residue obtained after the workup was purified two times by preparative TLC (dichloromethane/methanol/7.0 M $NH_3$ in methanol, 9/1/0.05; then acetone/methanol/7.0 M $NH_3$ in methanol, 9:1:0.05). The product was obtained as a white solid (35 mg, 29%).

$^1$H NMR (701 MHz, methanol-$d_4$) δ (ppm) 8.32 (d, J=4.94 Hz, 1H), 8.05 (s, 1H), 7.41 (d, J=3.48 Hz, 1H), 7.30-7.23 (m, 2H), 7.09 (d, J=4.88 Hz, 1H), 6.88-6.80 (m, 2H), 6.12 (d, J=3.54 Hz, 1H), 3.73 (tt, J=12.10, 3.90 Hz, 1H), 2.37-2.30 (m, 1H), 2.21 (s, 6H), 2.15-2.09 (m, 1H), 2.03-1.95 (m, 2H), 1.94-1.82 (m, 3H), 1.21-1.13 (m, 1H), 1.12-1.05 (m, 1H).

$^{13}$C NMR (176 MHz, methanol-$d_4$) δ (ppm) 163.2 (d, J=244.77 Hz), 149.8, 143.8, 138.9, 136.6, 132.3, 131.6 (d, J=3.08 Hz), 129.6 (d, J=8.05 Hz), 128.4, 126.1, 122.3, 118.8, 115.9 (d, J=21.66 Hz), 100.4, 63.5, 56.3, 41.6, 34.1, 33.7, 28.2, 28.2.

HRMS calculated for $C_{24}H_{27}FN_5$ [M+H]$^+$ 404.2260, found 404.2265.

Preparative Example 91: 1-((4-(4-fluorophenyl)-5-(1H-pyrrolo[2,3-b]pyridin-4-yl)-1H-imidazol-1-yl)methyl)cyclobutan-1-ol

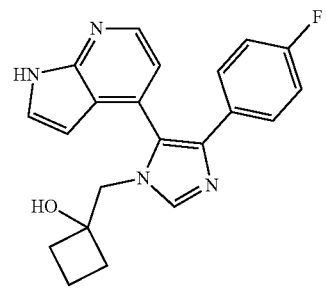 [SMILES: OC1(Cn2cnc(-c3ccc(F)cc3)c2-c2ccnc3[nH]ccc23)CCC1]

The compound was prepared according to General procedure A using 1H-pyrrolo[2,3-b]pyridine-4-carbaldehyde, 1-(aminomethyl)cyclobutan-1-ol, 1-fluoro-4-(isocyano(tosyl)methyl)benzene and $K_2CO_3$. Reaction time: 3 hours for the formation of the imine, then additional 14 hours for the cyclization step.

The residue obtained after the workup was purified by column chromatography (acetone/hexane, 4/1) and then by preparative TLC (acetone/hexane, 3:1). The product was obtained as a white solid (50 mg, 49%).

$^1$H NMR (701 MHz, acetone-d6) δ (ppm) 10.96 (s, 1H), 8.40 (d, J=4.77 Hz, 1H), 8.10 (s, 1H), 7.53-7.43 (m, 3H), 7.17 (d, J=4.73 Hz, 1H), 6.94-6.85 (m, 2H), 6.17 (dd, J=3.50, 1.78 Hz, 1H), 4.65 (br s, 1H), 4.13 (d, J=14.54 Hz, 1H), 3.97 (d, J=14.54 Hz, 1H), 1.95-1.90 (m, 1H), 1.90-1.81 (m, 2H), 1.79-1.73 (m, 1H), 1.49-1.43 (m, 1H), 0.90-0.83 (m, 1H).

$^{13}$C NMR (176 MHz, acetone-d6) δ 162.4 (d, J=243.60 Hz), 150.3, 144.1, 139.4, 136.9, 131.8 (d, J=3.38 Hz), 131.3, 129.1 (d, J=7.89 Hz), 127.6, 127.5, 121.0, 118.9, 115.5 (d, J=21.59 Hz), 100.6, 74.3, 52.6, 34.8, 34.7, 12.2.

HRMS calculated for $C_{21}H_{20}FN_4O$ [M+H]$^+$ 363.1616, found 363.1619.

Preparative Example 92: 4-(4-(4-fluorophenyl)-1-((1-methyl-1H-imidazol-4-yl)methyl)-1H-imidazol-5-yl)-1H-pyrrolo[2,3-b]pyridine

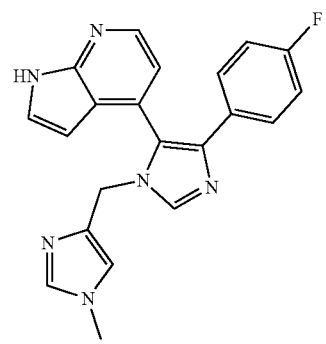 [SMILES: Cn1cnc(Cn2cnc(-c3ccc(F)cc3)c2-c2ccnc3[nH]ccc23)c1]

The compound was prepared according to General procedure A using 1H-pyrrolo[2,3-b]pyridine-4-carbaldehyde, (1-methyl-1H-imidazol-4-yl)methanamine, 1-fluoro-4-(isocyano(tosyl)methyl)benzene and K₂CO₃ (2 eq.). Reaction time: 3 hours for the formation of the imine, then additional 14 hours for the cyclization step. The residue obtained after the workup was purified by column chromatography (dichloromethane/methanol/7.0 M NH₃ in methanol, 9:1:0.05). The product was obtained as a white solid (80 mg, 83%).

¹H NMR (500 MHz, CDCl₃) δ (ppm) 10.10 (br s, 1H), 8.38 (d, J=4.9 Hz, 1H), 7.95 (s, 1H), 7.46-7.37 (m, 2H), 7.38-7.30 (m, 2H), 7.10 (d, J=4.9 Hz, 1H), 6.90-6.78 (m, 2H), 6.41 (s, 1H), 6.17 (d, J=3.5 Hz, 1H), 4.92 (q, J=14.9 Hz, 2H), 3.56 (s, 3H).

¹³C NMR (126 MHz, CDCl₃) δ (ppm) 162.06 (d, J=246.2 Hz), 148.97, 143.21, 138.24, 138.02, 137.87, 137.28, 130.97, 129.65 (d, J=2.1 Hz), 128.54 (d, J=8.0 Hz), 126.23, 124.80, 120.45, 118.65, 118.06, 115.30 (d, J=21.6 Hz), 100.89, 43.75, 33.57.

¹⁹F NMR (471 MHz, CDCl₃) δ (ppm) −115.28.

HRMS calculated for C₂₁H₁FN₆ [M+H]⁺ 373.1571, found 373.1575.

Preparative Example 93: 4-(4-(4-fluorophenyl)-1-((1-methyl-H-pyrazol-4-ylmethyl-1H-imidazol-5-yl-1H-pyrrolo[2,3-b]pyridine

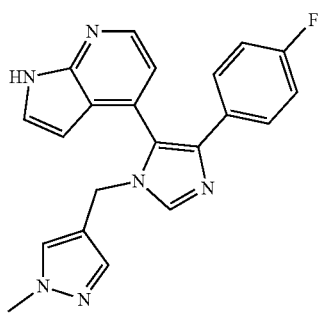 [SMILES: Cn1cc(Cn2cnc(-c3ccc(F)cc3)c2-c2ccnc3[nH]ccc23)cn1]

The compound was prepared according to General procedure A using 1H-pyrrolo[2,3-b]pyridine-4-carbaldehyde, (1-methyl-1H-pyrazol-4-yl)methanamine (CAS: 400877-05-6), 1-fluoro-4-(isocyano(tosyl)methyl)benzene and K₂CO₃ (2 eq.). Reaction time: 3 hours for the formation of the imine, then additional 14 hours for the cyclization step. The residue obtained after the workup was purified by column chromatography (dichloromethane/methanol, 92:8). The product was obtained as a white solid (80 mg, 75%).

¹H NMR (500 MHz, CDCl₃) δ (ppm) 10.36 (s, 1H), 8.43 (br s, 1H), 7.95 (s, 1H), 7.52-7.31 (m, 3H), 7.10 (s, 1H), 7.05 (d, J=4.5 Hz, 1H), 7.01 (s, 1H), 6.84 (t, J=8.4 Hz, 2H), 6.17 (d, J=3.5 Hz, 1H), 4.90 (q, J=15.1 Hz, 2H), 3.77 (s, 3H).

¹³C NMR (126 MHz, CDCl₃) δ (ppm) 162.12 (d, J=246.4 Hz), 149.04, 143.17, 138.59, 138.21, 137.57, 130.88, 129.49 (d, J=2.9 Hz), 129.40, 128.47 (d, J=8.1 Hz), 126.54, 124.80, 120.60, 118.09, 116.32, 115.37 (d, J=21.5 Hz), 100.67, 40.56, 39.14.

¹⁹F NMR (471 MHz, CDCl₃) δ (ppm) −115.05.

HRMS calculated for C₂₁H₁FN₆ [M+H]⁺ 373.1571, found 373.1575.

Preparative Example 94: 4-(4-(4-fluorophenyl)-1-((1-methyl-H-pyrazol-3-ylmethyl-1H-imidazol-5-yl-1H-pyrrolo[2,3-b]pyridine

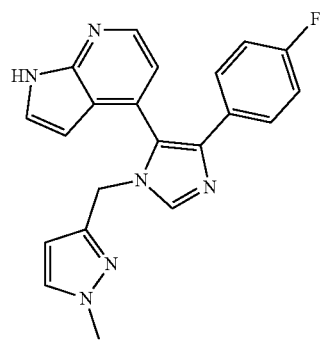 [SMILES: Cn1ccc(Cn2cnc(-c3ccc(F)cc3)c2-c2ccnc3[nH]ccc23)n1]

The compound was prepared according to General procedure A using 1H-pyrrolo[2,3-b]pyridine-4-carbaldehyde, (1-methyl-1H-pyrazol-3-yl)methanamine (CAS: 612511-81-6), 1-fluoro-4-(isocyano(tosyl)methyl)benzene (83 mg; 0.287 mmol) and K₂CO₃ (2 eq.). Reaction time: 3 hours for the formation of the imine, then additional 14 hours for the cyclization step. The residue obtained after the workup was purified by column chromatography (dichloromethane/methanol, 94:6). The product was obtained as a white solid (65 mg, 61%).

¹H NMR (500 MHz, CDCl₃) δ (ppm) 10.75 (s, 1H), 8.41 (d, J=4.9 Hz, 1H), 7.84 (s, 1H), 7.41 (dd, J=8.6, 5.4 Hz, 2H), 7.36 (d, J=3.5 Hz, 1H), 7.19 (d, J=2.3 Hz, 1H), 7.09 (d, J=4.8 Hz, 1H), 6.83 (t, J=8.7 Hz, 2H), 6.19 (d, J=3.5 Hz, 1H), 5.80 (d, J=2.3 Hz, 1H), 5.10-4.85 (m, 2H), 3.81 (s, 3H).

¹³C NMR (126 MHz, CDCl₃) δ (ppm) 161.96 (d, J=245.8 Hz), 149.18, 147.15, 143.05, 138.33, 138.08, 131.35, 131.12, 130.15 (d, J=3.1 Hz), 128.42 (d, J=7.9 Hz), 126.32, 124.93, 120.62, 118.07, 115.21 (d, J=21.4 Hz), 104.92, 100.78, 43.43, 39.02.

¹⁹F NMR (471 MHz, CDCl₃) δ (ppm) −115.64.

HRMS calculated for C₂₁H₁₈FN₆ [M+H]⁺ 373.1571, found 373.1569.

Preparative Example 95: 4-(1-cyclohexyl-4-(4-fluorophenyl)-2-iodo-1H-imidazol-5-yl)-1H-pyrrolo[2,3-b]pyridine

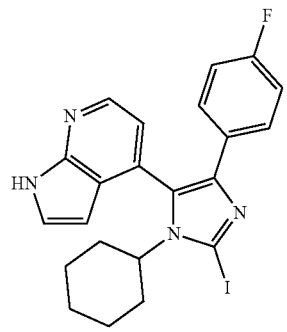 [SMILES: Fc1ccc(-c2nc(I)n(C3CCCCC3)c2-c2ccnc3[nH]ccc23)cc1]

To a cold solution (−78° C.) of 4-(1-cyclohexyl-4-(4-fluorophenyl)-1H-imidazol-5-yl)-1H-pyrrolo[2,3-b]pyridine (145 mg; 0.403 mmol) in tetrahydrofuran (10 mL) was added dropwise 1.5 M solution of n-BuLi in hexane (0.670 mL; 1.01 mmol) and the resulting mixture was stirred at −78° C. for 60 minutes. Then, a solution of iodine (61 mg; 0.483) in tetrahydrofuran (5 mL) was added dropwise and the resulting mixture was stirred at −78° C. for 30 minutes and then at 25° C. for 120 minutes. A saturated aqueous solution of NH$_4$Cl (20 mL) was added and the mixture was extracted with ethyl acetate (2×50 mL). The combined organic extracts were dried over MgSO$_4$, filtered, and the solvent was evaporated in vacuo.

The residue was purified by column chromatography (acetone/hexane, 3:7). The product was obtained as a white solid (75 mg, 38%).

$^1$H NMR (500 MHz, CDCl$_3$) δ (ppm) 10.38 (s, 1H), 8.43 (s, 1H), 7.39 (d, J=3.48 Hz, 1H), 7.26-7.21 (m, 2H), 7.07 (d, J=4.65 Hz, 1H), 6.80-6.72 (m, 2H), 6.24 (d, J=3.43 Hz, 1H), 4.02-3.89 (m, 1H), 2.12-1.92 (m, 1H), 1.89-1.81 (m, 1H), 1.80-1.62 (m, 4H), 1.58-1.52 (m, 1H), 1.19-1.06 (m, 2H), 1.04-0.92 (m, 1H).

$^{13}$C NMR (126 MHz, CDCl$_3$) δ (ppm) 162.0 (d, J=246.03 Hz), 148.7, 143.5, 142.7, 142.2, 132.3, 132.0, 129.7 (d, J=3.13 Hz), 128.2 (d, J=7.92 Hz), 126.7, 121.8, 119.0, 115.1 (dd, J=21.40, 2.25 Hz), 100.8, 53.6, 31.9, 26.3, 26.2, 25.0.

HRMS calculated for C$_{22}$H$_{21}$FIN$_4$ [M+H]$^+$ 487.0789, found 487.0792.

Preparative Example 96: 3-(dimethylamino)-1-(4-(4-(4-fluorophenyl-5-(1H-pyrrolo[2,3-b]pyridin-4-yl)-1H-imidazol-1-yl)piperidin-1-yl)propan-1-one

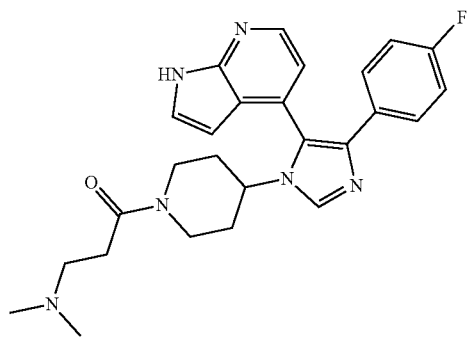 [SMILES: CN(C)CCC(=O)N1CCC(n2cnc(-c3ccc(F)cc3)c2-c2ccnc3[nH]ccc23)CC1]

To a solution of 4-(4-(4-fluorophenyl)-1-(piperidin-4-yl)-1H-imidazol-5-yl)-1H-pyrrolo[2,3-b]pyridine (100 mg; 0.2766 mmol) in acetonitrile (5 mL) was added K$_2$CO$_3$ (114 mg; 0.830 mmol), followed by 3-(dimethylamino)propanoyl chloride hydrochloride (52 mg; 0.3043 mmol) and the resulting mixture was stirred at 25° C. for 72 h. The solvent was evaporated, H$_2$O (20 mL) was added and the mixture was extracted with ethyl acetate (2×50 mL). The combined organic extracts were dried over MgSO$_4$, filtered, and the solvent was evaporated. The residue was purified by preparative TLC (dichloromethane/methanol/7 M NH$_3$ in methanol, 9:1:0.2). The product was obtained as a white solid (12 mg, 10%).

$^1$H NMR (300 MHz, methanol-d$_4$) δ (ppm) 8.34 (d, J=5.03 Hz, 1H), 8.09 (s, 1H), 7.47-7.38 (m, 1H), 7.28 (dd, J=8.54, 5.47 Hz, 2H), 7.13 (t, J=4.96 Hz, 1H), 6.86 (t, J=8.67 Hz, 2H), 6.18-6.10 (m, 1H), 4.59 (apparent t, J=14.93 Hz, 1H), 4.13-3.93 (m, 2H), 3.09-2.84 (m, 1H), 2.70-2.52 (m, 4H), 2.51-2.34 (m, 1H), 2.26 (s, 6H), 2.15-1.87 (m, 4H).

HRMS calculated for C$_{26}$H$_{30}$FN$_6$O [M+H]$^+$ 461.2460, found 461.2461.

Preparative Example 97: N-((1R,4s)-4-(4-(4-fluorophenyl)-5-(1H-pyrrolo[2,3-b]pyridin-4-yl-1H-imidazol-1-yl)cyclohexyl)ethenesulfonamide

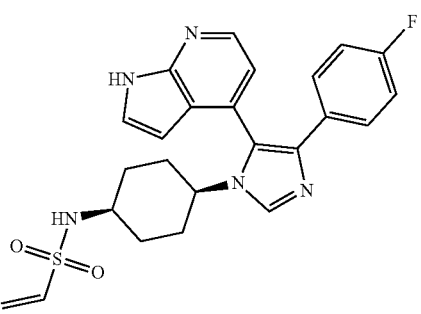 [SMILES: C=CS(=O)(=O)N[C@H]1CC[C@@H](n2cnc(-c3ccc(F)cc3)c2-c2ccnc3[nH]ccc23)CC1]

To a solution of cis-4-(4-(4-fluorophenyl)-5-(1H-pyrrolo[2,3-b]pyridin-4-yl)-1H-imidazol-1-yl)cyclohexan-1-amine (75 mg; 0.199 mmol) in dichloromethane (8 mL) was added triethylamine (0.168 mL; 1.198 mmol), followed by 2-(dimethylamino)ethane-1-sulfonyl chloride hydrochloride (50 mg; 0.239 mmol) and the resulting mixture was stirred at 25° C. for 16 h. Then, aqueous saturated solution of NaHCO$_3$ (25 mL) was added and the mixture was extracted with CH$_2$C2 (2×100 mL). The organic extracts were dried over MgSO$_4$, filtered, and the solvent was evaporated in vacuo. The residue was purified by column chromatography (acetone/hexane, 4:1). The product was obtained as a white solid (40 mg, 43%).

$^1$H NMR (500 MHz, acetone-d$_6$) δ (ppm) 10.87 (s, 1H), 8.36 (d, J=4.80 Hz, 1H), 8.00 (s, 1H), 7.49 (dd, J=3.49, 2.41 Hz, 1H), 7.44-7.39 (m, 2H), 7.08 (d, J=4.73 Hz, 1H), 6.93-6.83 (m, 2H), 6.69 (dd, J=16.53, 9.92 Hz, 1H), 6.33 (d, J=7.31 Hz, 1H), 6.14 (dd, J=3.59, 1.88 Hz, 1H), 6.09 (d, J=16.57 Hz, 1H), 5.91 (d, J=9.95 Hz, 1H), 3.77 (tt, J=11.75, 3.80 Hz, 1H), 3.49 (dt, J=6.97, 3.46 Hz, 2H), 2.27-2.16 (m, 2H), 1.96-1.86 (m, 3H), 1.84-1.76 (m, 1H), 1.54 (tt, J=13.64, 4.04 Hz, 1H), 1.45 (tt, J=13.67, 3.78 Hz, 1H).

$^{13}$C NMR (126 MHz, acetone-d$_6$) δ (ppm) 161.3 (d, J=242.99 Hz), 149.3, 143.3, 137.8, 136.9, 135.1, 131.7 (d, J=3.03 Hz), 130.9, 127.7 (d, J=7.78 Hz), 126.5, 124.4, 120.2, 117.6, 114.4 (d, J=21.37 Hz), 99.3, 53.7, 47.4, 30.1, 30.1, 27.9.

$^{19}$F NMR (471 MHz, acetone-d$_6$) δ (ppm) −118.41.

HRMS calculated for C$_{24}$H$_{25}$FN$_5$O$_2$S[M+H]$^+$ 466.1708, found 466.1709.

Preparative Example 98: 2-(dimethylamino)-N-((1R,4s)-4-(4-(4-fluorophenyl)-5-(1H-pyrrolo[2,3-b]pyridin-4-yl)-1H-imidazol-1-yl)cyclohexyl)ethane-1-sulfonamide

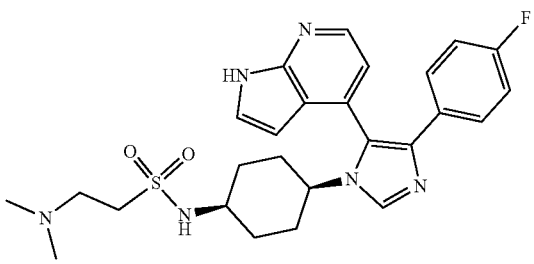 [SMILES: CN(C)CCS(=O)(=O)N[C@H]1CC[C@@H](n2cnc(-c3ccc(F)cc3)c2-c2ccnc3[nH]ccc23)CC1]

To a solution of N-((1R,4s)-4-(4-(4-fluorophenyl)-5-(1H-pyrrolo[2,3-b]pyridin-4-yl)-1H-imidazol-1-yl)cyclohexyl)ethenesulfonamide (66 mg; 0.142 mmol) in tetrahydrofuran (2 mL) and acetonitrile (5 mL) was added triethylamine (0.118 mL; 0.850 mmol), followed by dimethylamine hydrochloride (58 mg; 0.709 mmol) and the resulting mixture was stirred at 25° C. for 16 h. The solvent was evaporated, $H_2O$ (15 mL) was added, and the mixture was extracted with $CH_2Cl2$ (2×35 mL). The combined organic extracts were dried over $MgSO_4$, filtered, and the solvent was evaporated in vacuo. The residue was purified by column chromatography (dichloromethane/methanol/7 M $NH_3$ in methanol, 9:1:0.2). The product was obtained as a white solid (53 mg, 73%).

$^1$H NMR (500 MHz, DMSO-$d_6$) δ (ppm) 11.87 (s, 1H), 8.34 (d, J=4.78 Hz, 1H), 8.12 (s, 1H), 7.48 (t, J=2.95 Hz, 1H), 7.35 (d, J=8.35 Hz, 1H), 7.33-7.25 (m, 2H), 7.06 (d, J=4.79 Hz, 1H), 7.00-6.92 (m, 2H), 6.02 (dd, J=3.51, 1.83 Hz, 1H), 3.59-3.49 (m, 1H), 3.50-3.45 (m, 1H), 3.20-3.12 (m, 2H), 2.63 (t, J=7.52 Hz, 2H), 2.17 (s, 6H), 2.12-2.02 (m, 2H), 1.82-1.75 (m, 1H), 1.75-1.60 (m, 3H), 1.40 (tt, J=13.71, 3.83 Hz, 1H), 1.30 (tt, J=14.01, 3.96 Hz, 1H).

$^{13}$C NMR (126 MHz, DMSO-$d_6$) δ (ppm) 160.6 (d, J=243.04 Hz), 148.8, 143.0, 136.0, 135.6, 131.2 (d, J=2.85 Hz), 130.1, 127.4 (d, J=7.81 Hz), 127.3, 124.2, 119.7, 117.2, 114.8 (d, J=21.34 Hz), 98.6, 54.8, 53.3, 53.0, 49.9, 46.6, 44.8, 30.3, 28.1, 27.5.

$^{19}$F NMR (471 MHz, DMSO-$d_6$) δ (ppm) −116.50.

HRMS calculated for $C_{26}H_{32}FN_6O_2S[M+H]^+$ 511.2286, found 511.2289.

Preparative Example 99: 4-(4-(4-fluorophenyl)-1-((1-methyl-1H-pyrazol-5-ylmethyl-1H-imidazol-5-yl)-1H-pyrrolo[2,3-b]pyridine

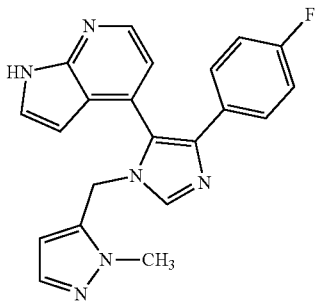 [SMILES: Cn1nccc1Cn1cnc(-c2ccc(F)cc2)c1-c1ccnc2[nH]ccc12]

The compound was prepared according to General procedure A using 1H-pyrrolo[2,3-b]pyridine-4-carbaldehyde, C-(2-methyl-2H-pyrazol-3-yl)-methylamine (CAS: 863548-52-1), 1-fluoro-4-(isocyano(tosyl)methyl)benzene and $K_2CO_3$ (2 eq.). Reaction time: 3 hours for the formation of the imine, then additional 14 hours for the cyclization step. The residue obtained after the workup was purified by column chromatography (dichloromethane/methanol, 94:6). The product was obtained as a white solid (50 mg, 24%).

$^1$H NMR (500 MHz, CDCl$_3$) δ (ppm) 9.98 (s, 1H), 8.41 (apparent s, 1H), 7.75 (apparent s, 1H), 7.41 (dd, J=8.59, 5.26 Hz, 2H), 7.36 (d, J=2.46 Hz, 1H), 7.32 (apparent s, 1H), 7.00 (apparent s, 1H), 6.85 (t, J=8.37 Hz, 2H), 6.16 (apparent s, 1H), 5.95 (apparents, 1H), 5.00 (dd, J=29.90, 12.15 Hz, 2H), 3.49 (s, 3H).

$^{13}$C NMR (126 MHz, CDCl$_3$) δ (ppm) 162.1 (d, J=246.37 Hz), 148.9, 143.4, 139.1, 138.8, 137.8, 136.3, 130.7, 129.8 (d, J=2.60 Hz), 128.4 (d, J=7.95 Hz), 126.6, 124.7, 120.5, 118.1, 115.4 (d, J=21.55 Hz), 107.0, 100.6, 40.9, 36.5.

$^{19}$F NMR (471 MHz, CDCl$_3$) δ (ppm) −115.03.

HRMS calculated for $C_{21}H_{18}FN_6$ $[M+H]^+$ 373.1571, found 373.1572.

Preparative Example 100: 3-(dimethylamino)-N-((1R,4s)-4-(4-(4-fluorophenyl)-5-(1H-pyrrolo[2,3-b]pyridin-4-yl)-1H-imidazol-1-yl)cyclohexyl)propane-1-sulfonamide

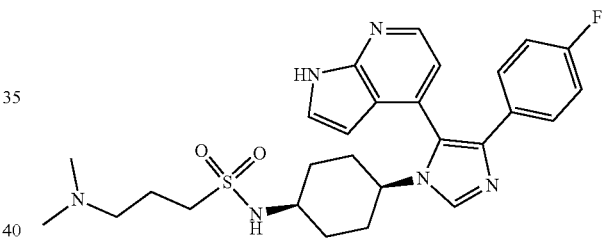

To a solution of cis-4-(4-(4-fluorophenyl)-5-(1H-pyrrolo[2,3-b]pyridin-4-yl)-1H-imidazol-1-yl)cyclohexan-1-amine (55 mg; 0.146 mmol) in tetrahydrofuran (1 mL) and dimethylformamide (0.50 mL) was added triethylamine (0.041 mL; 0.293 mmol), followed by 3-(dimethylamino)-1-propanesulfonyl chloride hydrochloride (58 mg; 0.709 mmol; CAS: 118646-42-7) and the resulting mixture was stirred at 25° C. for 16 h. The solvent was evaporated, $H_2O$ (10 mL) was added and the mixture was extracted with $CH_2Cl2$ (2×40 mL). The combined organic extracts were dried over $MgSO_4$, filtered, and the solvent was evaporated in vacuo. The residue was purified by preparative TLC (dichloromethane/methanol/7 M $NH_3$ in methanol, 9:1:0.2). The product was obtained as a white solid (16 mg, 21%).

$^1$H NMR (500 MHz, methanol-$d_4$) δ (ppm) 8.32 (d, J=4.89 Hz, 1H), 8.10 (s, 1H), 7.41 (d, J=3.52 Hz, 1H), 7.32-7.23 (m, 2H), 7.09 (d, J=4.91 Hz, 1H), 6.90-6.82 (m, 2H), 6.12 (d, J=3.52 Hz, 1H), 3.79 (tt, J=11.78, 3.81 Hz, 1H), 3.57 (t, J=3.34 Hz, 1H), 3.12-3.03 (m, 2H), 2.50-2.44 (m, 2H), 2.27 (s, 6H), 2.14-2.02 (m, 2H), 1.99-1.88 (m, 4H), 1.90-1.77 (m, 1H), 1.53 (tt, J=13.96, 3.98 Hz, 1H), 1.44 (tt, J=13.24, 3.56 Hz, 1H).

$^{13}$C NMR (126 MHz, methanol-$d_4$) δ (ppm) 163.3 (d, J=244.82 Hz), 149.8, 143.8, 138.8, 136.7, 132.3, 131.6 (d, J=3.38 Hz), 129.6 (d, J=8.06 Hz), 128.4, 126.1, 122.3, 118.8, 115.9 (d, J=21.80 Hz), 100.4, 58.6, 55.7, 51.6, 48.3 (HSQC), 45.3, 31.7, 31.7, 29.6, 29.1, 22.8.
$^{19}$F NMR (471 MHz, methanol-d$_4$) δ (ppm) −117.68.
HRMS calculated for C$_{27}$H$_{34}$FN$_6$O$_2$S[M+H]$^+$ 525.2442, found 525.2442.

Preparative Example 101: 4-(4-(4-fluorophenyl)-1-(pyridin-2-ylmethyl)-1H-imidazol-5-yl)-1H-pyrrolo[2,3-b]pyridine

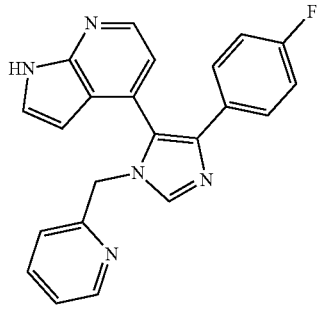 [SMILES: Fc1ccc(-c2ncn(Cc3ccccn3)c2-c2ccnc3[nH]ccc23)cc1]

The compound was prepared according to General procedure A using 1H-pyrrolo[2,3-b]pyridine-4-carbaldehyde, 2-aminomethyl pyridine, 1-fluoro-4-(isocyano(tosyl)methyl)benzene and K$_2$CO$_3$ (2 eq.). Reaction time: 3 hours for the formation of the imine, then additional 14 hours for the cyclization step. The residue obtained after the workup was purified two times by column chromatography (acetone, 100%; then ethylacetate/methanol, 9:1). The product was obtained as an off white solid (35 mg, 33%).
$^1$H NMR (500 MHz, acetone-d$_6$) δ (ppm) 10.82 (s, 1H), 8.39 (ddd, J=4.82, 1.94, 1.00 Hz, 1H), 8.24 (d, J=4.82 Hz, 1H), 7.95 (s, 1H), 7.58 (td, J=7.69, 1.78 Hz, 1H), 7.51-7.45 (m, 2H), 7.44-7.40 (m, 1H), 7.16 (ddd, J=7.54, 4.82, 1.10 Hz, 1H), 6.96 (d, J=4.81 Hz, 1H), 6.92-6.86 (m, 2H), 6.78 (dt, J=7.74, 0.94 Hz, 1H), 6.07 (dd, J=3.53, 1.85 Hz, 1H), 5.37-5.07 (m, 2H).
$^{13}$C NMR (126 MHz, acetone-d$_6$) δ (ppm) 162.3 (d, J=243.15 Hz), 157.5, 150.20, 150.17, 144.0, 139.9, 138.8, 137.5, 132.6 (d, J=3.13 Hz), 131.4, 128.8 (d, J=7.80 Hz), 127.3, 127.2, 126.1, 123.4, 121.9, 120.8, 120.8, 118.4, 115.4 (d, J=21.41 Hz), 100.6, 100.5, 51.2.
$^{19}$F NMR (471 MHz, acetone-d$_6$) δ (ppm) −118.16.
HRMS calculated for C$_{22}$H$_{17}$FN$_5$ [M+H]$^+$ 370.1463, found 370.1460.

Preparative Example 102: 4-(4-(4-fluorophenyl)-1-((1-methylpiperidin-4-yl)methyl)-1H-imidazol-5-yl)-1H-pyrrolo[2,3-b]pyridine

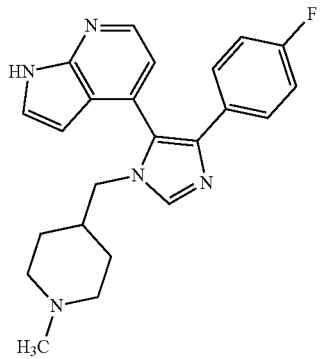 [SMILES: CN1CCC(Cn2cnc(-c3ccc(F)cc3)c2-c2ccnc3[nH]ccc23)CC1]

The compound was prepared according to General procedure A using 1H-pyrrolo[2,3-b]pyridine-4-carbaldehyde, C-(1-Methyl-piperidin-4-yl)-methylamine (CAS: 7149-42-0), 1-fluoro-4-(isocyano(tosyl)methyl)benzene and K$_2$CO$_3$ (2 eq.). Reaction time: 3 hours for the formation of the imine, then additional 16 hours for the cyclization step. The residue obtained after the workup was purified by column chromatography (dichloromethane/7 M NH$_3$ in methanol, 99:1), and then by preparative TLC (dichloromethane/methanol/7 M NH$_3$ in methanol, 9:1:0.2). The product was obtained as a white solid (35 mg, 32%).
$^1$H NMR (500 MHz, acetone-d$_6$) δ (ppm) 10.91 (s, 1H), 8.37 (d, J=4.78 Hz, 1H), 7.80 (s, 1H), 7.49 (dd, J=3.60, 2.02 Hz, 1H), 7.47-7.42 (m, 2H), 7.11 (d, J=4.77 Hz, 1H), 6.93-6.84 (m, 2H), 6.12 (dd, J=3.59, 1.75 Hz, 1H), 3.82 (ddd, J=67.03, 14.01, 6.93 Hz, 2H), 2.63 (t, J=11.24 Hz, 2H), 2.08 (s, 3H), 1.63 (t, J=11.62 Hz, 2H), 1.36-1.28 (m, 3H), 1.15-1.01 (m, 2H).
$^{13}$C NMR (126 MHz, acetone-d$_6$) δ (ppm) 162.3 (d, J=243.03 Hz), 150.3, 144.2, 139.5, 138.7, 132.7 (d, J=3.09 Hz), 131.9, 128.8 (d, J=7.91 Hz), 127.5, 127.3, 125.8, 120.9, 118.4, 115.4 (d, J=21.48 Hz), 100.5, 100.4, 55.7, 51.5, 46.4, 37.2, 29.5 (HMBC).
$^{19}$F NMR (471 MHz, acetone-d$_6$) δ (ppm) −118.32.
HRMS calculated for C$_{23}$H$_{25}$FN$_5$ [M+H]$^+$ 390.2089, found 390.2085.

Preparative Example 103: 4-((4-(4-fluorophenyl)-5-(1H-pyrrolo[2,3-b]pyridin-4-yl)-1H-imidazol-1-yl)methyl)oxazole

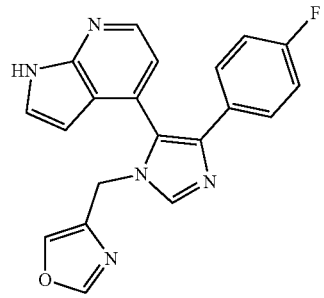 [SMILES: Fc1ccc(-c2ncn(Cc3cocn3)c2-c2ccnc3[nH]ccc23)cc1]

The compound was prepared according to General procedure A using 1H-pyrrolo[2,3-b]pyridine-4-carbaldehyde, 4-oxazolemethanamine hydrochloride (CAS: 1072806-60-0), 1-fluoro-4-(isocyano(tosyl)methyl)benzene and K$_2$CO$_3$ (3 eq.). Reaction time: 3 hours for the formation of the imine, then additional 16 hours for the cyclization step. The residue obtained after the workup was purified by column chromatography (acetone/hexane, 4:1). The product was obtained as a white solid (70 mg, 68%).
$^1$H NMR (500 MHz, acetone-d$_6$) δ (ppm) 10.88 (s, 1H), 8.34 (d, J=4.81 Hz, 1H), 8.04 (d, J=1.07 Hz, 1H), 7.90 (s, 1H), 7.50 (d, J=1.03 Hz, 1H), 7.48-7.43 (m, 3H), 7.13 (d, J=4.82 Hz, 1H), 6.93-6.82 (m, 2H), 6.10 (dd, J=3.57, 1.87 Hz, 1H), 5.09 (d, J=15.67 Hz, 1H), 4.96 (d, J=15.64 Hz, 1H).
$^{13}$C NMR (126 MHz, acetone-d$_6$) δ (ppm) 162.3 (d, J=243.35 Hz), 152.9, 150.2 (d, J=17.03 Hz), 144.1, 139.3, 138.7, 137.5, 137.2, 132.5 (d, J=3.21 Hz), 131.3, 128.9 (d, J=7.84 Hz), 127.4, 127.2, 125.8, 120.8 (d, J=3.05 Hz), 118.5, 115.4 (d, J=21.58 Hz), 100.5 (d, J=7.00 Hz), 41.6.
$^{19}$F NMR (471 MHz, acetone-d$_6$) δ (ppm) −118.14.
HRMS calculated for C$_{20}$H$_{15}$FN$_5$O[M+H]$^+$ 360.1255, found 360.1256.

Preparative Example 104: (R)-4-(4-(4-fluorophenyl)-1-((tetrahydrofuran-3-ylmethyl-1H-imidazol-5-yl-1H-pyrrolo[2,3-b]pyridine

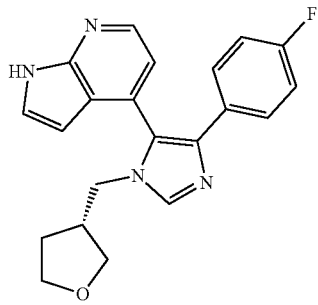 [SMILES: Fc1ccc(-c2ncn(C[C@H]3CCOC3)c2-c2ccnc3[nH]ccc23)cc1]

The compound was prepared according to General procedure A using 1H-pyrrolo[2,3-b]pyridine-4-carbaldehyde, (R)-(tetrahydrofuran-3-yl)methanamine hydrochloride (CAS: 1400744-17-3), 1-fluoro-4-(isocyano(tosyl)methyl)benzene and K$_2$CO$_3$ (3 eq.). Reaction time: 3 hours for the formation of the imine, then additional 16 hours for the cyclization step. The residue obtained after the workup was purified by column chromatography (acetone/hexane, 4:1). The product was obtained as a white solid (60 mg, 58%).

$^1$H NMR (500 MHz, acetone-d$_6$) δ (ppm) 10.93 (s, 1H), 8.38 (d, J=3.24 Hz, 1H), 7.88 (s, 1H), 7.53-7.47 (m, 1H), 7.48-7.42 (m, 2H), 7.14 (dd, J=4.81, 2.60 Hz, 1H), 6.95-6.82 (m, 2H), 6.14 (d, J=6.47 Hz, 1H), 4.00 (td, J=14.98, 7.69 Hz, 1H), 3.88 (td, J=13.93, 8.02 Hz, 1H), 3.65-3.55 (m, 1H), 3.54-3.45 (m, 2H), 3.27 (ddd, J=14.30, 8.74, 5.24 Hz, 1H), 2.35 (dp, J=13.62, 7.58 Hz, 1H), 1.77 (dtd, J=13.32, 7.95, 5.50 Hz, 1H), 1.43 (dt, J=13.28, 6.90 Hz, 1H).

$^{13}$C NMR (126 MHz, acetone-d$_6$) δ (ppm) 162.3 (d, J=243.32 Hz), 150.3, 144.3, 139.1, 138.8, 132.6 (d, J=3.13 Hz), 131.8, 128.8 (d, J=7.80 Hz), 127.6, 127.4, 125.7, 120.9, 118.40, 118.36, 115.4 (d, J=21.39 Hz), 100.5, 100.4, 71.4, 70.96, 67.6, 48.64, 48.59, 41.03, 40.99, 29.2 (HSQC).

$^{19}$F NMR (471 MHz, acetone-d$_6$) δ (ppm) −118.20.

HRMS calculated for C$_{21}$H$_{20}$FN$_4$O [M+H]$^+$ 363.1616, found 363.1618.

Preparative Example 105: (S)-4-(4-(4-fluorophenyl)-1-((tetrahydrofuran-3-yl)methyl)-1H-imidazol-5-yl)-1H-pyrrolo[2,3-b]pyridine

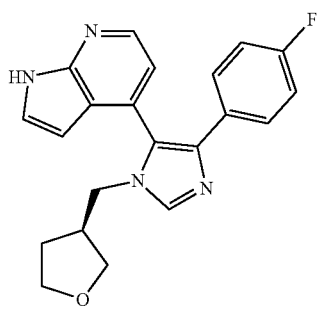 [SMILES: Fc1ccc(-c2ncn(C[C@@H]3CCOC3)c2-c2ccnc3[nH]ccc23)cc1]

The compound was prepared according to General procedure A using 1H-pyrrolo[2,3-b]pyridine-4-carbaldehyde, (S)-(tetrahydrofuran-3-yl)methanamine hydrochloride (CAS: 1403763-27-8), 1-fluoro-4-(isocyano(tosyl)methyl)benzene and K$_2$CO$_3$ (3 eq.). Reaction time: 3 hours for the formation of the imine, then additional 16 hours for the cyclization step. The residue obtained after the workup was purified by column chromatography (acetone/hexane, 4:1). The product was obtained as a light yellow solid (80 mg, 78%).

$^1$H NMR (500 MHz, acetone-d$_6$) δ (ppm) 10.92 (s, 1H), 8.39 (apparent s, 1H), 7.88 (s, 1H), 7.58-7.35 (m, 3H), 7.20-7.09 (m, 1H), 6.88 (apparent t, J=8.54 Hz, 2H), 6.14 (dd, J=9.57, 3.56 Hz, 1H), 4.01 (td, J=14.86, 7.58 Hz, 1H), 3.88 (td, J=13.82, 7.96 Hz, 1H), 3.66-3.54 (m, 1H), 3.54-3.45 (m, 2H), 3.32-3.23 (m, 1H), 2.35 (dq, J=13.78, 7.64, 6.86 Hz, 1H), 1.77 (dtd, J=13.29, 7.95, 5.51 Hz, 1H), 1.42 (dt, J=13.37, 6.92 Hz, 1H).

$^{13}$C NMR (126 MHz, acetone-d$_6$) δ (ppm) 162.3 (d, J=243.24 Hz), 150.3, 150.1, 144.3, 139.0, 132.6, 131.8, 128.8 (d, J=7.91 Hz), 127.6, 127.4, 120.9, 118.4, 115.4 (d, J=21.50 Hz), 100.5, 100.4, 71.04, 70.96, 67.6, 48.6, 41.02, 40.99, 29.9.

$^{19}$F NMR (471 MHz, acetone-d$_6$) δ (ppm) −118.19.

HRMS calculated for C$_{21}$H$_{20}$FN$_4$O [M+H]$^+$ 363.1616, found 363.1617.

Preparative Example 106: 4-(4-(4-fluorophenyl)-1-((1-methyl-1H-1,2,4-triazol-3-yl)methyl)-1H-imidazol-5-yl)-1H-pyrrolo[2,3-b]pyridine

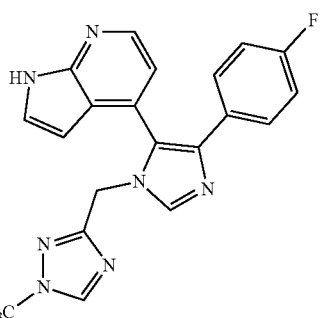

The compound was prepared according to General procedure A using 1H-pyrrolo[2,3-b]pyridine-4-carbaldehyde, (1-methyl-1H-1,2,4-triazol-3-yl)methanamine (CAS: 785760-73-8), 1-fluoro-4-(isocyano(tosyl)methyl)benzene and K$_2$CO$_3$ (2 eq.). Reaction time: 3 hours for the formation of the imine, then additional 16 hours for the cyclization step. The residue obtained after the workup was purified by column chromatography (dichloromethane/methanol, 9:1), and then by preparative TLC (dichloromethane/methanol, 9:1). The product was obtained as a white solid (12 mg, 11%).

$^1$H NMR (500 MHz, methanol-d$_4$) δ (ppm) 8.24 (d, J=4.69 Hz, 1H), 8.14 (s, 1H), 8.07 (s, 1H), 7.46-7.29 (m, 3H), 7.04 (d, J=4.93 Hz, 1H), 6.87 (apparent t, J=8.51 Hz, 2H), 6.00 (d, J=3.39 Hz, 1H), 5.29-5.08 (m, 2H), 3.70 (s, 3H).

Preparative Example 107: 4-(4-(4-fluorophenyl)-1-((5-methyl-4H-1,2,4-triazol-3-yl)methyl)-1H-imidazol-5-yl)-1H-pyrrolo[2,3-b]pyridine

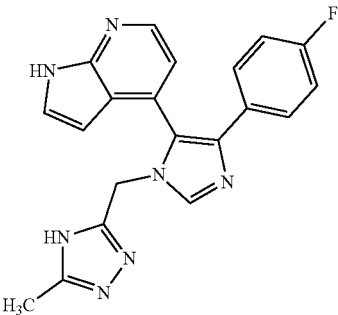 [SMILES: Cc1nnc(Cn2cnc(-c3ccc(F)cc3)c2-c2ccnc3[nH]ccc23)[nH]1]

The compound was prepared according to General procedure A using 1H-pyrrolo[2,3-b]pyridine-4-carbaldehyde, [(5-methyl-4H-1,2,4-triazol-3-yl)methyl]amine dihydrochloride (CAS: 131052-49-8), 1-fluoro-4-(isocyano(tosyl) methyl)benzene and $K_2CO$ (4 eq.). Reaction time: 3 hours for the formation of the imine, then additional 16 hours for the cyclization step. The residue obtained after the workup was purified by column chromatography (dichloromethane/methanol, 85:15). The product was obtained as a white solid (70 mg, 65%).

$^1$H NMR (500 MHz, DMSO-$d_6$) δ (ppm) 13.40 (s, 1H), 11.77 (s, 1H), 8.27 (d, J=4.85 Hz, 1H), 7.96 (s, 1H), 7.42 (apparent t, J=2.97 Hz, 1H), 7.36-7.27 (m, 2H), 7.03 (d, J=4.81 Hz, 1H), 7.00-6.94 (m, 2H), 5.92 (dd, J=3.51, 1.85 Hz, 1H), 5.23-4.80 (m, 2H), 2.25 (s, 3H).

$^{13}$C NMR (126 MHz, DMSO-$d_6$) δ (ppm) 160.7 (d, J=242.92 Hz), 158.7, 153.3, 148.7, 142.6, 138.8, 136.6, 131.0 (d, J=2.10 Hz), 129.4, 127.6 (d, J=7.92 Hz), 126.9, 124.9, 119.3, 117.0, 114.9 (d, J=21.38 Hz), 99.1, 42.3, 11.4.

$^{19}$F NMR (471 MHz, DMSO-$d_6$) δ (ppm) −116.28.

HRMS calculated for $C_{20}H_{17}FN_7$ [M+H]$^+$ 374.1524, found 374.1526.

Preparative Example 108: 4-((4-(4-fluorophenyl)-5-(1H-pyrrolo[2,3-b]pyridin-4-yl)-1H-imidazol-1-yl) methyl)-2-methylthiazole

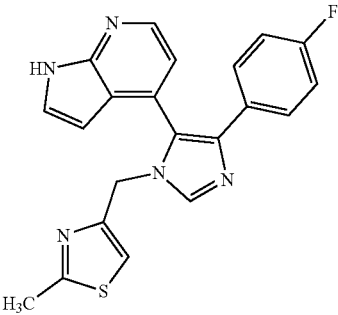 [SMILES: Cc1nc(Cn2cnc(-c3ccc(F)cc3)c2-c2ccnc3[nH]ccc23)cs1]

The compound was prepared according to General procedure A using 1H-pyrrolo[2,3-b]pyridine-4-carbaldehyde, [(2-methyl-1,3-thiazol-4-yl)methyl]amine dihydrochloride (CAS: 1072806-63-3), 1-fluoro-4-(isocyano(tosyl)methyl) benzene and $K_2CO_3$ (3 eq.). Reaction time: 3 hours for the formation of the imine, then additional 16 hours for the cyclization step. The residue obtained after the workup was purified by column chromatography (acetone/methanol, 95:5). The product was obtained as a pale yellow solid (40 mg, 36%).

$^1$H NMR (500 MHz, DMSO-$d_6$) δ (ppm) 11.76 (s, 1H), 8.27 (d, J=4.88 Hz, 1H), 7.99 (s, 1H), 7.42 (t, J=2.98 Hz, 1H), 7.37-7.30 (m, 2H), 7.03 (d, J=4.82 Hz, 1H), 7.00-6.93 (m, 2H), 6.77 (s, 1H), 5.93 (dd, J=3.49, 1.86 Hz, 1H), 5.22-4.93 (m, 2H), 2.52 (s, 3H).

$^{13}$C NMR (126 MHz, DMSO-$d_6$) δ (ppm) 165.9, 160.7 (d, J=242.99 Hz), 150.7, 148.7, 142.6, 138.7, 136.8, 131.0 (d, J=3.07 Hz), 129.6, 127.5 (d, J=8.18 Hz), 126.9, 124.7, 119.3, 117.0, 116.2, 114.9 (d, J=21.36 Hz), 99.0, 44.6, 18.6.

$^{19}$F NMR (471 MHz, DMSO-$d_6$) δ (ppm) −111.52.

HRMS calculated for $C_{21}H_{17}FN_5S$[M+H]$^+$ 390.1183, found 390.1186.

Preparative Example 109: 4-(1-((1H-pyrazol-3-yl) methyl)-4-(4-fluorophenyl)-1H-imidazol-5-yl)-1H-pyrrolo[2,3-b]pyridine

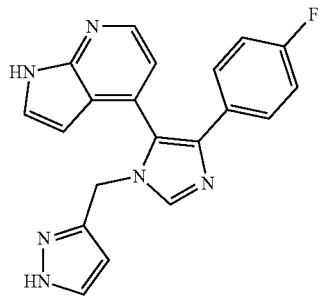 [SMILES: Fc1ccc(-c2ncn(Cc3cc[nH]n3)c2-c2ccnc3[nH]ccc23)cc1]

The compound was prepared according to General procedure A using 1H-pyrrolo[2,3-b]pyridine-4-carbaldehyde, C-(1H-pyrazol-3-yl)-methylamine (CAS: 37599-58-9), 1-fluoro-4-(isocyano(tosyl) methyl)benzene and $K_2CO_3$ (2 eq.). Reaction time: 3 hours for the formation of the imine, then additional 16 hours for the cyclization step. The residue obtained after the workup was purified two times by column chromatography (acetone/methanol, 95:5, and then acetone/methanol, 98:2). The product was obtained as a white solid (40 mg, 39%).

$^1$H NMR (500 MHz, methanol-$d_4$) δ (ppm) 8.25 (d, J=4.95 Hz, 1H), 7.96 (s, 1H), 7.45 (s, 1H), 7.36 (d, J=3.51 Hz, 1H), 7.34-7.28 (m, 2H), 7.03 (d, J=4.94 Hz, 1H), 6.90-6.84 (m, 2H), 6.06 (d, J=3.53 Hz, 1H), 5.82 (apparent s, 1H), 5.25-5.02 (m, 2H).

$^{13}$C NMR (126 MHz, methanol-$d_4$) δ (ppm) 163.3 (d, J=244.97 Hz), 149.7, 148.8, 143.5, 139.8, 139.5, 131.9, 131.6 (d, J=3.13 Hz), 130.7, 129.7 (d, J=8.02 Hz), 128.1, 126.6, 122.0, 118.7, 115.9 (d, J=21.80 Hz), 104.8, 100.8, 44.2.

$^{19}$F NMR (471 MHz, methanol-$d_4$) δ (ppm) −117.57.

HRMS calculated for $C_{20}H_{16}FN_6$ [M+H]$^+$ 359.1415, found 359.1412.

Preparative Example 110: 4-(1-((1H-imidazol-4-yl)methyl)-4-(4-fluorophenyl)-1H-imidazol-5-yl)-1H-pyrrolo[2,3-b]pyridine

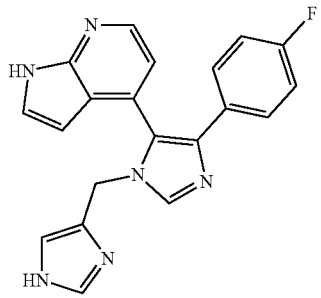 [SMILES: Fc1ccc(-c2ncn(Cc3c[nH]cn3)c2-c2ccnc3[nH]ccc23)cc1]

The compound was prepared according to General procedure A using 1H-pyrrolo[2,3-b]pyridine-4-carbaldehyde, (1H-imidazol-4-yl)methanamine dihydrochloride (CAS: 72631-80-2), 1-fluoro-4-(isocyano(tosyl)methyl)benzene and K$_2$CO$_3$ (4 eq.). Reaction time: 3 hours for the formation of the imine, then additional 16 hours for the cyclization step. The residue obtained after the workup was purified by column chromatography (dichloromethane/methanol, 85:15). The product was obtained as a white solid (80 mg, 78%).

$^1$H NMR (500 MHz, DMSO-d$_6$) δ (ppm) 11.98 (br s, 1H), 11.80 (s, 1H), 8.31 (d, J=4.79 Hz, 1H), 7.88 (s, 1H), 7.56 (s, 1H), 7.43 (t, J=2.97 Hz, 1H), 7.34-7.28 (m, 2H), 7.14 (d, J=4.79 Hz, 1H), 7.00-6.93 (m, 2H), 6.62 (s, 1H), 5.97 (dd, J=3.46, 1.85 Hz, 1H), 5.02-4.77 (m, 2H).

$^{13}$C NMR (126 MHz, DMSO-d$_6$) δ (ppm) 160.7 (d, J=242.89 Hz), 148.8, 142.7, 138.3, 136.7, 135.5, 131.3 (d, J=2.91 Hz), 129.8, 127.6 (d, J=8.04 Hz), 126.9, 124.7, 119.2, 117.1, 114.8 (d, J=21.38 Hz), 99.2, 42.2.

$^{19}$F NMR (471 MHz, DMSO-d$_6$) δ (ppm) −116.43.

HRMS calculated for C$_{20}$H$_{16}$FN$_6$ [M+H]$^+$ 359.1415, found 359.1414.

Preparative Example 111: 2-((4-(4-fluorophenyl)-5-(1H-pyrrolo[2,3-b]pyridin-4-yl)-1H-imidazol-1-yl)methyl)-5-methyl-1,3,4-oxadiazole

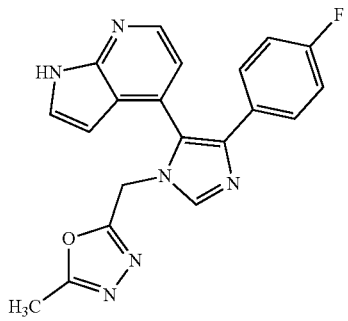 [SMILES: Cc1nnc(Cn2cnc(-c3ccc(F)cc3)c2-c2ccnc3[nH]ccc23)o1]

The compound was prepared according to General procedure A using 1H-pyrrolo[2,3-b]pyridine-4-carbaldehyde, (5-methyl-1,3,4-oxadiazol-2-yl)methanamine hydrochloride (CAS: 1172088-56-0), 1-fluoro-4-(isocyano(tosyl)methyl)benzene and K$_2$CO$_3$ (3 eq.). Reaction time: 3 hours for the formation of the imine, then additional 16 hours for the cyclization step. The residue obtained after the workup was purified by column chromatography (dichloromethane/methanol, 95:5), and then by two times preparative TLC (dichloromethane/methanol, 95:5, and then acetone). The product was obtained as a white solid (7 mg, 7%).

$^1$H NMR (500 MHz, methanol-d$_4$) δ (ppm) 8.29 (s, 1H), 8.12 (s, 1H), 7.41-7.31 (m, 3H), 7.09 (d, J=4.85 Hz, 1H), 6.92-6.85 (m, 2H), 6.01 (d, J=3.51 Hz, 1H), 5.50-5.34 (m, 2H), 2.31 (s, 3H).

$^{13}$C NMR (126 MHz, methanol-d$_4$) δ (ppm) 166.5, 163.5, 163.4 (d, J=245.48 Hz), 149.7, 143.7, 140.5, 139.9, 131.1 (d, J=3.31 Hz), 130.9, 129.6 (d, J=8.04 Hz), 128.4, 126.4, 121.9, 118.6, 116.0 (d, J=21.79 Hz), 100.4, 41.1, 10.3.

$^{19}$F NMR (471 MHz, methanol-d$_4$) δ (ppm) −117.12.

HRMS calculated for C$_{20}$H$_{16}$FN$_6$O[M+H]$^+$ 375.1364, found 375.1367.

Preparative Example 112: 4-((4-(4-fluorophenyl)-5-(1H-pyrrolo[2,3-b]pyridin-4-yl)-1H-imidazol-1-yl)methyl)-2-methyloxazole

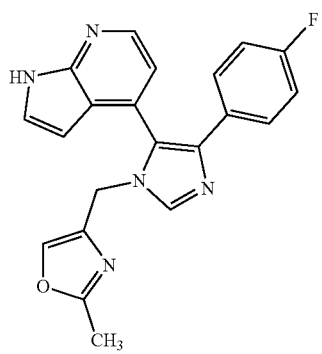 [SMILES: Cc1nc(Cn2cnc(-c3ccc(F)cc3)c2-c2ccnc3[nH]ccc23)co1]

The compound was prepared according to General procedure A using 1H-pyrrolo[2,3-b]pyridine-4-carbaldehyde, (2-methyl-1,3-oxazol-4-yl)methanamine (CAS: 1065073-45-1), 1-fluoro-4-(isocyano (tosyl)methyl)benzene and K$_2$CO$_3$ (2 eq.). Reaction time: 3 hours for the formation of the imine, then additional 16 hours for the cyclization step. The residue obtained after the workup was purified by column chromatography (acetone/methanol, 98:2). The product was obtained as an off white solid (65 mg, 61%).

$^1$H NMR (500 MHz, DMSO-d$_6$) δ (ppm) 11.80 (s, 1H), 8.31 (d, J=4.78 Hz, 1H), 7.94 (s, 1H), 7.43 (dd, J=3.47, 2.45 Hz, 1H), 7.39 (d, J=1.14 Hz, 1H), 7.35-7.28 (m, 2H), 7.09 (d, J=4.80 Hz, 1H), 7.01-6.94 (m, 2H), 5.94 (dd, J=3.40, 1.79 Hz, 1H), 4.97-4.76 (m, 2H), 2.29 (s, 3H).

$^{13}$C NMR (126 MHz, DMSO-d$_6$) δ (ppm) 161.3, 160.7 (d, J=242.93 Hz), 148.7, 142.7, 138.6, 136.9, 136.1, 135.7, 131.1 (d, J=3.12 Hz), 129.6, 127.5 (d, J=7.99 Hz), 127.0, 124.6, 119.3, 117.0, 114.8 (d, J=21.37 Hz), 99.0, 40.5, 13.3.

HRMS calculated for C$_{21}$H$_{17}$FN$_5$O[M+H]$^+$ 374.1412, found 374.1413.

Preparative Example 113: 4-(4-(4-fluorophenyl)-1-((1-methyl-1H-1,2,3-triazol-4-yl)methyl)-1H-imidazol-5-yl)-1H-pyrrolo[2,3-b]pyridine

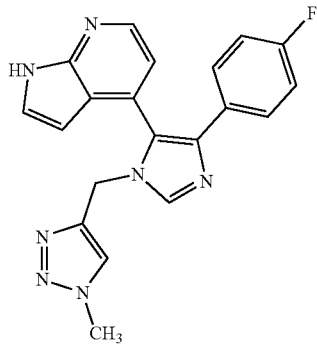 [SMILES: Cn1cc(Cn2cnc(-c3ccc(F)cc3)c2-c2ccnc3[nH]ccc23)nn1]

The compound was prepared according to General procedure A using 1H-pyrrolo[2,3-b]pyridine-4-carbaldehyde, (1-methyl-1H-1,2,3-triazol-4-yl)methanamine hydrochloride (CAS: 612511-67-8), 1-fluoro-4-(isocyano(tosyl) methyl)benzene and K$_2$CO$_3$ (3 eq.). Reaction time: 3 hours for the formation of the imine, then additional 16 hours for the cyclization step. The residue obtained after the workup was purified by column chromatography (dichloromethane/methanol, 9:1). The product was obtained as a light yellow solid (170 mg, 80%).

$^1$H NMR (500 MHz, acetone-d$_6$) δ (ppm) 10.90 (s, 1H), 8.36 (s, 1H), 7.90 (s, 1H), 7.50-7.43 (m, 3H), 7.42 (s, 1H), 7.12 (d, J=4.66 Hz, 1H), 6.88 (apparent t, J=8.84 Hz, 2H), 6.09 (dd, J=3.55, 1.74 Hz, 1H), 5.25-5.06 (m, 2H), 3.96 (s, 3H).

$^{13}$C NMR (126 MHz, acetone-d$_6$) δ (ppm) 162.3 (d, J=243.38 Hz), 150.2, 144.1, 144.0, 139.1, 132.5 (d, J=2.77 Hz), 131.3, 128.8 (d, J=7.82 Hz), 127.4, 127.2, 125.8, 124.5, 120.9, 118.6, 115.4 (d, J=21.47 Hz), 100.6, 100.5, 41.3, 36.6.

$^{19}$F NMR (471 MHz, acetone-d$_6$) δ (ppm) −118.11.

HRMS calculated for C$_{20}$H$_{17}$FN$_7$ [M+H]$^+$ 374.1524, found 374.1521.

Preparative Example 114: 2-((4-(4-fluorophenyl)-5-(1H-pyrrolo[2,3-b]pyridin-4-yl)-1H-imidazol-1-yl)methyl)morpholine

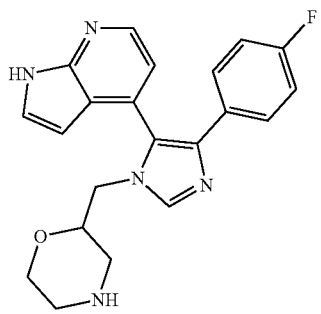 [SMILES: Fc1ccc(-c2ncn(CC3CNCCO3)c2-c2ccnc3[nH]ccc23)cc1]

The compound was prepared according to General procedure A using 1H-pyrrolo[2,3-b]pyridine-4-carbaldehyde, 1-morpholin-2-ylmethanamine (CAS: 116143-27-2), 1-fluoro-4-(isocyano(tosyl) methyl)benzene and K$_2$CO$_3$ (2 eq.). Reaction time: 3 hours for the formation of the imine, then additional 16 hours for the cyclization step. The residue obtained after the workup was purified two times by column chromatography (dichloromethane/methanol/7 M NH$_3$ in methanol, 85:15:2). The obtained solid was triturated with diethyl ether (10 mL) and dried in a vacuum. The product was obtained as a white solid (115 mg, 53%).

$^1$H NMR (500 MHz, DMSO-d$_6$) δ (ppm) 11.85 (s, 1H), 8.34 (d, J=4.76 Hz, 1H), 7.88 (d, J=7.21 Hz, 1H), 7.47 (dd, J=6.71, 3.49 Hz, 1H), 7.37-7.25 (m, 2H), 7.09 (dd, J=21.85, 4.87 Hz, 1H), 7.02-6.90 (m, 2H), 5.99 (d, J=25.31 Hz, 1H), 5.05 (br s, 1H), 3.97-3.87 (m, 1H), 3.84-3.62 (m, 2H), 3.47-3.15 (m, 3H, overlaped with H$_2$O), 2.72-2.62 (m, 1H), 2.61-2.54 (m, 1H), 2.22 (t, J=11.23 Hz, 1H).

$^{13}$C NMR (126 MHz, DMSO-d$_6$) δ (ppm) 160.7 (d, J=242.79 Hz), 148.8, 142.8, 139.0, 136.74, 136.68, 131.1, 129.8, 127.5 (d, J=7.90 Hz), 127.22, 127.19, 124.73, 124.66, 119.4, 117.2, 117.1, 114.8 (d, J=21.47 Hz), 99.0, 73.6, 66.0, 47.1, 44.2, 39.4 (HSQC).

$^{19}$F NMR (471 MHz, DMSO-d$_6$) δ (ppm) −116.4 (d, J=15.43 Hz).

HRMS calculated for C$_{21}$H$_{21}$FN$_5$O[M+H]$^+$ 378.1725, found 378.1722.

Preparative Example 115: 3-((4-(4-fluorophenyl)-5-(1H-pyrrolo[2,3-b]pyridin-4-yl)-1H-imidazol-1-yl)methyl)-5-methylisoxazole

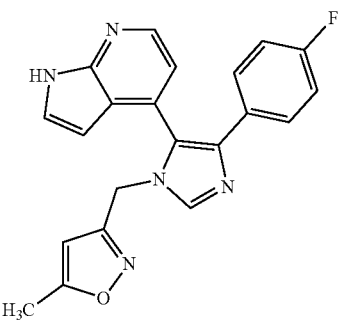 [SMILES: Cc1cc(Cn2cnc(-c3ccc(F)cc3)c2-c2ccnc3[nH]ccc23)no1]

The compound was prepared according to General procedure A using 1H-pyrrolo[2,3-b]pyridine-4-carbaldehyde, (5-methylisoxazol-3-yl)methylamine (CAS: 154016-48-5), 1-fluoro-4-(isocyano(tosyl)methyl)benzene and K$_2$CO$_3$ (2 eq.). Reaction time: 3 hours for the formation of the imine, then additional 16 hours for the cyclization step. The residue obtained after the workup was purified by column chromatography (acetone/hexane, 3:2), and then two times by preparative TLC (acetone/hexane, 1:1, and then dichloromethane/methanol, 95:5). The product was obtained as a white solid (40 mg, 19%).

$^1$H NMR (500 MHz, CDCl$_3$) δ (ppm) 10.32 (br s, 1H), 8.43 (s, 1H), 7.96 (s, 1H), 7.55-7.38 (m, 3H), 7.08 (d, J=4.43 Hz, 1H), 6.85 (t, J=8.48 Hz, 2H), 6.28-6.13 (m, 1H), 5.62 (s, 1H), 5.19-4.87 (m, 2H), 2.33 (s, 3H).

$^{13}$C NMR (126 MHz, CDCl$_3$) δ (ppm) 171.1, 162.2 (d, J=246.63 Hz), 159.5, 148.7, 142.9, 138.7, 138.3, 130.5, 129.5 (d, J=3.00 Hz), 128.5 (d, J=7.97 Hz), 126.7, 124.9, 120.7, 118.0, 115.4 (d, J=21.48 Hz), 100.7, 100.6, 41.4, 12.4.

$^{19}$F NMR (471 MHz, CDCl$_3$) δ (ppm) −114.87.

HRMS calculated for C$_{21}$H$_{17}$FN$_5$O[M+H]$^+$ 374.1412, found 374.1415.

Preparative Example 116: 4-(4-(4-fluorophenyl-1-((1-methyl-1H-imidazol-5-ylmethyl-1H-imidazol-5-yl)-1H-pyrrolo[2,3-b]pyridine

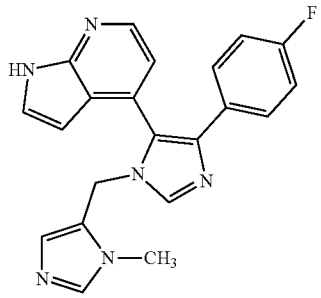 [SMILES: Cn1cncc1Cn1cnc(-c2ccc(F)cc2)c1-c1ccnc2[nH]ccc12]

The compound was prepared according to General procedure A using 1H-pyrrolo[2,3-b]pyridine-4-carbaldehyde, (1-methyl-1H-imidazol-5-yl)methylamine (CAS: 486414-86-2), 1-fluoro-4-(isocyano(tosyl)methyl)benzene and $K_2CO_3$ (2 eq.). Reaction time: 3 hours for the formation of the imine, then additional 16 hours for the cyclization step. The residue obtained after the workup was purified by column chromatography (dichloromethane/methanol/7 M $NH_3$ in methanol, 9:1:0.2). The product was obtained as a white solid (50 mg, 47%).

$^1$H NMR (500 MHz, DMSO-$d_6$) δ (ppm) 11.82 (s, 1H), 8.30 (d, J=4.81 Hz, 1H), 7.88 (s, 1H), 7.45 (apparent s, 1H), 7.40 (s, 1H), 7.37-7.29 (m, 2H), 7.05 (d, J=4.84 Hz, 1H), 6.97 (apparent t, J=8.77 Hz, 2H), 6.25 (s, 1H), 5.97 (d, J=2.84 Hz, 1H), 5.15-5.00 (m, 2H), 3.27 (s, 3H).

$^{13}$C NMR (126 MHz, DMSO-$d_6$) δ (ppm) 160.7 (d, J=243.24 Hz), 148.7, 142.7, 138.8, 138.2, 137.1, 131.0 (d, J=2.99 Hz), 129.6, 128.3, 127.6 (d, J=8.05 Hz), 127.2, 126.4, 124.6, 119.3, 117.0, 114.9 (d, J=21.33 Hz), 98.9, 38.5, 30.6.

$^{19}$F NMR (471 MHz, DMSO-$d_6$) δ (ppm) −116.20.

HRMS calculated for $C_{21}H_1FN_6$ [M+H]$^+$ 373.1571, found 373.1572.

Preparative Example 117: 4-(1-cyclohexyl-4-(p-tolyl-1H-imidazol-5-yl-1H-pyrrolo[2,3-b]pyridine

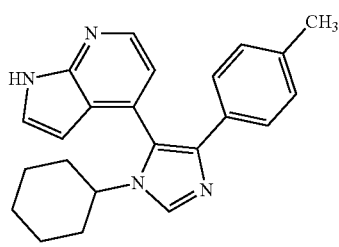 [SMILES: Cc1ccc(-c2ncn(C3CCCCC3)c2-c2ccnc3[nH]ccc23)cc1]

The compound was prepared according to General procedure A using 1H-pyrrolo[2,3-b]pyridine-4-carbaldehyde, cyclohexylamine (CAS: 108-91-8), 1-((isocyano(p-tolyl)methyl)sulfonyl)-4-methylbenzene (CAS: 1330529-37-7), $K_2CO_3$ (2 eq.) and methanol (3 mL). Reaction time: 3 hours for the formation of the imine, then additional 16 hours for the cyclization step. The reaction mixture was concentrated in vacuo and the residue obtained after the workup was purified by column chromatography (acetone/hexane, 2:3). The product was obtained as a white solid (40 mg, 46%).

$^1$H NMR (500 MHz, CD$_3$OD) δ (ppm) 8.29 (d, J=4.91 Hz, 1H), 8.01 (s, 1H), 7.39 (d, J=3.47 Hz, 1H), 7.15 (d, J=7.84 Hz, 2H), 7.05 (d, J=4.93 Hz, 1H), 6.92 (d, J=7.84 Hz, 2H), 6.12 (d, J=3.46 Hz, 1H), 3.72 (tt, J=12.16, 3.91 Hz, 1H), 2.21 (s, 3H), 2.07-1.98 (m, 1H), 1.98-1.89 (m, 1H), 1.84-1.69 (m, 4H), 1.64-1.56 (m, 1H), 1.26-1.04 (m, 3H).

$^{13}$C NMR (126 MHz, CD$_3$OD) δ (ppm) 149.7, 143.6, 139.7, 137.6, 136.4, 132.9, 132.4, 129.8, 128.1, 127.8, 125.7, 122.5, 118.9, 100.6, 56.8, 35.8, 35.1, 26.7, 26.7, 26.1, 21.1.

HRMS calculated for $C_{23}H_{25}N_4$ [M+H]$^+$ 357.2074, found 357.2077.

Preparative Example 118: 5-((4-(4-fluorophenyl)-5-(1H-pyrrolo[2,3-b]pyridin-4-yl)-1H-imidazol-1-yl)methyl)oxazole

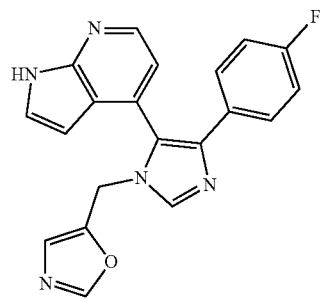 [SMILES: Fc1ccc(-c2ncn(Cc3cnco3)c2-c2ccnc3[nH]ccc23)cc1]

The compound was prepared according to General procedure A using 1H-pyrrolo[2,3-b]pyridine-4-carbaldehyde, oxazol-5-yl-methylamine (CAS: 847644-09-1), 1-fluoro-4-(isocyano(tosyl)methyl) benzene and $K_2CO_3$ (2 eq.). Reaction time: 3 hours for the formation of the imine, then additional 16 hours for the cyclization step. The residue obtained after the workup was purified by column chromatography (acetone/methanol, 95:5). The product was obtained as a white solid (45 mg, 44%).

$^1$H NMR (500 MHz, CDCl$_3$) δ (ppm) 10.62 (s, 1H), 8.43 (d, J=4.90 Hz, 1H), 7.83 (s, 1H), 7.76 (s, 1H), 7.52-7.33 (m, 3H), 7.05 (d, J=4.85 Hz, 1H), 6.94-6.76 (m, 2H), 6.63 (s, 1H), 6.17 (d, J=3.54 Hz, 1H), 5.04 (apparent q, J=16.01 Hz, 2H).

$^{13}$C NMR (126 MHz, CDCl$_3$) δ (ppm) 162.1 (d, J=246.18 Hz), 151.6, 149.2, 146.4, 143.3, 139.1, 138.0, 130.6, 130.0 (d, J=3.17 Hz), 128.4 (d, J=8.02 Hz), 126.7, 125.5, 124.7, 120.6, 118.0, 115.3 (d, J=21.63 Hz), 100.4, 40.0.

$^{19}$F NMR (471 MHz, CDCl$_3$) δ (ppm) −113.18−−116.87 (m).

HRMS calculated for $C_{20}H_{15}FN_5O$[M+H]$^+$ 360.1255, found 360.1258.

Preparative Example 119: 4-((4-(4-fluorophenyl)-5-(1H-pyrrolo[2,3-b]pyridin-4-yl)-1H-imidazol-1-yl)methyl)-1-methylpiperidin-4-ol

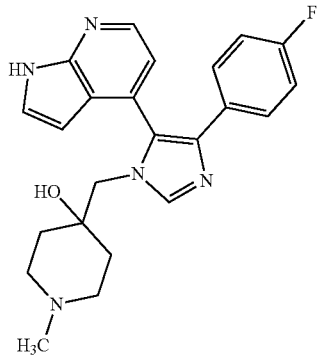 [SMILES: CN1CCC(O)(Cn2cnc(-c3ccc(F)cc3)c2-c2ccnc3[nH]ccc23)CC1]

The compound was prepared according to General procedure A using 1H-pyrrolo[2,3-b]pyridine-4-carbaldehyde, 4-(aminomethyl)-1-methylpiperidin-4-ol (2 eq.; CAS: 26228-68-2), 1-fluoro-4-(isocyano(tosyl)methyl)benzene and $K_2CO_3$ (2 eq.). Reaction time: 3 hours for the formation of the imine, then additional 16 hours for the cyclization step. The residue obtained after the workup was purified by column chromatography (dichloromethane/methanol/7 M $NH_3$ in methanol, 8:2:0.5), and then by preparative TLC (dichloromethane/methanol/7 M $NH_3$ in methanol, 85:10:5). The product was obtained as a white solid (35 mg, 30%).

$^1$H NMR (500 MHz, methanol-$d_4$) δ (ppm) 8.27 (d, J=4.93 Hz, 1H), 7.95 (s, 1H), 7.34 (d, J=3.51 Hz, 1H), 7.27-7.21 (m, 2H), 7.08 (d, J=4.95 Hz, 1H), 6.88-6.81 (m, 2H), 6.05 (d, J=3.51 Hz, 1H), 4.02 (d, J=14.61 Hz, 1H), 3.87 (d, J=14.61 Hz, 1H), 2.32-2.18 (m, 2H), 2.16-2.08 (m, 2H), 2.05 (s, 3H), 1.36-1.19 (m 4H), 1.05-0.97 (m, 1H).

$^{13}$C NMR (126 MHz, methanol-$d_4$) δ (ppm) 163.3 (d, J=245.06 Hz), 149.9, 143.6, 141.0, 139.0, 132.3, 131.6 (d, J=3.21 Hz), 129.9 (d, J=8.12 Hz), 128.3, 127.1, 121.9, 119.0, 115.9 (d, J=21.80 Hz), 100.9, 68.8, 56.5, 51.62, 51.57, 45.7, 35.2, 34.9.

HRMS calculated for $C_{23}H_{25}FN_5O[M+H]^+$ 406.2038, found 406.2040.

Preparative Example 120: 4-(4-(4-fluorophenyl)-1-((2-methyl-2H-1,2,3-triazol-4-yl)methyl)-1H-imidazol-5-yl)-1H-pyrrolo[2,3-b]pyridine

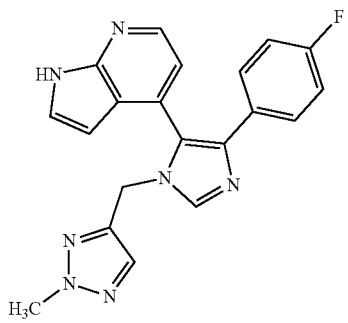 [SMILES: Cn1ncc(Cn2cnc(-c3ccc(F)cc3)c2-c2ccnc3[nH]ccc23)n1]

The compound was prepared according to General procedure A using 1H-pyrrolo[2,3-b]pyridine-4-carbaldehyde, (2-methyl-2H-1,2,3-triazol-4-yl)methanamine (CAS: 791584-15-1), 1-fluoro-4-(isocyano(tosyl)methyl)benzene and $K_2CO_3$ (2 eq.). Reaction time: 3 hours for the formation of the imine, then additional 16 hours for the cyclization step. The residue obtained after the workup was purified by column chromatography (acetone/methanol, 98:2). The product was obtained as a white solid (60 mg, 56%).

$^1$H NMR (500 MHz, CDCl$_3$) δ (ppm) 10.19 (s, 1H), 8.42 (s, 1H), 7.95 (s, 1H), 7.47-7.34 (m, 3H), 7.07 (d, J=4.82 Hz, 1H), 7.04 (s, 1H), 6.84 (apparent t, J=8.51 Hz, 2H), 6.16 (d, J=3.55 Hz, 1H), 5.06 (apparent q, J=15.37 Hz, 2H), 4.08 (s, 3H).

$^{13}$C NMR (126 MHz, CDCl$_3$) δ (ppm) 162.1 (d, J=246.20 Hz), 148.9, 143.2, 143.0, 138.4, 138.0, 133.0, 130.7, 129.5 (d, J=2.91 Hz), 128.5 (d, J=8.07 Hz), 126.6, 124.7, 120.6, 118.1, 115.4 (d, J=21.46 Hz), 100.7, 41.9, 40.9.

$^{19}$F NMR (471 MHz, CDCl$_3$) δ (ppm) −115.01.

HRMS calculated for $C_{20}H_{17}FN_7$ [M+H]$^+$ 374.1524, found 374.1527.

Preparative Example 121: 4-((4-(4-fluorophenyl)-5-(1H-pyrrolo[2,3-b]pyridin-4-yl)-1H-imidazol-1-yl)methyl)-2-(trifluoromethyl)oxazole

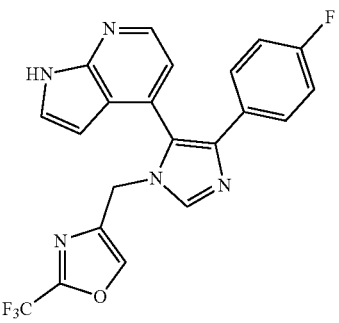 [SMILES: Fc1ccc(-c2ncn(Cc3coc(C(F)(F)F)n3)c2-c2ccnc3[nH]ccc23)cc1]

The compound was prepared according to General procedure A using 1H-pyrrolo[2,3-b]pyridine-4-carbaldehyde, [2-(trifluoromethyl)-1,3-oxazol-4-yl]methanamine (CAS: 1780694-01-0), 1-fluoro-4-(isocyano(tosyl)methyl)benzene and $K_2CO_3$ (2 eq.). Reaction time: 3 hours for the formation of the imine, then additional 16 hours for the cyclization step. The residue obtained after the workup was purified by column chromatography (acetone/hexane, 3:2). The product was obtained as a light yellow solid (50 mg, 41%).

$^1$H NMR (500 MHz, acetone-$d_6$) δ (ppm) 10.89 (br s, 1H), 8.35 (d, J=4.80 Hz, 1H), 7.96 (s, 1H), 7.76 (s, 1H), 7.49-7.44 (m, 3H), 7.11 (d, J=4.76 Hz, 1H), 6.92-6.86 (m, 2H), 6.06 (dd, J=3.51, 1.83 Hz, 1H), 5.24-5.07 (m, 2H).

$^{13}$C NMR (126 MHz, acetone-$d_6$) δ (ppm) 162.4 (d, J=243.40 Hz), 151.1 (q, $^1J_{C-F}$=43.74 Hz), 150.2, 144.2, 140.7, 139.4, 139.0, 138.9, 132.3 (d, J=2.70 Hz), 131.1, 128.8 (d, J=7.98 Hz), 127.5, 127.3, 125.7, 120.9, 118.4, 118.4 (q, $^1J_{C-F}$=269.23 Hz), 115.5 (d, J=21.63 Hz), 100.3, 100.2, 41.3.

$^{19}$F NMR (471 MHz, acetone-$d_6$) δ (ppm) −66.83, −117.97.

HRMS calculated for $C_{21}H_{14}F_4N_5O[M+H]^+$ 428.1129, found 428.1132.

Preparative Example 122: 4-(4-(4-fluorophenyl)-1-((1-methyl-1H-imidazol-2-yl)methyl)-1H-imidazol-5-yl)-1H-pyrrolo[2,3-b]pyridine

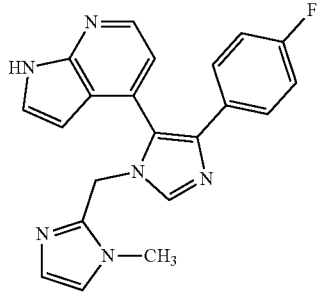 [SMILES: Cn1ccnc1Cn1cnc(-c2ccc(F)cc2)c1-c1ccnc2[nH]ccc12]

The compound was prepared according to General procedure A using 1H-pyrrolo[2,3-b]pyridine-4-carbaldehyde, (1-methyl-1H-imidazol-2-yl)methanamine (CAS: 124312-73-8), 1-fluoro-4-(isocyano(tosyl)methyl)benzene and $K_2CO_3$ (2 eq.). Reaction time: 3 hours for the formation of the imine, then additional 16 hours for the cyclization step. The residue obtained after the workup was purified by column chromatography (dichloromethane/methanol, 85:15). The product was obtained as a light brown solid (50 mg, 47%).

$^1$H NMR (500 MHz, CDCl$_3$) δ (ppm) 10.25 (s, 1H), 8.41 (s, 1H), 7.72 (s, 1H), 7.44-7.34 (m, 3H), 7.04 (d, J=4.70 Hz, 1H), 6.96 (s, 1H), 6.86-6.80 (m, 2H), 6.73 (d, J=1.18 Hz, 1H), 6.18 (d, J=3.47 Hz, 1H), 5.13-4.98 (m, 2H), 3.11 (s, 3H).

$^{13}$C NMR (126 MHz, CDCl$_3$) δ (ppm) 162.0 (d, J=246.10 Hz), 149.1, 143.4, 141.7, 138.9, 138.1, 130.8, 130.1 (d, J=3.20 Hz), 128.4 (d, J=7.88 Hz), 128.3, 126.6, 124.5, 122.3, 120.4, 118.0, 115.3 (d, J=21.52 Hz), 100.6, 41.7, 32.6.

$^{19}$F NMR (471 MHz, CDCl$_3$) δ (ppm) −115.46.

HRMS calculated for $C_{21}H_{18}FN_6$ [M+H]$^+$ 373.1571, found 373.1569.

Preparative Example 123: (1R,3s)-3-(4-(4-fluorophenyl)-5-(1H-pyrrolo[2,3-b]pyridin-4-yl)-1H-imidazol-1-yl)-N,N-dimethylcyclobutan-1-amine

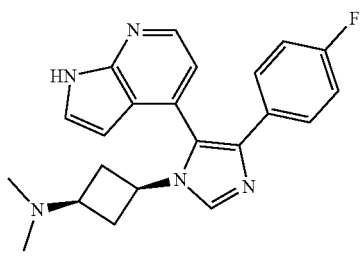 [SMILES: CN(C)[C@H]1C[C@@H](n2cnc(-c3ccc(F)cc3)c2-c2ccnc3[nH]ccc23)C1]

The compound was prepared according to General procedure A using 1H-pyrrolo[2,3-b]pyridine-4-carbaldehyde, cis-N$_1$,N$_1$-dimethylcyclobutane-1,3-diamine (CAS: 1821830-18-5), 1-fluoro-4-(isocyano(tosyl)methyl)benzene and $K_2CO_3$ (2 eq.). Reaction time: 3 hours for the formation of the imine, then additional 16 hours for the cyclization step. The residue obtained after the workup was purified by column chromatography (dichloromethane/methanol/7 M NH$_3$ in methanol, 85:15:2). The obtained solid was triturated with diethyl ether (5 mL), filtered and dried in vacuo. The product was obtained as a light yellow solid (75 mg, 58%).

$^1$H NMR (500 MHz, CD$_3$OD) δ (ppm) 8.30 (d, J=4.95 Hz, 1H), 8.16 (s, 1H), 7.40 (d, J=3.51 Hz, 1H), 7.34-7.25 (m, 2H), 7.07 (d, J=4.92 Hz, 1H), 6.91-6.83 (m, 2H), 6.09 (d, J=3.51 Hz, 1H), 4.25-4.15 (m, 1H), 2.58-2.48 (m, 2H), 2.47-2.40 (m, 1H), 2.27-2.20 (m, 2H), 2.18 (s, 6H).

$^{13}$C NMR (126 MHz, CD$_3$OD) δ (ppm) 163.3 (d, J=245.00 Hz), 149.7, 143.6, 139.3, 137.1, 132.1, 131.5 (d, J=3.22 Hz), 129.7 (d, J=7.96 Hz), 128.3, 126.4, 122.2, 118.7, 115.9 (d, J=21.81 Hz), 100.6, 55.6, 44.3, 41.8, 37.5, 36.9.

$^{19}$F NMR (471 MHz, CD$_3$OD) δ (ppm) −117.52.

HRMS calculated for $C_{22}H_{23}FN_5$ [M+H]$^+$ 376.1932, found 376.1930.

Preparative Example 124: (1S,3r)-3-(4-(4-fluorophenyl)-5-(1H-pyrrolo[2,3-b]pyridin-4-yl)-1H-imidazol-1-yl)-N,N-dimethylcyclobutan-1-amine

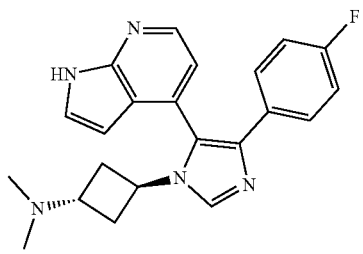 [SMILES: CN(C)[C@H]1C[C@H](n2cnc(-c3ccc(F)cc3)c2-c2ccnc3[nH]ccc23)C1]

The compound was prepared according to General procedure A using 1H-pyrrolo[2,3-b]pyridine-4-carbaldehyde, trans-N1,N1-dimethylcyclobutane-1,3-diamine (CAS: 1821832-50-1), 1-fluoro-4-(isocyano(tosyl)methyl)benzene and $K_2CO_3$ (2 eq.). Reaction time: 3 hours for the formation of the imine, then additional 16 hours for the cyclization step. The residue obtained after the workup was purified by column chromatography (dichloromethane/methanol/7 M NH$_3$ in methanol, 85:15:2), and then by preparative TLC (dichloromethane/methanol/7 M NH$_3$ in methanol, 9:1:0.2). The product was obtained as a white solid (75 mg, 58%).

$^1$H NMR (500 MHz, methanol-d$_4$) δ (ppm) 8.30 (d, J=4.91 Hz, 1H), 8.22 (s, 1H), 7.39 (d, J=3.51 Hz, 1H), 7.34-7.27 (m, 2H), 7.05 (d, J=4.88 Hz, 1H), 6.91-6.82 (m, 2H), 6.07 (d, J=3.50 Hz, 1H), 4.59 (tt, J=8.44, 6.06 Hz, 1H), 3.00-2.92 (m, 1H), 2.60-2.46 (m, 2H), 2.40-2.32 (m, 1H), 2.31-2.23 (m, 1H), 2.10 (s, 6H).

$^{13}$C NMR (126 MHz, methanol-d$_4$) δ (ppm) 163.3 (d, J=245.01 Hz), 149.7, 143.6, 139.5, 136.9, 132.2, 131.5 (d, J=3.17 Hz), 129.7 (d, J=8.10 Hz), 128.2, 126.6, 122.2, 118.7, 115.9 (d, J=21.76 Hz), 100.6, 58.6, 48.4, 42.3, 35.4, 34.8.

$^{19}$F NMR (471 MHz, methanol-d$_4$) δ (ppm) −115.45-−120.14 (m).

HRMS calculated for $C_{22}H_{23}FN_5$ [M+H]$^+$ 376.1932, found 376.1931.

Preparative Example 125: (1S,4r)-4-(4-(4-fluorophenyl)-5-(1H-pyrrolo[2,3-b]pyridin-4-yl)-1H-imidazol-1-yl)-N,N-dimethylcyclohexan-1-amine

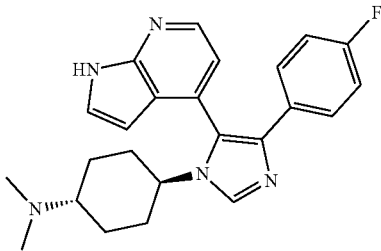 [SMILES: CN(C)[C@H]1CC[C@H](n2cnc(-c3ccc(F)cc3)c2-c2ccnc3[nH]ccc23)CC1]

The compound was prepared according to General procedure A using 1H-pyrrolo[2,3-b]pyridine-4-carbaldehyde, trans-$N_1,N_1$-dimethylcyclohexane-1,4-diamine hydrochloride (CAS: 1388893-25-1), 1-fluoro-4-(isocyano(tosyl)methyl)benzene and $K_2CO_3$ (4 eq.). Reaction time: 3 hours for the formation of the imine, then additional 16 hours for the cyclization step. The residue obtained after the workup was purified by column chromatography (dichloromethane/methanol/7 M $NH_3$ in methanol, 85:15:2). The product was obtained as a white solid (120 mg, 52%).

$^1$H NMR (500 MHz, methanol-$d_4$) δ (ppm) 8.38 (apparent s, 1H), 8.12 (s, 1H), 7.46 (d, J=3.51 Hz, 1H), 7.37-7.28 (m, 2H), 7.15 (d, J=4.85 Hz, 1H), 6.94-6.85 (m, 2H), 6.17 (d, J=3.52 Hz, 1H), 3.92-3.81 (m, 1H), 3.38-3.33 (m, 1H), 2.81 (s, 6H), 2.34-2.25 (m, 1H), 2.22-2.10 (m, 3H), 2.08-1.97 (m, 2H), 1.55 (qd, J=12.56, 3.72 Hz, 1H), 1.45 (qd, J=12.36, 4.26 Hz, 1H).

$^{13}$C NMR (126 MHz, methanol-$d_4$) δ (ppm) 163.3 (d, J=245.14 Hz), 149.8, 143.8, 139.1, 136.6, 132.0, 131.4 (d, J=2.97 Hz), 129.6 (d, J=7.97 Hz), 128.5, 126.1, 122.4, 118.9, 115.9 (d, J=21.71 Hz), 100.4, 64.9, 55.0, 40.4, 32.9, 32.6, 26.4.

$^{19}$F NMR (471 MHz, methanol-$d_4$) δ (ppm) −117.18-−117.76 (m).

HRMS calculated for $C_{24}H_{27}FN_5$ [M+H]$^+$ 404.2245, found 404.2244.

Preparative Example 126: 4-(1-((4-fluoro-1-methylpiperidin-4-yl)methyl)-4-(4-fluorophenyl)-1H-imidazol-5-yl)-1H-pyrrolo[2,3-b]pyridine

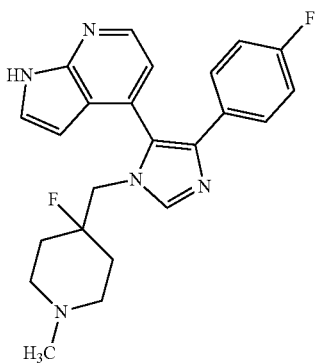 [SMILES: CN1CCC(F)(Cn2cnc(-c3ccc(F)cc3)c2-c2ccnc3[nH]ccc23)CC1]

The compound was prepared according to General procedure A using 1H-pyrrolo[2,3-b]pyridine-4-carbaldehyde, (4-fluoro-1-methylpiperidin-4-yl)methanamine dihydrochloride, 1-fluoro-4-(isocyano (tosyl)methyl)benzene and $K_2CO_3$ (6 eq.). Reaction time: 3 hours for the formation of the imine, then additional 16 hours for the cyclization step. The residue obtained after the workup was purified by column chromatography (dichloromethane/methanol/7 M $NH_3$ in methanol, 8:2:0.2), and then by preparative TLC (acetone/methanol/7 M $NH_3$ in methanol, 9:1:0.2). The product was obtained as an off-white solid (65 mg, 28%).

$^1$H NMR (500 MHz, CDCl$_3$) δ (ppm) 10.16 (s, 1H), 8.37 (d, J=4.87 Hz, 1H), 7.84 (d, J=2.58 Hz, 1H), 7.42-7.34 (m, 2H), 7.31 (dd, J=3.60, 1.50 Hz, 1H), 7.02 (d, J=4.88 Hz, 1H), 6.86-6.79 (m, 2H), 6.12 (d, J=3.36 Hz, 1H), 4.02 (ddd, J=55.56, 22.58, 15.24 Hz, 2H), 2.70-2.50 (m, 2H), 2.26 (s, 3H), 2.24-2.18 (m, 2H), 1.67-1.50 (m, 3H), 1.40-1.30 (m, 1H).

$^{13}$C NMR (126 MHz, CDCl$_3$) δ (ppm) 162.0 (d, J=245.63 Hz), 149.2, 143.5, 139.1 (d, J=4.58 Hz), 138.6, 130.9, 130.4 (d, J=3.13 Hz), 128.4 (d, J=7.99 Hz), 126.4, 125.4, 120.3, 118.1, 115.2 (d, J=21.42 Hz), 100.5, 52.8, 52.6, 50.5, 45.6, 32.2, 32.0.

$^{19}$F NMR (471 MHz, CDCl$_3$) δ (ppm) −115.67-−115.80 (m).

HRMS calculated for $C_{23}H_{24}F_2N_5$ [M+H]$^+$ 408.1994, found 408.1992.

Preparative Example 127: 4-((4-(4-fluorophenyl)-5-(1H-pyrrolo[2,3-b]pyridin-4-yl)-1H-imidazol-1-yl)methyl)thiazole

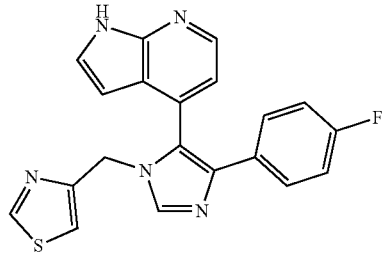 [SMILES: Fc1ccc(-c2ncn(Cc3cscn3)c2-c2ccnc3[nH]ccc23)cc1]

The compound was prepared according to General procedure A using 1H-pyrrolo[2,3-b]pyridine-4-carbaldehyde, thiazol-4-ylmethanamine dihydrochloride, 1-fluoro-4-(isocyano(tosyl)methyl)benzene. $Cs_2CO_3$ (6.5 eq.) was used instead of $K_2CO_3$ and MeCN (3 mL) was used as the solvent instead of DMF. Reaction time: 3 hours 30 minutes for the formation of the imine, then additional 13 hours for the cyclization step. The residue obtained after the workup was purified by column chromatography 3 times (hexane/acetone, 1:1; then ethyl acetate/methanol, 15:1; then acetone/dichloromethane, 4:1. The product was obtained as a white solid (4 mg, 4%).

$^1$H NMR (500 MHz, methanol-$d_4$) δ (ppm) 8.81 (d, J=2.0 Hz, 1H), 8.23 (d, J=4.9 Hz, 1H), 8.04 (s, 1H), 7.37-7.28 (m, 3H), 7.02 (d, J=4.9 Hz, 1H), 6.91-6.83 (m, 3H), 6.01 (d, J=3.5 Hz, 1H), 5.34 (d, J=15.3 Hz, 1H), 5.23 (d, J=15.4 Hz, 1H).

$^{13}$C NMR (126 MHz, methanol-$d_4$) δ (ppm) 163.31 (d, J=244.8 Hz), 155.93, 152.97, 149.64, 143.47, 140.26, 139.59, 131.94, 131.48 (d, J=3.2 Hz), 128.14, 126.45, 121.97, 118.58, 118.22, 115.94 (d, J=21.8 Hz), 100.68, 46.26.

$^{19}$F NMR (471 MHz, methanol-$d_4$) δ (ppm) −117.51.

Preparative Example 128: ethyl 2-(4-(4-fluorophenyl)-5-(1H-pyrrolo[2,3-b]pyridin-4-yl)-1H-imidazol-1-yl)acetate

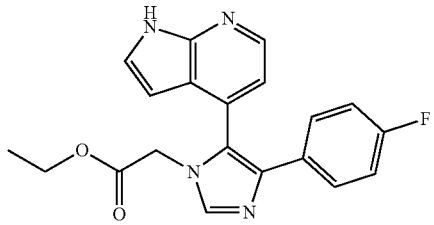 [SMILES: CCOC(=O)Cn1cnc(-c2ccc(F)cc2)c1-c1ccnc2[nH]ccc12]

The compound was prepared according to General procedure A using 1H-pyrrolo[2,3-b]pyridine-4-carbaldehyde, ethyl glycinate hydrochloride, 1-fluoro-4-(isocyano(tosyl)methyl)benzene and $K_2CO_3$. Reaction time: 2 hours for the formation of the imine, then additional 22 hours for the cyclization step. The residue obtained after the workup was purified by column chromatography (hexane/acetone, gradient from 2:1 to 1:1) and then by recrystallization from a mixture of ethyl acetate/hexane (1:1). The product was obtained as a white solid (303 mg, 30%).

$^1$H NMR (500 MHz, $CDCl_3$) δ (ppm) 10.44 (s, 1H), 8.40 (d, J=4.8 Hz, 1H), 7.99 (s, 1H), 7.47-7.39 (m, 2H), 7.37 (d, J=3.5 Hz, 1H), 7.07 (d, J=4.8 Hz, 1H), 6.90-6.80 (m, 2H), 6.18 (d, J=3.5 Hz, 1H), 4.73-4.44 (m, 2H), 4.10 (dd, J=7.1, 1.8 Hz, 2H), 1.15 (t, J=7.1 Hz, 3H).

$^{13}$C NMR (126 MHz, $CDCl_3$) δ (ppm) 167.35, 162.18 (d, J=246.5 Hz), 148.75, 142.89, 138.92, 138.15, 130.40, 129.42 (d, J=3.4 Hz), 128.55 (d, J=8.0 Hz), 126.74, 125.08, 120.67, 117.93, 115.38 (d, J=21.4 Hz), 100.69, 62.30, 46.93, 14.09.

$^{19}$F NMR (471 MHz, $CDCl_3$) δ (ppm) −114.93.

HRMS calculated for $C_{20}H_{18}FN_4O_2$ $[M+H]^+$ 365.1408, found 365.1411.

Preparative Example 129: 4-(4-(4-fluorophenyl)-1-((1-methylpyrrolidin-3-yl)methyl)-1H-imidazol-5-yl)-1H-pyrrolo[2,3-b]pyridine

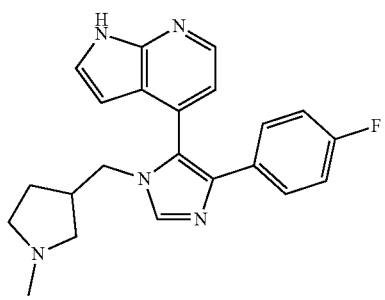 [SMILES: CN1CCC(Cn2cnc(-c3ccc(F)cc3)c2-c2ccnc3[nH]ccc23)C1]

The compound was prepared according to General procedure A using 1H-pyrrolo[2,3-b]pyridine-4-carbaldehyde, (1-methylpyrrolidin-3-yl)methanamine, 1-fluoro-4-(isocyano(tosyl)methyl)benzene and $K_2CO_3$. Reaction time: 5 hours for the formation of the imine, then additional 15 hours for the cyclization step. The solvent was evaporated and the residue was purified by column chromatography (dichloromethane/7 M $NH_3$ in methanol, 10:1). The product was obtained as a white solid (73 mg, 49%).

$^1$H NMR (500 MHz, methanol-$d_4$) δ (ppm) 8.22 (d, J=4.9 Hz, 1H), 7.87 (s, 1H), 7.29 (s, 1H), 7.23-7.15 (m, 2H), 7.08-6.99 (m, 1H), 6.81-6.72 (m, 2H), 6.03-5.94 (m, 1H), 3.97-3.89 (m, 1H), 3.87-3.77 (m, 1H), 2.37-2.23 (m, 3H), 2.19-2.04 (m, 4H), 2.04-1.92 (m, 1H), 1.68-1.57 (m, 1H), 1.29-1.16 (m, 1H).

$^{13}$C NMR (126 MHz, methanol-$d_4$) δ (ppm) 163.30 (d, J=245.1 Hz), 149.81, 143.74, 139.82, 139.68, 132.26, 131.53 (d, J=3.3 Hz), 129.71 (d, J=8.1 Hz), 128.34, 126.30, 121.91, 118.46, 115.94 (d, J=21.8 Hz), 100.67, 60.16, 56.34, 50.86, 42.03, 29.32.

$^{19}$F NMR (471 MHz, methanol-$d_4$) δ (ppm) −117.54.

HRMS calculated for $C_{22}H_{23}FN_5$ $[M+H]^+$ 376.1932, found 376.1933.

Preparative Example 130: 4-((4-(4-fluorophenyl)-5-(1H-pyrrolo[2,3-b]pyridin-4-yl)-1H-imidazol-1-yl)methyl)isothiazole

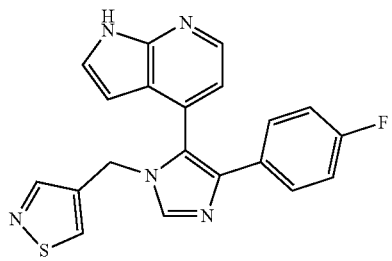 [SMILES: Fc1ccc(-c2ncn(Cc3cnsc3)c2-c2ccnc3[nH]ccc23)cc1]

The compound was prepared according to General procedure A using 1H-pyrrolo[2,3-b]pyridine-4-carbaldehyde, isothiazol-4-ylmethanamine hydrochloride, 1-fluoro-4-(isocyano(tosyl)methyl)benzene and $K_2CO_3$ and methanol (3 mL) instead of DMF. Reaction time: 1 hour 40 minutes for the formation of the imine, then additional 16 hours for the cyclization step. The solvent was evaporated and the residue was purified by column chromatography (hexane/acetone, 5:4) and then by preparative TLC 2 times (dichloromethane/methanol, 20:1; then pentane/propan-2-ol, 12:5). The product was obtained as a white solid (14 mg, 11%).

$^1$H NMR (500 MHz, methanol-$d_4$) δ (ppm) 8.30-8.23 (m, 2H), 8.09 (s, 1H), 7.94 (s, 1H), 7.36-7.28 (m, 3H), 7.01 (d, J=4.9 Hz, 1H), 6.90-6.83 (m, 2H), 5.98 (d, J=3.5 Hz, 1H), 5.38-5.21 (m, 2H).

$^{13}$C NMR (126 MHz, methanol-$d_4$) δ (ppm) 163.35 (d, J=245.2 Hz), 157.82, 149.68, 147.71, 143.58, 139.94, 136.13, 131.84, 131.36 (d, J=3.2 Hz), 129.64 (d, J=7.9 Hz), 128.38, 126.27, 121.90, 118.50, 115.98 (d, J=21.8 Hz), 100.49, 42.96.

$^{19}$F NMR (471 MHz, methanol-$d_4$) δ (ppm) −117.37.

HRMS calculated for $C_{20}H_{15}FN_5S$ $[M+H]^+$ 376.1027, found 376.1028.

Preparative Example 131: 4-(1-((2H-tetrazol-5-yl)methyl)-4-(4-fluorophenyl)-1H-imidazol-5-yl)-1H-pyrrolo[2,3-b]pyridine

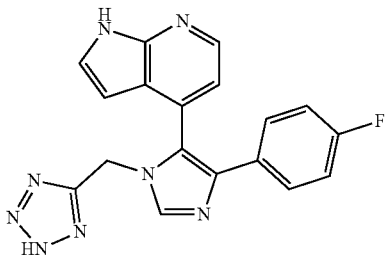 [SMILES: Fc1ccc(-c2ncn(Cc3nn[nH]n3)c2-c2ccnc3[nH]ccc23)cc1]

The compound was prepared according to General procedure A using 1H-pyrrolo[2,3-b]pyridine-4-carbaldehyde, (2H-tetrazol-5-yl)methanamine, 1-fluoro-4-(isocyano(tosyl)methyl)benzene and $K_2CO_3$. Reaction time: 2 hours for the formation of the imine, then additional 16 hours for the cyclization step. The solvent was evaporated and the residue was purified by column chromatography (THF/7 M $NH_3$ in methanol, 10:3). So obtained material was then recrystallized from a mixture of methanol/diethyl ether (1:10). The product was obtained as a white solid (99 mg, 64%).

$^1$H NMR (500 MHz, methanol-$d_4$) δ (ppm) 8.23 (d, J=4.9 Hz, 1H), 7.94 (s, 1H), 7.36-7.26 (m, 3H), 7.04 (d, J=4.9 Hz, 1H), 6.91-6.80 (m 2H), 6.06 (d, J=3.5 Hz, 1H), 5.40-5.17 (m 2H).
$^{13}$C NMR (126 MHz, methanol-$d_4$) δ (ppm) 163.27 (d, J=244.8 Hz), 149.66, 143.47, 139.90, 139.31, 131.64 (d, J=1.9 Hz), 129.96, 129.74 (d, J=8.1 Hz), 128.02, 126.71, 122.04, 118.80, 115.87 (d, J=21.8 Hz), 100.84, 41.81.
$^{19}$F NMR (471 MHz, methanol-$d_4$) δ (ppm) -117.70.
HRMS calculated for $C_{18}H_{14}FN_8$ [M+H]$^+$ 361.1320, found 361.1323.

Preparative Example 132: 2-(4-(4-fluorophenyl-5-(1H-pyrrolo[2,3-b]pyridin-4-yl-1H-imidazol-1-yl)-1-(pyrrolidin-1-yl)ethan-1-one

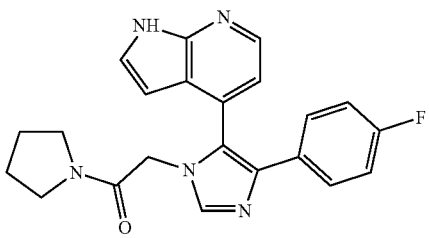 [SMILES: O=C(Cn1cnc(-c2ccc(F)cc2)c1-c1ccnc2[nH]ccc12)N1CCCC1]

The compound was prepared according to General procedure A using 1H-pyrrolo[2,3-b]pyridine-4-carbaldehyde, 2-amino-1-(pyrrolidin-1-yl)ethan-1-one, 1-fluoro-4-(isocyano(tosyl)methyl)benzene and $K_2CO_3$. Reaction time: 2 hours for the formation of the imine, then additional 16 hours for the cyclization step. The solvent was evaporated and the residue was purified by column chromatography (THF/7 M $NH_3$ in methanol, 10:3). So obtained material was then recrystallized from a mixture of methanol/diethyl ether (1:10). The product was obtained as a white solid (99 mg, 64%).

$^1$H NMR (500 MHz, methanol-$d_4$) δ (ppm) 8.28 (d, J=4.9 Hz, 1H), 7.92 (s, 1H), 7.40 (d, J=3.5 Hz, 1H), 7.38-7.28 (m, 2H), 7.06 (d, J=4.9 Hz, 1H), 6.92-6.84 (m, 2H), 6.13 (d, J=3.5 Hz, 1H), 4.80-4.76 (m, 1H), 4.67-4.59 (m, 1H), 3.27-3.18 (m, 2H), 3.02-2.90 (m, 2H), 1.82-1.64 (m, 4H).
$^{13}$C NMR (126 MHz, methanol-$d_4$) δ (ppm) 166.91, 163.31 (d, J=245.1 Hz), 149.77, 143.63, 141.15, 139.01, 131.79, 131.53 (d, J=3.2 Hz), 129.61 (d, J=7.9 Hz), 128.24, 126.73, 122.05, 118.77, 115.97 (d, J=21.7 Hz), 100.89, 48.06, 47.27, 46.81, 26.76, 24.85.
$^{19}$F NMR (471 MHz, methanol-$d_4$) δ (ppm) -117.56.
HRMS calculated for $C_{22}H_{21}FN_5O$ [M+H]$^+$ 390.1725, found 390.1728.

Preparative Example 133: 2-(4-(4-fluorophenyl-5-(1H-pyrrolo[2,3-b]pyridin-4-yl-1H-imidazol-1-yl)-N,N-dimethylacetamide

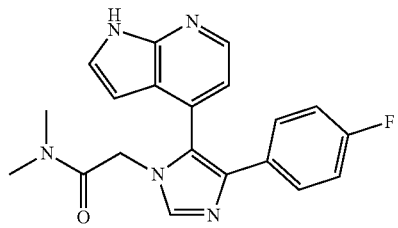 [SMILES: CN(C)C(=O)Cn1cnc(-c2ccc(F)cc2)c1-c1ccnc2[nH]ccc12]

The compound was prepared according to General procedure A using 1H-pyrrolo[2,3-b]pyridine-4-carbaldehyde, 2-amino-N,N-dimethylacetamide, 1-fluoro-4-(isocyano(tosyl)methyl)benzene and $K_2CO_3$. Reaction time: 2 hours for the formation of the imine, then additional 16 hours for the cyclization step. The solvent was evaporated and the residue was purified by column chromatography (dichloromethane/ethanol, 10:1). So obtained material was then recrystallized from a mixture of methanol/diethyl ether (1:10). The product was obtained as a white solid (77 mg, 56%).

$^1$H NMR (500 MHz, methanol-$d_4$) δ (ppm) 8.27 (d, J=4.9 Hz, 1H), 7.89 (s, 1H), 7.38 (d, J=3.5 Hz, 1H), 7.36-7.29 (m, 2H), 7.04 (d, J=5.0 Hz, 1H), 6.92-6.84 (m, 2H), 6.11 (d, J=3.5 Hz, 1H), 4.92 (d, J=16.7 Hz, 1H), 4.71 (d, J=16.7 Hz, 1H), 2.81 (s, 3H), 2.73 (s, 3H).
$^{13}$C NMR (126 MHz, methanol-$d_4$) δ (ppm) 168.69, 163.30 (d, J=244.9 Hz), 149.78, 143.57, 141.20, 138.98, 131.72, 131.59 (d, J=3.1 Hz), 129.68 (d, J=8.1 Hz), 128.16, 126.92, 121.96, 118.60, 115.94 (d, J=21.8 Hz), 100.90, 47.34, 36.44, 36.10.
$^{19}$F NMR (471 MHz, methanol-$d_4$) δ (ppm) -117.60.
HRMS calculated for $C_{20}H_{19}FN_5O$ [M+H]$^+$ 364.1568, found 364.1571.

Preparative Example 134: 3-bromo-4-(1-cyclohexyl-4-(4-fluorophenyl)-1H-imidazol-5-yl)-1H-pyrrolo[2,3-b]pyridine

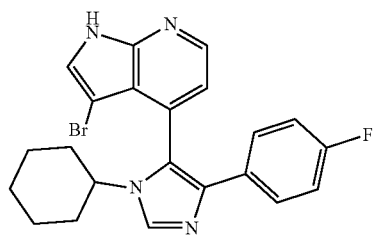 [SMILES: Fc1ccc(-c2ncn(C3CCCCC3)c2-c2ccnc3[nH]cc(Br)c23)cc1]

To a cold solution (−78° C.) of 4-(1-cyclohexyl-4-(4-fluorophenyl)-1H-imidazol-5-yl)-1H-pyrrolo[2,3-b]pyridine (148 mg; 0.411 mmol) in tetrahydrofuran (20 mL) were added 1,2-bis(dimethylamino)ethane (TMEDA; 0.185 mL; 143 mg; 1.23 mmol), then dropwise 2.5 M solution of n-BuLi in hexane (0.411 mL; 1.028 mmol) and the resulting mixture was stirred at −78° C. for 60 minutes. Then, a solution of bromine (98.5 mg; 0.617 mmol) in tetrahydrofuran (3 mL) was added and the resulting mixture was stirred at −78° C. for 40 minutes. A saturated aqueous solution of $NH_4Cl$ (15 mL) and solution of $Na_2S_2O_3$ (0.50 g) in water (15 mL) were added and the mixture was extracted with ethyl acetate (2×25 mL). The combined organic extracts were dried over $MgSO_4$, filtered, and the solvent was evaporated in vacuo. The residue was purified by column chromatography (dichloromethane/acetone, 5:1). So obtained material was triturated with $Et_2O$. The product was obtained as a white solid (27 mg, 15%).

$^1$H NMR (500 MHz, methanol-$d_4$) δ (ppm) 8.38 (d, J=4.8 Hz, 1H), 8.01 (s, 1H), 7.54 (s, 1H), 7.30-7.23 (m, 2H), 7.13 (d, J=4.8 Hz, 1H), 6.87-6.83 (m, 2H), 3.52-3.46 (m, 1H), 2.15-2.11 (m, 1H), 1.99-1.95 (m, 1H), 1.89-1.83 (m, 1H), 1.81-1.71 (m, 2H), 1.68-1.62 (m, 1H), 1.62-1.57 (m, 1H), 1.24-1.17 (m 1H), 1.14-1.02 (m 2H).

$^{13}$C NMR (126 MHz, methanol-$d_4$) δ (ppm) 163.16 (d, J=244.7 Hz), 148.69, 144.94, 139.37, 135.79, 132.66, 131.81, 129.47 (d, J=8.0 Hz), 128.48, 123.93, 120.90, 119.60, 115.84 (d, J=21.6 Hz), 88.18, 57.21, 36.18, 34.35, 26.71, 26.53, 26.16.

$^{19}$F NMR (471 MHz, methanol-$d_4$) δ (ppm) −117.96.

HRMS calculated for $C_{22}H_{21}BrFN_4$ [M+H]$^+$ 361.1823, found 361.1827.

Preparative Example 135: 4-(2-bromo-1-cyclohexyl-4-(4-fluorophenyl)-1H-imidazol-5-yl)-1H-pyrrolo[2,3-b]pyridine

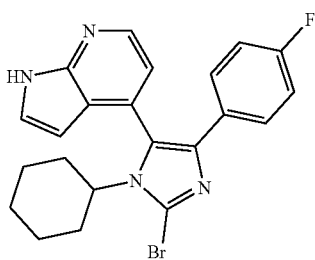 [SMILES: Fc1ccc(-c2nc(Br)n(C3CCCCC3)c2-c2ccnc3[nH]ccc23)cc1]

To a cold solution (−78° C.) of 4-(1-cyclohexyl-4-(4-fluorophenyl)-1H-imidazol-5-yl)-1H-pyrrolo[2,3-b]pyridine (66 mg; 0.183 mmol) in tetrahydrofuran (11 mL) were added 1,2-bis(dimethylamino)ethane (TMEDA; 0.0824 mL; 63.8 mg; 0.549 mmol), then dropwise 1.33 M solution of n-BuLi in hexane (0.372 mL; 0.494 mmol) and the resulting mixture was stirred at −78° C. for 60 minutes. Then, a solution of bromotrichloromethane (61.7 mg; 0.311 mmol) in tetrahydrofuran (2 mL) was added and the resulting mixture was stirred at −78° C. for 60 minutes and then at 25° C. for 30 minutes. A saturated aqueous solution of $NH_4Cl$ (20 mL) was added and the mixture was extracted with ethyl acetate (3×25 mL). The combined organic extracts were dried over $MgSO_4$, filtered, and the solvent was evaporated in vacuo. The residue was purified by column chromatography 2 times (hexane/ethyl acetate, 1:1; then hexane/acetone, 3:1). The product was obtained as a white solid (24 mg, 30%).

$^1$H NMR (300 MHz, CDCl$_3$) δ (ppm) 10.18 (s, 1H), 8.42 (s, 1H), 7.41 (d, J=3.6 Hz, 1H), 7.26-7.18 (m, 2H), 7.10 (d, J=4.9 Hz, 1H), 6.79 (t, J=8.8 Hz, 2H), 6.27 (d, J=3.5 Hz, 1H), 3.96-3.71 (m, 1H), 2.33-2.13 (m, 1H), 2.13-1.89 (m, 1H), 1.89-1.67 (m, 4H), 1.64-1.51 (m, 1H), 1.18-0.94 (m, 3H).

$^{13}$C NMR (126 MHz, CDCl$_3$) δ (ppm) 162.03 (d, J=246.4 Hz), 147.68, 141.79, 139.51, 129.53, 129.50, 128.28 (d, J=7.9 Hz), 127.01, 115.22 (d, J=21.6 Hz), 100.95, 31.53, 26.18, 26.12, 24.98.

$^{19}$F NMR (471 MHz, methanol-$d_4$) δ (ppm) −115.17.

HRMS calculated for $C_{22}H_{21}BrFN_4$ [M+H]$^+$ 439.0928, found 439.0925.

Preparative Example 136: 4-(1-cyclohexyl-4-(4-fluorophenyl)-2-(methylthio)-1H-imidazol-5-yl)-1H-pyrrolo[2,3-b]pyridine

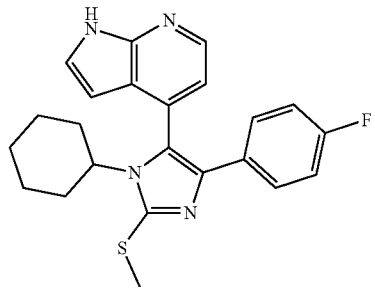 [SMILES: CSc1nc(-c2ccc(F)cc2)c(-c2ccnc3[nH]ccc23)n1C1CCCCC1]

To a solution of 4-(2-bromo-1-cyclohexyl-4-(4-fluorophenyl)-1H-imidazol-5-yl)-1H-pyrrolo[2,3-b]pyridine (66 mg; 0.183 mmol) in DMF (1.5 mL) was added sodium methanethiolate (80.0 mg, 1.14 mmol)) and the resulting mixture was stirred at 90° C. for 16 hours. Ethyl acetate (40 mL) was added and the mixture was washed with an aqueous solution of LiCl (10% w/w, 20 mL) and then with water (25 mL). The organic part was dried over $MgSO_4$, filtered, and the solvent was evaporated in vacuo. The residue was purified by column chromatography two times (dichloromethane/acetone, 20:1; then hexane/ethyl acetate, 4:3). The product was obtained as a beige solid (6 mg, 26%).

$^1$H NMR (300 MHz, CDCl$_3$) δ (ppm) 9.84 (s, 1H), 8.41 (d, J=5.0 Hz, 1H), 7.36-7.29 (m, 2H), 7.05 (d, J=5.0 Hz, 1H), 6.85-6.74 (m, 2H), 6.26 (d, J=3.2 Hz, 1H), 3.76 (s, 1H), 2.30-2.13 (m, 1H), 2.14-1.95 (m, 1H), 1.83-1.72 (m, 4H), 1.62-1.49 (m, 1H), 1.17-0.98 (m, 3H).

HRMS calculated for $C_{23}H_{24}FN_4S$ [M+H]$^+$ 407.1700, found 407.1703.

Preparative Example 137: 4-methylbenzenesulfinic acid

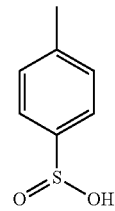

To sodium 4-methylbenzenesulfinate (2.23 g, 12.52 mmol) was added water (17 mL) and the mixture was stirred for 15 minutes. Then 2-methoxy-2-methylpropane (5 mL) and concentrated HCl (1.04 mL) were added and the resulting mixture was stirred for 15 minutes. The organic phase was separated, diluted with toluene (10 mL) and concentrated in vacuo to the volume of approx. 5 mL. The precipitate was collected by filttation, washed with hexane (2×10 mL) and dried in vacuo. The product was obtained as an off-white solid (1.43 g, 73%). So obtained material was used directly in the next step.

Preparative Example 138: N-((3-chloro-4-fluorophenyl)(tosyl)methyl)formamide

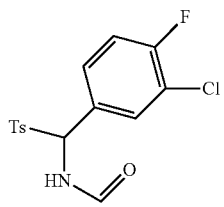 [SMILES: Cc1ccc(S(=O)(=O)C(NC=O)c2ccc(F)c(Cl)c2)cc1]

To a solution of 4-methylbenzenesulfinic acid (1005 mg, 6.44 mmol) in toluene/acetonitrile (1.5+1.5 mL) were added formamide (427 µL, 10.7 mmol), 3-chloro-4-fluorobenzaldehyde (680 mg, 4.29 mmol) and chlorotrimethylsilane (598 µL, 4.72 mmol) and the mixture was stirred at 50° C. for 12 hours. Then, water (3 mL) and 2-methoxy-2-methylpropane (4 mL) were added and the mixture was stirred at 0° C. (ice bath) for 15 minutes. The precipitate was collected by filtration, washed with water (10 mL) and dried in vacuo. The product was obtained as a white solid (701 mg, 48%).

NMR shifts for major rotamer:
$^1$H NMR (500 MHz, DMSO-$d_6$) δ (ppm) 9.75 (d, J=10.6 Hz, 1H), 7.97 (s, 1H), 7.87-7.83 (m, 1H), 7.76-7.70 (m, 2H), 7.63-7.59 (m, 1H), 7.49-7.42 (m, 3H), 6.54 (d, J=10.5 Hz, 1H), 2.42 (s, 3H).
$^{19}$F NMR (471 MHz, DMSO-$d_6$) δ (ppm) −114.98.

NMR is in agreement with the published data. (patent: US2016/0257690 Å1)

Preparative Example 139: 2-chloro-1-fluoro-4-(isocyano(tosyl)methyl)benzene

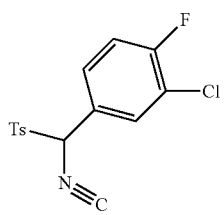

To a solution of N-((3-chloro-4-fluorophenyl)(tosyl) methyl)formamide (653 mg, 1.92 mmol) in THF (11 mL) was added POCl$_3$ (763 mg, 4.98 mmol) and the mixture was stirred for 30 minutes at 25° C. Then, 2,6-lutidine (1.79 mL, 15.3 mmol) was added dropwise at 0° C. and the resulting mixture was stirred at 25° C. for 18 hours. Ethyl acetate (50 mL) was added and the organic phase was washed with a saturated aqueous solution of NaHCO$_3$ (30 mL) and then by a solution of K$_2$CO$_3$ (3.3 g) in water (50 mL). The organic phase was dried over MgSO$_4$, filtered, and the solvent was evaporated in vacuo. So obtained crude product was directly used in the next step (cyclization).

Preparative Example 140:4-(1-benzyl-4-(3-chloro-4-fluorophenyl)-1H-imidazol-5-yl)-1H-pyrrolo[2,3-b]pyridine

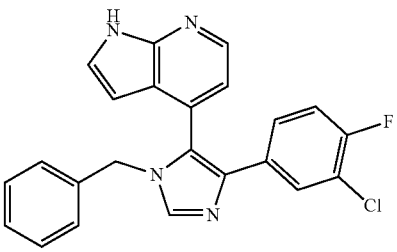 [SMILES: Fc1ccc(-c2ncn(Cc3ccccc3)c2-c2ccnc3[nH]ccc23)cc1Cl]

The compound was prepared according to General procedure A using 1H-pyrrolo[2,3-b]pyridine-4-carbaldehyde (140 mg, 0.958 mmol), benzylamine (256 mg, 2.40 mmol), 2-chloro-1-fluoro-4-(isocyano(tosyl)methyl)benzene (prepared as described above, used as crude) and K$_2$CO$_3$ (199 mg, 1.44 mmol). Reaction time: 100 minutes for the formation of the imine, then additional 16 hours for the cyclization step. The residue obtained after the workup was purified by column chromatography two times (hexane/ethyl acetate, 10:4; then pentane/acetone, 3:1) and then by recrystallization from chloroform. The product was obtained as a white solid (147 mg, 38%).

$^1$H NMR (500 MHz, CDCl$_3$) δ (ppm) 10.03 (s, 1H), 8.34 (s, 1H), 7.78 (s, 1H), 7.65 (dd, J=7.2, 2.1 Hz, 1H), 7.34 (d, J=3.5 Hz, 1H), 7.24-7.19 (m, 3H), 7.18-7.11 (m, 1H), 6.94 (d, J=4.7 Hz, 1H), 6.91-6.81 (m, 3H), 6.14 (d, J=3.5 Hz, 1H), 5.05 (d, J=15.4 Hz, 1H), 4.93 (d, J=15.4 Hz, 1H).
$^{13}$C NMR (126 MHz, CDCl$_3$) δ (ppm) 157.18 (d, J=248.5 Hz), 148.61, 142.87, 138.40, 137.63, 135.84, 131.30 (d, J=3.8 Hz), 130.90, 129.01, 128.86, 128.35, 127.16, 126.55, 126.22 (d, J=7.0 Hz), 125.62, 121.04 (d, J=17.8 Hz), 120.59, 117.97, 116.38 (d, J=21.2 Hz), 100.70, 49.66.
$^{19}$F NMR (471 MHz, CDCl$_3$) δ (ppm) −118.09.
HRMS calculated for C$_{23}$H$_{17}$ClFN$_4$ [M+H]$^+$ 403.1120, found 403.1116.

Preparative Example 141: 4-(4-(3-chloro-4-fluorophenyl)-1-((1-methylpiperidin-4-yl)methyl)-1H-imidazol-5-yl)-1H-pyrrolo[2,3-b]pyridine

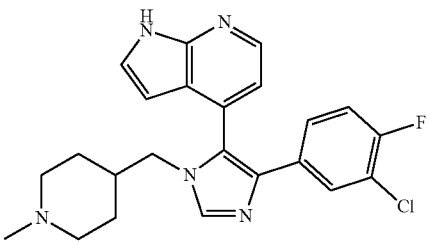 [SMILES: CN1CCC(Cn2cnc(-c3ccc(F)c(Cl)c3)c2-c2ccnc3[nH]ccc23)CC1]

The compound was prepared according to General procedure A using 1H-pyrrolo[2,3-b]pyridine-4-carbaldehyde (140 mg, 0.958 mmol), (1-methylpiperidin-4-yl)methanamine (246 mg, 1.92 mmol, 2 eq.), 2-chloro-1-fluoro-4-(isocyano(tosyl)methyl)benzene (prepared as described above, used as crude) and K₂CO₃ (265 mg, 1.92 mmol, 2 eq.). Reaction time: 100 minutes for the formation of the imine, then additional 20 hours for the cyclization step. The residue obtained after the workup was purified by column chromatography (dichloromethane/7 M NH₃ in methanol, gradient from 1:0 to 13:1) and then by recrystallization from hexane/Et₂O/acetone (1+1+03 mL). The product was obtained as a beige solid (226 mg, 38%).

$^1$H NMR (500 MHz, methanol-d$_4$) δ (ppm) 8.34 (d, J=4.9 Hz, 1H), 7.95 (s, 1H), 7.48-7.39 (m, 2H), 7.18-7.12 (m, 2H), 7.03-6.93 (m, 1H), 6.09 (d, J=3.5 Hz, 1H), 4.02-3.89 (m, 1H), 3.89-3.74 (m, 1H), 2.76-2.60 (m, 2H), 1.78-1.63 (m, 2H), 1.33 (s, 3H), 1.13-0.95 (m, 2H).

$^{13}$C NMR (126 MHz, methanol-d$_4$) δ (ppm) 158.23 (d, J=247.6 Hz), 149.85, 143.80, 140.45, 138.07, 132.92 (d, J=3.9 Hz), 131.84, 129.71, 128.57, 127.77 (d, J=7.1 Hz), 127.17, 121.82, 121.57 (d, J=18.1 Hz), 118.46, 117.35 (d, J=21.4 Hz), 100.53, 52.04, 46.10, 37.33, 30.13, 30.02.

$^{19}$F NMR (471 MHz, CDCl3) δ (ppm) −120.41−−120.49 (m).

HRMS calculated for C₂₃H₂₄ClFN₅ [M+H]⁺ 424.1699, found 424.1700.

Preparative Example 142: (1R,4r)-4-(4-(3-chloro-4-fluorophenyl)-5-(1H-pyrrolo[2,3-b]pyridin-4-yl)-1H-imidazol-1-yl)-N,N-dimethylcyclohexan-1-amine

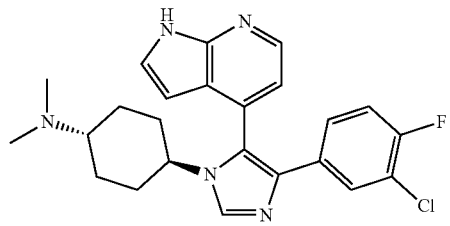 [SMILES: CN(C)[C@H]1CC[C@H](n2cnc(-c3ccc(F)c(Cl)c3)c2-c2ccnc3[nH]ccc23)CC1]

The compound was prepared according to General procedure A using 1H-pyrrolo[2,3-b]pyridine-4-carbaldehyde (140 mg, 0.958 mmol), (1r,4r)-N',N'-dimethylcyclohexane-1,4-diamine hydrochloride (342 mg, 1.92 mmol, 2 eq.), 2-chloro-1-fluoro-4-(isocyano(tosyl)methyl)benzene (prepared as described above, used as crude) and K₂CO₃ (530 mg, 3.83 mmol, 4 eq.). Reaction time: 2 hours for the formation of the imine, then additional 20 hours for the cyclization step. The residue obtained after the workup was purified by column chromatography (dichloromethane/7 M NH₃ in methanol, gradient from 1:0 to 12:1) and then by recrystallization from hexane/acetone. The product was obtained as a white solid (140 mg, 33%).

$^1$H NMR (500 MHz, methanol-d$_4$) δ (ppm) 8.37 (d, J=4.9 Hz, 1H), 8.09 (s, 1H), 7.46 (d, J=3.5 Hz, 1H), 7.43 (dd, J=7.2, 2.2 Hz, 1H), 7.17-7.10 (m, 2H), 7.02-6.94 (m, 1H), 6.14 (d, J=3.5 Hz, 1H), 3.80-3.69 (m, 1H), 2.40-2.30 (m, 1H), 2.23 (s, 6H), 2.18-2.12 (m, 1H), 2.05-1.83 (m, 5H), 1.26-1.03 (m, 2H).

$^{13}$C NMR (126 MHz, methanol-d$_4$) δ (ppm) 158.19 (d, J=247.6 Hz), 149.83, 143.86, 137.42, 136.91, 132.95 (d, J=3.9 Hz), 131.86, 129.65, 128.63, 127.70 (d, J=7.2 Hz), 126.76, 122.21, 121.55 (d, J=17.9 Hz), 118.72, 117.33 (d, J=21.5 Hz), 100.29, 63.51, 56.44, 41.62, 34.07, 33.71, 28.18, 28.15.

$^{19}$F NMR (471 MHz, methanol-d$_4$) δ (ppm) −120.59.

HRMS calculated for C₂₄H₂₆ClFN₅ [M+H]⁺ 438.1855, found 438.1859.

Preparative Example 143: 4-(4-(3-chloro-4-fluorophenyl)-1-((1-methyl-1H-pyrazol-3-yl)methyl)-1H-imidazol-5-yl)-1H-pyrrolo[2,3-b]pyridine

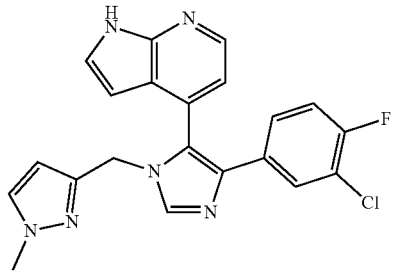 [SMILES: Cn1ccc(Cn2cnc(-c3ccc(F)c(Cl)c3)c2-c2ccnc3[nH]ccc23)n1]

The compound was prepared according to General procedure A using 1H-pyrrolo[2,3-b]pyridine-4-carbaldehyde (140 mg, 0.958 mmol), (1-methyl-1H-pyrazol-3-yl)methanamine (213 mg, 1.92 mmol, 2 eq.), 2-chloro-1-fluoro-4-(isocyano(tosyl)methyl)benzene (prepared as described above, used as crude) and K₂CO₃ (265 mg, 1.92 mmol, 2 eq.). Reaction time: 100 minutes for the formation of the imine, then additional 20 hours for the cyclization step. The residue obtained after the workup was purified by column chromatography (hexane/acetone, gradient from 4:1 to 1:4). The product was obtained as a white solid (207 mg, 53%).

$^1$H NMR (500 MHz, Methanol-d$_4$) δ (ppm) 8.28 (d, J=5.0 Hz, 1H), 7.97 (s, 1H), 7.45 (dd, J=7.2, 2.2 Hz, 1H), 7.38 (d, J=3.5 Hz, 1H), 7.33 (d, J=2.3 Hz, 1H), 7.20-7.13 (m, 1H), 7.07 (d, J=5.0 Hz, 1H), 7.01-6.94 (m, 1H), 6.03 (d, J=3.5 Hz, 1H), 5.74 (d, J=2.3 Hz, 1H), 5.12 (d, J=15.4 Hz, 1H), 5.02 (d, J=15.3 Hz, 1H), 3.71 (s, 3H).

$^{13}$C NMR (126 MHz, Methanol-d$_4$) δ (ppm) 158.23 (d, J=247.9 Hz), 149.74, 148.53, 143.55, 140.10, 138.02, 133.09, 132.93 (d, J=3.8 Hz), 131.55, 129.67, 128.24, 127.74 (d, J=7.2 Hz), 127.16, 121.93, 121.65, 121.50, 118.63, 117.35 (d, J=21.6 Hz), 105.55, 100.68, 44.22, 38.71.

HRMS calculated for C₂₁H₁₇ClFN₆ [M+H]⁺ 407.1182, found 407.1184.

Preparative Example 144: 3-chloro-4-(1-cyclohexyl-4-(4-fluorophenyl)-1H-imidazol-5-yl)-1H-pyrrolo[2,3-b]pyridine

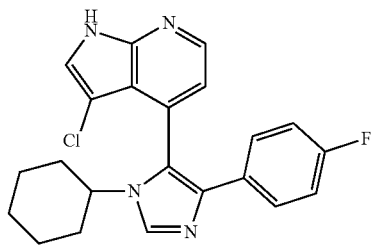 [SMILES: Fc1ccc(-c2ncn(C3CCCCC3)c2-c2ccnc3[nH]cc(Cl)c23)cc1]

To a cold solution (−78° C.) of 4-(1-cyclohexyl-4-(4-fluorophenyl)-1H-imidazol-5-yl)-1H-pyrrolo[2,3-b]pyridine (35 mg; 0.0971 mmol) in tetrahydrofuran (10 mL) were added 1,2-bis(dimethylamino)ethane (TMEDA; 0.0437 mL; 33.9 mg; 0.291 mmol), then dropwise 1.6 M solution of n-BuLi in hexane (0.152 mL; 0.243 mmol) and the resulting mixture was stirred at −78° C. for 45 minutes. Then, a solution of 1-chloropyrrolidine-2,5-dione (NCS, 19.5 mg; 0.146 mmol) in tetrahydrofuran (2.5 mL) was added and the resulting mixture was stirred at −78° C. for 15 minutes. A saturated aqueous solution of NH$_4$Cl (5 mL), and solution of Na$_2$S$_2$O$_3$ (0.20 g) in water (15 mL) were added and the mixture was extracted with ethyl acetate (2×25 mL). The combined organic extracts were dried over MgSO$_4$, filtered, and the solvent was evaporated in vacuo. The residue was purified by column chromatography two times (hexane/acetone, 5:1; then hexane/ethyl acetate, 1:2). So obtained material was dissolved in ethyl acetate (7 mL) and washed with water (5×5 mL). The organic phase was dried over MgSO$_4$, filtered, and the solvent was evaporated in vacuo. The product was obtained as a white solid (8 mg; 21%).

$^1$H NMR (500 MHz, methanol-d$_4$) δ (ppm) 8.38 (d, J=4.8 Hz, 1H), 8.01 (s, 1H), 7.48 (s, 1H), 7.30-7.24 (m, 2H), 7.11 (d, J=4.8 Hz, 1H), 6.88-6.84 (m, 2H), 3.58-3.51 (m, 1H), 2.12-2.04 (m, 1H), 2.01-1.94 (m, 1H), 1.88-1.82 (m, 1H), 1.81-1.72 (m, 2H), 1.70-1.64 (m, 1H), 1.65-1.57 (m, 2H), 1.24-1.18 (m 2H).

$^{13}$C NMR (126 MHz, methanol-d$_4$) δ (ppm) 163.19 (d, J=244.8 Hz), 148.31, 145.11, 139.19, 135.95, 132.11, 131.64, 131.37, 129.57 (d, J=7.9 Hz), 125.79, 125.06, 124.39, 120.76, 119.11, 118.42, 115.86 (d, J=21.5 Hz), 104.45, 57.23, 36.04, 34.39, 26.71, 26.54, 26.14.

HRMS calculated for C$_{22}$H$_{21}$ClFN$_4$ [M+H]$^+$ 395.1433, found 395.1430.

Preparative Example 145: 4-(4-(4-fluorophenyl)-1-(1-(1-methyl-1H-pyrazol-4-yl)ethyl-1H-imidazol-5-yl)-1H-pyrrolo[2,3-b]pyridine

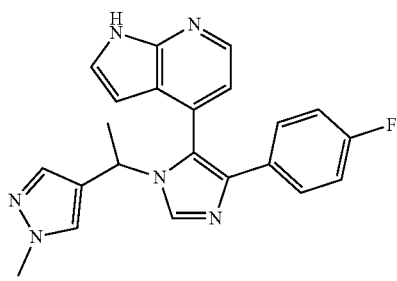 [SMILES: CC(c1cnn(C)c1)n1cnc(-c2ccc(F)cc2)c1-c1ccnc2[nH]ccc12]

The compound was prepared according to General procedure A using 1H-pyrrolo[2,3-b]pyridine-4-carbaldehyde, 1-(1-methyl-1H-pyrazol-4-yl)ethan-1-amine (2 eq.), 1-fluoro-4-(isocyano(tosyl)methyl) benzene and K$_2$CO$_3$. Reaction time: 3.5 hours for the formation of the imine, then additional 14 hours for the cyclization step. The residue obtained after the workup was purified by column chromatography (hexane/acetone, 1:2). So obtained material was then recrystallized from a mixture of hexane/acetone (1:1) and the crystals were washed with acetone (0.5 mL). The product was obtained as a white solid (28 mg, 14%).

Mixture of 2 rotamers:

$^1$H NMR (500 MHz, methanol-d$_4$) δ (ppm) 8.31 (dd, J=20.7, 4.9 Hz, 2H), 7.97 (d, J=14.5 Hz, 2H), 7.43 (d, J=5.8 Hz, 2H), 7.38 (d, J=3.5 Hz, 1H), 7.34-7.25 (m, 6H), 7.16 (s, 1H), 7.13 (d, J=4.9 Hz, 1H), 7.05 (d, J=4.9 Hz, 1H), 6.86 (d, J=3.3 Hz, 4H), 6.16 (d, J=3.5 Hz, 1H), 6.04 (d, J=3.5 Hz, 1H), 5.21 (dd, J=18.7, 7.0 Hz, 2H), 3.81 (s, 3H), 3.74 (s, 3H), 1.74 (dd, J=19.3, 7.0 Hz, 6H).

$^{13}$C NMR (126 MHz, methanol-d$_4$) δ (ppm) 163.27 (d, J=246.5 Hz), 149.76, 143.68, 143.66, 139.19, 139.10, 138.12, 138.05, 137.22, 137.17, 132.34, 132.25, 131.54, 131.52, 130.38, 130.32, 129.67, 129.61, 129.55, 128.41, 128.27, 126.15, 124.28, 123.89, 122.37, 119.02, 118.83, 116.01, 115.83, 100.63, 100.44, 38.89, 38.80, 22.69, 22.64.

$^{19}$F NMR (471 MHz, methanol-d$_4$) δ (ppm) −117.64.

HRMS calculated for C$_{22}$H$_2$FN$_6$ [M+H]$^+$ 387.1728, found 387.1725.

Preparative Example 146: 4-(4-(4-fluorophenyl)-1-(1-phenylethyl)-1H-imidazol-5-yl)-1H-pyrrolo[2,3-b]pyridine

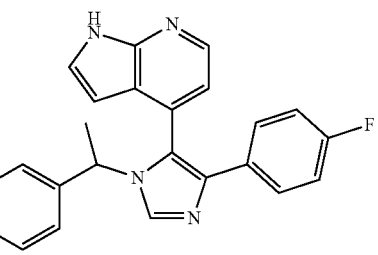

The compound was prepared according to General procedure A using 1H-pyrrolo[2,3-b]pyridine-4-carbaldehyde, 1-phenylethan-1-amine, 1-fluoro-4-(isocyano(tosyl)methyl) benzene and K$_2$CO$_3$. Reaction time: 3.5 hours for the formation of the imine, then additional 14 hours for the cyclization step. The residue obtained after the workup was purified by column chromatography (hexane/acetone, 2:1) and then by preparative TLC (ethyl acetate/dichloromethane, 3:1). The product was obtained as a white solid (7 mg, 6%).

Mixture of 2 rotamers:

$^1$H NMR (500 MHz, methanol-d$_4$) δ (ppm) 8.44-8.29 (m, 3H), 8.06 (d, J=4.8 Hz, 1H), 7.50 (d, J=3.5 Hz, 1H), 7.37-7.27 (m, 4H), 7.27-7.17 (m, 4H), 7.15 (d, J=3.5 Hz, 1H), 7.13-7.03 (m, 3H), 6.95-6.79 (m, 8H), 6.57 (d, J=4.9 Hz, 1H), 6.29 (d, J=3.5 Hz, 1H), 5.67 (d, J=3.5 Hz, 1H), 5.37 (q, J=7.1 Hz, 1H), 5.20 (q, J=7.1 Hz, 1H), 1.93-1.81 (m, 6H).

$^{13}$C NMR (126 MHz, methanol-d$_4$) δ (ppm) 163.54 (d, J=245.7 Hz), 163.51 (d, J=245.7 Hz), 149.65, 149.54, 143.40, 143.37, 142.77, 141.94, 138.28, 138.16, 136.99, 131.37, 130.22, 130.09, 129.95, 129.87, 129.75, 129.69, 129.63, 129.05, 128.90, 128.69, 128.00, 127.18, 127.02, 126.96, 126.81, 122.33, 122.23, 119.28, 118.59, 116.21, 116.04, 116.03, 100.63, 100.26, 57.61, 57.50, 22.34, 22.09.

$^{19}$F NMR (471 MHz, methanol-d$_4$) δ (ppm) −116.60, −116.64.

HRMS calculated for C$_{24}$H$_{20}$FN$_4$ [M+H]$^+$ 383.1667, found 383.1666.

Preparative Example 147: 4-(1-cyclohexyl-4-(4-fluorophenyl)-1H-imidazol-5-yl)-5-fluoro-1H-pyrrolo[2,3-b]pyridine

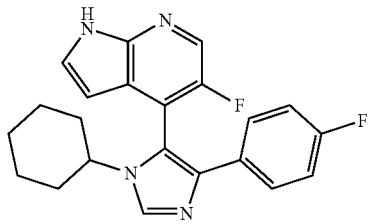 [SMILES: Fc1ccc(-c2ncn(C3CCCCC3)c2-c2c(F)cnc3[nH]ccc23)cc1]

The compound was prepared according to General procedure A using 5-fluoro-1H-pyrrolo[2,3-b]pyridine-4-carbaldehyde (1 eq.), cyclohexanamine, 1-fluoro-4-(isocyano(tosyl)methyl)benzene and $K_2CO_3$. Methanol (2.5 mL) was used as a solvent instead of DMF. Reaction time: 4.5 hours for the formation of the imine, then additional 14 hours for the cyclization step. The solvent was evaporated and the residue was purified by column chromatography (hexane/acetone, 2:1). The product was obtained as a white solid (17 mg, 17%).

$^1$H NMR (500 MHz, methanol-$d_4$) δ (ppm) 8.30 (s, 1H), 8.11 (s, 1H), 7.49 (s, 1H), 7.32 (dt, 2H), 6.91 (dt, J=8.9 Hz, 2H), 6.08 (s, 1H), 3.65 (tt, J=11.8, 3.7 Hz, 1H), 2.09 (d, J=12.6 Hz, 1H), 1.96-1.85 (m, 2H), 1.85-1.80 (m, 1H), 1.80-1.73 (m, 2H), 1.67-1.61 (m, 1H), 1.32-1.20 (m, 2H), 1.16-1.06 (m, 1H).

$^{13}$C NMR (126 MHz, methanol-$d_4$) δ (ppm) 161.94 (d, J=245.1 Hz), 154.05, 152.13, 145.17, 138.53, 136.00, 131.00, 130.75, 130.11, 130.09, 129.17, 127.94 (d, J=7.9 Hz), 121.05, 121.03, 118.21, 116.93, 116.80, 114.60 (d, J=21.8 Hz), 99.18, 99.14, 56.02, 34.13, 33.77, 25.30, 25.24, 24.66.

$^{19}$F NMR (471 MHz, methanol-$d_4$) δ (ppm) –117.45, 142.39.

HRMS calculated for $C_{22}H_{21}F_2N_4$ [M+H]$^+$ 379.1729, found 379.1727.

Preparative Example 148: 3-fluoro-1H-pyrrolo[2,3-b]pyridine-4-carbaldehyde

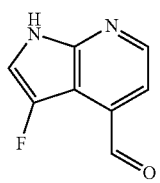

To a solution of 1H-pyrrolo[2,3-b]pyridine-4-carbaldehyde in DMF (1.20 mL) was added AcOH (0.40 mL) and the mixture was stirred at 40° C. while a solution of SelectFluor (177 mg, 0.697 mmol, CAS: 140681-55-6) in DMF (0.8 mL) was added over 1 hour. Then, the resulting mixture was stirred for additional 70 minutes at 40° C. Ethyl acetate (40 mL) was added and the organic phase was washed with saturated aqueous solution of $NaHCO_3$ (2×25 mL) and then with 10% aqueous solution of LiCl (15 mL). The organic extract was dried over $MgSO_4$, filtered, and the solvent was evaporated in vacuo. The residue obtained after the workup was purified by column chromatography (hexane/acetone, 3:1). The product was obtained as a yellow solid (9 mg, 14%, ca. 85% purity). So obtained material was used in the next step (cyclization).

$^1$H NMR (500 MHz, acetone-$d_6$) δ (ppm) 10.58 (d, J=2.8 Hz, 1H), 8.51 (d, J=4.9 Hz, 1H), 7.66 (d, J=2.3 Hz, 1H), 7.62 (d, J=4.9 Hz, 1H).

$^{13}$C NMR (126 MHz, acetone-$d_6$) δ (ppm) 190.99 (d, J=10.8 Hz), 144.95, 144.82, 143.01, 134.51 (d, J=5.6 Hz), 115.07, 112.63 (d, J=27.6 Hz), 107.64 (d, J=14.6 Hz).

$^{19}$F NMR (471 MHz, acetone-$d_6$) δ (ppm) –165.78.

Preparative Example 149: 4-(1-cyclohexyl-4-(4-fluorophenyl)-1H-imidazol-5-yl)-3-fluoro-1H-pyrrolo[2,3-b]pyridine

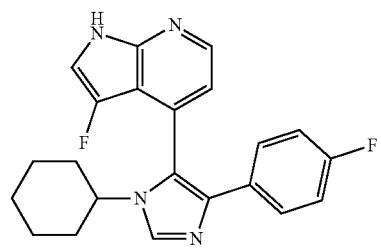 [SMILES: Fc1ccc(-c2ncn(C3CCCCC3)c2-c2ccnc3[nH]cc(F)c23)cc1]

The compound was prepared according to General procedure A using 3-fluoro-1H-pyrrolo[2,3-b]pyridine-4-carbaldehyde (27 mg, 0.165 mmol, prepared as described above), cyclohexanamine (40.9 mg, 0.413 mmol), 1-fluoro-4-(isocyano(tosyl)methyl)benzene (47.6 mg, 0.165 mmol) and $K_2CO_3$ (34 mg, 0.248 mmol). Reaction time: 2 hours for the formation of the imine, then additional 20 hours for the cyclization step. The residue obtained after the workup was purified by column chromatography (hexane/acetone, 10:4). The product was obtained as a white solid (19 mg, 31%).

$^1$H NMR (500 MHz, $CDCl_3$) δ 9.32 (s, 1H), 8.43 (d, 1H), 7.93 (s, 1H), 7.36 (dd, J=8.8, 5.4 Hz, 2H), 7.14 (d, J=2.2 Hz, 1H), 7.05 (d, J=4.8 Hz, 1H), 6.89-6.81 (m, 2H), 3.72-3.66 (m, 1H), 2.13-2.07 (m, 1H), 2.00-1.94 (m, 1H), 1.85-1.75 (m, 2H), 1.74-1.67 (m, 1H), 1.66-1.62 (m, 1H), 1.60-1.53 (m, 1H), 1.20-1.08 (m, 3H).

$^{13}$C NMR (126 MHz, $CDCl_3$) δ (ppm) 162.06 (d, J=246.2 Hz), 144.96, 144.69, 143.06 (d, J=248.2 Hz), 137.72, 134.59, 129.66 (d, J=26.8 Hz), 128.59 (d, J=7.9 Hz), 123.42, 119.16, 115.34 (d, J=21.5 Hz), 109.51 (d, J=12.4 Hz), 108.97 (d, J=26.3 Hz), 55.95, 35.48, 33.78, 25.84, 25.65, 25.23.

$^{19}$F NMR (471 MHz, $CDCl_3$) δ (ppm) –115.32, –170.20.

HRMS calculated for $C_{22}H_{21}F_2N_4$ [M+H]$^+$ 379.1729, found 379.1727.

Preparative Example 150: 4-((4-(4-fluorophenyl)-5-(1H-pyrrolo[2,3-b]pyridin-4-yl)-1H-imidazol-1-yl)methyl)-1,3-dihydro-2H-imidazol-2-one

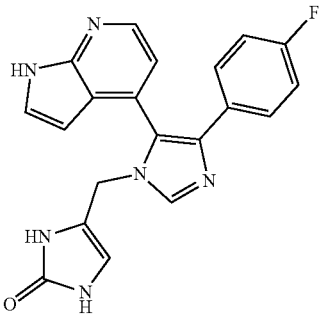 [SMILES: O=c1[nH]cc(Cn2cnc(-c3ccc(F)cc3)c2-c2ccnc3[nH]ccc23)[nH]1]

The compound was prepared according to General procedure A using 1H-pyrrolo[2,3-b]pyridine-4-carbaldehyde (150 mg, 1.03 mmol), 4-(aminomethyl)-1,3-dihydro-2H-imidazol-2-one dihydrochloride (318 mg, 1.71 mmol), 1-fluoro-4-(isocyano(tosyl)methyl)benzene (247 mg, 0.855 mmol) and $K_2CO_3$ [709 mg, 5.13 mmol (413 mg was added together with amine, 296 mg was added together with the TOSMIC reagent)]. Methanol (9.0 mL) was used as a solvent instead of DMF. Reaction time: 2 hours for the formation of the imine, then additional 18 hours for the cyclization step. The solvent was evaporated and the residue was purified by column chromatography two times (dichloromethane/methanol, gradient from 10:1 to 4:1; then acetone/methanol, 5:1). So obtained material was triturated with methanol (0.3 mL). The product was obtained as a yellow solid (58 mg, 18%).

$^1$H NMR (500 MHz, methanol-$d_6$) δ (ppm) 8.29 (d, J=5.0 Hz, 1H), 7.93 (s, 1H), 7.38 (d, J=3.5 Hz, 1H), 7.36-7.27 (m, 2H), 7.08 (d, J=5.0 Hz, 1H), 6.96-6.82 (m, 2H), 6.08 (d, J=3.5 Hz, 1H), 5.59 (s, 1H), 4.95-4.84 (m, 2H).

$^{13}$C NMR (126 MHz, DMSO-$d_6$) δ (ppm) 163.34 (d, J=245.2 Hz), 156.81, 149.66, 143.52, 139.81, 139.70, 131.95, 131.42, 131.39, 129.67 (d, J=7.9 Hz), 128.26, 126.31, 122.06, 118.63, 118.55, 115.97 (d, J=21.8 Hz), 109.80, 100.62, 42.06.

$^{19}$F NMR (471 MHz, DMSO-$d_6$) δ (ppm) −118.20.

HRMS calculated for $C_{20}H_{16}FN_6O$ [M+H]$^+$ 375.1364, found 375.1366.

Preparative Example 151: 4-(4-(4-fluorophenyl-1-((2-methyl-2H-tetrazol-5-yl)methyl)-1H-imidazol-5-yl)-1H-pyrrolo[2,3-b]pyridine

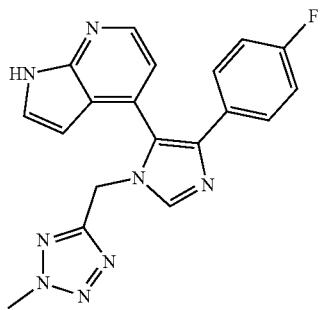 [SMILES: Cn1nnc(Cn2cnc(-c3ccc(F)cc3)c2-c2ccnc3[nH]ccc23)n1]

The compound was prepared according to General procedure A using 1H-pyrrolo[2,3-b]pyridine-4-carbaldehyde (50 mg, 342 mmol), (2-methyl-2H-tetrazol-5-yl)methanamine hydrochloride (102 mg, 0.684 mmol), 1-fluoro-4-(isocyano(tosyl)methyl)benzene (98.9 mg, 0.342 mmol) and $K_2CO_3$ (189 mg, 1.37 mmol). Methanol (2.0 mL) was used as a solvent instead of DMF. Reaction time: 3.5 hours for the formation of the imine, then additional 21 hours for the cyclization step. The solvent was evaporated and the residue was purified by column chromatography (hexane/acetone, 2:3). So obtained material was recrystallized from methanol/$Et_2O$ (0.3+0.8 mL). The product was obtained as a white solid (16 mg, 13%).

$^1$H NMR (500 MHz, DMSO-$d_6$) δ (ppm) 11.78 (s, 1H), 8.26 (d, J=4.8 Hz, 1H), 8.07 (s, 1H), 7.46-7.39 (m, 1H), 7.38-7.29 (m, 2H), 7.03-6.93 (m, 3H), 5.88-5.81 (m, 1H), 5.41 (d, J=16.1 Hz, 1H), 5.27 (d, J=16.2 Hz, 1H), 4.17 (s, 3H).

$^{13}$C NMR (126 MHz, DMSO-$d_6$) δ (ppm) 162.01, 160.77 (d, J=243.0 Hz), 148.65, 142.68, 138.94, 137.00, 130.86 (d, J=2.9 Hz), 129.13, 127.46 (d, J=7.9 Hz), 127.01, 124.66, 119.29, 116.96, 114.92 (d, J=21.4 Hz), 98.72.

$^{19}$F NMR (471 MHz, DMSO-$d_6$) δ (ppm) −116.10.

HRMS calculated for $C_{19}H_{16}FN_8$ [M+H]$^+$ 375.1476, found 375.1473.

Preparative Example 152: 5-((4-(4-fluorophenyl)-5-(1H-pyrrolo[2,3-b]pyridin-4-yl)-1H-imidazol-1-yl)methyl)-2-methylthiazole

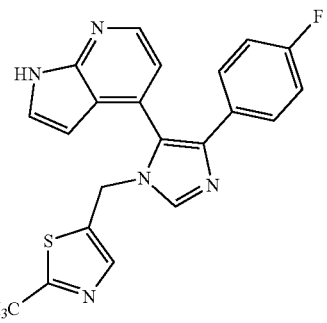

The compound was prepared according to General procedure A using 1H-pyrrolo[2,3-b]pyridine-4-carbaldehyde, (2-methylthiazol-5-yl)methanamine (2 eq.), 1-fluoro-4-(isocyano(tosyl)methyl)benzene and $K_2CO_3$. Reaction time: 2 hours for the formation of the imine, then additional 22 hours for the cyclization step. The residue obtained after the workup was purified by column chromatography (dichloromethane/acetone, 2:3). So obtained material was recrystallized from methanol/diethyl ether (0.2+0.5 mL). The product was obtained as a white solid (13 mg, 14%).

$^1$H NMR (500 MHz, methanol-$d_4$) δ (ppm) 8.29 (d, J=4.9 Hz, 1H), 8.05 (s, 1H), 7.36 (d, J=3.5 Hz, 1H), 7.32 (s, 2H), 7.07 (d, J=4.9 Hz, 1H), 6.94-6.83 (m, 3H), 6.00 (d, J=3.5 Hz, 1H), 5.41 (d, J=15.8 Hz, 1H), 5.31 (d, J=15.8 Hz, 1H), 2.50 (s, 3H).

$^{13}$C NMR (126 MHz, methanol-$d_4$) δ (ppm) 169.58, 163.38 (d, J=245.4 Hz), 149.74, 143.62, 141.65, 139.99, 139.75, 135.05, 131.64, 131.30 (d, J=3.2 Hz), 129.68 (d, J=8.0 Hz), 128.27, 126.20, 121.91, 118.55, 115.99 (d, J=21.9 Hz), 100.60, 42.68, 18.66.

$^{19}$F NMR (471 MHz, methanol-d$_4$) δ (ppm) −117.31.
HRMS calculated for C$_{21}$H$_{17}$FN$_5$S [M+H]$^+$ 390.1183, found 390.1181.

Preparative Example 153: 4-(1-((1H-1,2,3-triazol-4-yl)methyl)-4-(4-fluorophenyl)-1H-imidazol-5-yl)-1H-pyrrolo[2,3-b]pyridine

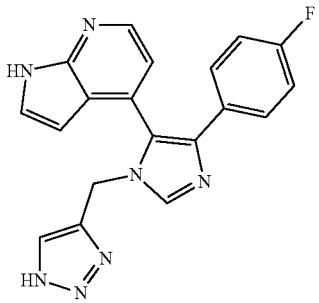 [SMILES: Fc1ccc(-c2ncn(Cc3c[nH]nn3)c2-c2ccnc3[nH]ccc23)cc1]

The compound was prepared according to General procedure A using 1H-pyrrolo[2,3-b]pyridine-4-carbaldehyde, (1H-1,2,3-triazol-4-yl)methanamine hydrochloride (2 eq.), 1-fluoro-4-(isocyano(tosyl)methyl)benzene and K$_2$CO$_3$ (4 eq.). Reaction time: 2 hours for the formation of the imine, then additional 20 hours for the cyclization step. The residue obtained after the workup was purified by column chromatography (dichloromethane/methanol, 10:1) and then by preparative TLC (dichloromethane/methanol, 9:1). The product was obtained as a white solid (10 mg, 10%).

$^1$H NMR (500 MHz, methanol-d$_4$) δ (ppm) 8.27 (d, J=4.9 Hz, 1H), 8.03 (s, 1H), 7.35 (d, J=3.5 Hz, 1H), 7.34-7.28 (m, 2H), 7.20 (s, 1H), 7.05 (d, J=4.9 Hz, 1H), 6.90-6.82 (m, 2H), 6.02 (d, J=3.5 Hz, 1H), 5.31 (d, J=15.6 Hz, 1H), 5.21 (d, J=15.7 Hz, 1H).
$^{13}$C NMR (126 MHz, methanol-d$_4$) δ (ppm) 163.32 (d, J=245.1 Hz), 149.69, 143.55, 139.96, 139.65, 131.78, 131.46, 131.43, 129.67 (d, J=8.1 Hz), 128.22, 126.37, 121.95, 118.63, 115.95 (d, J=21.8 Hz), 100.64, 41.64.
$^{19}$F NMR (471 MHz, methanol-d$_4$) δ (ppm) −117.45.
HRMS calculated for C$_{19}$H$_{15}$FN$_7$ [M+H]$^+$ 360.1367, found 360.1366.

Preparative Example 154: 4-(1-((1H-1,2,4-triazol-3-yl)methyl)-4-(4-fluorophenyl)-1H-imidazol-5-yl)-1H-pyrrolo[2,3-b]pyridine

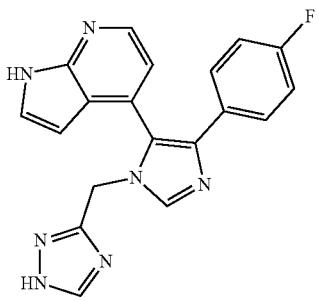 [SMILES: Fc1ccc(-c2ncn(Cc3nc[nH]n3)c2-c2ccnc3[nH]ccc23)cc1]

The compound was prepared according to General procedure A using 1H-pyrrolo[2,3-b]pyridine-4-carbaldehyde, (1H-1,2,4-triazol-3-yl)methanamine hydrochloride (2 eq.), 1-fluoro-4-(isocyano(tosyl)methyl)benzene and K$_2$CO$_3$ (4 eq.). Reaction time: 2 hours for the formation of the imine, then additional 21 hours for the cyclization step. The residue obtained after the workup was purified by column chromatography (dichloromethane/methanol, 8:1). The product was obtained as a white solid (36 mg, 35%).

$^1$H NMR (500 MHz, methanol-d$_4$) δ (ppm) 8.27-8.18 (m, 2H), 8.04 (s, 1H), 7.37-7.25 (m, 3H), 7.01 (d, J=5.0 Hz, 1H), 6.93-6.83 (m, 2H), 6.03 (d, J=3.5 Hz, 1H), 5.29 (d, J=15.6 Hz, 1H), 5.16 (d, J=15.8 Hz, 1H).
$^{13}$C NMR (126 MHz, methanol-d$_4$) δ (ppm) 163.31 (d, J=244.9 Hz), 149.65, 143.44, 140.29, 139.46, 131.61, 131.51 (d, J=3.3 Hz), 129.65 (d, J=8.1 Hz), 128.05, 126.59, 122.02, 118.64, 115.94 (d, J=21.8 Hz), 100.69, 43.65.
$^{19}$F NMR (471 MHz, methanol-d$_4$) δ (ppm) −117.52.
HRMS calculated for C$_{19}$H$_{15}$FN$_7$ [M+H]$^+$ 360.1367, found 360.1365.

Preparative Example 155: 4-(2-chloro-1-cyclohexyl-4-(4-fluorophenyl)-1H-imidazol-5-yl)-1H-pyrrolo[2,3-b]pyridine

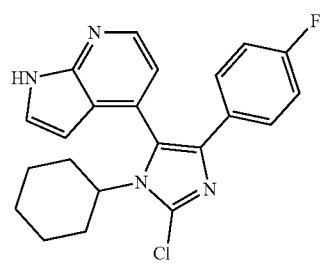 [SMILES: Fc1ccc(-c2nc(Cl)n(C3CCCCC3)c2-c2ccnc3[nH]ccc23)cc1]

To a cold solution (−78° C.) of 4-(1-cyclohexyl-4-(4-fluorophenyl)-1H-imidazol-5-yl)-1H-pyrrolo[2,3-b]pyridine (91 mg; 0.252 mmol) in tetrahydrofuran (10 mL) were added 1,2-bis(dimethylamino)ethane (TMEDA; 0.113 mL; 88.0 mg; 0.757 mmol), then dropwise 2.5 M solution of n-BuLi in hexane (0.272 mL; 0.680 mmol) and the resulting mixture was stirred at −78° C. for 60 minutes. Then, a solution of perchloroethane (101 mg; 0.428 mmol) in tetrahydrofuran (2.0 mL) was added and the resulting mixture was stirred at −78° C. for 60 minutes. A saturated aqueous solution of NH$_4$Cl (5 mL) and water (25 mL) were added and the mixture was extracted with ethyl acetate (2×30 mL). The combined organic extracts were dried over MgSO$_4$, filtered, and the solvent was evaporated in vacuo. The residue was purified by column chromatography (hexane/acetone, 2:1). The product was obtained as a white solid (54 mg; 54%).

$^1$H NMR (300 MHz, CDCl$_3$) δ (ppm) 10.19 (s, 1H), 8.43 (d, J=5.0 Hz, 1H), 7.40 (d, J=3.6 Hz, 1H), 7.31-7.20 (m, 3H), 7.07 (d, J=5.0 Hz, 1H), 6.87-6.72 (m, 2H), 6.26 (d, J=3.5 Hz, 1H), 3.86-3.60 (m, 1H), 2.32-2.15 (m, 1H), 2.15-1.94 (m, 1H), 1.89-1.69 (m, 4H), 1.65-1.51 (m, 1H), 1.17-0.94 (m, 3H).
$^{13}$C NMR (126 MHz, CDCl$_3$) δ (ppm) 162.01 (d, J=246.4 Hz), 147.89, 141.97, 137.68, 132.55, 132.23, 129.56 (d, J=3.2 Hz), 128.25 (d, J=8.1 Hz), 127.00, 125.86, 121.93, 118.57, 115.23 (d, J=21.5 Hz), 100.81, 57.98, 31.38, 26.10, 26.03, 24.99.
$^{19}$F NMR (471 MHz, CDCl$_3$) δ (ppm) −115.25.
HRMS calculated for C$_{22}$H$_{21}$ClFN$_4$ [M+H]$^+$ 395.1433, found 395.1433.

Preparative Example 156: 4-(1-((1H-imidazol-2-yl)methyl)-4-(4-fluorophenyl)-1H-imidazol-5-yl)-1H-pyrrolo[2,3-b]pyridine

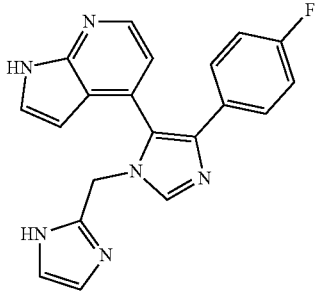 [SMILES: Fc1ccc(-c2ncn(Cc3ncc[nH]3)c2-c2ccnc3[nH]ccc23)cc1]

The compound was prepared according to General procedure A using 1H-pyrrolo[2,3-b]pyridine-4-carbaldehyde (50 mg, 0.342 mmol, 1 eq.), (1H-imidazol-2-yl)methanamine dihydrochloride (91.4 mg, 0.684 mmol, 2 eq.), 1-fluoro-4-(isocyano(tosyl)methyl)benzene (98.9 mg, 0.342 mmol) and $K_2CO_3$ (284 mg, 2.05 mmol, 6 eq.). Reaction time: 2 hours for the formation of the imine, then additional 18 hours for the cyclization step. The residue obtained after the workup was purified by column chromatography (dichloromethane/methanol, gradient from 8:1 to 6:1). So obtained material was triturated with methanol (1 mL), the solid was dried in vacuo. The product was obtained as a white solid (12 mg, 10%).

$^1$H NMR (500 MHz, methanol-$d_4$) δ (ppm) 8.21 (d, J=5.0 Hz, 1H), 7.96 (s, 1H), 7.37-7.27 (m, 3H), 6.91 (d, J=4.9 Hz, 1H), 6.90-6.76 (m, 4H), 6.03 (d, J=3.5 Hz, 1H), 5.24 (d, J=15.6 Hz, 1H), 5.09 (d, J=15.8 Hz, 1H).

$^{13}$C NMR (126 MHz, methanol-$d_4$) δ (ppm) 163.33 (d, J=245.2 Hz), 149.64, 143.56, 143.45, 140.00, 139.66, 131.47, 129.62 (d, J=8.1 Hz), 128.13, 126.43, 122.01, 118.51, 115.94 (d, J=21.7 Hz), 100.63, 43.93.

$^{19}$F NMR (471 MHz, methanol-$d_4$) δ (ppm) −117.46.

HRMS calculated for $C_{20}H_{16}FN_6$ [M+H]$^+$ 359.1415, found 359.1417.

Preparative Example 157: (1R,3R)-3-(4-(4-fluorophenyl)-5-(1H-pyrrolo[2,3-b]pyridin-4-yl)-1H-imidazol-1-yl)cyclohexan-1-ol

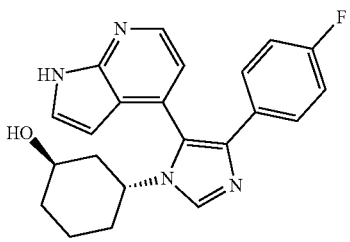 [SMILES: O[C@@H]1CCC[C@@H](n2cnc(-c3ccc(F)cc3)c2-c2ccnc3[nH]ccc23)C1]

The compound was prepared according to General procedure A using 1H-pyrrolo[2,3-b]pyridine-4-carbaldehyde (50 mg, 0.342 mmol, 1 eq.), (1R,3R)-3-aminocyclohexan-1-ol hydrochloride (104 mg, 0.684 mmol, 2 eq.), 1-fluoro-4-(isocyano(tosyl)methyl)benzene (98.9 mg, 0.342 mmol) and $K_2CO_3$ (165 mg, 1.20 mmol, 3.5 eq.). Reaction time: 2 hours for the formation of the imine, then additional 18 hours for the cyclization step. The residue obtained after the workup was purified by column chromatography (dichloromethane/acetone, 1:2). The product was obtained as a beige solid (30 mg, 23%).

$^1$H NMR (500 MHz, acetone-$d_6$) δ (ppm) 10.92 (s, 1H), 8.37 (s, 1H), 7.95 (s, 1H), 7.51-7.35 (m, 3H), 7.11-7.03 (m, 1H), 6.89-6.80 (m, 2H), 6.14-6.08 (m, 1H), 4.25 (s, 1H), 4.14 (d, J=25.4 Hz, 1H), 2.10-1.98 (m, 3H), 1.94-1.71 (m, 2H), 1.71-1.41 (m, 5H).

$^{13}$C NMR (126 MHz, acetone-$d_6$) δ (ppm) 162.20 (d, J=242.9 Hz), 150.23, 144.16, 144.11, 136.15, 132.79, 131.99, 128.78, 128.75, 128.72, 128.69, 127.35 (d, J=9.0 Hz), 127.23, 127.16, 121.22, 118.59, 118.48, 115.36 (d, J=21.6 Hz), 100.60, 100.39, 66.40, 66.30, 50.93, 50.88, 41.73, 41.07, 35.56, 34.94, 32.37, 32.32, 20.44, 20.36.

$^{19}$F NMR (471 MHz, acetone-$d_6$) δ (ppm) −118.49.

HRMS calculated for $C_{22}H_{22}FN_4O$ [M+H]$^+$ 377.1772, found 377.1769.

Preparative Example 158: (1S,3S)-3-(4-(4-fluorophenyl)-5-(1H-pyrrolo[2,3-b]pyridin-4-yl)-1H-imidazol-1-yl)cyclohexan-1-ol

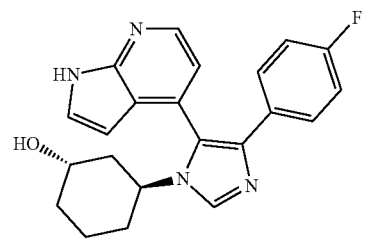 [SMILES: O[C@H]1CCC[C@H](n2cnc(-c3ccc(F)cc3)c2-c2ccnc3[nH]ccc23)C1]

The compound was prepared according to General procedure A using 1H-pyrrolo[2,3-b]pyridine-4-carbaldehyde (50 mg, 0.342 mmol, 1 eq.), (1S,3S)-3-aminocyclohexan-1-ol hydrochloride (104 mg, 0.684 mmol, 2 eq.), 1-fluoro-4-(isocyano(tosyl)methyl)benzene (98.9 mg, 0.342 mmol) and $K_2CO_3$ (165 mg, 1.20 mmol, 3.5 eq.). Reaction time: 2 hours for the formation of the imine, then additional 18 hours for the cyclization step. The residue obtained after the workup was purified by column chromatography (dichloromethane/acetone, 1:2). The product was obtained as a beige solid (22 mg, 17%).

$^1$H NMR (500 MHz, acetone-$d_6$) δ (ppm) 10.91 (s, 1H), 8.41-8.29 (m, 1H), 7.94 (s, 1H), 7.51-7.34 (m, 3H), 7.11-7.03 (m, 1H), 6.92-6.81 (m, 2H), 6.17-6.06 (m, 1H), 4.31-4.20 (m, 1H), 4.14 (d, J=25.3 Hz, 1H), 2.11-1.95 (m, 3H), 1.93-1.71 (m, 2H), 1.71-1.41 (m, 5H).

$^{13}$C NMR (126 MHz, acetone-$d_6$) δ (ppm) 162.20 (d, J=243.1 Hz), 150.23, 144.17, 144.12, 137.90, 136.15, 132.79, 131.99, 128.78, 128.75, 128.72, 128.69, 127.35 (d, J=9.0 Hz), 127.22, 125.42, 121.20, 118.59, 118.47, 115.36 (d, J=21.4 Hz), 100.60, 100.39, 66.40, 66.30, 50.92, 50.88, 41.72, 41.06, 35.56, 34.94, 32.37, 32.32, 31.98, 20.44, 20.36.

$^{19}$F NMR (471 MHz, acetone-$d_6$) δ (ppm) −118.49.

HRMS calculated for $C_{22}H_{22}FN_4O$ [M+H]$^+$ 377.1772, found 377.1774.

Preparative Example 159: 3-((4-(4-fluorophenyl)-5-(1H-pyrrolo[2,3-b]pyridin-4-yl)-1H-imidazol-1-yl)methyl)isoxazole

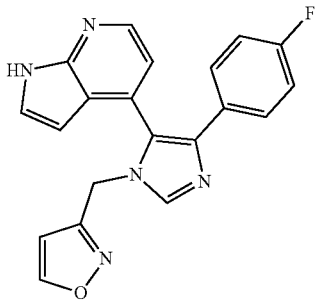 [SMILES: Fc1ccc(-c2ncn(Cc3ccon3)c2-c2ccnc3[nH]ccc23)cc1]

The compound was prepared according to General procedure A using 1H-pyrrolo[2,3-b]pyridine-4-carbaldehyde, isoxazol-3-ylmethanamine (2 eq.), 1-fluoro-4-(isocyano(tosyl)methyl)benzene and K$_2$CO. Reaction time: 2 hours for the formation of the imine, then additional 16 hours for the cyclization step. The solvent was evaporated and the residue was purified by column chromatography (hexane/acetone, gradient from 4:5 to 1:2). So obtained material was then recrystallized from diethyl ether and then purified by preparative TLC (ethyl acetate/acetone, 3:1). The product was obtained as a white solid (17 mg, 17%).

$^1$H NMR (500 MHz, methanol-d$_4$) δ (ppm) 8.47 (d, J=1.7 Hz, 1H), 8.26 (d, J=5.0 Hz, 1H), 8.06 (s, 1H), 7.38-7.27 (m, 3H), 7.04 (d, J=5.0 Hz, 1H), 6.93-6.82 (m, 2H), 6.08-6.03 (m, 2H), 5.34 (d, J=16.1 Hz, 1H), 5.20 (d, J=16.1 Hz, 1H).

$^{13}$C NMR (126 MHz, methanol-d$_4$) δ (ppm) 163.37 (d, J=245.2 Hz), 161.32, 160.39, 149.74, 143.57, 140.24, 139.78, 131.37, 131.33, 129.70 (d, J=8.0 Hz), 128.28, 126.55, 121.92, 118.61, 115.98 (d, J=21.8 Hz), 104.27, 100.64, 42.02.

$^{19}$F NMR (471 MHz, methanol-d$_4$) δ (ppm) −117.31.

HRMS calculated for C$_{20}$H$_{15}$FN$_5$O [M+H]$^+$ 360.1255, found 360.1252.

Preparative Example 160: 4-(4-(4-fluorophenyl)-1-((1-(trifluoromethyl)-1H-pyrazol-4-yl)methyl)-1H-imidazol-5-yl)-1H-pyrrolo[2,3-b]pyridine

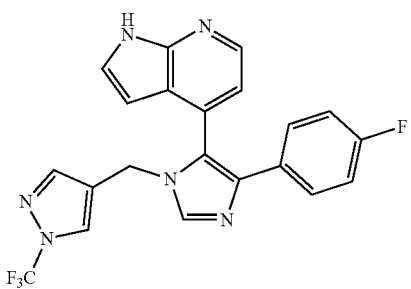 [SMILES: Fc1ccc(-c2ncn(Cc3cnn(C(F)(F)F)c3)c2-c2ccnc3[nH]ccc23)cc1]

The compound was prepared according to General procedure A using 1H-pyrrolo[2,3-b]pyridine-4-carbaldehyde, (1-(trifluoromethyl)-1H-pyrazol-4-yl)methanamine hydrochloride (2 eq.), 1-fluoro-4-(isocyano(tosyl)methyl)benzene and K$_2$CO$_3$ (3.5 eq.). Reaction time: 2 hours for the formation of the imine, then additional 16 hours for the cyclization step. The solvent was evaporated and the residue was purified by column chromatography (hexane/acetone, 10:8). So obtained material was then recrystallized from hexane/diethyl ether (1.5+1.5 mL). The product was obtained as a white solid (61 mg, 17%).

$^1$H NMR (500 MHz, methanol-d$_4$) δ (ppm) 8.30 (d, J=4.9 Hz, 1H), 8.05 (s, 1H), 7.49 (s, 1H), 7.40-7.29 (m, 4H), 7.08 (d, J=4.9 Hz, 1H), 6.92-6.82 (m, 2H), 5.96 (d, J=3.5 Hz, 1H), 5.19-5.05 (m, 2H).

$^{13}$C NMR (126 MHz, methanol-d$_4$) δ (ppm) 163.33 (d, J=245.2 Hz), 149.67, 144.05, 143.62, 139.93, 139.79, 131.99, 131.37 (d, J=3.3 Hz), 129.61 (d, J=8.0 Hz), 128.97, 128.39, 126.14, 121.96, 121.49, 119.11 (q, J=786.5, 261.9 Hz), 118.50, 115.97 (d, J=21.8 Hz), 100.44, 40.59.

$^{19}$F NMR (471 MHz, methanol-d$_4$) δ (ppm) −62.26, −117.40.

HRMS calculated for C$_{21}$H$_{15}$F$_4$N$_6$ [M+H]$^+$ 427.1289, found 427.1291.

Preparative Example 161: N-(2-(dimethylamino)ethyl)-2-(4-(4-fluorophenyl)-5-(1H-pyrrolo[2,3-b]pyridin-4-yl)-1H-imidazol-1-yl)acetamide

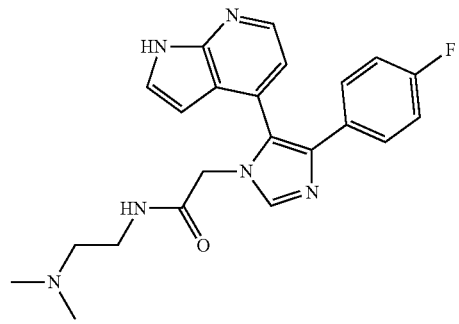 [SMILES: CN(C)CCNC(=O)Cn1cnc(-c2ccc(F)cc2)c1-c1ccnc2[nH]ccc12]

A mixture of ethyl 2-(4-(4-fluorophenyl)-5-(1H-pyrrolo[2,3-b]pyridin-4-yl)-1H-imidazol-1-yl)acetate (39 mg, 0.107 mmol) and N',N'-dimethylethane-1,2-diamine (220 µL, 2.08 mmol) was stirred in a pressure tube at 100° C. for 3.5 hours. Volatile compounds were evaporated and the residue was purified by column chromatography (dichloromethane/7 M NH$_3$ in methanol, 6:1) and then by preparative TLC (dichloromethane/7 M NH$_3$ in methanol, 6:1). The product was obtained as a beige solid (27 mg, 62%).

$^1$H NMR (500 MHz, methanol-d$_4$) δ (ppm) 8.28 (d, J=5.0 Hz, 1H), 7.95 (s, 1H), 7.37 (d, J=3.5 Hz, 1H), 7.35-7.29 (m, 2H), 7.08 (d, J=4.9 Hz, 1H), 6.91-6.82 (m, 2H), 6.10 (d, J=3.5 Hz, 1H), 4.69 (d, J=16.6 Hz, 1H), 4.54 (d, J=16.4 Hz, 1H), 3.19-3.06 (m, 2H), 2.20-2.08 (m, 8H).

$^{13}$C NMR (126 MHz, methanol-d$_4$) δ (ppm) 168.88, 163.28 (d, J=244.9 Hz), 149.75, 143.60, 141.10, 139.25, 131.59, 131.51 (d, J=3.2 Hz), 129.61 (d, J=8.1 Hz), 128.16, 126.65, 122.05, 118.68, 115.95 (d, J=21.8 Hz), 100.96, 58.75, 45.39, 37.98.

$^{19}$F NMR (471 MHz, methanol-d$_4$) δ (ppm) −117.44.

HRMS calculated for C$_{22}$H$_{24}$FN$_6$O [M+H]$^+$ 407.1990, found 407.1986.

Preparative Example 162: 2-(4-(4-fluorophenyl-5-(1H-pyrrolo[2,3-b]pyridin-4-yl)-1H-imidazol-1-yl-N-((4-methylthiazol-2-yl)methyl)acetamide

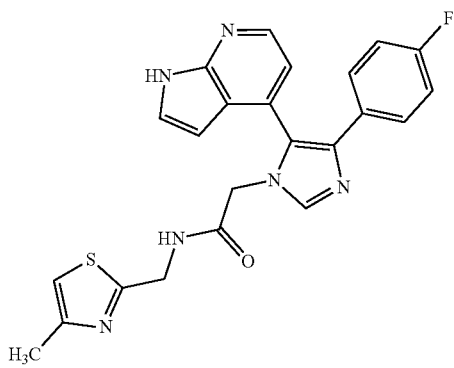 [SMILES: Cc1csc(CNC(=O)Cn2cnc(-c3ccc(F)cc3)c2-c2ccnc3[nH]ccc23)n1]

A mixture of ethyl 2-(4-(4-fluorophenyl)-5-(1H-pyrrolo[2,3-b]pyridin-4-yl)-1H-imidazol-1-yl)acetate (41 mg, 0.113 mmol) and (4-methylthiazol-2-yl)methanamine (112 mg, 0.874 mmol) was stirred in a pressure tube at 90° C. for 11 hours and then at 100° C. for 4 hours. Volatile compounds were evaporated and the residue was purified by column chromatography (acetone/methanol, 20:1). So obtained material was triturated with diethyl ether, the solid was dried in vacuo. The product was obtained as a beige solid (18 mg, 36%).

$^1$H NMR (500 MHz, methanol-$d_4$) δ (ppm) 8.22 (d, J=4.9 Hz, 1H), 7.96 (s, 1H), 7.35-7.30 (m, 3H), 7.04 (d, J=5.0 Hz, 1H), 6.98 (q, J=1.1 Hz, 1H), 6.91-6.85 (m, 2H), 6.07 (d, J=3.5 Hz, 1H), 4.83 (br s, 1H), 4.62 (d, J=16.9 Hz, 1H), 4.45 (d, J=9.5 Hz, 2H), 2.36 (d, J=1.0 Hz, 3H).

$^{13}$C NMR (126 MHz, methanol-$d_4$) δ (ppm) 169.33, 169.24, 163.32 (d, J=244.9 Hz), 153.34, 149.77, 147.92, 143.59, 141.15, 139.33, 131.50 (d, J=3.4 Hz), 131.45, 129.67 (d, J=7.9 Hz), 128.17, 126.72, 122.04, 118.62, 115.95 (d, J=21.8 Hz), 115.39, 100.95, 41.51, 16.62.

$^{19}$F NMR (471 MHz, methanol-$d_4$) δ (ppm) −117.49.

HRMS calculated for $C_{23}H_{20}FN_6OS[M+H]^+$ 447.1398, found 477.1402.

Preparative Example 163: ethyl 1-cyclohexyl-4-(4-fluorophenyl)-5-(1H-pyrrolo[2,3-b]pyridin-4-yl)-1H-imidazole-2-carboxylate

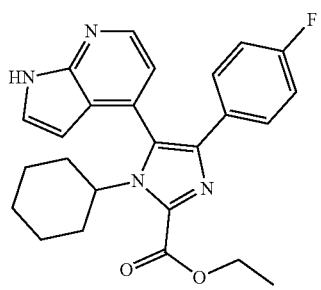 [SMILES: CCOC(=O)c1nc(-c2ccc(F)cc2)c(-c2ccnc3[nH]ccc23)n1C1CCCCC1]

To a cold solution (−78° C.) of 4-(1-cyclohexyl-4-(4-fluorophenyl)-1H-imidazol-5-yl)-1H-pyrrolo[2,3-b]pyridine (191 mg; 0.530 mmol) in tetrahydrofuran (30 mL) were added 1,2-bis(dimethylamino)ethane (0.318 mL; 246 mg; 2.12 mmol), then dropwise 1.2 M solution of n-BuLi in hexane (1.325 mL; 1.59 mmol) and the resulting mixture was stirred at −78° C. for 60 minutes. Then, a solution of ethyl chloroformate (230 mg; 2.12 mmol) in tetrahydrofuran (4.0 mL) was added dropwise and the resulting mixture was allowed to warm to −68° C. over 60 minutes. Then, EtOH (4 mL) and 21% solution of NaOEt in EtOH (0.80 mL) were added and the resulting mixture was stirred at 25° C. for 10 minutes. A saturated aqueous solution of NH$_4$Cl (10 mL) was added and the solvents were removed in vacuo. Water (30 mL) was added and the mixture was extracted with ethyl acetate (2×40 mL). The combined organic extracts were dried over MgSO$_4$, filtered, and the solvent was evaporated in vacuo. The residue was purified by column chromatography (hexane/acetone, 3:1). The product was obtained as a orange wax (120 mg, 52%).

$^1$H NMR (500 MHz, CDCl$_3$) δ (ppm) 10.69 (s, 1H), 8.45 (s, 1H), 7.40 (d, J=3.5 Hz, 1H), 7.32-7.27 (m, 2H), 7.11 (d, J=4.8 Hz, 1H), 6.80-6.74 (m, 2H), 6.19 (d, J=3.5 Hz, 1H), 4.55-4.46 (m, 2H), 4.45-4.36 (m, 1H), 2.19-2.14 (m, 1H), 2.05-1.94 (m, 1H), 1.89-1.83 (m, 1H), 1.80-1.64 (m, 3H), 1.54-1.50 (s, 1H), 1.48 (t, J=7.1 Hz, 3H), 1.14-1.00 (m 3H).

$^{13}$C NMR (126 MHz, CDCl$_3$) δ (ppm) 162.13 (d, J=246.3 Hz), 159.83, 148.69, 142.65, 139.17, 137.32, 132.34, 129.67 (d, J=3.3 Hz), 129.62, 128.84 (d, J=8.1 Hz), 126.87, 121.61, 118.62, 115.09 (d, J=21.5 Hz), 100.59, 62.02, 59.47, 32.05, 31.64, 26.26, 26.20, 24.87, 14.52.

$^{19}$F NMR (471 MHz, CDCl$_3$) δ (ppm) −115.17.

HRMS calculated for $C_{25}H_{26}FN_4O_2 [M+H]^+$ 433.2034, found 433.2038.

Preparative Example 164: 1-((4-(4-fluorophenyl)-5-(1H-pyrrolo[2,3-b]pyridin-4-yl)-1H-imidazol-1-yl)methyl)-N,N-dimethylcyclobutan-1-amine

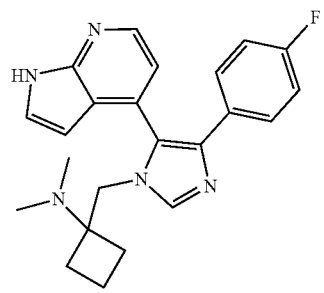 [SMILES: CN(C)C1(Cn2cnc(-c3ccc(F)cc3)c2-c2ccnc3[nH]ccc23)CCC1]

The compound was prepared according to General procedure A using 1H-pyrrolo[2,3-b]pyridine-4-carbaldehyde, 1-(aminomethyl)-N,N-dimethylcyclobutan-1-amine (2 eq.), 1-fluoro-4-(isocyano(tosyl) methyl)benzene and K$_2$CO$_3$. Reaction time: 2.5 hours for the formation of the imine, then additional 18 hours for the cyclization step. The residue obtained after the workup was purified by column chromatography (acetone/triethylamine, gradient from 100:1 to 100:2). So obtained material was then recrystallized from hexane/acetone (1.5+0.3 mL). The product was obtained as a white solid (30 mg, 27%).

$^1$H NMR (500 MHz, DMSO-$d_6$) δ (ppm) 11.80 (s, 1H), 8.34 (d, J=4.8 Hz, 1H), 8.02 (s, 1H), 7.50-7.44 (m, 1H), 7.36-7.28 (m, 2H), 7.10 (d, J=4.8 Hz, 1H), 7.01-6.93 (m, 2H), 6.00 (dd, J=3.5, 1.8 Hz, 1H), 4.07 (d, J=14.8 Hz, 1H), 3.93 (d, J=14.8 Hz, 1H), 1.92 (s, 6H), 1.87-1.80 (m, 2H), 1.45-1.33 (m, 3H), 0.96-0.88 (m, 1H).

$^{13}$C NMR (126 MHz, DMSO-d$_6$) δ (ppm) 160.65 (d, J=242.9 Hz), 148.84, 142.77, 139.10, 136.25, 131.25 (d, J=3.0 Hz), 130.21, 127.65 (d, J=7.8 Hz), 127.18, 125.44, 119.39, 117.33, 114.78 (d, J=21.1 Hz), 99.10, 63.33, 46.40, 37.11, 25.80, 25.65, 12.46.

$^{19}$F NMR (471 MHz, DMSO-d$_6$) δ (ppm) −116.51.

HRMS calculated for C$_{23}$H$_{25}$FN$_5$ [M+H]$^+$ 390.2089, found 390.2088.

Preparative Example 165: 1-cyclohexyl-4-(4-fluorophenyl)-5-(1H-pyrrolo[2,3-b]pyridin-4-yl)-1H-imidazole-2-carboxamide

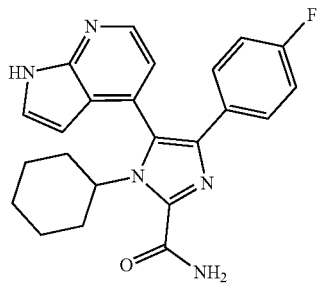 [SMILES: NC(=O)c1nc(-c2ccc(F)cc2)c(-c2ccnc3[nH]ccc23)n1C1CCCCC1]

A mixture of ethyl 1-cyclohexyl-4-(4-fluorophenyl)-5-(1H-pyrrolo[2,3-b]pyridin-4-yl)-1H-imidazole-2-carboxylate (32 mg, 0.0740 mmol) and 7 M solution of NH$_3$ in methanol (5 mL) was stirred in a pressure tube at 90° C. for 14 hours. The solvent was evaporated and the residue was purified by column chromatography (hexane/acetone, 10:4). So obtained material was then recrystallized from hexane/dichloromethane. The product was obtained as a white solid (13 mg, 43%).

$^1$H NMR (500 MHz, CDCl$_3$) δ (ppm) 10.29 (s, 1H), 8.44 (d, J=5.0 Hz, 1H), 7.63 (s, 1H), 7.40 (d, J=3.6 Hz, 1H), 7.30-7.21 (m, 2H), 7.13 (d, J=4.9 Hz, 1H), 6.83-6.77 (m, 2H), 6.24 (d, J=3.5 Hz, 1H), 5.61 (br s, 1H), 4.55 (br s, 1H), 2.90 (br s, 2H), 2.36-2.21 (m, 1H), 2.08 (br s, 1H), 1.87-1.80 (m, 1H), 1.78-1.64 (m, 3H), 1.53-1.47 (m, 1H), 1.17-1.02 (m, 3H).

$^{13}$C NMR (126 MHz, CDCl$_3$) δ (ppm) 162.14 (d, J=246.8 Hz), 161.10, 147.84, 141.93, 138.98, 137.74, 133.25, 129.58 (d, J=3.2 Hz), 129.02, 128.45 (d, J=8.0 Hz), 127.04, 122.06, 118.72, 115.31 (d, J=21.4 Hz), 100.90, 59.25, 32.06, 31.56, 26.22, 26.17, 24.82.

$^{19}$F NMR (471 MHz, CDCl$_3$) δ (ppm) −114.92.

HRMS calculated for C$_{23}$H$_{23}$FN$_5$O [M+H]$^+$ 404.1881, found 404.1884.

Preparative Example 166: (1-cyclohexyl-4-(4-fluorophenyl)-5-(1H-pyrrolo[2,3-b]pyridin-4-yl)-1H-imidazol-2-yl)methanol

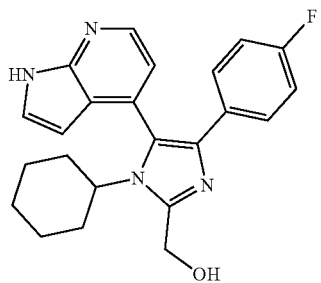 [SMILES: OCc1nc(-c2ccc(F)cc2)c(-c2ccnc3[nH]ccc23)n1C1CCCCC1]

To a cold solution (−78° C.) of ethyl 1-cyclohexyl-4-(4-fluorophenyl)-5-(1H-pyrrolo[2,3-b]pyridin-4-yl)-1H-imidazole-2-carboxylate (24 mg, 0.0555 mmol) in tetrahydrofuran (3.0 mL) was added 2 M solution of LiAlH$_4$ in tetrahydrofuran (41.6 µL; 0.0832 mmol) and the resulting mixture was stirred at 25° C. for 15 minutes. A saturated aqueous solution of NH$_4$Cl (5 mL) and water (15 mL) were added and the mixture was extracted with ethyl acetate (3×20 mL). The combined organic extracts were dried over MgSO$_4$, filtered, and the solvent was evaporated in vacuo. The residue was purified by column chromatography (hexane/acetone, 1:1). The product was obtained as a white solid (10 mg, 46%).

$^1$H NMR (500 MHz, methanol-d$_4$) δ (ppm) 8.30 (d, J=4.9 Hz, 1H), 7.42 (d, J=3.5 Hz, 1H), 7.26-7.17 (m, 2H), 7.11 (d, J=4.9 Hz, 1H), 6.84-6.74 (m, 2H), 6.16 (d, J=3.5 Hz, 1H), 4.84 (s, 2H), 4.12-4.03 (m, 1H), 2.04-1.93 (m, 2H), 1.90-1.84 (m, 1H), 1.78-1.62 (m, 3H), 1.57-1.50 (m, 1H), 1.20-1.09 (m, 2H), 0.99-0.88 (m, 1H).

$^{13}$C NMR (126 MHz, methanol-d$_4$) δ (ppm) 163.13 (d, J=244.6 Hz), 149.62, 148.79, 143.40, 137.99, 133.80, 131.62 (d, J=3.2 Hz), 129.62 (d, J=8.0 Hz), 128.33, 127.23, 123.33, 119.96, 115.74 (d, J=21.8 Hz), 100.73, 59.46, 57.98, 34.21, 33.96, 27.26, 27.14, 26.16.

$^{19}$F NMR (471 MHz, methanol-d$_4$) δ (ppm) −117.94.

HRMS calculated for C$_{23}$H$_{24}$FN$_4$O [M+H]$^+$ 391.1929, found 391.1931.

Preparative Example 167: 2-((4-(4-fluorophenyl)-5-(1H-pyrrolo[2,3-b]pyridin-4-yl)-1H-imidazol-1-yl)methyl)-4-methylmorpholine

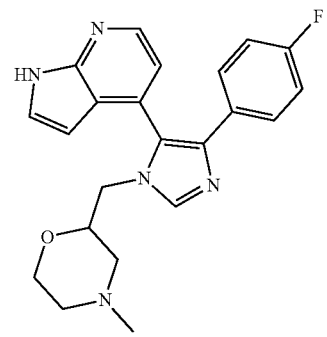 [SMILES: CN1CCOC(Cn2cnc(-c3ccc(F)cc3)c2-c2ccnc3[nH]ccc23)C1]

The compound was prepared according to General procedure A using 1H-pyrrolo[2,3-b]pyridine-4-carbaldehyde, (4-methylmorpholin-2-yl)methanamine (2 eq.), 1-fluoro-4-(isocyano(tosyl)methyl) benzene and K$_2$CO$_3$. Reaction time: 2 hours for the formation of the imine, then additional 16 hours for the cyclization step. The solvent was evaporated and the residue was purified by column chromatography (acetone/triethylamine/methanol, 100:5:2). So obtained material was then recrystallized from hexane/acetone (2.0+ 0.5 mL). The product was obtained as a white solid (44 mg, 33%).

$^1$H NMR (500 MHz, methanol-d$_4$) δ (ppm) 8.32 (apparent t, J=5.5 Hz, 1H), 7.91 (d, J=3.7 Hz, 1H), 7.45-7.36 (m, 1H), 7.36-7.24 (m, 2H), 7.13 (dd, J=34.1, 5.0 Hz, 1H), 6.98-6.83 (m, 2H), 6.09 (dd, J=31.9, 3.4 Hz, 1H), 4.13-4.03 (m, 1H), 4.02-3.91 (m, 1H), 3.82-3.74 (m, 1H), 3.52-3.43 (m, 1H), 3.41-3.34 (m, 1H), 2.55 (apparent t, J=10.0 Hz, 1H), 2.42-2.24 (m, 1H), 2.12 (d, J=6.7 Hz, 3H), 2.00 (apparent t, J=11.7 Hz, 1H), 1.61 (q, J=10.4 Hz, 1H).

$^{13}$C NMR (126 MHz, Methanol-d$_4$) δ (ppm) 163.29 (d, J=245.3 Hz), 149.82, 143.67, 140.69, 139.33, 132.03, 131.54, 129.77, 129.70, 129.64, 128.31, 126.55, 126.38, 122.03, 118.75, 118.63, 115.93 (d, J=21.8 Hz), 100.82, 100.71, 75.02, 67.20, 58.10, 55.32, 46.06.

$^{19}$F NMR (471 MHz, methanol-d$_4$) δ (ppm) −113.69 (d, J=13.9 Hz).

HRMS calculated for C$_{22}$H$_{23}$FN$_5$O[M+H]$^+$ 392.1881, found 392.1884.

Preparative Example 168: 6-((4-(4-fluorophenyl)-5-(1H-pyrrolo[2,3-b]pyridin-4-yl)-1H-imidazol-1-yl)methyl)morpholin-3-one

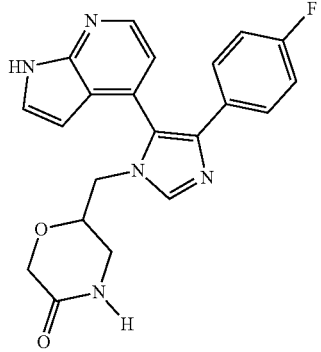 [SMILES: O=C1COC(Cn2cnc(-c3ccc(F)cc3)c2-c2ccnc3[nH]ccc23)CN1]

The compound was prepared according to General procedure A using 1H-pyrrolo[2,3-b]pyridine-4-carbaldehyde, 6-(aminomethyl)morpholin-3-one (2 eq.), 1-fluoro-4-(isocyano(tosyl)methyl)benzene and K$_2$CO$_3$. Reaction time: 2 hours for the formation of the imine, then additional 16 hours for the cyclization step. The residue obtained after the workup was purified by column chromatography (acetone). The product was obtained as a white solid (34 mg, 30%).

$^1$H NMR (500 MHz, methanol-d$_4$) δ (ppm) 8.33 (d, J=4.9 Hz, 1H), 7.98 (s, 1H), 7.41 (d, J=3.5 Hz, 1H), 7.34-7.27 (m, 2H), 7.15 (dd, J=15.6, 5.0 Hz, 1H), 6.91-6.84 (m, 2H), 6.11 (d, J=3.4 Hz, 1H), 4.22-4.12 (m, 1H), 4.11-4.00 (m, 2H), 3.95 (t, J=16.6 Hz, 1H), 3.83-3.65 (m, 1H), 3.05-2.89 (m, 2H).

$^{13}$C NMR (126 MHz, methanol-d$_4$) δ (ppm) 170.53, 163.33 (d, J=245.1 Hz), 149.81, 143.76, 140.58, 140.50, 139.35, 131.84, 131.46 (d, J=3.3 Hz), 129.69 (d, J=8.1 Hz), 128.43 (d, J=10.4 Hz), 122.03, 118.79 (d, J=13.2 Hz), 115.96 (d, J=21.8 Hz), 100.64 (d, J=19.3 Hz), 72.88, 67.97 (d, J=12.2 Hz), 48.07, 44.16 (d, J=9.2 Hz).

$^{19}$F NMR (471 MHz, methanol-d$_4$) δ (ppm) −117.48 (d, J=5.2 Hz).

HRMS calculated for C$_{21}$H$_{19}$FN$_5$O$_2$ [M+H]$^+$ 392.1517, found 392.1519.

Preparative Example 169: 1-(1-cyclohexyl-4-(4-fluorophenyl)-5-(1H-pyrrolo[2,3-b]pyridin-4-yl)-1H-imidazol-2-yl)-N,N-dimethylmethanamine

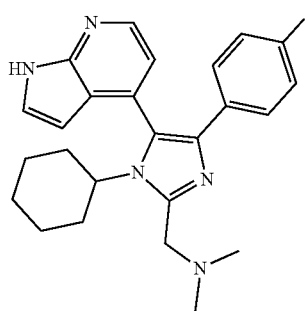

To a cold solution (−78° C.) of 4-(1-cyclohexyl-4-(4-fluorophenyl)-1H-imidazol-5-yl)-1H-pyrrolo[2,3-b]pyridine (74 mg; 0.205 mmol) in tetrahydrofuran (8 mL) were added 1,2-bis(dimethylamino)ethane (0.092 mL; 71.6 mg; 0.616 mmol), then dropwise 1.6 M solution of n-BuLi in hexane (0.320 mL; 0.513 mmol), and the resulting mixture was stirred at −78° C. for 50 minutes. Then, a suspension of N-methyl-N-methylenemethanaminium iodide (114 mg; 0.616 mmol) in tetrahydrofuran (5.0 mL) was added and the resulting mixture was allowed to warm to 25° C. and stirred for 20 hours. Then, water (20 mL) was added and pH was adjusted to ca. 1 using concentrated (35%) aqueous solution of HCl and the resulting mixture was stirred at 25° C. for 6 hours. A saturated aqueous solution of NaHCO$_3$ (20 mL) was added and the mixture was extracted with ethyl acetate (2×40 mL). The combined organic extracts were dried over MgSO$_4$, filtered, and the solvent was evaporated in vacuo. The residue was purified by column chromatography (ethyl acetate/7 M NH$_3$ in methanol, gradient from 10:0 to 10:1) and then by preparative TLC (dichloromethane/acetone, 4:1+0.5% 7 M NH$_3$ in methanol). The product was obtained as an orange wax (4.5 mg; 5%).

$^1$H NMR (500 MHz, methanol-d$_4$) δ (ppm) 8.29 (d, J=5.0 Hz, 1H), 7.41 (d, J=3.5 Hz, 1H), 7.22-7.17 (m, 2H), 7.14 (d, J=4.9 Hz, 1H), 6.83-6.76 (m, 2H), 6.13 (d, J=3.5 Hz, 1H), 4.25-4.17 (m, 1H), 3.74-3.65 (m, 2H), 2.34 (s, 6H), 2.01-1.94 (m, 1H), 1.93-1.84 (m, 1H), 1.82-1.76 (m, 1H), 1.76-1.68 (m, 1H), 1.64-1.57 (m, 1H), 1.55-1.46 (m, 2H), 1.21-1.13 (m, 2H), 0.87-0.77 (m, 1H).

$^{13}$C NMR (126 MHz, methanol-d$_4$) δ (ppm) 163.08 (d, J=244.7 Hz), 149.56, 147.28, 143.27, 138.02, 134.29, 131.69 (d, J=3.3 Hz), 129.63 (d, J=8.0 Hz), 128.26, 126.97, 123.57, 120.31, 115.66 (d, J=21.7 Hz), 100.85, 59.71, 57.39, 45.56, 34.11, 33.62, 27.39, 27.25, 26.24.

$^{19}$F NMR (471 MHz, methanol-d$_4$) δ (ppm) −118.08.

HRMS calculated for C$_{25}$H$_{29}$FN$_5$ [M+H]$^+$ 418.2402, found 418.2403.

Preparative Example 170: 4-(1-cyclohexyl-4-(4-fluorophenyl)-1H-imidazol-5-yl)-1H-pyrrolo[2,3-b]pyridin-6-amine

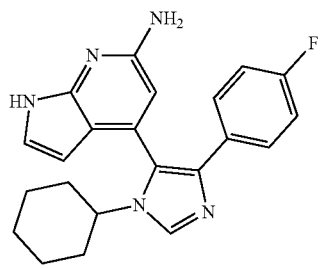 [SMILES: Nc1cc(-c2c(-c3ccc(F)cc3)ncn2C2CCCCC2)c2cc[nH]c2n1]

To a degassed solution of 5-bromo-1-cyclohexyl-4-(4-fluorophenyl)-1H-imidazole (45.0 mg; 0.133 mmol) in dioxane/H$_2$O (1.8 mL+0.30 mL) were added 4-(4,4,5,5-tetramethyl-1,3,2-dioxaborolan-2-yl)-1H-pyrrolo[2,3-b]pyridine (55.0 mg; 0.213 mmol), sodium methoxide (28.7 mg; 0.532 mmol), methanesulfonato(tri-t-butylphosphino)(2'-amino-1,1'-biphenyl-2-yl)palladium(II) (7.6 mg; 13.3 µmol; CAS:1445086-17-8) and the resulting mixture was stirred at 90° C. for 15 hours. The solvent was evaporated and the residue was purified by column chromatography (acetone/hexane, 1:1) and then by preparative TLC (dichloromethane/acetone, 2:1). The product was obtained as a white solid (19 mg, 38%).

$^1$H NMR (500 MHz, methanol-$d_4$) δ 7.98 (s, 1H), 7.38-7.34 (m, 2H), 6.97 (d, J=3.5 Hz, 1H), 6.91-6.85 (m, 2H), 6.34 (s, 1H), 5.90 (d, J=3.5 Hz, 1H), 3.82-3.74 (m, 1H), 2.06-1.95 (m, 2H), 1.83-1.76 (m, 3H), 1.75-1.68 (m, 1H), 1.66-1.60 (m, 1H), 1.30-1.20 (m, 2H), 1.18-1.10 (m, 1H).

$^{13}$C NMR (126 MHz, methanol-$d_4$) δ 163.16 (d, J=244.4 Hz), 157.42, 148.76, 138.05, 136.25, 134.53, 131.78, 131.75, 129.54 (d, J=7.9 Hz), 126.61, 122.80, 115.81 (d, J=21.7 Hz), 113.99, 106.01, 100.49, 35.87, 35.10, 26.74, 26.69, 26.13.

$^{19}$F NMR (471 MHz, methanol-$d_4$) δ (ppm) −118.10

HRMS calculated for $C_{22}H_{23}FN_5$[M+H]$^+$ 376.1932, found 376.1934.

Preparative Example 171: 1-cyclohexyl-4-(3,4-difluorophenyl)-1H-imidazole

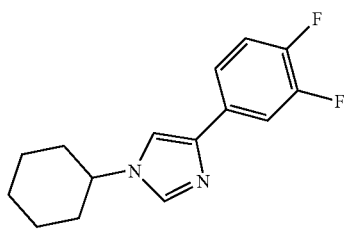 [SMILES: Fc1ccc(-c2cn(C3CCCCC3)cn2)cc1F]

To a degassed solution of 1-cyclohexyl-4-iodo-1H-imidazole (281 mg; 1.02 mmol) in 1-butanol/H$_2$O (10.0 mL+2.0 mL) were added (3,4-difluorophenyl)boronic acid (322 mg; 2.04 mmol), K$_3$PO$_4$ (758 mg; 3.57 mmol), (2-dicyclohexylphosphino-2',6'-dimethoxybiphenyl) [2-(2'-amino-1,1'-biphenyl)]palladium(II) methanesulfonate (39.8 mg; 0.051 mmol; CAS:1445085-82-4 and the resulting mixture was stirred at 90° C. for 2 hours and then at 100° C. for 4 hours and then at 110° C. for 14 hours. The solvent was evaporated in vacuo. The residue was mixed with water (100 mL) and extracted with ethyl acetate (3×50 mL). The combined organic extracts were dried over MgSO$_4$, filtered, and the solvent was evaporated in vacuo. The residue was purified by column chromatography (ethyl acetate/hexane, 1:1). The product was obtained as a yellow wax (158 mg, 59%).

$^1$H NMR (500 MHz, CDCl$_3$) δ (ppm) 9.34 (s, 1H), 7.82-7.78 (m, 1H), 7.74-7.67 (m, 1H), 7.34 (s, 1H), 7.31-7.27 (m, 1H), 4.44-4.33 (m, 1H), 2.30-2.22 (m, 2H), 2.00-1.95 (m, 2H), 1.85-1.70 (m, 3H), 1.52 (q, J=13.0 Hz, 2H), 1.36-1.26 (m, 1H).

$^{13}$C NMR (126 MHz, Chloroform-d) δ (ppm) 151.54, 151.51, 151.38, 149.65, 149.51, 134.78, 133.91, 124.04, 124.01, 123.98, 123.95, 117.99, 117.85, 116.54, 116.38, 101.49, 58.37, 33.62, 25.66, 25.05.

$^{19}$F NMR (471 MHz, CDCl$_3$) δ (ppm) −134.66 (d, J=21.3 Hz), −135.24 (d, J=20.9 Hz).

HRMS calculated for $C_{15}H_{16}F_2N_2$ [M+H]$^+$ 263.1354, found 263.1357.

Preparative Example 172: 5-bromo-1-cyclohexyl-4-(3,4-difluorophenyl)-1H-imidazole

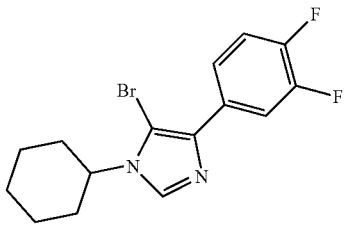 [SMILES: Fc1ccc(-c2ncn(C3CCCCC3)c2Br)cc1F]

To a cold solution (0° C.) of 1-cyclohexyl-4-(3,4-difluorophenyl)-1H-imidazole (158 mg; 0.602 mmol) in dichloromethane (15 mL) was added N-bromosuccinimide (113 mg; 0.632 mmol) and the resulting mixture was stirred at 0° C. for 60 minutes. Water (80 mL) and Na$_2$S$_2$O$_3$ (50 mg) were added and the mixture was extracted with ethyl acetate (3×50 mL). The combined organic extracts were dried over MgSO$_4$, filtered, and the solvent was evaporated in vacuo. The residue obtained after the workup was purified by column chromatography (ethyl acetate/hexane, 1:3). The product was obtained as a white solid (138 mg, 67%).

$^1$H NMR (500 MHz, CDCl$_3$) δ (ppm) 8.35 (s, 1H), 7.82 (ddd, J=11.5, 7.6, 2.2 Hz, 1H), 7.79-7.73 (m, 1H), 7.29-7.20 (m, 1H), 4.17-4.10 (m, 1H), 2.24-2.14 (m, 2H), 1.99 (dt, J=14.0, 3.3 Hz, 2H), 1.84-1.68 (m, 3H), 1.48 (qt, J=13.1, 3.5 Hz, 2H), 1.38-1.29 (m, 1H).

$^{13}$C NMR (126 MHz, CDCl$_3$) δ (ppm) 151.45 (dd, J=10.9, 9.8 Hz), 149.48 (dd, J=11.2, 5.4 Hz), 134.74, 134.22, 127.08, 123.87 (dd, J=6.4, 3.7 Hz), 117.84 (d, J=17.6 Hz), 116.38 (d, J=19.2 Hz), 101.32, 58.19, 33.64, 25.67, 25.08.

$^{19}$F NMR (471 MHz, CDCl$_3$) δ (ppm) −136.77 (d, J=21.4 Hz), −137.18 (d, J=16.3 Hz).

HRMS calculated for $C_{15}H_{16}BrF_2N_2$ [M+H]$^+$ 341.0459, found 341.0457.

Preparative Example 173: 4-(1-cyclohexyl-4-(3,4-difluorophenyl)-1H-imidazol-5-yl-1H-pyrrolo[2,3-b]pyridine

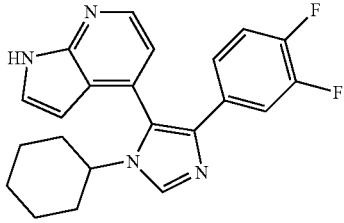 [SMILES: Fc1ccc(-c2ncn(C3CCCCC3)c2-c2ccnc3[nH]ccc23)cc1F]

To a degassed solution of 5-bromo-1-cyclohexyl-4-(3,4-difluorophenyl)-1H-imidazole (30.0 mg; 0.0879 mmol) in dioxane/H$_2$O (2.4 mL+0.40 mL) were added 4-(4,4,5,5-tetramethyl-1,3,2-dioxaborolan-2-yl)-1H-pyrrolo[2,3-b]pyridine (34.3 mg; 0.140 mmol), sodium methoxide (19.0 mg; 0.351 mmol), methanesulfonato(tri-t-butylphosphino)(2'-amino-1,1'-biphenyl-2-yl)palladium(II) (5.0 mg; 8.8 μmol; CAS:1445086-17-8) and the resulting mixture was stirred at 100° C. for 16 hours. Water (30 mL) was added and the mixture was extracted with ethyl acetate (3×20 mL). The combined organic extracts were dried over MgSO$_4$, filtered, and the solvent was evaporated in vacuo. The residue was purified by column chromatography (acetone/hexane, 1:3). The product was obtained as a yellow solid (12 mg, 36%).

$^1$H NMR (500 MHz, CDCl$_3$) δ (ppm) 10.63 (s, 1H), 8.51 (s, 1H), 8.47 (d, J=4.9 Hz, 1H), 7.47 (d, J=3.5 Hz, 1H), 7.25-7.18 (m, 2H), 7.09 (d, J=5.0 Hz, 1H), 6.97 (q, J=8.5 Hz, 1H), 6.18 (d, J=3.5 Hz, 1H), 3.72 (tt, J=12.1, 3.8 Hz, 1H), 2.10-2.02 (m, 1H), 1.99-1.92 (m, 1H), 1.87-1.70 (m, 4H), 1.67-1.61 (m, 1H), 1.21-1.05 (m, 3H).

$^{13}$C NMR (126 MHz, CDCl$_3$) δ (ppm) 151.24 (dd, J=26.8, 12.6 Hz), 149.26 (dd, J=29.2, 12.8 Hz), 148.32, 142.60, 134.73, 134.07, 129.65, 127.71, 125.19, 123.43 (dd, J=6.4, 3.7 Hz), 121.09, 117.81, 117.77, 117.63, 116.03 (d, J=19.1 Hz), 100.06, 56.75, 34.98, 34.31, 25.60, 25.56, 24.92.

$^{19}$F NMR (471 MHz, CDCl$_3$) δ (ppm) −136.97 (dt, J=19.9, 9.8 Hz), −137.98.

HRMS calculated for C$_{22}$H$_{21}$F$_2$N$_4$ [M+H]$^+$ 379.1729, found 379.1732.

Preparative Example 174: 1-benzyl-1H-imidazole

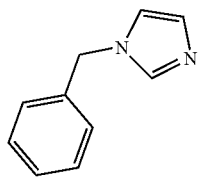 [SMILES: c1ccc(Cn2ccnc2)cc1]

NaH (60% in mineral oil, 1.85 g, 46.27 mmol) was added portionwise to a solution of imidazole (3.00 g, 44.06 mmol) in DMF (25 mL) at 0° C. and the mixture was stirred at 0° C. for 15 min. Benzyl bromide (5.23 mL, 44.06 mmol) was added dropwise and the resulting reaction mixture was stirred at 25° C. for 3 hours. The reaction mixture was quenched with water (150 mL), and extracted with EtOAc (2×200 mL). The organic extracts were washed with brine (100 mL), dried over MgSO$_4$, filtered, and the solvents were evaporated in vacuo. The residue was purified by column chromatography (dichloromethane/methanol, 20/1). The product was obtained as light orange solid (6.76 g, 97%).

$^1$H NMR (500 MHz, CDCl$_3$) δ (ppm) 7.54 (s, 1H), 7.37-7.27 (m, 3H), 7.17-7.12 (m, 2H), 7.07 (s, 1H), 6.89 (d, J=1.37 Hz, 1H), 5.10 (s, 2H).

$^{13}$C NMR (126 MHz, CDCl$_3$) δ (ppm) 137.5, 136.2, 129.8, 129.0, 128.3, 127.4, 119.4, 50.9.

HRMS calculated for C$_{10}$H$_{11}$N$_2$ [M+H]$^+$ 159.0917, found 159.0915.

Preparative Example 175: 1-benzyl-4,5-diiodo-1H-imidazole

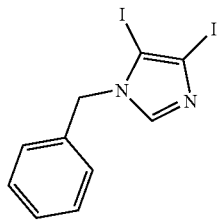 [SMILES: Ic1ncn(Cc2ccccc2)c1I]

To a solution of 1-benzyl-1H-imidazole (2.50 g; 15.80 mmol) in DMF (20 mL) was added N-iodosuccinimide (8.17 g; 36.34 mmol) and the resulting mixture was stirred at 80° C. for 15 hours. A saturated aqueous solution of Na$_2$S$_2$O$_3$ (110 mL) was added and the mixture was extracted with ethyl acetate (2×200 mL). The layers were separated and the organic phase was washed with H$_2$O (100 mL).

The combined organic extracts were dried over MgSO$_4$, filtered, and the solvent was evaporated in vacuo. The residue was purified by column chromatography (hexane/ethyl acetate; 7:3). The product was obtained as a white solid (2.40 g; 37%).

$^1$H NMR (500 MHz, CDCl$_3$) δ (ppm) 7.62 (s, 1H), 7.41-7.32 (m, 3H), 7.18-7.11 (m, 2H), 5.16 (s, 2H).

$^{13}$C NMR (126 MHz, CDCl$_3$) δ (ppm) 141.4, 134.9, 129.2, 128.7, 127.5, 96.3, 83.0, 53.5.

HRMS calculated for C$_{10}$H$_9$I$_2$N$_2$ [M+H]$^+$ 410.8850, found 410.8853.

Preparative Example 176: 1-benzyl-4-iodo-1H-imidazole

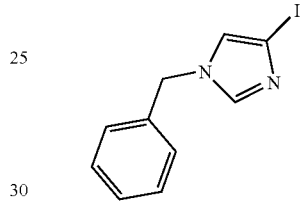

To a cold solution (0° C.) of 1-benzyl-4,5-diiodo-1H-imidazole (2.40 g; 5.85 mmol) in tetrahydrofuran (20 mL) was added dropwise 2 M solution of MeMgCl in tetrahydrofuran (3.22 mL; 6.43 mmol) and the resulting mixture was stirred at 0° C. for 30 minutes. A saturated aqueous solution of NH$_4$Cl (30 mL) was added and the mixture was extracted with ethyl acetate (2×100 mL). The combined organic extracts were dried over MgSO$_4$, filtered, and the solvent was evaporated in vacuo. The residue was purified by column chromatography (hexane/ethyl acetate; 1:1). The product was obtained as a white solid (1.38 g, 83%).

$^1$H NMR (500 MHz, CDCl$_3$) δ (ppm) 7.51 (d, J=1.44 Hz, 1H), 7.40-7.32 (m, 3H), 7.20-7.16 (m, 2H), 6.98 (d, J=1.55 Hz, 1H), 5.10 (s, 2H).

$^{13}$C NMR (126 MHz, CDCl$_3$) δ (ppm) 139.0, 135.3, 129.3, 128.8, 127.7, 125.0, 81.8, 51.4.

HRMS calculated for C$_{10}$H$_{10}$IN$_2$ [M+H]$^+$ 284.9883, found 284.9884.

Preparative Example 177: 1-benzyl-4-(3,4-difluorophenyl)-1H-imidazole

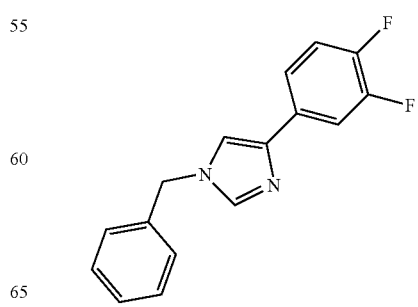

To a degassed solution of 1-benzyl-4-iodo-1H-imidazole (139 mg; 0.489 mmol) in 1-butanol/H$_2$O (5.0 mL+1.0 mL) were added (3,4-difluorophenyl)boronic acid (155 mg; 0.979 mmol), K$_3$PO$_4$ (364 mg; 0.171 mmol), (2-dicyclohexylphosphino-2',6'-dimethoxybiphenyl) [2-(2'-amino-1,1'-biphenyl)]palladium(II) methanesulfonate (19.1 mg; 0.0245 mmol; CAS:1445085-82-4) and the resulting mixture was stirred at 110° C. for 2.5 hours. The solvent was evaporated in vacuo, the residue was mixed with water (50 mL) and extracted with ethyl acetate (3×30 mL). The combined organic extracts were dried over MgSO$_4$, filtered, and the solvent was evaporated in vacuo. The residue was purified by column chromatography (ethyl acetate/hexane, 2:3). The product was obtained as a yellow wax (90 mg, 68%).

$^1$H NMR (500 MHz, CDCl$_3$) δ (ppm) 8.04 (s, 1H), 7.58 (ddd, J=11.6, 7.6, 2.1 Hz, 1H), 7.53-7.48 (m, 1H), 7.42-7.35 (m, 3H), 7.26 (s, 1H, overlapped with CDCl$_3$), 7.25 (d, J=1.7 Hz, 1H), 7.17-7.11 (m, 2H), 5.21 (s, 2H).

$^{13}$C NMR (126 MHz, CDCl$_3$) δ (ppm) 151.32 (dd, J=101.4, 12.9 Hz), 149.34 (dd, J=102.3, 12.8 Hz), 139.42, 137.57, 135.14, 129.66, 129.38, 128.93, 127.85, 121.56-121.11 (m), 117.73 (d, J=17.6 Hz), 115.48, 114.25 (d, J=18.8 Hz), 51.83.

$^{19}$F NMR (471 MHz, CDCl$_3$) δ (ppm) −137.58 (dt, J=20.7, 9.9 Hz), −139.38.

HRMS calculated for C$_{16}$H$_{13}$F$_2$N$_2$ [M+H]$^+$ 271.1041, found 271.1043.

Preparative Example 178: 1-benzyl-5-bromo-4-(3,4-difluorophenyl)-1H-imidazole

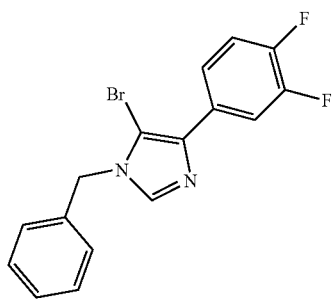 [SMILES: Fc1ccc(-c2ncn(Cc3ccccc3)c2Br)cc1F]

To a cold solution (0° C.) of 1-benzyl-4-(3,4-difluorophenyl)-1H-imidazole (100 mg; 0.370 mmol) in dichloromethane (5 mL) was added N-bromosuccinimide (69.1 mg; 0.388 mmol) and the resulting mixture was stirred at 0° C. for 30 minutes. Water (30 mL) and Na$_2$S$_2$O$_3$ (50 mg) were added and the mixture was extracted with ethyl acetate (3×20 mL). The combined organic extracts were dried over MgSO$_4$, filtered, and the solvent was evaporated in vacuo. The residue obtained after the workup was purified by column chromatography (ethyl acetate/hexane, gradient from 1:3 to 1:1). The product was obtained as a white solid (87 mg, 67%).

$^1$H NMR (300 MHz, CDCl$_3$) δ (ppm) 7.91-7.86 (m, 1H), 7.87-7.79 (m, 1H), 7.78-7.71 (m, 1H), 7.45-7.33 (m, 3H), 7.25-7.15 (m, 3H), 5.22 (s, 2H).

HRMS calculated for C$_{16}$H$_{12}$BrF$_2$N$_2$ [M+H]$^+$ 349.0146, found 349.0147.

Preparative Example 179: 4-(1-benzyl-4-(3,4-difluorophenyl)-1H-imidazol-5-yl)-1H-pyrrolo[2,3-b]pyridine

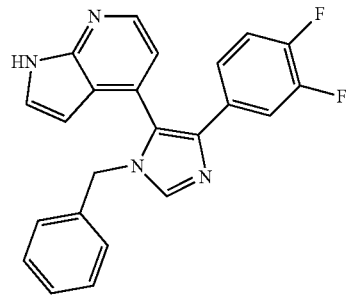 [SMILES: Fc1ccc(-c2ncn(Cc3ccccc3)c2-c2ccnc3[nH]ccc23)cc1F]

To a degassed solution of 5-bromo-1-cyclohexyl-4-(3,4-difluorophenyl)-1H-imidazole (37.3 mg; 0.107 mmol) in dioxane/H$_2$O (2.4 mL+0.40 mL) were added 4-(4,4,5,5-tetramethyl-1,3,2-dioxaborolan-2-yl)-1H-pyrrolo[2,3-b]pyridine (44.4 mg; 0.182 mmol), sodium methoxide (23.1 mg; 0.427 mmol), methanesulfonato(tri-t-butylphosphino)(2'-amino-1,1'-biphenyl-2-yl)palladium(II) (6.1 mg; 10.7 μmol; CAS:1445086-17-8) and the resulting mixture was stirred at 100° C. for 15 hours. The solvent was evaporated and the residue was purified by column chromatography (acetone/hexane, gradient from 1:2 to 1:1). So obtained material was recrystallized from acetone/hexane/chloroform. The product was obtained as a white solid (23 mg, 56%).

$^1$H NMR (500 MHz, CDCl$_3$) δ (ppm) 10.15 (s, 1H), 8.34 (d, J=4.9 Hz, 1H), 7.99 (s, 1H), 7.37 (d, J=3.5 Hz, 1H), 7.31 (ddd, J=11.9, 7.7, 2.1 Hz, 1H), 7.24-7.19 (m, 3H), 7.17-7.12 (m, 1H), 6.96 (d, J=5.1 Hz, 1H), 6.95-6.90 (m, 1H), 6.90-6.87 (m, 2H), 6.15 (d, J=3.5 Hz, 1H), 5.18-4.91 (m, 2H).

$^{13}$C NMR (126 MHz, CDCl$_3$) δ (ppm) 151.06 (dd, J=77.3, 12.8 Hz), 149.09 (dd, J=79.1, 12.7 Hz), 147.94, 142.16, 138.22, 137.06, 135.29, 130.93, 130.12-129.89 (m), 129.11, 128.58, 127.32, 127.07, 125.47, 122.89 (dd, J=6.4, 3.5 Hz), 120.95, 117.88, 117.36 (d, J=17.4 Hz), 115.75 (d, J=18.9 Hz), 100.70, 50.00.

$^{19}$F NMR (471 MHz, CDCl$_3$) δ (ppm) −137.69 (d, J=21.7 Hz), −139.34 (d, J=21.2 Hz).

HRMS calculated for C$_{23}$H$_{17}$F$_2$N$_4$ [M+H]$^+$ 387.1416, found 387.1416.

Preparative Example 180: 2-(1-benzyl-1H-imidazol-4-yl)-5-fluoropyridine

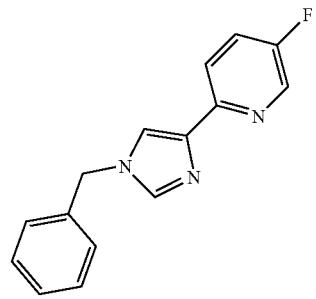 [SMILES: Fc1ccc(-c2cn(Cc3ccccc3)cn2)nc1]

To a cold solution (−30° C.) of 1-benzyl-4-iodo-1H-imidazole (800 mg; 2.81 mmol) in tetrahydrofuran (15 mL) was added 2 M solution of MeMgCl in tetrahydrofuran (1.83 mL; 3.66 mmol) and the resulting mixture was stirre at 0° C. for 2 hours. Trimethyl borate (314 mL, 2.81 mmol) was added dropwise at −60° C. and the resulting reaction mixture was stirred at 0° C. for 3 hours. The solvent was evaporated in vacuo to afford the crude boronate as a white solid (1.05 g, 4.56 mmol). To a degassed solution of the crude boronate (1.05 g, 4.56 mmol) in dioxane/H$_2$O (20 mL+4 mL) were added 5-fluoro-2-iodopyridine (752 mg, 3.37 mmol), K$_3$PO$_4$ (1.79 g; 8.43 mmol), bis(di-tert-butyl(4-dimethylaminophenyl)phosphine)dichloropalladium(II) (CAS: 887919-35-9, 50 mg, 0.070 mmol), palladium(II)acetate (19 mg, 0.0843 mmol), (4-(N,N-dimethylamino)phenyl)di-tert-butyl phosphine (CAS: 932710-63-9, 52 mg, 0.196 mmol) and the resulting mixture was stirred at 100° C. for 16 hours.

The solvent was evaporated in vacuo, the residue was mixed with water (100 mL), and the mixture was extracted with EtOAc (2×100 mL). The combined organic extracts were dried over MgSO$_4$, filtered, and the solvents were evaporated in vacuo. The residue was purified by column chromatography (hexane/acetone, 1/1). The product was obtained as a light orange solid (350 mg, 49% over 2 steps).

$^1$H NMR (500 MHz, CDCl$_3$) δ (ppm) 8.35 (s, 1H), 7.98 (dd, J=9.13, 4.57 Hz, 1H), 7.60 (s, 1H), 7.53 (s, 1H), 7.41 (td, J=8.52, 2.82 Hz, 1H), 7.38-7.31 (m, 3H), 7.24-7.20 (m, 2H), 5.14 (s, 2H).

$^{13}$C NMR (126 MHz, CDCl$_3$) δ (ppm) 158.5 (d, J=253.96 Hz), 149.7, 142.0, 137.6, 137.2 (d, J=23.92 Hz), 135.7, 129.2, 128.6, 127.7, 123.6 (d, J=18.47 Hz), 120.2, 118.0, 51.5.

$^{19}$F NMR (471 MHz, CDCl$_3$) δ (ppm) −129.98.

HRMS calculated for C$_{15}$H$_{13}$FN$_3$ [M+H]$^+$ 254.1088, found 254.1090.

Preparative Example 181: 2-(1-benzyl-5-bromo-1H-imidazol-4-yl)-5-fluoropyridine

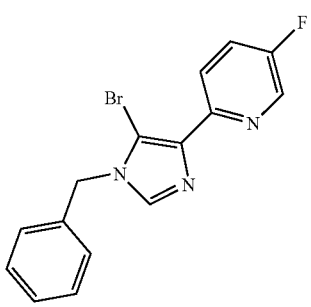 [SMILES: Fc1ccc(-c2ncn(Cc3ccccc3)c2Br)nc1]

A solution of N-bromosuccinimide (236 mg; 1.33 mmol) in dichloromethane (5 mL) was added to a solution of 2-(1-benzyl-1H-imidazol-4-yl)-5-fluoropyridine (350 mg; 1.38 mmol) in dichloromethane (20 mL) at 25° C. and the mixture was stirred at 25° C. for 16 hours. The solvent was evaporated and the residue was purified by column chromatography (hexane/acetone, 3:2). The product was obtained as a white solid (270 mg, 59%).

$^1$H NMR (500 MHz, CDCl$_3$) δ (ppm) 8.51 (d, J=2.90 Hz, 1H), 8.05 (dd, J=8.81, 4.46 Hz, 1H), 7.78 (s, 1H), 7.45 (td, J=8.48, 2.91 Hz, 1H), 7.40-7.31 (m, 3H), 7.25-7.18 (m, 2H), 5.23 (s, 2H).

$^{13}$C NMR (126 MHz, CDCl$_3$) δ (ppm) 158.6 (d, J=255.99 Hz), 148.51, 148.48, 138.0, 137.6, 137.3 (d, J=23.71 Hz), 135.0, 129.2, 128.6, 127.5, 123.4 (d, J=18.56 Hz), 122.4 (d, J=4.30 Hz), 50.2.

$^{19}$F NMR (471 MHz, CDCl$_3$) δ (ppm) −128.79.

HRMS calculated for C$_{15}$H$_{12}$BrFN$_3$ [M+H]$^+$ 332.0193, found 332.0196.

Preparative Example 182: 4-(1-(1,4-dimethyl-1,4-diazepan-6-yl)-4-(4-fluorophenyl)-1H-imidazol-5-yl)-1H-pyrrolo[2,3-b]pyridine

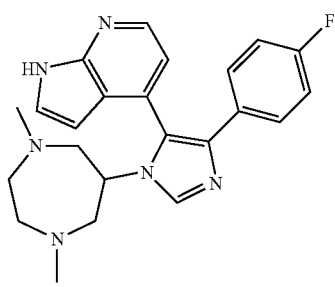 [SMILES: CN1CCN(C)CC(n2cnc(-c3ccc(F)cc3)c2-c2ccnc3[nH]ccc23)C1]

The compound was prepared according to General procedure A using 1H-pyrrolo[2,3-b]pyridine-4-carbaldehyde, 1,4-dimethyl-1,4-diazepan-6-amine (CAS: 129295-47-2), 1-fluoro-4-(isocyano(tosyl)methyl)benzene and K$_2$CO$_3$ (2 eq.). Reaction time: 3 hours for the formation of the imine, then additional 16 hours for the cyclization step. The residue obtained after the workup was purified by column chromatography (dichloromethane/methanol/7 M NH$_3$ in methanol, 9:1:0.2). The product was obtained as a white solid (60 mg, 52%).

$^1$H NMR (500 MHz, DMSO-d$_6$) δ (ppm) 11.90 (s, 1H), 8.35 (d, J=4.7 Hz, 1H), 8.15 (s, 1H), 7.50 (t, J=3.0 Hz, 1H), 7.35-7.27 (m, 2H), 7.05 (d, J=4.7 Hz, 1H), 7.00-6.93 (m, 2H), 6.05 (dd, J=3.5, 1.8 Hz, 1H), 3.86 (p, J=6.2 Hz, 1H), 2.87-2.75 (m, 3H), 2.68 (dd, J=13.5, 5.4 Hz, 1H), 2.63-2.55 (m, 2H), 2.49-2.42 (m, 2H), 2.22 (s, 3H), 2.17 (s, 3H).

$^{13}$C NMR (126 MHz, DMSO-d$_6$) δ (ppm) 160.64 (d, J=243.0 Hz), 148.76, 142.96, 135.92, 135.70, 131.14 (d, J=3.1 Hz), 130.03, 127.35 (d, J=7.9 Hz), 127.35, 124.17, 119.78, 117.36, 114.85 (d, J=21.4 Hz), 98.67, 62.63, 62.17, 59.07, 53.51, 46.95, 46.91.

$^{19}$F NMR (471 MHz, DMSO-d$_6$) δ (ppm) −116.50.

HRMS calculated for C$_{23}$H$_{26}$FN$_6$ [M+H]$^+$ 405.2197, found 405.2195.

Preparative Example 183: N-((5-fluoropyridin-2-yl)(tosyl)methyl)formamide

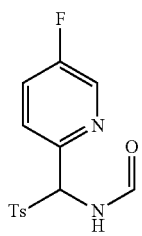 [SMILES: Cc1ccc(S(=O)(=O)C(NC=O)c2ccc(F)cn2)cc1]

To a solution of 4-methylbenzenesulfinic acid (1038 mg, 6.65 mmol) in toluene/acetonitrile (2+2 mL) were added formamide (440 μL, 11.1 mmol), 5-fluoropicolinaldehyde (554 mg, 4.43 mmol) and chlorotrimethylsilane (617 μL, 4.87 mmol) and the mixture was stirred at 50° C. for 3 hours. Then, water (6 mL) and 2-methoxy-2-methylpropane (6 mL) were added and the mixture was stirred at 0° C. (ice bath) for 15 minutes. The precipitate was collected by filtration, washed with water (50 mL), then washed with Et$_2$O (10 mL) and dried in vacuo. The product was obtained as a white solid (820 mg, 48%).

NMR shifts for major rotamers:
$^1$H NMR (300 MHz, DMSO-d$_6$) δ (ppm) 9.54 (d, J=10.2 Hz, 1H), 8.57 (d, J=2.7 Hz, 1H), 8.03 (d, J=1.3 Hz, 1H), 7.93-7.78 (m, 2H), 7.66-7.56 (m, 2H), 7.45-7.37 (m, 2H), 6.58 (d, J=10.3 Hz, 1H), 2.41 (s, 3H).

Preparative Example 184: 4-(1-benzyl-4-(5-fluoro-pyridin-2-yl)-1H-imidazol-5-yl)-1H-pyrrolo[2,3-b]pyridine

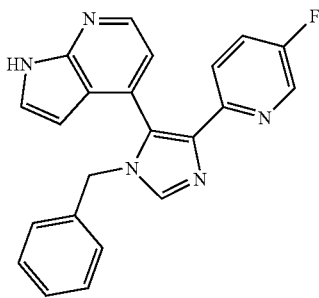 [SMILES: Fc1ccc(-c2ncn(Cc3ccccc3)c2-c2ccnc3[nH]ccc23)nc1]

Dichloromethane (5.0 mL) and 1H-pyrrolo[2,3-b]pyridine-4-carbaldehyde (52 mg, 0.357 mmol) were added to a mixture of N-((5-fluoropyridin-2-yl)(tosyl)methyl)formamide (100 mg, 0.324 mmol) and 5-(2-hydroxyethyl)-3,4-dimethylthiazol-3-ium iodide (14 mg, 0.0486 mmol, CAS: 16311-69-6), and the mixture was stirred at 35° C. for 5 min. Triethylamine (0.678 mL, 4.865 mmol) was added in one portion and the reaction mixture was stirred at 35° C. for additional 45 min. The solvents were evaporated in vacuo, ethanol (8 mL), acetic acid (92 μL, 1.622 mmol) and benzylamine (177 μL, 1.622 mmol) were added to the residue and the resulting mixture was stirred at reflux for 16 hours. The reaction mixture was cooled to 25° C., quenched with water (25 mL), and extracted with EtOAc (2×35 mL). The combined organic extracts were dried over MgSO$_4$, filtered, and the solvents were evaporated in vacuo. The residue was purified by column chromatography two times (dichloromethane/methanol, gradient from 98:2 to 95:5; then acetone/hexane, 1:1 to 95:5). The product was obtained as a pale yellow solid (70 mg, 59%).

$^1$H NMR (500 MHz, CDCl$_3$) δ (ppm) 10.32 (s, 1H), 8.32 (d, J=4.9 Hz, 1H), 8.19 (d, J=2.9 Hz, 1H), 7.79 (s, 1H), 7.52 (dd, J=8.8, 4.4 Hz, 1H), 7.31 (d, J=3.6 Hz, 1H), 7.25-7.16 (m, 4H), 6.99 (d, J=4.9 Hz, 1H), 6.94-6.84 (m, 2H), 6.12 (d, J=3.6 Hz, 1H), 5.11-4.92 (m, 2H).

$^{13}$C NMR (126 MHz, CDCl$_3$) δ (ppm) 158.23 (d, J=255.5 Hz), 149.42 (d, J=3.5 Hz), 148.60, 142.43, 138.88, 138.59, 137.45 (d, J=23.4 Hz), 136.00, 131.55, 128.94, 128.25, 127.44, 127.15, 126.20, 123.00 (d, J=18.6 Hz), 122.07 (d, J=3.4 Hz), 120.78, 118.04, 100.70, 49.57.

$^{19}$F NMR (471 MHz, CDCl$_3$) δ (ppm) -129.99.

HRMS calculated for C$_{22}$H$_{17}$FN$_5$ [M+H]$^+$ 370.1463, found 370.1466.

II. Biological Activity

Primary CLL Cells and Non-Malignant Controls

Primary cells were isolated from peripheral blood (PB) of CLL patients monitored and treated at the Dept. of Internal Medicine—Hematology and Oncology, University Hospital Brno according to international criteria. All samples including age-matched non-malignant controls were taken after written informed consent in accordance with the Declaration of Helsinki under protocols approved by the Ethical Committee of the University Hospital Brno. Cells were separated using non-B cell depletion techniques (RosetteSep kits, StemCell). The separation efficiency was assessed by flow-cytometry. All tested CLL samples contained ≥98% leukemic B cells and the nonmalignant controls contained 70-80% B cells. Freshly isolated cells were used in case of experiments presented in Example II.4 (Table 3). Data presented in Example II.1 (Table 1) are based on work with primary PB CLL cells from one sampling of a CLL patient "GH" (preparative examples 1-95) and "HN" (96-179), which were aliquoted (50×10$^6$ per vial) and viably frozen in a freezing medium (10% DMSO, 20% FBS, 70% RPMI-1640) and stored longterm in a liquid nitrogen tank. The cells were thawed 2 hours prior to experiment, freezing medium was removed by centrifugation and cells were kept in normal culture conditions.

Cell Culture Conditions, Cell Lines

The leukemia and lymphoma-derived cell lines [MEC-1 cell line (derived from chronic lymphocytic leukemia—CLL), Nalm-16 (acute lymphocytic leukemia—ALL), K562 (chronic myeloid leukemia—CML), HL-60 (acute myeloid leukemia—AML), Maver-1 and Mino (mantle cell lymphoma—MCL), BL-41 (Burkitt lymphoma—BL), WSU-NHL (follicular lymphoma—FL), SUDHL (diffuse large B-cell lymphoma—DLBCL)], primary CLL cells and non-malignant control primary cells were cultured in suspension in flasks under the following conditions: RPMI 1640 medium (Hyclone) supplemented with 10% fetal bovine serum (FBS, Gibco) and 1% penicillin/streptomycin (Life Technologies), 37° C., 5% CO$_2$ and 95% relative humidity, with optimal culture cell density 5×10$^6$ cells/mL in case of primary cells and 0.5-1×10$^6$ cells/mL in case of cell lines. The adherent cell lines [A375 (derived from malignant melanoma), MDA-MB-231 and MCF-7 (breast cancer), MIA-PA-CA and PANC1 (pancreatic cancer), PC3 (prostate cancer), OVCAR4 (ovarian cancer) and HEPG2 (hepatocellular carcinoma)] were cultured on plates under the same conditions using RPMI1640 or DMEM medium (Gibco) according to instructions provided by the distributor (DSMZ/ATCC).

Example II.1: Cytotoxicity

Cell Treatment

Cytotoxicity of compounds of formula I was tested in two models representative for leukemia (primary CLL cells) and lymphoma (Maver-1 cells). The primary CLL cells and Maver-1 cells (MCL-derived) were incubated with inhibitors at 100 μM concentration or corresponding amount of solvent (DMSO, Sigma Aldrich) as 0.1×10$^6$ cells/200 μl per well in a 96-well plate. Experiments were performed in technical duplicates. Viability of cells was assessed after 6 hours in case of primary CLL cells and after 24 hours in case of Maver-1 cells.

Viability Assessment

Viability of cells was assessed by flow cytometric analysis (Accuri C6 flow cytometer, BD Biosciences) according to TMRE staining (Tetramethylrhodamine, 2 M, 15 min at room temperature; Invitrogen), which is able to determine mitochondrial membrane potential in cells and therefore measure cell viability as well as induction of apoptosis in cells. Apoptosis-induced reduction of mitochondrial potential is detected as lower TMRE fluorescence. Viable cells (TMRE positive) were assessed in each experiment and obtained results were normalized to control (no inhibitor) condition. Relative values are presented, showing ratio to the effect of PF670462 (as the closest prior art). Relative value <1 indicates a higher cytotoxicity than PF670462.

Table 1 shows cytotoxicity data of compounds of formula I, expressed relative to PF670462 which is structurally closest compound proposed for the treatment of chronic lymphocytic leukaemia (CLL). Results obtained from primary CLL cells and MCL-derived Maver-1 cell line are presented.

TABLE 1

| | | Viability of cells Compound of formula I (100 μM), relative to PF670462 (100 μM) | |
|---|---|---|---|
| Preparative example number | Compound of formula I | CLL primary cells | Maver-1 cells (mantle cell lymphoma) |
| | 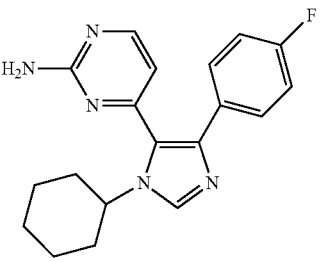<br>PF670462 = standard | 1.00 | 1.00 |
| 3 | 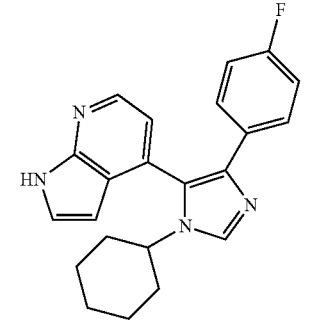 [SMILES: Fc1ccc(-c2ncn(C3CCCCC3)c2-c2ccnc3[nH]ccc23)cc1] | 0.30 | 0.27 |
| 28 | 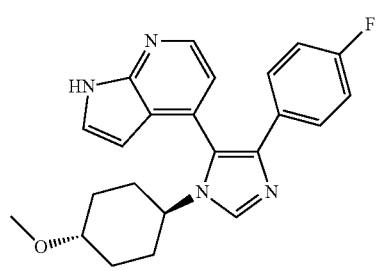 [SMILES: CO[C@H]1CC[C@H](n2cnc(-c3ccc(F)cc3)c2-c2ccnc3[nH]ccc23)CC1] | 0.67 | n.d. |
| 31 | 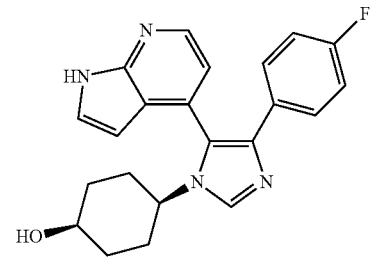 [SMILES: O[C@H]1CC[C@@H](n2cnc(-c3ccc(F)cc3)c2-c2ccnc3[nH]ccc23)CC1] | 0.78 | n.d. |

TABLE 1-continued

| Preparative example number | Compound of formula I | Viability of cells Compound of formula I (100 μM), relative to PF670462 (100 μM) | |
|---|---|---|---|
| | | CLL primary cells | Maver-1 cells (mantle cell lymphoma) |
| 32 | | 0.67 | n.d. |
| 33 | | 0.63 | 0.12 |
| 75 | | 0.83 | 0.66 |
| 74 | | 0.73 | 0.46 |
| 34 | | 0.55 | 0.89 |

TABLE 1-continued

| Preparative example number | Compound of formula I | Viability of cells Compound of formula I (100 μM), relative to PF670462 (100 μM) | |
|---|---|---|---|
| | | CLL primary cells | Maver-1 cells (mantle cell lymphoma) |
| 78 | | 0.87 | n.d. |
| 79 | | 0.86 | n.d. |
| 68 | | 0.81 | n.d. |
| 69 | | 0.84 | 0.85 |
| 70 | | 0.72 | 0.11 |

TABLE 1-continued

| Preparative example number | Compound of formula I | Viability of cells Compound of formula I (100 μM), relative to PF670462 (100 μM) | |
|---|---|---|---|
| | | CLL primary cells | Maver-1 cells (mantle cell lymphoma) |
| 71 | | 0.87 | 0.87 |
| 35 | | 0.60 | 0.44 |
| 36 | | 0.68 | 0.01 |
| 37 | | 0.51 | n.d. |
| 14 | | 0.77 | 0.70 |

TABLE 1-continued

| Preparative example number | Compound of formula I | Viability of cells Compound of formula I (100 μM), relative to PF670462 (100 μM) | |
|---|---|---|---|
| | | CLL primary cells | Maver-1 cells (mantle cell lymphoma) |
| 11 | | 0.30 | 0.06 |
| 13 | | 0.47 | n.d. |
| 19 | | 0.22 | 0.33 |
| 12 | | 0.80 | n.d. |
| 16 | | 0.67 | n.d. |

TABLE 1-continued

| Preparative example number | Compound of formula I | Viability of cells Compound of formula I (100 μM), relative to PF670462 (100 μM) | |
|---|---|---|---|
| | | CLL primary cells | Maver-1 cells (mantle cell lymphoma) |
| 18 | | 0.33 | n.d. |
| 17 | | 0.52 | n.d. |
| 29 | | 0.21 | 0.03 |
| 23 | | 0.37 | 0.46 |
| 22 | | 0.17 | 0.27 |

TABLE 1-continued

| Preparative example number | Compound of formula I | Viability of cells Compound of formula I (100 μM), relative to PF670462 (100 μM) | |
|---|---|---|---|
| | | CLL primary cells | Maver-1 cells (mantle cell lymphoma) |
| 47 | | 0.78 | n.d. |
| 50 | | 0.63 | 0.48 |
| 30 | | 0.69 | n.d. |
| 24 | | 0.30 | n.d. |
| 20 | | 0.68 | n.d. |

TABLE 1-continued
| Preparative example number | Compound of formula I | Viability of cells Compound of formula I (100 μM), relative to PF670462 (100 μM) | |
|---|---|---|---|
| | | CLL primary cells | Maver-1 cells (mantle cell lymphoma) |
| 21 | 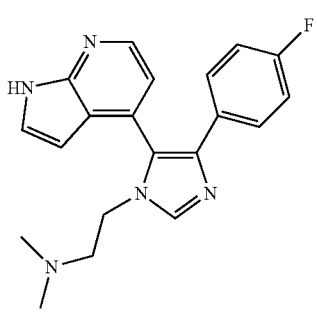 | 0.72 | n.d. |
| 15 | 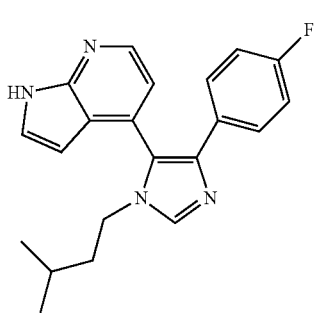 [SMILES: CC(C)CCn1cnc(-c2ccc(F)cc2)c1-c1ccnc2[nH]ccc12] | 0.13 | n.d. |
| 25 | 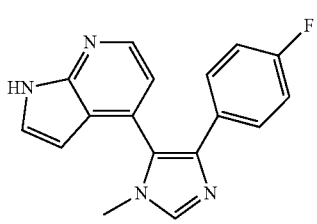 [SMILES: Cn1cnc(-c2ccc(F)cc2)c1-c1ccnc2[nH]ccc12] | 0.81 | n.d. |
| 80 | 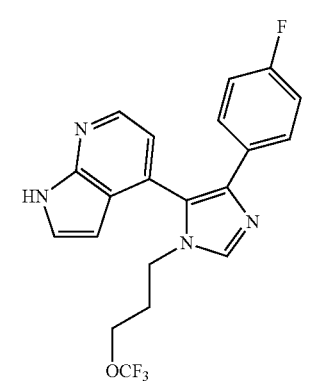 [SMILES: Fc1ccc(-c2ncn(CCCOC(F)(F)F)c2-c2ccnc3[nH]ccc23)cc1] | 0.49 | 0.42 |

TABLE 1-continued

| Preparative example number | Compound of formula I | Viability of cells Compound of formula I (100 μM), relative to PF670462 (100 μM) | |
|---|---|---|---|
| | | CLL primary cells | Maver-1 cells (mantle cell lymphoma) |
| 81 | | 0.60 | 0.10 |
| 82 | | 0.80 | n.d. |
| 83 | | 0.78 | n.d. |
| 84 | | 0.48 | 0.08 |

TABLE 1-continued

| Preparative example number | Compound of formula I | Viability of cells Compound of formula I (100 μM), relative to PF670462 (100 μM) | |
|---|---|---|---|
| | | CLL primary cells | Maver-1 cells (mantle cell lymphoma) |
| 85 | [structure: 7-azaindole linked to imidazole bearing 4-fluorophenyl and N-(4-trifluoromethoxybenzyl)] | 0.01 | 0.04 |
| 86 | [structure: 7-azaindole linked to imidazole bearing 4-fluorophenyl and N-quinuclidinyl] | 0.76 | n.d. |
| 87 | [structure: 7-azaindole linked to imidazole bearing 4-fluorophenyl and N-phenethyl] | 0.10 | 0.03 |

TABLE 1-continued

| Preparative example number | Compound of formula I | Viability of cells Compound of formula I (100 μM), relative to PF670462 (100 μM) | |
|---|---|---|---|
| | | CLL primary cells | Maver-1 cells (mantle cell lymphoma) |
| 88 | | 0.15 | 0.05 |
| 89 | | 0.59 | 0.70 |
| 90 | | 0.23 | 0.52 |
| 91 | | n.d. | 0.69 |

TABLE 1-continued

| Preparative example number | Compound of formula I | Viability of cells Compound of formula I (100 μM), relative to PF670462 (100 μM) | |
|---|---|---|---|
| | | CLL primary cells | Maver-1 cells (mantle cell lymphoma) |
| 92 | | n.d. | 0.81 |
| 93 | | n.d. | 0.75 |
| 94 | | n.d. | 0.81 |
| 8 | | 0.32 | 0.04 |

TABLE 1-continued

| Preparative example number | Compound of formula I | Viability of cells Compound of formula I (100 μM), relative to PF670462 (100 μM) | |
|---|---|---|---|
| | | CLL primary cells | Maver-1 cells (mantle cell lymphoma) |
| 1 | | 0.18 | 0.06 |
| 2 | | 0.37 | 0.32 |
| 4 | | 0.21 | 0.21 |
| 9 | | 0.50 | 0.30 |
| 5 | | 0.24 | 0.54 |

TABLE 1-continued

| Preparative example number | Compound of formula I | Viability of cells Compound of formula I (100 μM), relative to PF670462 (100 μM) | |
|---|---|---|---|
| | | CLL primary cells | Maver-1 cells (mantle cell lymphoma) |
| 7 | | 0.34 | 0.84 |
| 10 | | 0.61 | 0.46 |
| 6 | | 0.37 | 0.42 |
| 44 | | 0.81 | n.d. |
| 42 | | 0.76 | 0.12 |

TABLE 1-continued

| Preparative example number | Compound of formula I | Viability of cells Compound of formula I (100 μM), relative to PF670462 (100 μM) | |
|---|---|---|---|
| | | CLL primary cells | Maver-1 cells (mantle cell lymphoma) |
| 67 | | 0.66 | 0.71 |
| 61 | | 0.35 | 0.02 |
| 95 | | 0.02 | 0.01 |
| 39 | | 0.10 | 0.02 |
| 56 | | 0.67 | 0.79 |

TABLE 1-continued

| Preparative example number | Compound of formula I | Viability of cells Compound of formula I (100 μM), relative to PF670462 (100 μM) | |
|---|---|---|---|
| | | CLL primary cells | Maver-1 cells (mantle cell lymphoma) |
| 60 | | 0.93 | 0.84 |
| 97 | | 0.18 | 0.01 |
| 98 | | 0.16 | 0.03 |
| 100 | | 0.01 | 0.00 |

TABLE 1-continued

| Preparative example number | Compound of formula I | Viability of cells Compound of formula I (100 μM), relative to PF670462 (100 μM) | |
|---|---|---|---|
| | | CLL primary cells | Maver-1 cells (mantle cell lymphoma) |
| 102 | | 0.68 | 0.69 |
| 106 | | n.d. | 0.07 |
| 108 | | 0.74 | 0.82 |
| 109 | | 0.87 | 0.31 |

TABLE 1-continued

| Preparative example number | Compound of formula I | Viability of cells Compound of formula I (100 μM), relative to PF670462 (100 μM) | |
|---|---|---|---|
| | | CLL primary cells | Maver-1 cells (mantle cell lymphoma) |
| 114 | | 0.78 | 0.27 |
| 119 | | 0.87 | n.d. |
| 123 | | 0.58 | 0.78 |
| 124 | | 0.55 | 0.53 |

TABLE 1-continued
| Preparative example number | Compound of formula I | Viability of cells Compound of formula I (100 µM), relative to PF670462 (100 µM) | |
|---|---|---|---|
| | | CLL primary cells | Maver-1 cells (mantle cell lymphoma) |
| 125 | 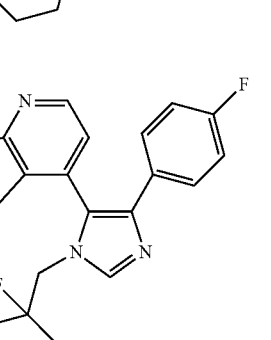 | 0.28 | 0.26 |
| 126 | 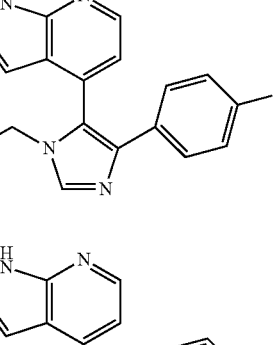 | 0.64 | 0.71 |
| 127 | 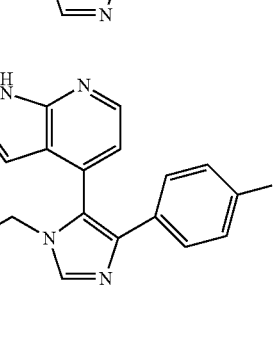 | n.d. | 0.72 |
| 129 | 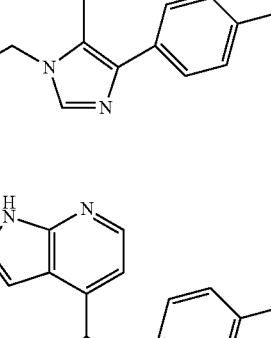 | 0.78 | 0.86 |
| 130 | 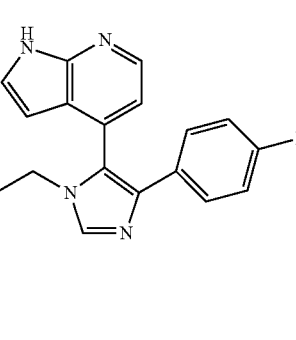 | 0.89 | n.d. |

TABLE 1-continued

| Preparative example number | Compound of formula I | Viability of cells Compound of formula I (100 μM), relative to PF670462 (100 μM) | |
|---|---|---|---|
| | | CLL primary cells | Maver-1 cells (mantle cell lymphoma) |
| 134 | | 0.22 | 0.01 |
| 135 | | 0.09 | 0.00 |
| 136 | | 0.47 | 0.00 |
| 140 | | 0.01 | 0.00 |
| 141 | | 0.43 | 0.00 |

TABLE 1-continued

| Preparative example number | Compound of formula I | Viability of cells Compound of formula I (100 μM), relative to PF670462 (100 μM) | |
|---|---|---|---|
| | | CLL primary cells | Maver-1 cells (mantle cell lymphoma) |
| 142 | | 0.05 | 0.00 |
| 143 | | 0.66 | n.d. |
| 144 | | 0.36 | 0.01 |
| 145 | | n.d. | 0.42 |
| 146 | | 0.16 | 0.00 |
| 147 | | 0.08 | 0.03 |

TABLE 1-continued

| Preparative example number | Compound of formula I | Viability of cells Compound of formula I (100 μM), relative to PF670462 (100 μM) | |
|---|---|---|---|
| | | CLL primary cells | Maver-1 cells (mantle cell lymphoma) |
| 149 | | 0.11 | 0.00 |
| 152 | | n.d. | 0.62 |
| 153 | | 1.17 | 0.87 |
| 155 | | 0.01 | 0.00 |
| 158 | | 0.76 | n.d. |

TABLE 1-continued

| Preparative example number | Compound of formula I | Viability of cells Compound of formula I (100 μM), relative to PF670462 (100 μM) | |
|---|---|---|---|
| | | CLL primary cells | Maver-1 cells (mantle cell lymphoma) |
| 163 | (structure: 7-azaindole-imidazole with 4-fluorophenyl, N-cyclohexyl, ethyl ester) | 0.57 | 0.10 |
| 165 | (structure: 7-azaindole-imidazole with 4-fluorophenyl, N-cyclohexyl, carboxamide) | 0.00 | 0.00 |
| 166 | (structure: 7-azaindole-imidazole with 4-fluorophenyl, N-cyclohexyl, CH₂OH) | 0.07 | 0.04 |
| 169 | (structure: 7-azaindole-imidazole with 4-fluorophenyl, N-cyclohexyl, CH₂N(CH₃)₂) | 0.12 | 0.00 |
| 170 | (structure: 7-azaindole with NH₂, imidazole with 4-fluorophenyl, N-cyclohexyl) | 0.56 | 0.06 |

TABLE 1-continued

| Preparative example number | Compound of formula I | Viability of cells Compound of formula I (100 μM), relative to PF670462 (100 μM) | |
|---|---|---|---|
| | | CLL primary cells | Maver-1 cells (mantle cell lymphoma) |
| 173 | | 0.02 | 0.01 |
| 179 | | 0.01 | 0.00 |
| 184 | | n.d. | 0.57 |

Example II.2: Cytotoxicity of Selected Compounds of Formula I on a Panel of Cell Lines Cytotoxicity of selected compounds of formula I was tested on a panel of cell lines representative for main types of leukemia and lymphoma, selection of epithelial solid tumors and melanoma.

Cell Treatment

The tested cell lines were incubated with inhibitors at 30 μM concentration or corresponding amount of solvent (DMSO, Sigma Aldrich) in standard culture conditions, seeded as $10^5$ cells/500 μl per well in a 24-well plate. Experiments were performed in technical duplicates and 2-3 biological repetitions per cell line. Viability of cells was assessed after 24 hours.

Viability Assessment

Viability of cells was assessed by flow cytometric analysis (Accuri C6, BD Biosciences) according to TMRE staining (details in Example II.1). Viable cells (TMRE positive) were assessed in each experiment and obtained results were normalized to control (no inhibitor) condition. Relative values are presented as a mean value, showing ratio to the effect of control. Relative value <1=lower viability than control condition.

The tested compounds were the following:

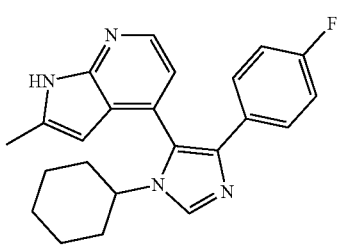

Prep. Example 39

-continued
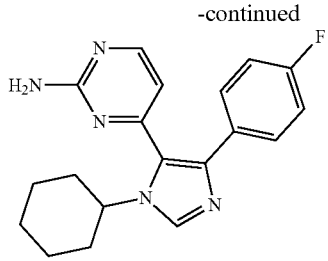
PF670462 = standard
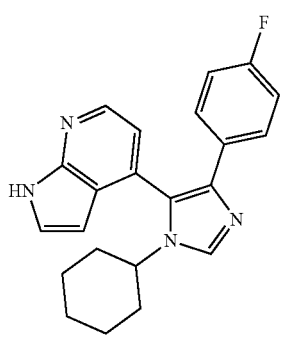
Prep. Example 3
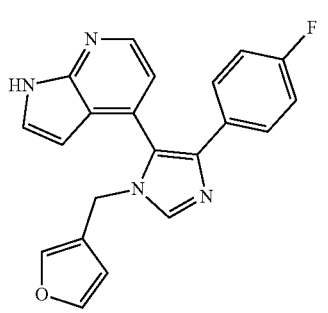
Prep. Example 37
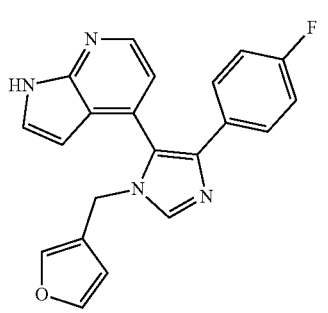
Prep. Example 23
Prep. Example 24
-continued
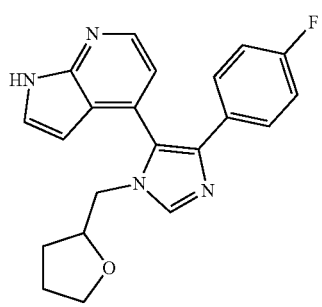
Prep. Example 27
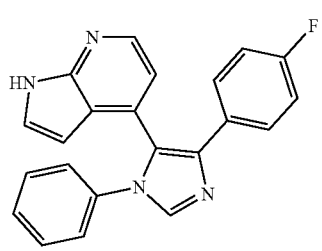
Prep. Example 47
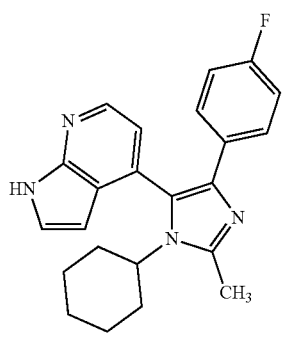
Prep. Example 61
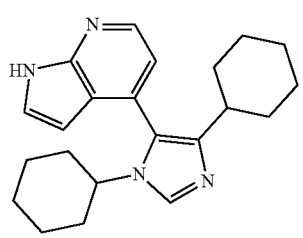
Prep. Example 67
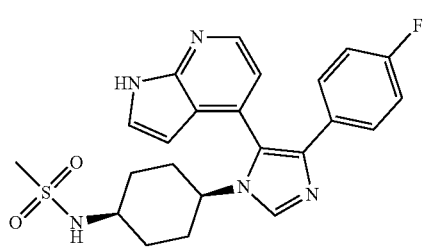
Prep. Example 74

Prep. Example 81

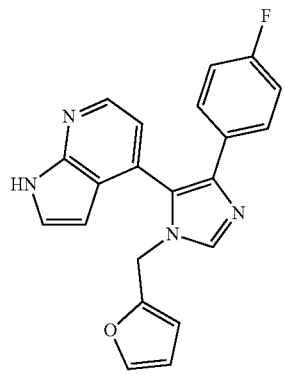

Prep. Example 95

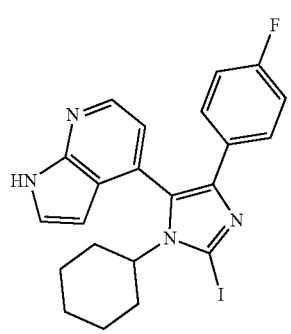

Prep. Example 97

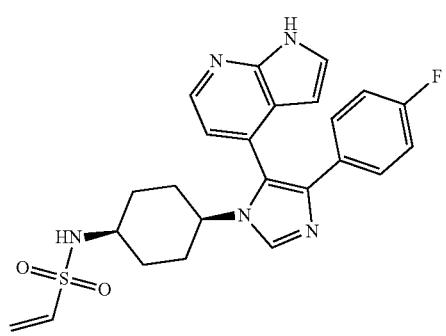

Prep. Example 106

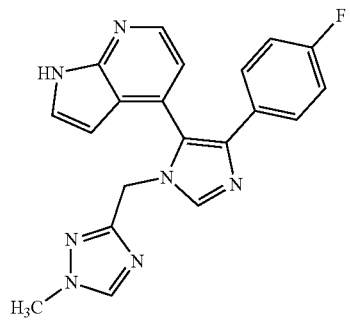

Prep. Example 140

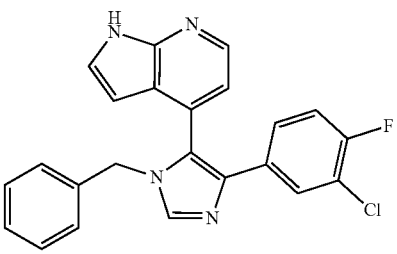

Prep. Example 147

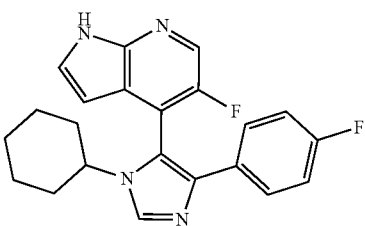

Prep. Example 149

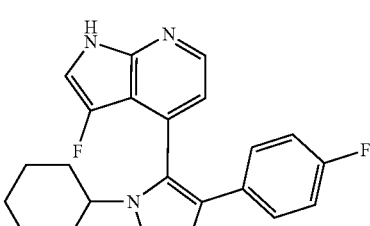

Prep. Example 173

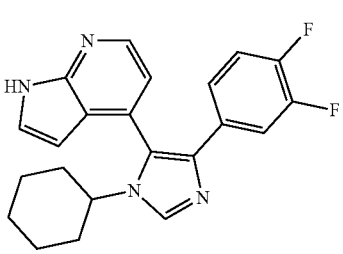

Table 2 shows average viability of cancer cell lines on selected compounds of formula I. The tested concentration was 30 µM, and the results are expressed as cell viability relative to control (Ctrl). PF670462 (PF) is included for comparison. (n.d.=not determined). Abbreviations: leukemia types—chronic lymphocytic leukemia (CLL), acute lymphocytic leukaemia (ALL), chronic myeloid leukaemia (CML), acute myeloid leukaemia (AML), lymphoma types—mantle cell lymphoma (MCL), Burkitt lymphoma (BL), diffuse large B-cell lymphoma (DLBCL), and follicular lymphoma (FL).

TABLE 2

| Disease Type | Cancer/ Cell line | Ctrl | PF | 3 | 39 | 37 | 23 | 24 | 27 | 47 | 61 | 67 | 74 |
|---|---|---|---|---|---|---|---|---|---|---|---|---|---|
| CLL | primary CLL | 1 | 1.03 | 0.69 | 0.48 | 0.39 | 0.68 | 0.85 | n.d. | 0.81 | 0.7 | n.d. | n.d. |
| CLL | MEC-1 | 1 | 0.92 | 0.43 | 0.22 | n.d. | 0.84 | n.d. | n.d. | n.d. | 0.41 | n.d. | n.d. |
| ALL | Nalm16 | 1 | 0.94 | 0.32 | 0.06 | 0.50 | 0.20 | 0.75 | n.d. | 0.57 | 0.06 | 0.40 | 0.78 |
| CML | K562 | 1 | 0.97 | 0.81 | 0.73 | n.d. | n.d. | n.d. | n.d. | n.d. | 0.80 | n.d. | n.d. |
| AML | HL60 | 1 | 0.98 | 0.72 | 0.62 | n.d. | n.d. | n.d. | n.d. | n.d. | 0.63 | n.d. | n.d. |

TABLE 2-continued

| Disease Type | Cancer/Cell line | Ctrl | | | | | | | | | | |
|---|---|---|---|---|---|---|---|---|---|---|---|---|
| MCL | Maver1 | 1 | 0.85 | 0.54 | 0.02 | n.d. | 0.71 | 0.72 | 0.78 | n.d. | 0.52 | 0.73 | 0.84 |
| MCL | Mino | 1 | 0.84 | 0.38 | 0.26 | n.d. | 0.65 | 0.80 | n.d. | n.d. | 0.28 | 0.72 | n.d. |
| BL | BL-41 | 1 | 0.82 | 0.17 | 0.10 | 0.75 | 0.57 | 0.76 | n.d. | 0.73 | 0.22 | 0.76 | n.d. |
| FL | WSU-NHL | 1 | 1.1 | n.d. | 0.88 | n.d. | n.d. | n.d. | n.d. | n.d. | n.d. | 0.84 | n.d. |
| DLBCL | SUDHL | 1 | 0.93 | 0.18 | 0.24 | 0.89 | 0.67 | n.d. | n.d. | n.d. | 0.24 | n.d. | n.d. |
| Breast cancer | MDA-MB-231 | 1 | 0.99 | 0.69 | 0.71 | n.d. | n.d. | n.d. | n.d. | n.d. | 0.46 | n.d. | n.d. |
| Breast cancer | MCF-7 | 1 | 0.55 | 0.53 | n.d. | n.d. | 0.31 | n.d. | n.d. | n.d. | 0.39 | n.d. | 0.72 |
| Pancreatic cancer | PANC1 | 1 | 0.93 | 0.65 | 0.44 | 0.67 | n.d. | n.d. | n.d. | 0.83 | 0.81 | n.d. | n.d. |
| Pancreatic cancer | MIA-PA-CA | 1 | 1.04 | 0.61 | 0.56 | n.d. | n.d. | n.d. | n.d. | n.d. | 0.58 | n.d. | n.d. |
| Melanoma | A375 | 1 | 0.94 | 0.64 | 0.16 | n.d. | n.d. | n.d. | n.d. | n.d. | 0.20 | 0.55 | n.d. |
| Ovarian cancer | OVCAR4 | 1 | 0.95 | 0.73 | 0.42 | 0.82 | n.d. | n.d. | 0.84 | 0.76 | 0.77 | n.d. | n.d. |
| Prostate cancer | PC3 | 1 | 1.15 | n.d. | 0.29 | n.d. | n.d. | n.d. | n.d. | n.d. | 0.71 | n.d. | n.d. |
| Hepatocellular carcinoma | HEPG2 | 1 | 0.78 | 0.47 | 0.55 | n.d. | n.d. | n.d. | 0.85 | n.d. | 0.60 | n.d. | n.d. |

| Disease Type | Cancer/Cell line | Ctrl | Preparative example number | | | | | | | |
|---|---|---|---|---|---|---|---|---|---|---|
| | | | 95 | 149 | 147 | 97 | 173 | 81 | 106 | 140 |
| CLL | primary CLL | 1 | 0.02 | 0.68 | 0.37 | 0.51 | 0.62 | 0.77 | n.d. | 0.60 |
| CLL | MEC-1 | 1 | 0.00 | 0.33 | 0.38 | 0.01 | 0.09 | n.d. | n.d. | 0.67 |
| CML | K562 | 1 | 0.01 | n.d. | n.d. | n.d. | n.d. | n.d. | n.d. | n.d. |
| AML | HL60 | 1 | 0.02 | 0.79 | 0.84 | 0.68 | 0.77 | n.d. | n.d. | 0.78 |
| MCL | Maver1 | 1 | 0.01 | 0.01 | 0.00 | 0.01 | 0.00 | 0.51 | 0.54 | 0.07 |
| MCL | Mino | 1 | 0.00 | 0.01 | 0.01 | 0.00 | 0.01 | 0.37 | 0.85 | 0.03 |
| BL | BL-41 | 1 | 0.00 | 0.22 | 0.21 | 0.11 | 0.05 | n.d. | n.d. | 0.44 |
| FL | WSU-NHL | 1 | 0.00 | 0.26 | 0.38 | 0.02 | 0.16 | 0.68 | 0.82 | 0.56 |
| DLBCL | SUDHL | 1 | 0.00 | 0.21 | 0.01 | 0.68 | 0.03 | n.d. | n.d. | 0.11 |
| Breast cancer | MDA-MB-231 | 1 | 0.02 | n.d. | n.d. | 0.53 | n.d. | n.d. | n.d. | 0.86 |
| Breast cancer | MCF-7 | 1 | 0.01 | 0.65 | 0.41 | 0.28 | 0.52 | 0.68 | 0.65 | 0.43 |
| Pancreatic cancer | PANC1 | 1 | 0.10 | n.d. | 0.67 | 0.50 | n.d. | n.d. | n.d. | 0.77 |
| Pancreatic cancer | MIA-PA-CA | 1 | 0.01 | 0.87 | 0.45 | 0.23 | 0.74 | n.d. | 0.68 | 0.29 |
| Melanoma | A375 | 1 | 0.16 | n.d. | 0.85 | 0.17 | n.d. | n.d. | 0.79 | 0.80 |
| Ovarian cancer | OVCAR4 | 1 | 0.07 | n.d. | 0.69 | 0.78 | n.d. | n.d. | 0.89 | 0.87 |
| Prostate cancer | PC3 | 1 | 0.01 | 0.86 | 0.57 | 0.74 | n.d. | n.d. | n.d. | 0.67 |
| Hepatocellular carcinoma | HEPG2 | 1 | 0.05 | 0.77 | 0.41 | 0.39 | 0.58 | 0.58 | 0.24 | 0.22 |

Example II.3: Blocking of Migration

Migration Assay and Cell Treatment

The migration assay was performed in HTS Transwell®-96 well plates (Corning Incorporated) with 5.0 μm pore size polycarbonate membranes. Cell migration was induced by 200 ng/ml of CCL19 (R&D Systems, 361-MI-025) recombinant chemokine, which is involved in CLL cell homing to lymphoid organs, a process crucial for the pathogenesis of CLL or other leukemias and lymphomas. Maver-1 cells ($0.3 \times 10^5$ cells/well) were seeded according to manufacturer's instructions and incubated for 4 h with the inhibitors at final concentration 3 μM or with corresponding amount of DMSO. The absolute number of transmigrated cells was quantified by Accuri C6 flow cytometer (BD Biosciences). Obtained values are presented in FIG. 3 as Relative migration=ratio of cell counts in the inhibitor-treated and control conditions. Experiments were performed in technical duplicates.

Example II.4: Specificity of Cytotoxic Activity to Cancer Cells

To prove that compounds of formula I selectively target cancer cells, the cytotoxicity towards cancer cells (primary CLL cells) and their nonmalignant counterparts (primary healthy B cells) was tested with the compound described in preparative example 3. PF670462, which is the structurally closest compound proposed for the treatment of chronic lymphocytic leukaemia (CLL), was used as a negative control. Ibrutinib (PCI-32765, DC Chemicals), a drug used for therapy of CLL with described cytotoxic effects towards primary CLL cells (Amin N A, Balasubramanian S, Saiya-Cork K, Shedden K, Hu N, Malek S N. Clin Cancer Res. 2017; 23(4):1049-1059), was used as a positive control. Obtained data show that the cytotoxic effects are dose-dependent (FIG. 1), caused by apoptosis (FIG. 2) and selective to cancer cells (Table 3, FIG. 4).

Cell Treatment

Both primary CLL cells and primary nonmalignant control cells were incubated for 6 hours with inhibitors PF670462 or preparative example 3 at 30 μM concentration. Corresponding amount of solvent (DMSO) was used as a control (data presented in Table 3). For the experiment presented in FIG. 1, the cells were incubated for 6 h with indicated doses of inhibitors (PF670462, prep. example 3 or ibrutinib) or DMSO as a control. To confirm by an independent method that compound of preparative example 3 induces apoptosis in primary CLL cells, the cells were treated overnight by 10 μM concentration of the compound, PF670462 inhibitor or DMSO (FIG. 2).

Viability Assessment—Induction of Apoptosis

Viability and induction of apoptosis in primary CLL and nonmalignant control cells was assessed by flow cytometric analysis (Accuri C6, BD Biosciences) according to TMRE staining (details in Example II.1, data presented in FIG. 1, Table 3 and FIG. 4). Viable cells (TMRE positive) were assessed in each experiment and obtained results were normalized to control (no inhibitor) condition. Alternatively (FIG. 2), induction of apoptosis was assessed by western blotting analysis (performed essentially as described in Bryja V, Schulte G, Arenas E. *Cell Signal*. 2007; 19(3):610-616) and detection of cleaved PARP protein by cs-9541 antibody (Cell Signaling). Actin was detected as a loading control (cs-4970, Cell Signaling), Anti-Rabbit IgG, F(ab')2 fragment—Peroxidase conjugated secondary antibody (A6667, Sigma) and Immobilon Western Chemilluminiscent HRP Substrate (Millipore) were used for signal detection. Cleaved PARP serves as a sensitive apoptosis marker.

Table 3 shows that 30 μM PF670462 inhibitor is not able to induce apoptosis in primary CLL cells or nonmalignant control (healthy) cells, in contrast to compound described in preparative example 3. Average cell viability is presented. Cytotoxic effect of the tested compound (prep. example 3) is selective towards cancer cells—it is significantly stronger in case of primary CLL cells compared to healthy cells. Data are presented in graphs in FIG. 4.

TABLE 3

|  | Primary CLL | Primary healthy cells | Significantly different from control? | Significantly different effect on CLL vs healthy cells? |
|---|---|---|---|---|
|  | Viability - mean % of control | | One sample t-test, CLL/healthy | Unpaired t-test |
| PF670462 | 98.3% (N = 8) | 95.5% (N = 4) | No/no | No |
| Prep. Example 3 | 37.3% (N = 8) | 80.9% (N = 4) | Yes/yes | Yes |
| Significantly different effect of tested compounds? Unpaired t-test | Yes | Yes | | |

FIG. 1 shows that the apoptosis of primary CLL cells is induced dose-dependently by compound from preparatory example 3 but not PF670462. Compound from preparatory example 3 shows similar cytotoxic effects as ibrutinib.

FIG. 2 confirms that the effects observed for compound described in preparatory example 3 (Table 3) are caused by induction of apoptosis in primary CLL cells. Increased PARP cleavage, a sensitive apoptosis marker, is detectable after overnight incubation of primary CLL cells with 10 μM inhibitor from preparatory example 3, but not in case of PF670462 treatment. FIGS. 2A and B show data obtained by western blotting analysis of cleaved PARP (A) and flow cytometric analysis (B) from the same primary sample to illustrate that the methods are complementary. C-D show the same for another 4 primary CLL samples.

Example II.5: Pharmacokinetic Profiles of Selected Compounds

In order to demonstrate that the compounds are orally bioavailable, pharmacokinetic studies were carried out as described below.

Male Balb/c mice (10-12 weeks old, body weight 24.1 to 30.8 g and average body weight across all groups 26.8 g, SD=1.7 g) were used in this study. The animals were randomly assigned to the treatment groups before the pharmacokinetic study; all animals were fasted for 4 h before dosing. The time points indicated in Table 4 were set for this pharmacokinetic study. Each of the time point treatment group included 4 animals. There was also control group of 2 animals. The compounds were dosed orally as the corresponding dihydrochlorides dissolved in physiological saline (c=3-4 mg/mL) at the dose of 20 mg/kg.

Mice were injected IP with 2,2,2-tribromoethanol at the dose of 150 mg/kg prior to drawing the blood. Blood collection was performed from the orbital sinus in microtainers containing $K_2EDTA$. Animals were sacrificed by cervical dislocation after the blood samples collection. All samples were immediately processed, flash-frozen and stored at −70° C. until subsequent analysis.

Plasma samples (50 μL) were mixed with 200 μL of internal standard solution. After mixing by pipetting and centrifuging for 4 min at 6,000 rpm, 0.5 μL of each supernatant was injected into LC-MS/MS system.

Preparation of Calibration Standards

The analyzed compound (as a dihydrochloride salt) was dissolved in DMSO, and the resulting solution with concentration of 2 mg/mL was used for calibration standards preparation (stock solution). A series of calibration standards was prepared by consecutively dilution of stock compound solution with blank mouse plasma to a final concentration of 40 000, 20 000, 10 000, 5 000, 2 500, 1000, 500, 250, 100, 50, and 20 ng/mL. Standard plasma samples (50 μL) were mixed with 200 μL of internal standard. After mixing by pipetting and centrifuging for 4 min at 6,000 rpm, 0.5 μL of each supernatant was injected into LC-MS/MS system. Signal corresponding to the free base was analyzed and quantified (Table 4).

Calibration Curve

The regression analysis of the analyzed compound was performed by plotting the peak area ratio (y-axis) against the compound concentration in calibration standards (x-axis, ng/mL). The validity of the calibration curve (relationship between peak area ratio and compound concentration) was proved by the correlation coefficient (R) calculated for the quadratic regression.

The concentrations of the analyzed compound in plasma samples below the lower limit of quantitation (LLOQ—5 ng/mL to 20 ng/mL) were designated as zero.

TABLE 4

| compound Prep. Example | conc. at 15 min [μM] | conc. at 30 min [μM] | conc. at 60 min [μM] | conc. at 120 min [μM] | conc. at 240 min [μM] | conc. at 600 min [μM] | R |
|---|---|---|---|---|---|---|---|
| 107 | 4.78 | 2.42 | 2.30 | 0.43 | 0.24 | 0 | 0.9999 |
| 94 | 0.44 | 0.21 | 0.18 | 0.07 | 0 | 0 | 0.9994 |
| 92 | 9.52 | 6.63 | 4.52 | 0.79 | 0.05 | 0 | 0.9998 |
| 82 | 1.37 | 0.26 | 0.09 | 0.04 | 0.02 | 0 | 0.9999 |
| 123 | 1.35 | 0.92 | 0.52 | 0.13 | 0 | 0 | 0.9999 |
| 103 | 2.17 | 0.58 | 0.13 | 0.08 | 0.04 | 0 | 0.9998 |
| 122 | 2.73 | 0.73 | 0.30 | 0.16 | 0.04 | 0 | 0.9999 |
| 113 | 8.01 | 3.53 | 1.03 | 1.12 | 0.25 | 0 | 0.9998 |
| 102 | 0.62 | 0.72 | 0.40 | 0.53 | 0.48 | 0 | 0.9997 |
| 151 | 18.90 | 7.24 | 3.98 | 0.77 | 0.41 | 0 | 0.9997 |
| 154 | 13.88 | 8.76 | 7.86 | 2.45 | 0.52 | 0 | 0.9999 |
| 126 | 2.38 | 1.83 | 0.84 | 0.76 | 0.38 | 0 | 0.9999 |

The invention claimed is:
1. Compound of general formula I

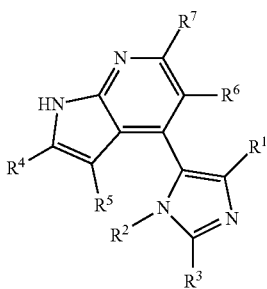

wherein:
R1 is selected from the group consisting of C6-C14 aryl, C4-C8 cycloalkyl, C3-C10 heteroaryl comprising at least one heteroatom selected from S, O, N, and C3-C7 cycloheteroalkyl comprising at least one heteroatom selected from S, O, N, wherein the aryl, cycloalkyl, cycloheteroalkyl or heteroaryl may optionally be substituted by at least one substituent selected independently from C1-C4 alkyl, halogen, OH, O(C1-C4 alkyl), O(C5-C6 aryl or heteroaryl), SH, S(C1-C4 alkyl), CN, NH2, NH(C1-C4 alkyl), N(C1-C4 alkyl)2, CF3, C2F5, OCF3, OC2F5;
R2 is selected from the group consisting of
linear or branched C1-C10 alkyl, preferably C1-C6 alkyl,
linear or branched C1-C10 alkenyl, preferably C1-C6 alkenyl,
C3-C8 cycloalkyl, preferably, C4-C7 cycloalkyl, wherein optionally 1-2 carbon atoms are replaced by a heteroatom selected from S, O, N,
C3-C8 cycloalkenyl, wherein optionally 1-2 carbon atoms are replaced by a heteroatom selected from S, O, N,
C3-C8-cycloalkyl-C1-C4-alkyl, wherein optionally 1-2 carbon atoms are replaced by a heteroatom selected from S, O, N,
C6-C14 aryl,
C6-C14-aryl-C1-C4-alkyl,
C3-C10 heteroaryl comprising at least one heteroatom selected from S, O, N, and
C3-C10-heteroaryl-C1-C4-alkyl comprising at least one heteroatom selected from S, O, N in the aromatic ring, wherein each of the listed substituents can optionally be substituted by at least one substituent selected independently from C1-C4 alkyl, halogen, OH, HO—C1-C4 alkyl, O(C1-C4 alkyl), (C1-C4 alkyl)-O—C1-C4 alkyl, O(C5-C6 aryl or heteroaryl), SH, S(C1-C4 alkyl), S(C5-C6 aryl or heteroaryl), CF3, CF3—(C1-C4 alkyl)-, C2F5, OCF3, CF3O—(C1-C4 alkyl)-, OC2F5, amino (NH2), NO2, N3, C1-C4 alkylamino, di(C1-C4 alkyl)amino, (C5-C6 aryl or heteroaryl)amino, di(C5-C6 aryl or heteroaryl)amino, NH2—(C1-C4 alkyl)-, (C1-C4 alkyl)-NH—C1-C4 alkyl, (C1-C4 alkyl)2-N—C1-C4-alkyl, =O, =S, CN, =N—OH, =N—O(C1-C4 alkyl), —COOH, HOOC—(C1-C4 alkyl)-, —CONH2, —CONH(C1-C4 alkyl), —CON(C1-C4 alkyl)2, NH2CO—(C1-C4 alkyl)-, (C1-C4 alkyl)-CONH—(C1-C4 alkyl)-, (C1-C4 alkyl)2N—CO—(C1-C4 alkyl)-, —COO(C1-C4 alkyl), (C1-C4 alkyl)-COO(C1-C4 alkyl)-, (C1-C4 alkyl)-O—CO—(C1-C4 alkyl)-, NH2S(O)2—(C1-C4 alkyl)-, (C1-C4 alkyl)-S(O)2NH(C1-C4 alkyl)-, (C1-C4 alkyl)2N—S(O)2—(C1-C4 alkyl)-, (C1-C4 alkyl)NH—S(O)2—(C1-C4 alkyl)-, —CO(C1-C4 alkyl), —CO(C5-C6 aryl or heteroaryl), (C1-C4 alkyl)-S(O)2—, (C1-C4 alkyl)-S(O)—, (C1-C4 alkyl)-S(O)2—NH—, (C1-C4 alkyl)-S(O)2—N(C1-C4 alkyl)-, (C1-C4 alkyl)-O—CO—, (C1-C4 alkyl)-NH—CO—, (C1-C4 alkyl)2N—CO—, (C1-C4 alkyl)-NH—(SO)2—, (C1-C4 alkyl)2N—(SO)2—, (C1-C4 alkyl)-CO—NH—, (C1-C4 alkyl)-CO—N(C1-C4 alkyl)-, (C1-C4 alkyl)-OCO—NH—, (C1-C4 alkyl)-OCO—N(C1-C4 alkyl)-, (C1-C4 alkyl)-CO—NH—CO—, (C1-C4 alkyl)-CO—N(C1-C4 alkyl)-CO—, NH2—CO—NH—, (C1-C4 alkyl)-NH—CO—NH—, (C1-C4 alkyl)2N—CO—NH—, NH2—CO—N(C1-C4 alkyl)-, (C1-C4 alkyl)-NH—CO—N(C1-C4 alkyl)-, (C1-C4 alkyl)2N—CO—N(C1-C4 alkyl)-, NH2—S(O)2—NH—, (C1-C4 alkyl)-NH—S(O)2—NH—, (C1-C4 alkyl)2N—S(O)2—NH—, NH2—S(O)2—N(C1-C4 alkyl)-, (C1-C4 alkyl)-NH—S(O)2—N(C1-C4 alkyl)-, (C1-C4 alkyl)2N—S(O)2—N(C1-C4 alkyl)-, (C1-C4 alkyl)2N—(C1-C4 alkylene)-CO—, (C1-C4 alkyl)2N—(C1-C4 alkylene)-SO2—, (C1-C4 alkyl)2N—(C1-C4 alkylene)-SO2—NH—, (C1-C4 alkyl)2N—(C1-C4 alkylene)-NH—SO2—;
R3 is selected from the group consisting of hydrogen, halogen, CF3, C2F5, CN, C1-C4 alkyl, said alkyl being optionally substituted by at least one substituent selected from C1-C4 alkyl, halogen, OH, NH2, NH(C1-C4 alkyl), NH(C5-C6 aryl or heteroaryl), N(C1-C4 alkyl)2, N(C5-C6 aryl or heteroaryl)2, O(C1-C4 alkyl), O(C5-C6 aryl or heteroaryl), SH, S(C1-C4 alkyl), S(C5-C6 aryl or heteroaryl), $OCF_3$, $OC_2F_5$, COO(C1-C4 alkyl), CONH(C1-C4 alkyl), CON(C1-C4 alkyl), $CF_3$, and $C_2F_5$;

R4 is selected the group consisting of hydrogen, $CF_3$, $C_2F_5$, CN, and C1-C4 alkyl, optionally substituted by at least one substituent selected from C1-C4 alkyl, halogen, OH, O(C1-C4 alkyl), O(C5-C6 aryl or heteroaryl), SH, S(C1-C4 alkyl), S(C5-C6 aryl or heteroaryl), $OCF_3$, $OC_2F_5$, $CF_3$, $C_2F_5$;

R5 is selected from H, C1-C2 alkyl, halogen;

R6 is selected from H, C1-C2 alkyl, halogen;

R7 is selected from H, halogen, OH, O(C1-C4 alkyl), $CF_3$, $C_2F_5$, CN, $NH_2$, NH(C1-C4 alkyl), N(C1-C4 alkyl)$_2$, C1-C4 alkyl, where alkyl is optionally substituted by at least one substituent selected from C1-C4 alkyl, halogen, OH, O(C1-C4 alkyl), O(C5-C6 aryl or heteroaryl), SH, S(C1-C4 alkyl), S(C5-C6 aryl or heteroaryl), $OCF_3$, $OC_2F_5$, $CF_3$, $C_2F_5$;

or pharmaceutically acceptable salts thereof.

2. Compound according to claim 1, wherein R1 is a C6-C10 aryl substituted by one or two halogens, preferably at least one of them being fluorine.

3. Compound according to claim 1, wherein R1 is a C4-C6 heteroaryl substituted by one or two halogens, preferably at least one of them being fluorine.

4. Compound according to claim 1, wherein R2 is selected from

C3-C8 cycloalkyl, preferably C4-C7 cycloalkyl, wherein optionally 1-2 carbon atoms are replaced by a heteroatom selected from S, O, N, and which is optionally substituted by one or more substituents selected independently from halogen, hydroxy, methoxy, ethoxy, methyl, ethyl, propyl, isopropyl, amino, methylamino, dimethylamino, hydroxymethyl, hydroxyethyl, hydroxypropyl, methoxymethyl, methoxyethyl, methoxypropyl, dimethylaminomethyl, dimethylaminoethyl, dimethylaminopropyl, methylsulfonamido, methylcarbonyl, methylaminocarbonyl, ethylsulfonamido, ethylcarbonyl, ethylaminocarbonyl, methoxycarbonyl, ethoxycarbonyl, dimethylaminoethylsulfonamido, dimethylaminoethylcarbonyl, dimethylaminopropylsulfonamido, dimethylaminopropylcarbonyl, $OCF_3$, $OC_2F_5$, $CF_3$, $C_2F_5$;

C3-C8-cycloalkyl-C1-C2-alkyl, wherein optionally 1-2 carbon atoms are replaced by a heteroatom selected from S, O, N, and which is optionally substituted by one or more substituents selected independently from halogen, hydroxy, methoxy, ethoxy, methyl, ethyl, propyl, isopropyl, amino, methylamino, dimethylamino, hydroxymethyl, hydroxyethyl, hydroxypropyl, methoxymethyl, methoxyethyl, methoxypropyl, dimethylaminomethyl, dimethylaminoethyl, dimethylaminopropyl, methylsulfonamido, methylcarbonyl, methylaminocarbonyl, ethylsulfonamido, ethylcarbonyl, ethylaminocarbonyl, methoxycarbonyl, ethoxycarbonyl, dimethylaminoethylsulfonamido, dimethylaminoethylcarbonyl, dimethylaminopropylsulfonamido, dimethylaminopropylcarbonyl, $OCF_3$, $OC_2F_5$, $CF_3$, $C_2F_5$;

C6-C14-aryl, which is optionally substituted by one or more substituents selected independently from halogen, hydroxy, methoxy, ethoxy, methyl, ethyl, propyl, isopropyl, amino, methylamino, dimethylamino, hydroxymethyl, hydroxyethyl, hydroxypropyl, methoxymethyl, methoxyethyl, methoxypropyl, dimethylaminomethyl, dimethylaminoethyl, dimethylaminopropyl, methylsulfonamido, methylcarbonyl, methylaminocarbonyl, ethylsulfonamido, ethylcarbonyl, ethylaminocarbonyl, methoxycarbonyl, ethoxycarbonyl, dimethylaminoethylsulfonamido, dimethylaminoethylcarbonyl, dimethylaminopropylsulfonamido, dimethylaminopropylcarbonyl, $OCF_3$, $OC_2F_5$, $CF_3$, $C_2F_5$;

C6-C14-aryl-C1-C2-alkyl, which is optionally substituted by one or more substituents selected independently from halogen, hydroxy, methoxy, ethoxy, methyl, ethyl, propyl, isopropyl, amino, methylamino, dimethylamino, hydroxymethyl, hydroxyethyl, hydroxypropyl, methoxymethyl, methoxyethyl, methoxypropyl, dimethylaminomethyl, dimethylaminoethyl, dimethylaminopropyl, methylsulfonamido, methylcarbonyl, methylaminocarbonyl, ethylsulfonamido, ethylcarbonyl, ethylaminocarbonyl, methoxycarbonyl, ethoxycarbonyl, dimethylaminoethylsulfonamido, dimethylaminoethylcarbonyl, dimethylaminopropylsulfonamido, dimethylaminopropylcarbonyl, $OCF_3$, $OC_2F_5$, $CF_3$, $C_2F_5$;

C3-C10-heteroaryl comprising one or two or three heteroatoms selected from S, O, N in the aromatic ring, and which is optionally substituted by one or more substituents selected independently from halogen, hydroxy, methoxy, ethoxy, methyl, ethyl, propyl, isopropyl, amino, methylamino, dimethylamino, hydroxymethyl, hydroxyethyl, hydroxypropyl, methoxymethyl, methoxyethyl, methoxypropyl, dimethylaminomethyl, dimethylaminoethyl, dimethylaminopropyl, methylsulfonamido, methylcarbonyl, methylaminocarbonyl, ethylsulfonamido, ethylcarbonyl, ethylaminocarbonyl, methoxycarbonyl, ethoxycarbonyl, dimethylaminoethylsulfonamido, dimethylaminoethylcarbonyl, dimethylaminopropylsulfonamido, dimethylaminopropylcarbonyl, $OCF_3$, $OC_2F_5$, $CF_3$, $C_2F_5$;

C3-C10-heteroaryl-C1-C2-alkyl comprising one or two or three heteroatoms selected from S, O, N in the aromatic ring, and which is optionally substituted by one or more substituents selected independently from halogen, hydroxy, methoxy, ethoxy, methyl, ethyl, propyl, isopropyl, amino, methylamino, dimethylamino, hydroxymethyl, hydroxyethyl, hydroxypropyl, methoxymethyl, methoxyethyl, methoxypropyl, dimethylaminomethyl, dimethylaminoethyl, dimethylaminopropyl, methylsulfonamido, methylcarbonyl, methylaminocarbonyl, ethylsulfonamido, ethylcarbonyl, ethylaminocarbonyl, methoxycarbonyl, ethoxycarbonyl, dimethylaminoethylsulfonamido, dimethylaminoethylcarbonyl, dimethylaminopropylsulfonamido, dimethylaminopropylcarbonyl, $OCF_3$, $OC_2F_5$, $CF_3$, $C_2F_5$;

C1-C6 alkyl, which is optionally substituted by one or more substituents selected independently from halogen, hydroxy, methoxy, ethoxy, amino, methylamino, dimethylamino, hydroxymethyl, hydroxyethyl, hydroxypropyl, methoxymethyl, methoxyethyl, methoxypropyl, dimethylaminomethyl, dimethylaminoethyl, dimethylaminopropyl, methylsulfonamido, methylcarbonyl, methylaminocarbonyl, ethylsulfonamido, ethylcarbonyl, ethylaminocarbonyl, methoxycarbonyl, ethoxycarbonyl, dimethylaminoethylsulfonamido, dimethylaminoethylcarbonyl, dimethylaminopropylsulfonamido, dimethylaminopropylcarbonyl, $OCF_3$, $OC_2F_5$, $CF_3$, $C_2F_5$.

5. Compound according to claim 1, wherein R2 is selected from

C3-C6-heteroaryl-methyl wherein the heteroaryl comprises one heteroatom selected from O, S, N and is optionally substituted by one or more substituents selected independently from halogen, hydroxy, methoxy, ethoxy, methyl, ethyl, propyl, isopropyl, amino, methylamino, dimethylamino, hydroxymethyl, hydroxyethyl, hydroxypropyl, methoxymethyl, methoxyethyl, methoxypropyl, dimethylaminomethyl, dimethylaminoethyl, dimethylaminopropyl, methylsulfonamido, methylcarbonyl, methylaminocarbonyl, ethylsulfonamido, ethylcarbonyl, ethylaminocarbonyl, methoxycarbonyl, ethoxycarbonyl, dimethylaminoethylsulfonamido, dimethylaminoethylcarbonyl, dimethylaminopropylsulfonamido, dimethylaminopropylcarbonyl, $OCF_3$, $OC_2F_5$, $CF_3$, $C_2F_5$;

C3-C6-heteroaryl wherein the heteroaryl comprises one or two or three heteroatoms selected from O, S, N, preferably N, and is optionally substituted by one or more substituents selected independently from halogen, hydroxy, methoxy, ethoxy, methyl, ethyl, propyl, isopropyl, amino, methylamino, dimethylamino, hydroxymethyl, hydroxyethyl, hydroxypropyl, methoxymethyl, methoxyethyl, methoxypropyl, dimethylaminomethyl, dimethylaminoethyl, dimethylaminopropyl, methylsulfonamido, methylcarbonyl, methylaminocarbonyl, ethylsulfonamido, ethylcarbonyl, ethylaminocarbonyl, methoxycarbonyl, ethoxycarbonyl, dimethylaminoethylsulfonamido, dimethylaminoethylcarbonyl, dimethylaminopropylsulfonamido, dimethylaminopropylcarbonyl, $OCF_3$, $OC_2F_5$, $CF_3$, $C_2F_5$;

cyclohexyl or cyclohexylmethyl wherein the cyclohexyl ring is optionally substituted by one or more substituents selected independently from halogen, hydroxy, methoxy, ethoxy, methyl, ethyl, propyl, isopropyl, amino, methylamino, dimethylamino, hydroxymethyl, hydroxyethyl, hydroxypropyl, methoxymethyl, methoxyethyl, methoxypropyl, dimethylaminomethyl, dimethylaminoethyl, dimethylaminopropyl, methylsulfonamido, methylcarbonyl, methylaminocarbonyl, ethylsulfonamido, ethylcarbonyl, ethylaminocarbonyl, methoxycarbonyl, ethoxycarbonyl, dimethylaminoethylsulfonamido, dimethylaminoethylcarbonyl, dimethylaminopropylsulfonamido, dimethylaminopropylcarbonyl, $OCF_3$, $OC_2F_5$, $CF_3$, $C_2F_5$;

cyclopentyl or cyclopentylmethyl wherein the cyclopentyl ring is optionally substituted by one or more substituents selected independently from halogen, hydroxy, methoxy, ethoxy, methyl, ethyl, propyl, isopropyl, amino, methylamino, dimethylamino, hydroxymethyl, hydroxyethyl, hydroxypropyl, methoxymethyl, methoxyethyl, methoxypropyl, dimethylaminomethyl, dimethylaminoethyl, dimethylaminopropyl, methylsulfonamido, methylcarbonyl, methylaminocarbonyl, ethylsulfonamido, ethylcarbonyl, ethylaminocarbonyl, methoxycarbonyl, ethoxycarbonyl, dimethylaminoethylsulfonamido, dimethylaminoethylcarbonyl, dimethylaminopropylsulfonamido, dimethylaminopropylcarbonyl, $OCF_3$, $OC_2F_5$, $CF_3$, $C_2F_5$;

cyclobutyl or cyclobutylmethyl wherein the cyclobutyl ring is optionally substituted by one or more substituents selected independently from halogen, hydroxy, methoxy, ethoxy, methyl, ethyl, propyl, isopropyl, amino, methylamino, dimethylamino, hydroxymethyl, hydroxyethyl, hydroxypropyl, methoxymethyl, methoxyethyl, methoxypropyl, dimethylaminomethyl, dimethylaminoethyl, dimethylaminopropyl, methylsulfonamido, methylcarbonyl, methylaminocarbonyl, ethylsulfonamido, ethylcarbonyl, ethylaminocarbonyl, methoxycarbonyl, ethoxycarbonyl, dimethylaminoethylsulfonamido, dimethylaminoethylcarbonyl, dimethylaminopropylsulfonamido, dimethylaminopropylcarbonyl, $OCF_3$, $OC_2F_5$, $CF_3$, $C_2F_5$;

C1-C6 alkyl, substituted by halogen, OH, O(C1-C3 alkyl), $OCF_3$, $OC_2F_5$, $CF_3$, $C_2F_5$;

benzyl, optionally substituted by one or more substituents selected independently from halogen, hydroxy, methoxy, ethoxy, methyl, ethyl, propyl, isopropyl, amino, methylamino, dimethylamino, hydroxymethyl, hydroxyethyl, hydroxypropyl, methoxymethyl, methoxyethyl, methoxypropyl, dimethylaminomethyl, dimethylaminoethyl, dimethylaminopropyl, methylsulfonamido, methylcarbonyl, methylaminocarbonyl, ethylsulfonamido, ethylcarbonyl, ethylaminocarbonyl, methoxycarbonyl, ethoxycarbonyl, dimethylaminoethylsulfonamido, dimethylaminoethylcarbonyl, dimethylaminopropylsulfonamido, dimethylaminopropylcarbonyl, $OCF_3$, $OC_2F_5$, $CF_3$, $C_2F_5$;

C5-C6 cycloalkyl, wherein 1-2 carbon atoms, preferably 1 carbon atom, are replaced by a heteroatom selected from S, O, N; optionally substituted by one or more substituents selected independently from halogen, hydroxy, methoxy, ethoxy, methyl, ethyl, propyl, isopropyl, amino, methylamino, dimethylamino, hydroxymethyl, hydroxyethyl, hydroxypropyl, methoxymethyl, methoxyethyl, methoxypropyl, dimethylaminomethyl, dimethylaminoethyl, dimethylaminopropyl, methylsulfonamido, methylcarbonyl, methylaminocarbonyl, ethylsulfonamido, ethylcarbonyl, ethylaminocarbonyl, methoxycarbonyl, ethoxycarbonyl, dimethylaminoethylsulfonamido, dimethylaminoethylcarbonyl, dimethylaminopropylsulfonamido, dimethylaminopropylcarbonyl, $OCF_3$, $OC_2F_5$, $CF_3$, $C_2F_5$;

C5-C6-cycloalkyl-C1-C2-alkyl, wherein 1-2 carbon atoms, preferably 1 carbon atom, are replaced by a heteroatom selected from S, O, N; optionally substituted by one or more substituents selected independently from halogen, hydroxy, methoxy, ethoxy, methyl, ethyl, propyl, isopropyl, amino, methylamino, dimethylamino, hydroxymethyl, hydroxyethyl, hydroxypropyl, methoxymethyl, methoxyethyl, methoxypropyl, dimethylaminomethyl, dimethylaminoethyl, dimethylaminopropyl, methylsulfonamido, methylcarbonyl, methylaminocarbonyl, ethylsulfonamido, ethylcarbonyl, ethylaminocarbonyl, methoxycarbonyl, ethoxycarbonyl, dimethylaminoethylsulfonamido, dimethylaminoethylcarbonyl, dimethylaminopropylsulfonamido, dimethylaminopropylcarbonyl, $OCF_3$, $OC_2F_5$, $CF_3$, $C_2F_5$.

6. Compound according to claim 1, wherein R1 is p-fluoro-phenyl or m-chloro-p-fluoro-phenyl, and R2 is cyclohexyl, cyclohexylmethyl, cyclobutyl, cyclobutylmethyl, methyl, ethyl, propyl, butyl, piperidinyl, piperidinylmethyl, tetrahydrofuryl, tetrahydrofurylmethyl, morpholinyl, morpholinylmethyl, phenyl, benzyl, thiophenyl, thiophenylmethyl, oxazolyl, oxazolylmethyl, thiazolyl, thiazolylmethyl, isothiazolyl, isothiazolylmethyl, isoxazolyl, isoxazolylmethyl, triazolyl, triazolylmethyl, pyrazolyl, pyrazolylmethyl, imidazolyl, imidazolylmethyl, pyridyl, pyridylmethyl, furyl or furanylmethyl, wherein the substituent group of R2 is optionally further substituted by one or more substituents selected independently from hydroxy, methoxy, ethoxy, methyl, ethyl, propyl, isopropyl, amino, methylamino, dimethylamino, hydroxymethyl, hydroxyethyl, hydroxypropyl, methoxymethyl, methoxyethyl, methoxypropyl, dimethylaminomethyl, dimethylaminoethyl, dimethylaminopropyl, methylsulfonamido, methylcarbonyl, methylaminocarbonyl, ethylsulfonamido, ethylcarbonyl, ethylaminocarbonyl, methoxycarbonyl, ethoxycarbonyl, dimethylaminoethylsulfonamido, dimethylaminoethylcarbonyl, dimethylaminopropylsulfonamido, dimethylaminopropylcarbonyl, $OCF_3$, $OC_2F_5$, $CF_3$, $C_2F_5$.

7. Compound according to claim 1, wherein R3 is hydrogen, halogen, methyl, ethyl, propyl, isopropyl, tert-butyl.

8. Compound according to claim 1, wherein R4 is hydrogen or C1 to C4 alkyl optionally substituted by OH, O(C1-C4 alkyl).

9. Compound according to claim 1, wherein:

R1 is monohalogenated or dihalogenated phenyl or pyridyl; wherein preferably at least one halogen is fluorine;

R3 is hydrogen, methyl or iodine;

R4, R5, R6, and R7 are hydrogens.

10. Compound according to claim 1, wherein:

R1 is monohalogenated or dihalogenated phenyl or pyridyl; wherein preferably at least one halogen is fluorine;

R3 is hydrogen, methyl or iodine;

R4, R5, R6, and R7 are hydrogens;

R2 is C3-C10-heteroaryl-C1-C3-alkyl comprising at least one heteroatom selected from S, O, N in the aromatic ring or C3-C8-cycloalkyl-C1-C3-alkyl, wherein optionally 1-2 carbon atoms in the cycloalkyl part are replaced by a heteroatom selected from S, O, N, wherein the heteroaryl or cycloalkyl is optionally substituted by halogen, hydroxy, methoxy, ethoxy, methyl, ethyl, propyl, isopropyl, amino, methylamino, dimethylamino, methylsulfonamido, methylcarbonyl, methylaminocarbonyl, ethylsulfonamido, ethylcarbonyl, ethylaminocarbonyl, methoxycarbonyl, ethoxycarbonyl, dimethylaminoethylsulfonamido, dimethylaminoethylcarbonyl, dimethylaminopropylsulfonamido, dimethylaminopropylcarbonyl, $OCF_3$, $OC_2F_5$, $CF_3$, $C_2F_5$.

11. Compound according to claim 1, wherein:

R1 is monohalogenated or dihalogenated phenyl or pyridyl; wherein preferably at least one halogen is fluorine;

R3 is hydrogen, methyl or iodine;

R4, R5, R6, and R7 are hydrogens;

R2 is C3-C10-heteroaryl comprising at least one heteroatom selected from S, O, N in the aromatic ring or C3-C8-cycloalkyl, wherein optionally 1-2 carbon atoms in the cycloalkyl part are replaced by a heteroatom selected from S, O, N, wherein the heteroaryl or cycloalkyl is optionally substituted by halogen, hydroxy, methoxy, ethoxy, methyl, ethyl, propyl, isopropyl, amino, methylamino, dimethylamino, methylsulfonamido, methylcarbonyl, methylaminocarbonyl, ethylsulfonamido, ethylcarbonyl, ethylaminocarbonyl, methoxycarbonyl, ethoxycarbonyl, dimethylaminoethylsulfonamido, dimethylaminoethylcarbonyl, dimethylaminopropylsulfonamido, dimethylaminopropylcarbonyl, $OCF_3$, $OC_2F_5$, $CF_3$, $C_2F_5$.

12. Compound according to claim 1, selected from

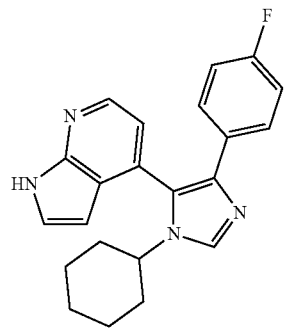

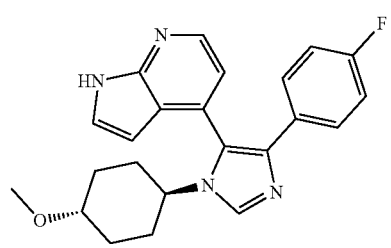

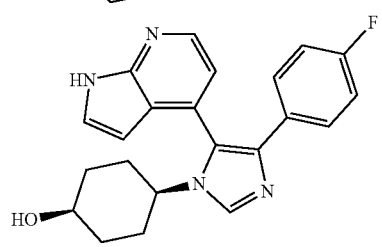

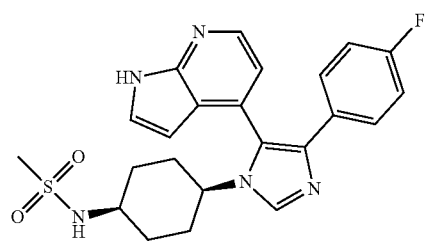

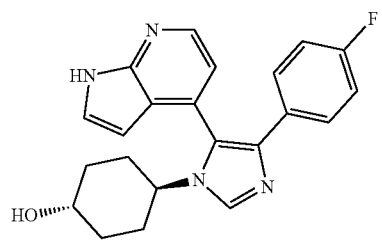

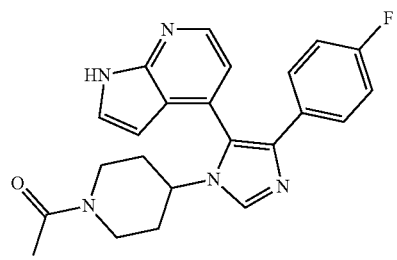

205
-continued
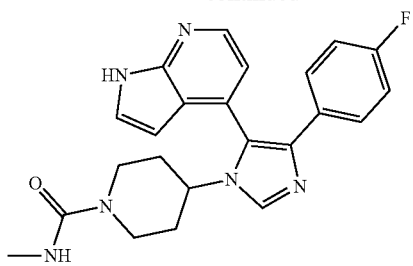
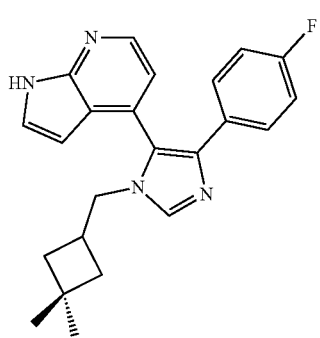
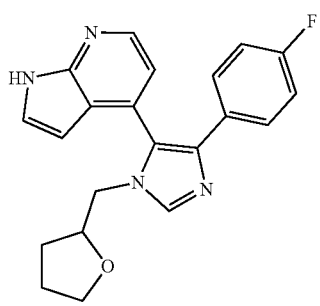
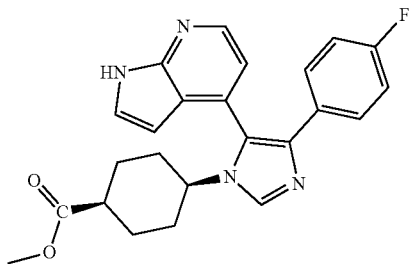
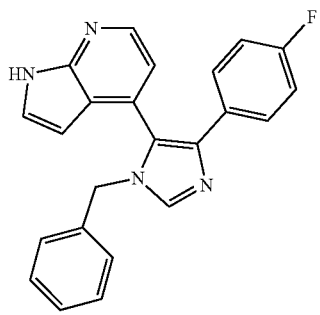
206
-continued
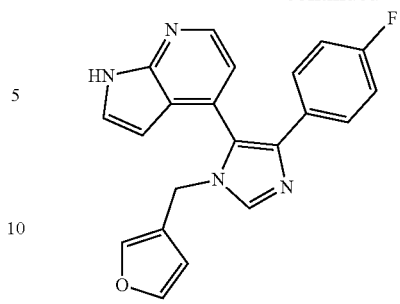
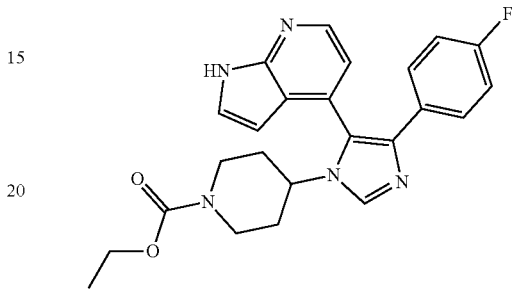
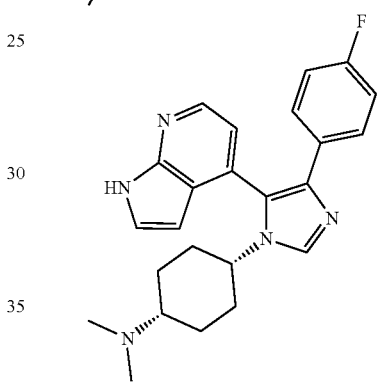
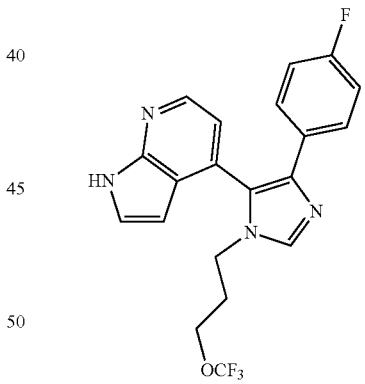
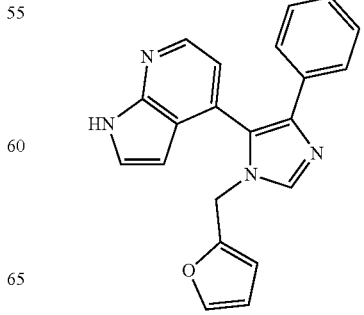

207
-continued
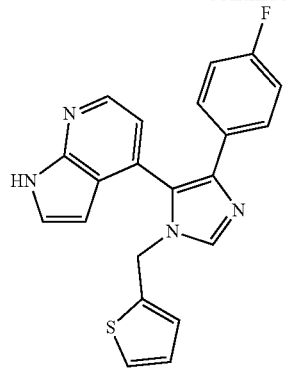
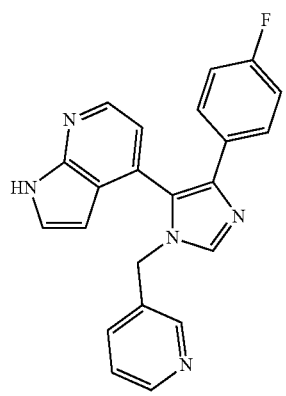
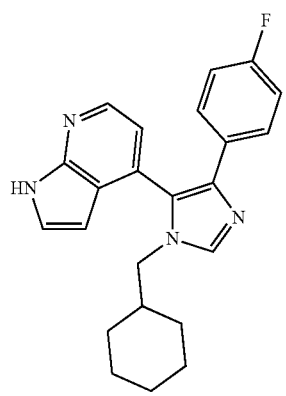
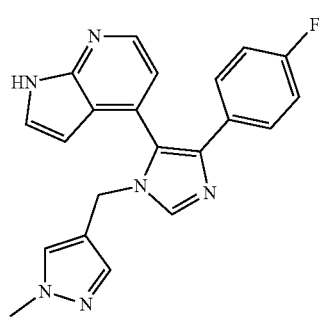
208
-continued
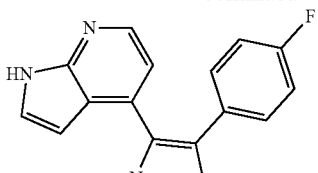
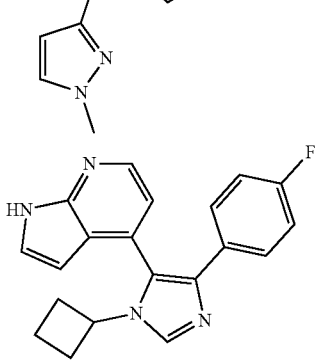
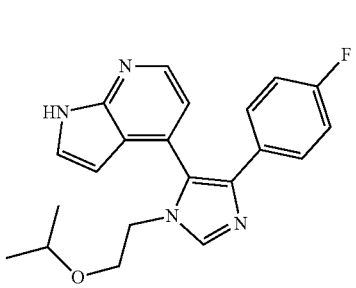
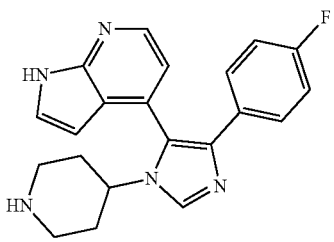
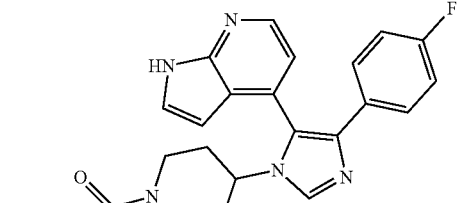
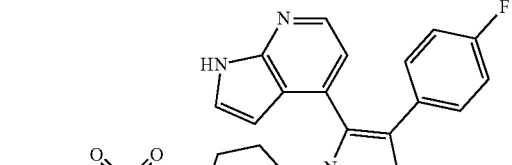

209
-continued
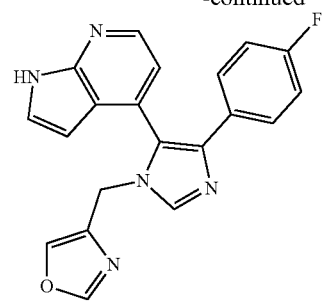
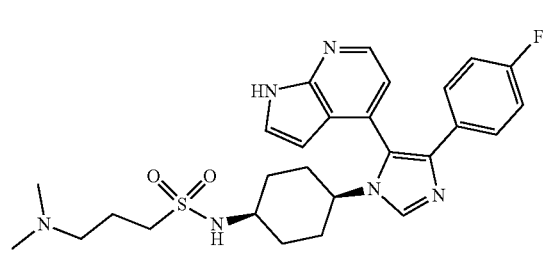
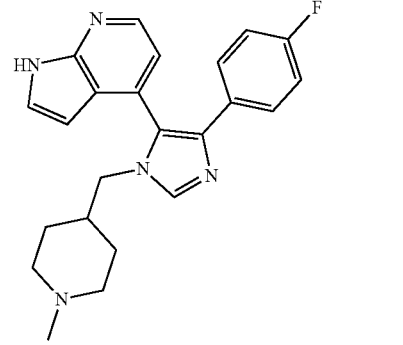
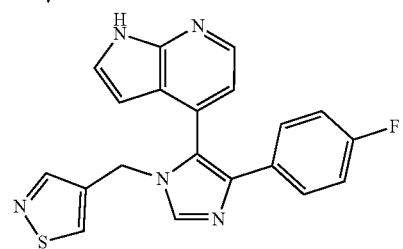
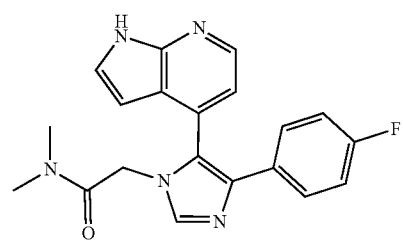
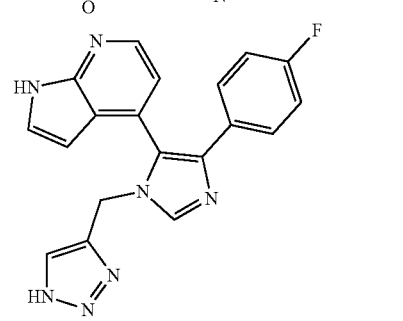
210
-continued
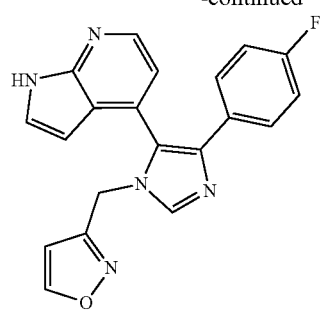
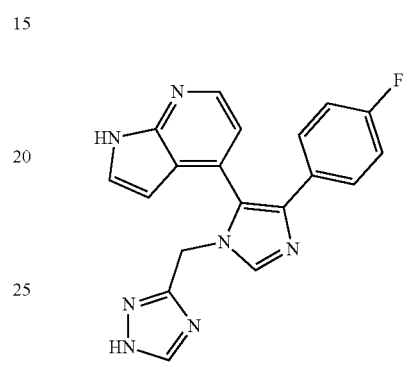
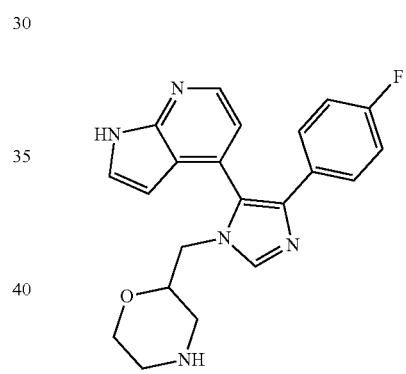
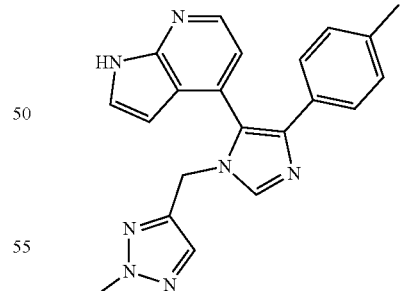
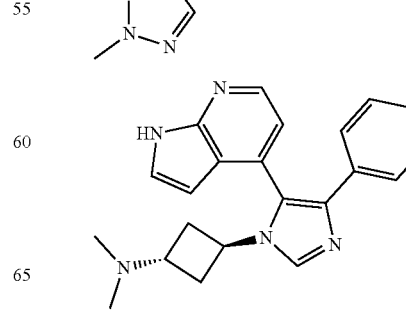
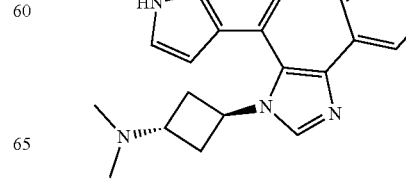

211
-continued
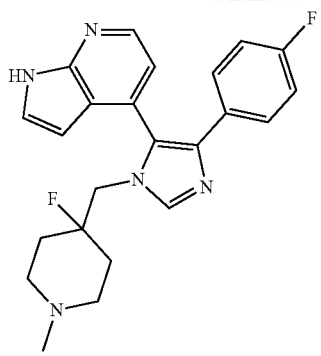
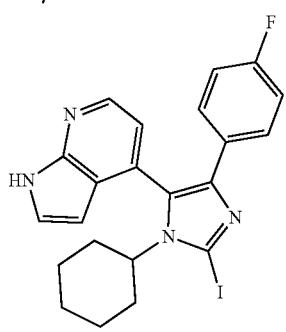
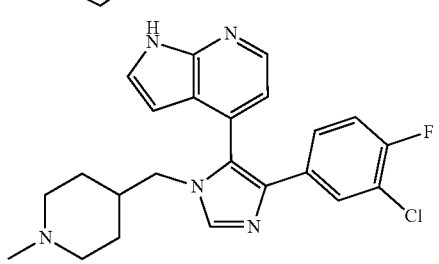
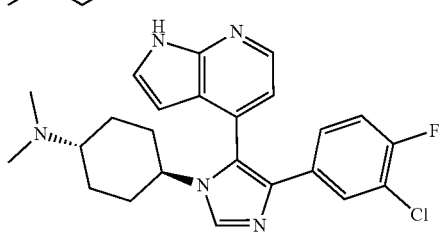
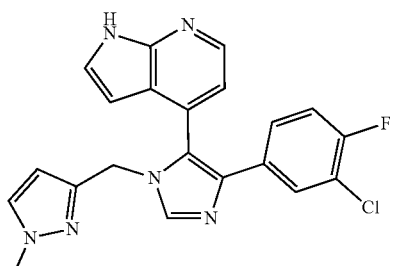
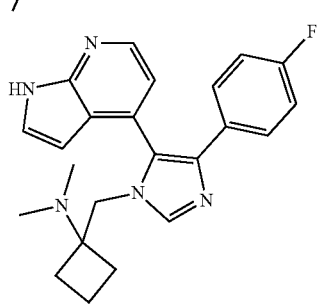
212
-continued
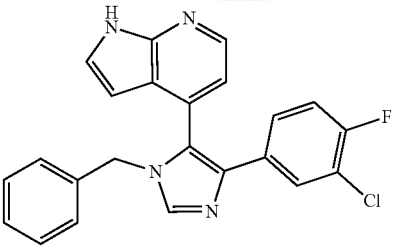
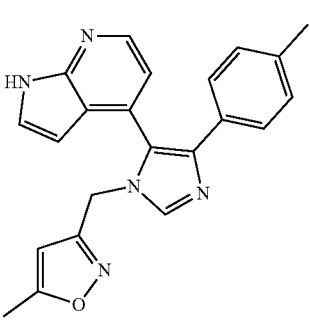
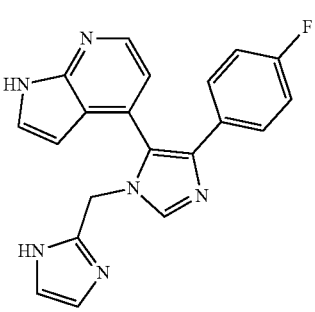
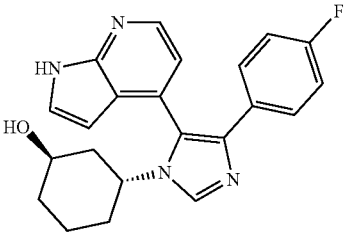
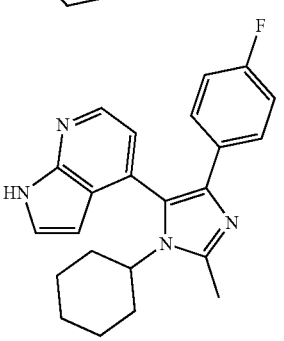
or a pharmaceutically acceptable salt thereof.

13. Compound according to claim 1, which is selected from the following:
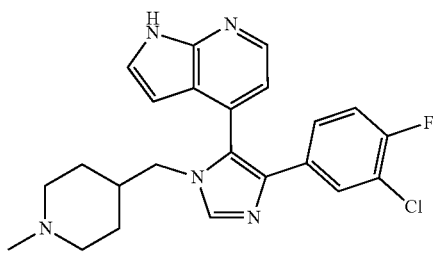
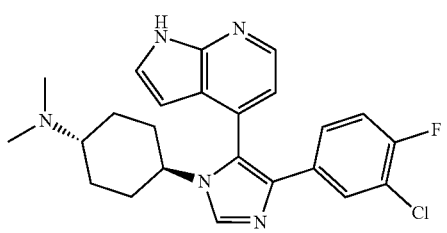
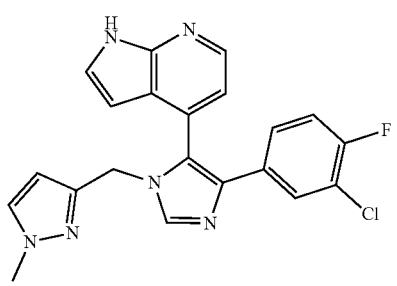
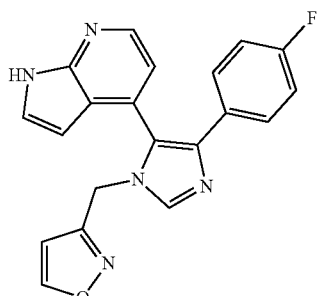
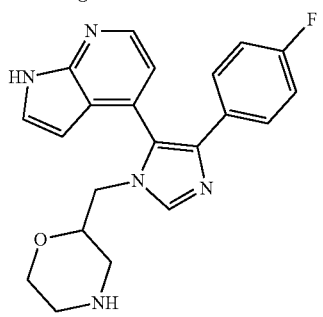
-continued
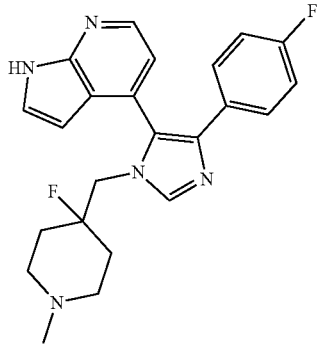
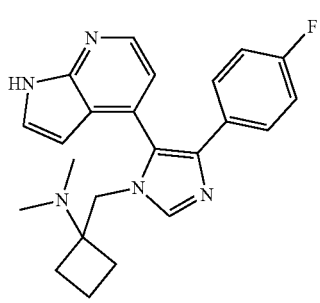
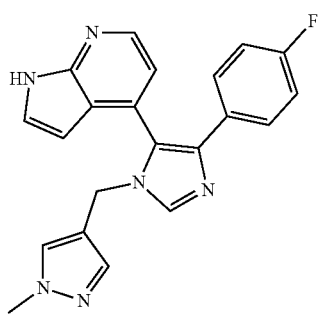
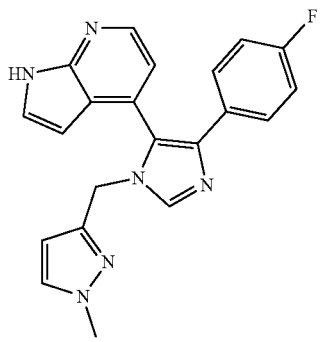
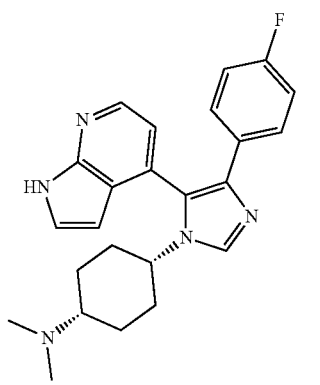

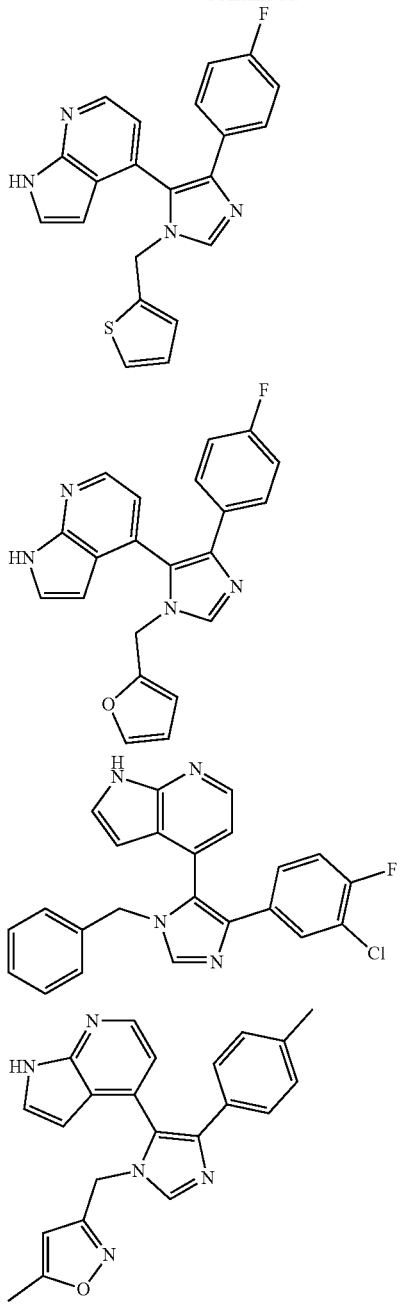
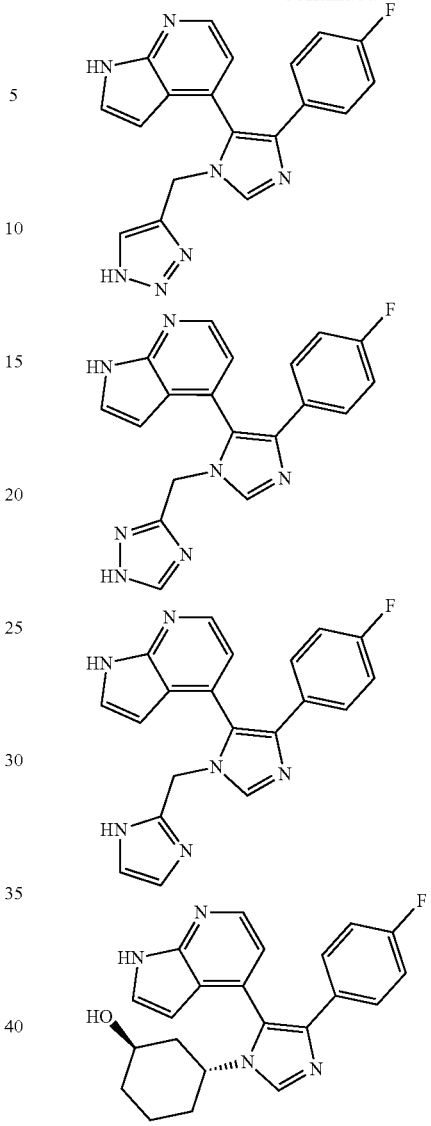
or a pharmaceutically acceptable salt thereof.
14. A pharmaceutical preparation comprising at least one compound of formula I according to claim 1, and at least one pharmaceutically acceptable auxiliary substance selected from pharmaceutically acceptable solvents, fillers, binders.
* * * * *